(12) United States Patent
Barr et al.

(10) Patent No.: US 9,745,265 B2
(45) Date of Patent: Aug. 29, 2017

(54) 4-HETEROARYL SUBSTITUTED BENZOIC ACID COMPOUNDS AS RORGAMMAT INHIBITORS AND USES THEREOF

(71) Applicant: Merck Sharp & Dohme Corp., Rahway, NJ (US)

(72) Inventors: Kenneth J. Barr, Boston, MA (US); Corey E. Bienstock, Natick, MA (US); John K. Maclean, Brookline, MA (US); Hongjun Zhang, Newton, MA (US); Richard T. Beresis, Shanghai (CN); Dongshan Zhang, Shanghai (CN); Neville J. Anthony, Northborough, MA (US); Blair T. Lapointe, Brookline, MA (US); Yuan Tian, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/421,048

(22) PCT Filed: Aug. 14, 2013

(86) PCT No.: PCT/US2013/054887
§ 371 (c)(1),
(2) Date: Feb. 11, 2015

(87) PCT Pub. No.: WO2014/028589
PCT Pub. Date: Feb. 20, 2014

(65) Prior Publication Data
US 2015/0218096 A1   Aug. 6, 2015

(30) Foreign Application Priority Data

Aug. 15, 2012  (WO) ................ PCT/CN2012/080131

(51) Int. Cl.
| | | |
|---|---|---|
| C07D 209/26 | (2006.01) |
| C07D 231/56 | (2006.01) |
| C07D 471/04 | (2006.01) |
| C07D 401/04 | (2006.01) |
| C07D 403/04 | (2006.01) |
| C07D 409/04 | (2006.01) |
| C07D 413/04 | (2006.01) |
| C07D 417/04 | (2006.01) |
| C07D 401/06 | (2006.01) |
| C07D 403/06 | (2006.01) |
| C07D 405/06 | (2006.01) |
| C07D 413/06 | (2006.01) |
| A61K 31/404 | (2006.01) |
| A61K 31/416 | (2006.01) |
| A61K 31/437 | (2006.01) |
| A61K 31/4439 | (2006.01) |
| A61K 31/5377 | (2006.01) |
| C07D 405/12 | (2006.01) |

(52) U.S. Cl.
CPC .......... *C07D 209/26* (2013.01); *A61K 31/404* (2013.01); *A61K 31/416* (2013.01); *A61K 31/437* (2013.01); *A61K 31/4439* (2013.01); *A61K 31/5377* (2013.01); *C07D 231/56* (2013.01); *C07D 401/04* (2013.01); *C07D 401/06* (2013.01); *C07D 403/04* (2013.01); *C07D 403/06* (2013.01); *C07D 405/06* (2013.01); *C07D 405/12* (2013.01); *C07D 409/04* (2013.01); *C07D 413/04* (2013.01); *C07D 413/06* (2013.01); *C07D 417/04* (2013.01); *C07D 471/04* (2013.01)

(58) Field of Classification Search
None
See application file for complete search history.

(56) References Cited

U.S. PATENT DOCUMENTS

| 4,670,447 A | 6/1987 | Strupczewski |
| 5,639,780 A | 6/1997 | Lau et al. |
| 6,133,290 A | 10/2000 | Krushinski, Jr. et al. |

(Continued)

FOREIGN PATENT DOCUMENTS

| EP | 0429257 A2 | 5/1991 |
| EP | 2181710 A1 | 5/2010 |

(Continued)

OTHER PUBLICATIONS

Caplus 1981:406959.*

(Continued)

*Primary Examiner* — Heidi Reese
(74) *Attorney, Agent, or Firm* — Goodwin Procter LLP

(57) ABSTRACT

The present invention relates to compounds according to Formula I (Formula I), and pharmaceutically acceptable salts or solvates thereof. Such compounds can be used in the treatment of RORgammaT-mediated diseases or conditions.

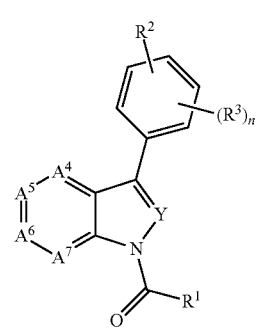

29 Claims, No Drawings

(56) References Cited

U.S. PATENT DOCUMENTS

| | | | |
|---|---|---|---|
| 7,355,042 | B2 | 4/2008 | Edgar et al. |
| 7,514,465 | B2 | 4/2009 | Kuo et al. |
| 7,696,229 | B2 | 4/2010 | Dunn et al. |
| 7,772,252 | B2 | 8/2010 | Hendrix et al. |
| 9,095,583 | B2 * | 8/2015 | Karstens ............... C07D 231/56 |
| 9,273,070 | B2 | 3/2016 | Knochel et al. |
| 2006/0030612 | A1 | 2/2006 | Steffan et al. |
| 2006/0100218 | A1 | 5/2006 | Ibrahim et al. |
| 2009/0124616 | A1 | 5/2009 | Song et al. |
| 2009/0233955 | A1 | 9/2009 | Frazee et al. |
| 2010/0317863 | A1 | 12/2010 | Kuzmich et al. |
| 2011/0150864 | A1 | 6/2011 | Bignan et al. |
| 2011/0263046 | A1 | 10/2011 | Deuschle et al. |
| 2015/0191434 | A1 | 7/2015 | Barr et al. |
| 2015/0210687 | A1 | 7/2015 | Barr et al. |
| 2015/0218169 | A1 | 8/2015 | Barr et al. |
| 2015/0297566 | A1 | 10/2015 | Karstens et al. |

FOREIGN PATENT DOCUMENTS

| | | |
|---|---|---|
| EP | 2487159 A1 | 8/2012 |
| JP | 2007238463 A | 9/2007 |
| WO | WO-96/37467 A1 | 11/1996 |
| WO | WO-2006/052190 A1 | 5/2006 |
| WO | WO-2006/063167 A1 | 6/2006 |
| WO | WO-2007/103308 A2 | 9/2007 |
| WO | WO-2007/144327 A2 | 12/2007 |
| WO | WO-2008/132434 A2 | 11/2008 |
| WO | WO-2008/138889 A2 | 11/2008 |
| WO | WO-2008/153858 A1 | 12/2008 |
| WO | WO-2009/015067 A2 | 1/2009 |
| WO | WO-2010/050837 A1 | 5/2010 |
| WO | WO-2010/068483 A2 | 6/2010 |
| WO | WO-2010/150837 A1 | 12/2010 |
| WO | WO-2011/014775 A1 | 2/2011 |
| WO | WO-2011/103189 A1 | 8/2011 |
| WO | WO-2011/146313 A1 | 11/2011 |
| WO | WO-2012/064744 A2 | 5/2012 |
| WO | WO-2012/077932 A2 | 6/2012 |
| WO | WO-2012/106995 A1 | 8/2012 |
| WO | WO-2012/176763 A1 | 12/2012 |

OTHER PUBLICATIONS

Annunziato et al., "Type 17 T helper cells—origins, features and possible roles in rheumatic disease," 5 Nat. Rev. Rheumatol. 325-31 (2009).

Boaventura et al., "Human mucosal leishmaniasis: Neutrophils infiltrate areas of tissue damage that express high levels of Th17-related cytokines," 40 Eur. J. Immunol. 2830-36 (2010).

Bundgaard (ed.), Design of Prodrugs, Elsevier (1985).

Buonocore et al., "Innate lymphoid cells drive interleukin-23-dependent innate intestinal pathology," 464 Nature 1371-75 (2010).

Eberl et al., "An essential function for the nuclear receptor RORγt in the generation of fetal lymphoid tissue inducer cells," 5(1) Nat. Immunol. 64-73 (2004).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

Higuchi et al. (eds.), Pro-drugs as Novel Delivery Systems, 14 A.C.S. Symposium Series (1975).

Hirose et al., "RORγ: the third member of ROR/RZR orphan receptor subfamily that is highly expressed in skeletal muscle," 205 Biochem. Biophys. Res. Comm. 1976-83 (1994).

Hueber et al., "Cutting Edge: Mast Cells Express IL-17A in Rheumatoid Arthritis Synovium," 184 J. Immunol. 3336-40 (2010).

Ivanov et al., "The Orphan Nuclear Receptor RORγt Directs the Differentiation Program of Proinflammatory IL-17+ T Helper Cells," 126 Cell 1121-33 (2006).

Jia et al., "The T helper type 17/regulatory T cell imbalance in patients with acute Kawasaki disease," 162 Clin. Exp. Immunol. 131-37 (2010).

Jin et al., "Structural Basis for Hydroxycholesterols as Natural Ligands of Orphan Nuclear Receptor RORγ," 24(5) Mol. Endocrinol. 923-29 (2010).

Kastelein et al., "Discovery and Biology of IL-23 and IL-27: Related but Functionally Distinct Regulators of Inflammation," 25 Annu. Rev. Immunol. 221-42 (2007).

Kurebayashi et al., "Selective LXXLL peptides antagonize transcriptional activation by the retinoid-related orphan receptor RORγ," 315 Biochem. Biophys. Res. Comm. 919-27 (2004).

Louten et al., "Development and function of TH17 cells in health and disease," 123(5) J. Allergy Clin. Immunol. 1004-11 (2009).

Miossec et al., "Interleukin-17 and Type 17 Helper T Cells," 361(9) New Eng. J. Med. 888-98 (2009.

Roche (ed.), Bioreversible Carriers in Drug Design, Pergamon Press (1987).

Sun et al., "Requirement for RORγ in Thymocyte Survival and Lymphoid Organ Development," 288 Science 2369-72 (2000).

Sutton et al., "Interleukin-1 and IL-23 Induce Innate IL-17 Production from γδ T Cells, Amplifying Th17 Responses and Autoimmunity," 31 Immunity 331-41 (2009).

Wang et al., "Identification of SR1078, a Synthetic Agonist for the Orphan Nuclear Receptors RORα and RORγ," 5(11) ACS Chem. Biol. 1029-34 (2010).

Wang et al., "Modulation of Retinoic Acid Receptor-related Orphan Receptor α and γ Activity by 7-Oxygenated Sterol Ligands," 285(7) J. Bio. Chem. 5013-25 (2010).

Xie et al., "RORγt Recruits Steroid Receptor Coactivators to Ensure Thymocyte Survival," 175(6) J. Immunol. 3800-09 (2005).

Yang et al., "T Helper 17 Lineage Differentiation is Programmed by Orphan Nuclear Receptors RORα and RORγ," 28 Immunity 29-39 (2008).

Zhou et al., "Use of Homogeneous Time-Resolved Fluorescence Energy Transfer in the Measurement of Nuclear Receptor Activation," 25 Methods 54-61 (2001).

PCT International Search Report (PCT Article 18 and Rules 43 and 44) for PCT/US2013/054887, Mar. 18, 2014.

PCT Written Opinion of the International Searching Authority (PCT Rule 43bis.1) for PCT/US2013/054887, Mar. 18, 2014.

U.S. Appl. No. 14/752,195, RORgammaT Inhibitors, filed Jun. 26, 2015.

U.S. Appl. No. 14/421,052, N-Alkylated Indole and Indazole Compounds as RORgammaT Inhibitors and Uses Thereof, filed Feb. 11, 2015.

U.S. Appl. No. 14/421,057, 3-Cyclohexenyl and Cyclohexyl Subsituted Indole and Indazole Compounds as RORgammaT Inhibitors and Uses Thereof, filed Feb. 11, 2015.

U.S. Appl. No. 14/421,062, 3-Aminocycloalkyl Compounds as RORgammaT Inhibitors and Uses Thereof, filed Feb. 11, 2015.

Chen, Hua-Sin et al., "Synthesis and antiplatelet activity of ethyl 4-(1-benzyl-1H-indazol-3-yl)benzoate (YD-3) derivatives," Bioorganic & Medicinal Chemistry, vol. 16, pp. 1262-1278, (2008).

Varnavas et al., "Anthranilic acid based CCK1 receptor antagonists: preliminary investigation on their second 'touch point,'" 40(6) Euro. J. Med. Chem. 563-81 (2005).

International Search Report and Written Opinion for PCT/US2013/054893, mailed Feb. 14, 2014 (5 pages).

Lee et al., "Synthesis of 1-Benzyl-3-(5'-hydroxymethyl-2'-furyl)indazole Analogues as Novel Antiplatelet Agents," 44 J. Med. Chem. 3746-49 (2001).

André et al., "Disruption of retinoid-related orphan receptor β changes circadian behaviour, causes retinal degeneration and leads to vacillans phenotype in mice," 17(14) The EMBO J. 3867-77 (1998).

Becker-André et al., "Identification of nuclear receptor mRNAs by RT-PCR amplification of conserved zinc-finger motif sequences," 194(3) Biochem. Biophys. Res. Comm. 1371-79 (1993).

Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).

Burris et al., "Targeting Orphan Nuclear Receptors for Treatment of Metabolic Diseases and Autoimmunity," 19(1) Chem. Biol. 51-59 (2012).

Cai et al., "Pivotal Role of Dermal IL-17-Producing γδ T Cells in Skin Inflammation", Immunity (2011) vol. 35, pp. 596-610.

Carlberg et al., "RZRs, a new family of retinoid-related orphan receptors that function as both monomers and homodimers," 8 Mol. Endocrinol. 757-70 (1994).

D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10/1002/art, American College of Rheumatology, (2016) pp. 1-27.

Dr. Baeton, et al., "Secukinumab, an Interleukin-17A Inhibitor, in Ankylosing Spondylitis", The New England Journal of Medicine, (2015) vol. 373, pp. 2534-2548.

Dussault et al., "Orphan nuclear receptor RORα-deficient mice display the cerebellar defects of staggerer," 70 Mech. Develop. 147-53 (1998).

El-Sawy et al., "Synthesis, antimicrobial and anti-cancer activities of some new N-ethyl, N-benzyl and N-benzoyl-3-indolyl heterocycles," 62 Acta Pharm. 157-179 (2012).

Extended European Search Report, EP Application No. 12744370.3, Sep. 9, 2014.

Giguére et al., "Isoform-specific amino-terminal domains dictate DNA-binding properties of RORα, a novel family of orphan hormone nuclear receptors," 8 Genes & Develop. 538-53 (1994).

Guo et al., "Stereospecific microbial reduction of ethyl 1-benzyl-3-oxo-piperidine-4-carboxylate," 17(13) Tetrahedron: Asymmetry 2015-2020 (2006).

Hirose et al., "Benzoheterocyclic derivatives. XI. Synthesis and pharmacological actions of indoline derivatives. 2," CA76:46035 (1971).

Huh et al., "Small molecule inhibitors of RORγt: Targeting Th17 cells and other applications," 42 Eur. J. Immunol. 2232-2237 (2012).

Inamoto et al., "Palladium-Catalyzed C-H Activation/Intramolecular Amination Reaction: A New Route to 3-Aryl/Alkylindazoles," 9(15) Org. Letts. 2931-34 (2007).

Julia et al., "Research in the indole series. IX. Certain 3-indolylsuccinic acids and the corresponding succinimides and pyrrolidines," CA61:92261 (1964).

Krueger, "A welcome surprise in psoriasis", Nature Medicine, (2012) vol. 18, No. 12, pp. 1750-1751.

Larhed et al., "Rapid Microwave-Assisted Suzuki Coupling on Solid-Phase," 37(45) Tetrahedron Letters 8219-22 (1996).

Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.

Martinez, "Th17-biased RORγt transgenic mice become susceptible to a viral model for multiple sclerosis", Brain, Behavior, and Immunity, (2014) vol. 43, pp. 86-97.

Medvedev et al., "Cloning of a cDNA encoding the murine orphan receptor RZR/RORγ and characterization of its response element," 181 Gene 199-206 (1996).

Nakajima, et al., "IL-17A as an Inducer for Th2 Immune Responses in Murine Atopic Dermatitis Models", Journal of Investigative Dermatology, (2014) vol. 134, pp. 2122-2130.

Ortiz et al., "TOR: a new orphan receptor expressed in the thymus that can modulate retinoid and thyroid hormone signals," 9 Mol. Endocrinol. 1679-91 (1995).

Papp et al. "Brodalumab, an Anti-Interleukin-17-Receptor Antibody for Psoriasis", The New England Journal of Medicine, (2012) vol. 366, Iss. 13, 9 pgs.

Reckenbeil et al., "Supramolekulare Phosphorylierung kationischer Alkohole mit 3-Arylindol-4-carboxamidin-Struktur," Liebigs Ann. Chem. 1219-29 (1994).

Skepner, et al., "Pharmacologic Inhibition of RORγt RegulatesTh17 Signature Gene Expression and Suppresses Cutaneous Inflammation in Vivo", The Journal of Immunology, (2014) pp. 1-12.

Smith, "The Bench-to-Bedside Story of IL-17 and the Therapeutic Efficacy of its Targeting in Spondyloarthritis", Curr Rheumatol Rep. (2016) vol. 18, pp. 1-10.

Solt et al., "Action of RORs and their ligands in (patho)physiology," 23(12) Trends in Endocrinology and Metabolism, pp. 619-627 (2012).

Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.

Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. pp. 4072-4080 (1999).

Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).

Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).

Xiao, et al., "Small-Molecule RORγt Antagonists Inhibit T Helper 17 Cell Transcriptional Network by Divergent Mechanisms", Immunity (2014) vol. 40, pp. 477-489.

International Search Report and Written Opinion for PCT/US2013/054902, mailed Feb. 28, 2014 (5 pages).

International Search Report and Written Opinion for PCT/US2013/054911 dated Mar. 4, 2014 (9 pages).

International Search Report from PCT/CN2012/071017, mailed May 24, 2012.

Cheng et al., "Design and synthesis of heterocyclic malonyl-CoA decarboxylase inhibitors," 16 Bioorg. Med. Chem. Lett. 695-700 (2006).

Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).

Database Caplus [Online] Chemical Abstracts Service, Columbus, Ohio, US; Kusakabe, Kanekazu et al: "Preparation of condensed pyrazole compounds as TTK protein kinase inhibitors", retrieved from STN Database accession No. 2011:1578140 ; & Kusakabe, Kanekazu et al: "Preparation of condensed pyrazole comopunds as TTK protein kinase inhibitors", Jpn. Kokai Tokkyo Koho, 134PP. Coden: JKXXAF.

* cited by examiner

4-HETEROARYL SUBSTITUTED BENZOIC ACID COMPOUNDS AS RORGAMMAT INHIBITORS AND USES THEREOF

CROSS REFERENCE TO RELATED APPLICATIONS

This application is a national stage of International (PCT) Patent Application Serial No. PCT/US2013/054887, filed Aug. 14, 2013, which claims the benefit of and priority to Patent Application Serial No. PCT/CN2012/080131, filed Aug. 15, 2012.

BACKGROUND OF THE INVENTION

Upon activation by antigen-presenting cells naïve T helper cells undergo clonal expansion and will ultimately differentiate in cytokine secreting effector T cells, such as Th1 and Th2 subtypes. A third and distinct effector subset has been identified, which plays a key role in providing immunity to bacteria and fungi at mucosal surfaces (Kastelein et al., Annu. Rev. Immunol. 25: 221-242, 2007). This effector T helper cell subset can be distinguished based on its ability to produce large quantities of IL-17/F, IL-21 and IL-22, and is named Th17 (Miossec et al., New Eng. J. Med. 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., Immunity 9: 797-806, 1998). RORgammaT belongs to the nuclear hormone receptor superfamily (Hirose et al., Biochem. Biophys. Res. Comm. 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., Science 288: 2369-2372, 2000; Eberl et al., Nat Immunol. 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., Cell 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., Cell 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., Immunity 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., Nature 464: 1371-1375, 2010). In addition, RORgammaT was shown to play a crucial role in other non-Th17 cells, such as mast cells (Hueber et al., J. Immunol. 184: 3336-3340, 2010). Finally, RORgammaT expression and secretion of Th17-type of cytokines was reported for Lymphoid Tissue Inducer cells, NK T-cells, NK cells (Eberl et al., Nat. Immunol. 5: 64-73, 2004), and gamma-delta T-cells (Sutton et al., Nat. Immunol. 31: 331-341, 2009; Louten et al., J. Allergy Clin. Immunol. 123: 1004-1011, 2009), suggesting an important function for RORgammaT in these subtypes of cells.

Based on the role of IL-17 producing cells (either Th17 or non-Th17 cells), RORgammaT has been identified as a key mediator in the pathogenesis of several diseases (Louten et al., J. Allergy Clin. Immunol. 123: 1004-1011, 2009; Annuziato et al., Nat. Rev. Rheumatol. 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., Cell 126:1121-33, 2006; Buonocore et al., Nature 464: 1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease, Crohn's disease, and asthma (Annunziato et al., Nat. Rev. Immunol. 5: 325-331, 2009; Louten et al., J. Allergy Clin. Immunol. 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., Clin. Exp. Immunol. 162: 131-137, 2010) and Hashimoto's thyroiditis (Figueroa-Vega et al., J. Clin. Endocrinol. Metab. 95: 953-62, 2010). Another example includes infectious diseases, such as but not limited to mucosal leishmaniasis (Boaventura et al., Eur. J. Immunol. 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., ACS Chem. Biol. 5:1029-1034, 2010). In addition, antagonists have been reported such as 7-oxygenated sterols (Wang et al., J. Biol. Chem. 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT and thereby antagonize RORgammaT-mediated transcriptional activity, their use for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

The present invention provides a compound according to Formula I

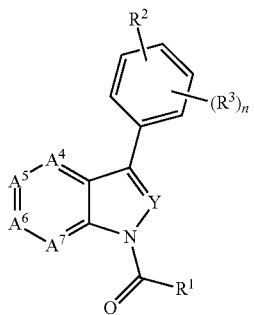

I or a pharmaceutically acceptable salt or solvate thereof, wherein:
Y is CH, $CR^a$, or N;
n=0, 1, 2, 3 or 4;
$A^4$ is $CR^4$ or N,
$A^5$ is $CR^5$ or N,
$A^6$ is $CR^6$ or N,
$A^7$ is $CR^7$ or N,
with the proviso that no more than two of $A^4$-$A^7$ can be N;
$R^a$ is $(C_{1-4})$alkyl or $(C_{3-7})$cycloalkyl;
$R^1$ is
  (i) $(C_{3-12})$carbocyclyl$(C_{0-4})$alkyl;
  (ii) a 4- to 12-membered heterocyclyl$(C_{0-4})$alkyl, or
  (iii) $(C_{1-4})$alkoxy,
  each optionally substituted with one, two, three, four or five $R^8$;
$R^2$ is hydroxycarbonyl, hydroxycarbonyl$(C_{1-10})$alkyl, $(C_{1-10})$alkylsulfoxyaminocarbonyl, or carbamoyl;
$R^3$ is hydrogen, halogen, cyano, nitro, hydroxy, $(C_{1-4})$alkoxy, $(C_{1-4})$alkylcarbonyloxy, $(C_{1-4})$alkylsulfonylamino, $(C_{1-4})$alkylcarbonylamino, $(C_{0-4})$alkylamino, $(C_{1-4})$alkyl, hydroxyl$(C_{1-4})$alkyl or $(C_{1-4})$alkoxy, wherein $(C_{1-4})$alkyl and $(C_{1-4})$alkoxy are optionally substituted with one or more halogen;
$R^4$-$R^7$ independently are hydrogen, halogen, amino, cyano, hydroxy, $(C_{1-3})$alkoxy, $(C_1$-4)alkyl, $(C_{0-10})$alkylaminocarbonyl, $(C_{0-6})$alkyoxycarbonylamino, (di)$(C_{1-6})$alkylaminocarbonyl, $(C_{1-6})$alkylcarbonylamino, $(C_{1-4})$alkylamino, amino$(C_{1-4})$alkyl or formaldehyde, wherein $(C_{1-3})$alkoxy, $(C_{1-4})$alkyl, $(C_{0-10})$alkyl)aminocarbonyl, (di)$(C_{1-6})$alkylaminocarbonyl, $(C_{1-4})$alkylamino and amino$(C_{1-4})$alkyl are optionally substituted with one or more halogen, hydroxyl or $(C_{1-3})$alkoxy; or a group having the formula

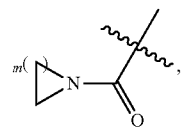

optionally substituted with one or more of the following: $(C_{1-10})$alkyl, halogen, amino, cyano, hydroxy, $(C_{1-3})$alkoxy, and wherein m is 1, 2, 3, or 4;
$R^6$ is, additionally,
  (i) $(C_{3-7})$cycloalkyl or $(C_{3-5})$heterocycloalkyl, both optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;
  (ii) $(C_{2-9})$heteroaryl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;
  (iii) $(C_{6-14})$aryl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;
  (iv) $(C_{3-5})$heterocycloalkylcarbonyl or $(C_{3-5})$heterocycloalkylcarbonyl$(C_{1-4})$alkyl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;
  (v) $(C_{3-5})$heterocycloalkylamino, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;
  (vi) $(C_{3-5})$cycloalkylaminocarbonyl or di$(C_{3-5})$cycloalkylaminocarbonyl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;
  (vii) $(C_{3-5})$cycloalkylcarbonylamino, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, (di)$(C_{1-6})$ alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl and $(C_{1-3})$alkoxy are optionally substituted with one or more halogen, amino or hydroxyl;

(viii) $(C_{3-5})$cycloalkyl$(C_{1-4})$alkyl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$ alkoxycarbonyl, $(di)(C_{1-6})$alkylaminocarbonyl, $(C_{1-4})$ alkyl and $(C_{1-3})$alkoxy are optionally substituted with one or more halogen, amino or hydroxyl;

(ix) $(C_{3-5})$cycloalkylamino, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$ alkoxycarbonyl, $(di)(C_{1-6})$alkylaminocarbonyl, $(C_{1-4})$ alkyl and $(C_{1-3})$alkoxy are optionally substituted with one or more halogen, amino or hydroxyl;

(x) $(C_{3-5})$cycloalkylcarbonyl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$ alkoxycarbonyl, $(di)(C_{1-6})$alkylaminocarbonyl, $(C_{1-4})$ alkyl and $(C_{1-3})$alkoxy are optionally substituted with one or more halogen, amino or hydroxyl;

(xi) $(C_{2-9})$heteroaryl$(C_{1-4})$alkyl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$ alkoxycarbonyl, $(di)(C_{1-6})$alkylaminocarbonyl, $(C_{1-4})$ alkyl and $(C_{1-3})$alkoxy are optionally substituted with one or more halogen, amino or hydroxyl;

(xii) $(C_{2-9})$heteroarylcarbonyl, optionally substituted with one or more groups selected from halogen, amino, amino$(C_{1-4})$alkyl, cyano, nitro, hydroxyl, oxo (=O), $H_2NC(O)$, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$ alkoxycarbonyl, $(di)(C_{1-6})$alkylaminocarbonyl, $(C_{1-4})$ alkyl and $(C_{1-3})$alkoxy are optionally substituted with one or more halogen, amino or hydroxyl;

(xiii)

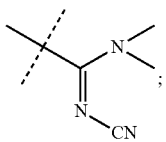

(xiv) $(C_{2-4})$alkynyl, optionally substituted with one or more $(C_{1-4})$alkyl, which $(C_{1-4})$alkyl may be substituted with hydroxyl or amino; or (xv) $(C_{1-6})$alkoxycarbonylamino,
$(C_{1-6})$alkylcarbonylamino,
$(C_{1-6})$alkylsulfonylamino$(C_{0-4})$alkyl,
$(C_{1-6})$alkylaminocarbonylamino,
$(C_{1-6})$alkyoxycarbonylamino$(C_{0-4})$alkyl,
Hydroxycarbonyl$(C_{1-4})$alkylamino,
Hydroxycarbonyl,
$(C_{1-6})$alkylamino,
(C1-6)alkoxyamino,
(C0-6)alkylaminocarbonyl(C1-6)alkyl, or
di(C1-6)alkylaminocarbonyl(C1-6)alkyl, each optionally substituted with one or more $(C_{1-4})$ alkyl, hydroxyl or amino; and $R^8$ is halogen, cyano, amino, nitro, hydroxy, oxo(=O), $H_2NC(O)$—, $di(C_{1-3})$alkylamino, $(C_{1-3})$alkoxycarbonyl, $(di)(C_{1-6})$alkylaminocarbonyl, $(C_{1-4}$ alkyl, $(C_{3-7})$ cycloalkyl, $(C_{3-5})$heterocycloalkyl, $(C_{1-4})$alkenyl, $(C_{3-6})$cycloalkoxy or $(C_{1-3})$alkoxy, wherein $(C_{1-3})$ alkoxycarbonyl, $(di)(C_{1-6})$alkylaminocarbonyl, $(C_{1-4}$ alkyl and $(C_{1-3})$alkoxy are optionally substituted with one, two or three halogens.

In a first embodiment of the compound having Formula I is a compound having Formula Ia

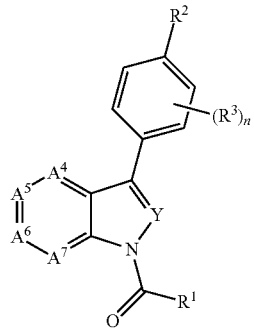

and a pharmaceutically acceptable salt or solvate thereof.

In a second embodiment of the compound having Formula I is a compound having Formula Ib

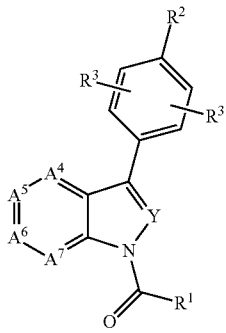

and a pharmaceutically acceptable salt or solvate thereof.

In a first subset of the second embodiment is a compound wherein Y is N.

In a third embodiment of the compound having Formula I is a compound having Formula Ic

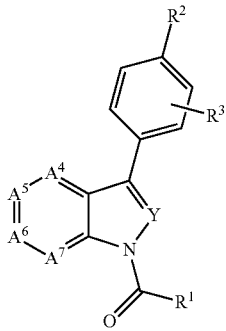

and a pharmaceutically acceptable salt or solvate thereof.

In a fourth embodiment of the compound having Formula I is a compound having Formula Id

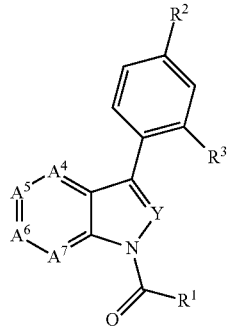

and a pharmaceutically acceptable salt or solvate thereof.

In a first subset of the fourth embodiment is a compound wherein Y is N.

In a first subset of the first embodiment is a compound having Formula Ie

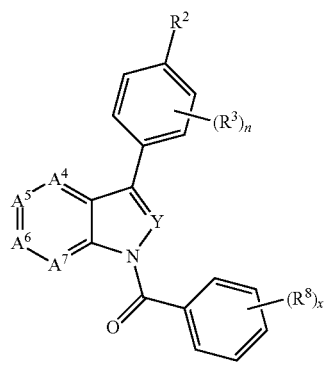

wherein x is 0, 1, 2, 3, 4 or 5; and a pharmaceutically acceptable salt or solvate thereof.

In a second subset is a compound having Formula If

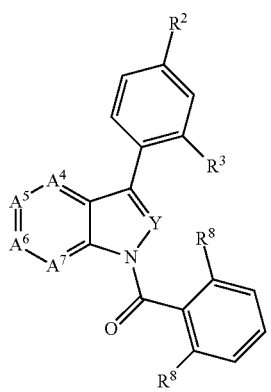

and a pharmaceutically acceptable salt or solvate thereof.

In a third subset is a compound having Formula Ig

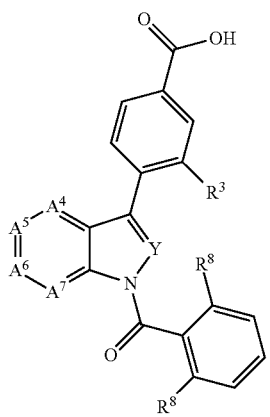

and a pharmaceutically acceptable salt or solvate thereof.

In a fourth subset is a compound having Formula Ih

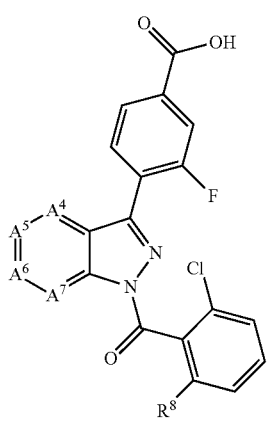

and a pharmaceutically acceptable salt or solvate thereof.

In a fifth subset is a compound having Formula Ii

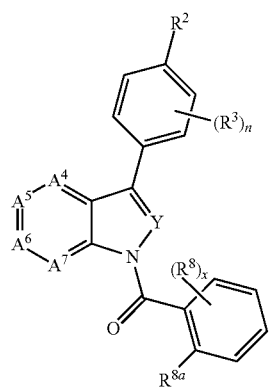

wherein
$R^{8a}$ is $(C_{3-7})$cycloalkyl or $(C_{3-5})$heterocycloalkyl, and x is 1 or 2,
and a pharmaceutically salt or solvate thereof.

In a preferred embodiment $R^{8a}$ is a $(C_{3-6})$cycloalkyl which includes but is not limited to cyclopropyl, cyclobutyl, cyclopentyl and cyclohexyl. In a preferred embodiment $R^{8a}$ is cyclopropyl or cyclobutyl.

In another preferred embodiment $R^{8a}$ is a $(C_{3-5})$heterocycloalkyl having one heteroatom such as O or N, which includes but is not limited to morpholinyl, azetidinyl, or oxetanyl.

In a fifth subset of the first embodiment is a compound wherein $A^4, A^5, A^6, A^7$ are selected from the group consisting of: (i) $CR^4, CR^5, CR^6, CR^7$; (ii) N, $CR^5, CR^6, CR^7$; (iii) $CR^4$, N, $CR^6, CR^7$; (iv) $CR^4, CR^5$, N, $CR^7$; (v) $CR^4, CR^5, CR^6$, N; (vi) N, N, $CR^6, CR^7$; (vii) $CR^4$, N, N, $CR^7$; (viii) $CR^4, CR^5$, N, N; (ix) N, $CR^5$, N, $CR^7$; (x) $CR^4$, N, $CR^6$, N; and (xi) N, $CR^5, CR^6$, N.

In a sixth subset is a compound wherein $A^4, A^5, A^6, A^7$ are selected from the group consisting of: (i) $CR^4, CR^5, CR^6, CR^7$; (ii) N, $CR^5, CR^6, CR^7$; and (iii) $CR^4$, N, $CR^6, CR^7$.

In a seventh subset is a compound wherein $A^4, A^5, A^6, A^7$ is (i) $CR^4, CR^5, CR^6, CR^7$, or (ii) N, $CR^5, CR^6, CR^7$; and Y is N.

In an eighth subset is a compound wherein $R^1$ is (i) $(C_{3-7})$cycloalkyl or $(C_{3-5})$heterocycloalkyl, both optionally substituted with one, two, three, four or five $R^8$;

(ii) $(C_{2-9})$heteroaryl$(C_{0-4})$alkyl, optionally substituted with one, two, three, four or five $R^8$; or (iii) $(C_{6-14})$aryl$(C_{0-4})$alkyl, optionally substituted with one, two, three, four or five $R^8$.

In a ninth subset is a compound wherein $R^1$ is (i) $(C_{2-9})$heteroaryl, or (ii) $(C_{6-14})$aryl, optionally substituted with one, two, three, four or five $R^8$.

In a tenth subset is a compound wherein $R^1$ is $(C_{6-14})$aryl, optionally substituted with one or two $R^8$.

In an eleventh subset is a compound wherein $R^1$ is phenyl, optionally substituted with one or two $R^8$.

In a twelfth subset is a compound wherein $R^2$ is C(O)OH.

In a thirteenth subset is a compound wherein $R^6$ is

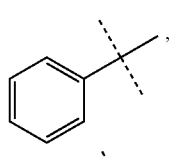

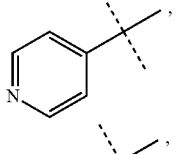

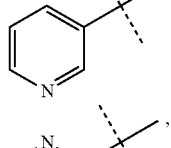

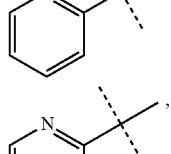

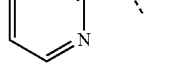

-continued

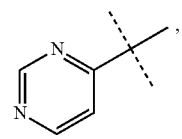

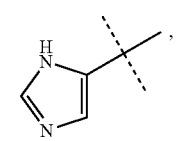

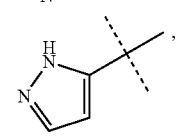

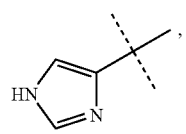

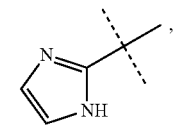

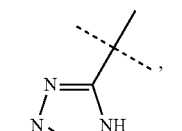

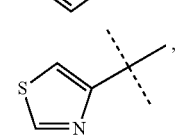

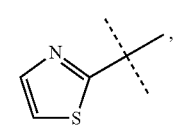

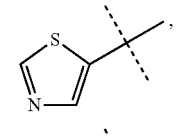

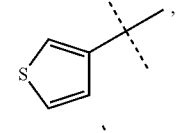

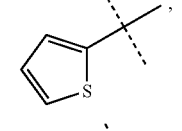

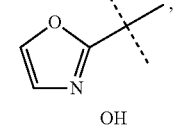

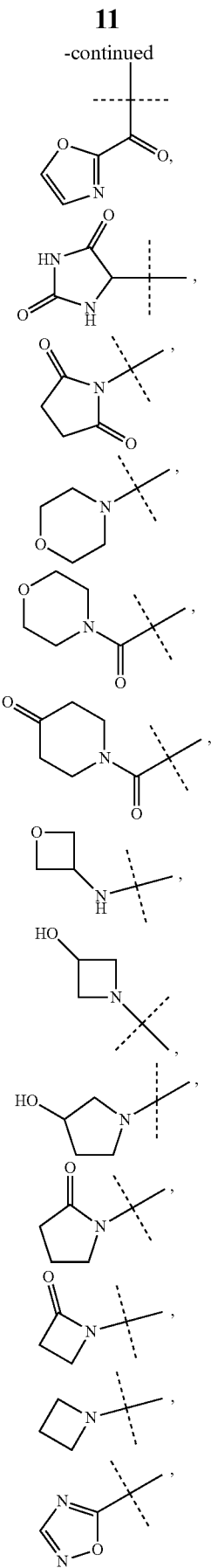
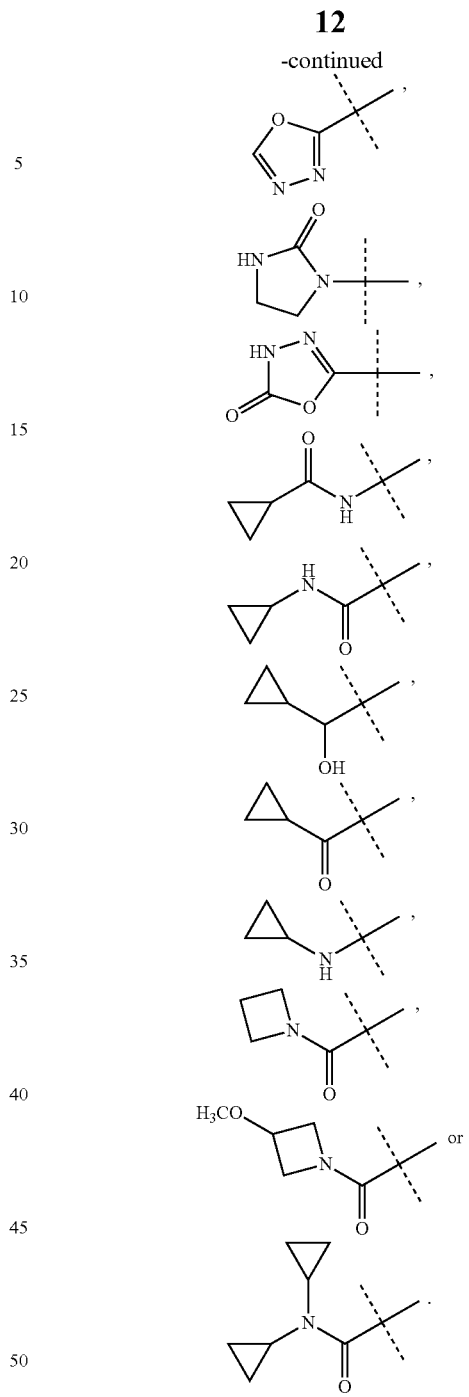

A still further embodiment of the compounds of Formula I, Ia, Ib, Ic, Id, Ie, If, Ig and Ih, are compounds wherein one of $R^4$, $R^5$, $R^6$, and $R^7$ is other than hydrogen.

The invention also relates to those compounds wherein all specific definitions for $A^1$ through $A^4$, $R^1$ through $R^8$, $R^a$, Y, m, n and x and all substituent groups in the various aspects of the inventions defined hereinabove occur in any combination within the definition of the compound of Formula I.

Non-limiting examples of the compounds of the present invention include:

(E)-4-(1-(2-chloro-6-(prop-1-enyl)benzoyl)-1H-pyrazolo[4,3-b]pyridin-3-yl)-3-fluorobenzoic acid;

4-(1-(2-chloro-6-(trifluoromethyl)benzoyl)-4-formyl-1H-indazol-3-yl)benzoic acid;

4-(1-(2-chloro-6-(trifluoromethyl)benzoyl)-1H-pyrazolo[4,3-b]pyridin-3-yl)-1H-indazole-7-carboxylic acid;
4-(1-(2-chloro-6-cyclopropoxybenzoyl)-1H-pyrazolo[4,3-b]pyridin-3-yl)benzoic acid;
3-fluoro-4-(1-(2-phenylpropanoyl)-1H-indazol-3-yl)benzoic acid;
3-fluoro-4-[1-(methoxyacetyl)-1H-indazol-3-yl]benzoic acid;
3-fluoro-4-[1-(pyridin-3-ylcarbonyl)-1H-indazol-3-yl]benzoic acid;
3-fluoro-4-{1-[(2-oxopyrrolidin-1-yl)acetyl]-1H-indazol-3-yl}benzoic acid;
3-fluoro-4-[1-(naphthalen-1-ylcarbonyl)-1H-indazol-3-yl]benzoic acid;
3-fluoro-4-{1-[(1-methyl-1H-indol-2-yl)carbonyl]-1H-indazol-3-yl}benzoic acid;
4-{1-[(2-bromo-3-methylphenyl)carbonyl]-1H-indazol-3-yl}-3-fluorobenzoic acid;
4-[1-(2,3-dihydro-1H-inden-4-ylcarbonyl)-1H-indazol-3-yl]-3-fluorobenzoic acid;
4-(1-{[3-(tertbutoxycarbonyl)-3-azabicyclo[3.1.0]hex-6-yl]carbonyl}-1H-indazol-3-yl)-3-fluorobenzoic acid;
4-[1-(2,3-dihydro-1-benzofuran-7-ylcarbonyl)-1H-indazol-3-yl]-3-fluorobenzoic acid;
4-[1-(1-benzofuran-7-ylcarbonyl)-1H-indazol-3-yl]-3-fluorobenzoic acid;
4-{1-[(2-bromo-3-chlorophenyl)carbonyl]-1H-indazol-3-yl}-3-fluorobenzoic acid;
3-fluoro-4-(1-(tetrahydrofuran-2-carbonyl)-1H-indazol-3-yl)benzoic acid;
4-(1-(2-chloro-6-(trifluoromethyl)benzoyl)-6-(morpholine-4-carbonyl)-1H-indazol-3-yl)benzoic acid;
4-(1-(2-chloro-6-(trifluoromethyl)benzoyl)-6-((2S,6R)-2,6-dimethylmorpholine-4-carbonyl)-1H-indazol-3-yl)-3-fluorobenzoic acid;
4-(1-(2-chloro-6-(trifluoromethyl)benzoyl)-6-(4-oxopiperidine-1-carbonyl)-1H-indazol-3-yl)-3-fluorobenzoic acid;
2-acetamido-4-(1-(2-chloro-6-(trifluoromethyl)benzoyl)-1H-indazol-3-yl)benzoic acid;
4-(1-(2-chloro-6-(trifluoromethyl)benzoyl)-1H-pyrazolo[4,3-b]pyridin-3-yl)-2-(methylsulfonamido)benzoic acid;
4-(1-(2-chloro-6-(trifluoromethyl)benzoyl)-6-(3-hydroxyazetidin-1-yl)-1H-indazol-3-yl)benzoic acid;
4-(6-(azetidin-1-yl)-1-(2-chloro-6-(trifluoromethyl)benzoyl)-1H-indazol-3-yl)-3-fluorobenzoic acid;
4-(1-(2-chloro-6-(trifluoromethyl)benzoyl)-6-(cyclopropylamino)-1H-indazol-3-yl)-3-fluorobenzoic acid;
4-(1-(2-chloro-6-(trifluoromethyl)benzoyl)-6-(oxetan-3-ylamino)-1H-indazol-3-yl)-3-fluorobenzoic acid;
4-(1-(2-chloro-6-(trifluoromethyl)benzoyl)-6-(3-hydroxypyrrolidin-1-yl)-1H-indazol-3-yl)-3-fluorobenzoic acid;
4-(1-(2-chloro-6-(trifluoromethyl)benzoyl)-6-morpholino-1H-indazol-3-yl)benzoic acid;
4-(1-(2-chloro-6-(trifluoromethyl)benzoyl)-6-(methoxycarbonylamino)-1H-indazol-3-yl)-3-fluorobenzoic acid;
4-(1-(2-chloro-6-(trifluoromethyl)benzoyl)-6-(N-methylacetamido)-1H-indazol-3-yl)-3-fluorobenzoic acid;
4-(1-(2-chloro-6-(trifluoromethyl)benzoyl)-6-(cyclopropanecarboxamido)-1H-indazol-3-yl)-3-fluorobenzoic acid;
4-(1-(2-chloro-6-(trifluoromethyl)benzoyl)-6-(methylsulfonamido)-1H-indazol-3-yl)-3-fluorobenzoic acid;
4-(1-(2-chloro-6-(trifluoromethyl)benzoyl)-6-(3-methylureido)-1H-indazol-3-yl)-3-fluorobenzoic acid;
4-(6-acetamido-1-(2-chloro-6-(trifluoromethyl)benzoyl)-1H-indazol-3-yl)-3-fluorobenzoic acid;
4-(1-(2-chloro-6-(trifluoromethyl)benzoyl)-6-(N-methylmethylsulfonamido)-1H-indazol-3-yl)-3-fluorobenzoic acid;
4-(1-(2-chloro-6-(trifluoromethyl)benzoyl)-6-(1,3-dimethylureido)-1H-indazol-3-yl)-3-fluorobenzoic acid;
4-(1-(2-chloro-6-(trifluoromethyl)benzoyl)-6-(2-oxo-imidazolidin-1-yl)-1H-indazol-3-yl)-3-fluorobenzoic acid;
4-(1-(2-chloro-6-(trifluoromethyl)benzoyl)-6-(2-oxoazetidin-1-yl)-1H-indazol-3-yl)-3-fluorobenzoic acid;
4-(6-(2-carboxyethylamino)-1-(2-chloro-6-(trifluoromethyl)benzoyl)-1H-indazol-3-yl)-3-fluorobenzoic acid;
4-(1-(2-chloro-6-(trifluoromethyl)benzoyl)-6-(3-methyl-2-oxoimidazolidin-1-yl)-1H-indazol-3-yl)-3-fluorobenzoic acid;
4-(1-(2-chloro-6-(trifluoromethyl)benzoyl)-6-(2-oxopyrrolidin-1-yl)-1H-indazol-3-yl)-3-fluorobenzoic acid;
4-(1-(2-chloro-6-(trifluoromethyl)benzoyl)-6-(morpholine-4-carbonyl)-1H-indazol-3-yl)benzoic acid;
3-(4-carboxyphenyl)-1-(2-chloro-6-(trifluoromethyl)benzoyl)-1H-indazole-6-carboxylic acid;
4-(1-(2-chloro-6-(trifluoromethyl)benzoyl)-6-(cyclopropylcarbamoyl)-1H-pyrazolo[4,3-b]pyridin-3-yl)-3-fluorobenzoic acid;
4-(1-(2-chloro-6-(trifluoromethyl)benzoyl)-6-(cyclopropyl(methyl)carbamoyl)-1H-pyrazolo[4,3-b]pyridin-3-yl)-3-fluorobenzoic acid;
4-(1-(2-chloro-6-(trifluoromethyl)benzoyl)-6-(cyclopropyl(hydroxy)methyl)-1H-pyrazolo[4,3-b]pyridin-3-yl)-3-fluorobenzoic acid;
4-(1-(2-chloro-6-(trifluoromethyl)benzoyl)-6-(cyclopropane-carbonyl)-1H-pyrazolo[4,3-b]pyridin-3-yl)-3-fluorobenzoic acid;
4-(1-(2-chloro-6-(trifluoromethyl)benzoyl)-6-(hydroxy(oxazol-2-yl)methyl)-1H-pyrazolo[4,3-b]pyridine-3-yl)-3-fluorobenzoic acid;
4-(1-(2-chloro-6-(trifluoromethyl)benzoyl)-6-(oxazole-2-carbonyl)-1H-pyrazolo[4,3-b]pyridin-3-yl)-3-fluorobenzoic acid;
sodium 4-(1-(2-chloro-6-(trifluoromethyl)benzoyl)-6-(5-methyloxazol-2-yl)-1H-indazol-3-yl)benzoate;
4-(1-(2-chloro-6-(trifluoromethyl)benzoyl)-6-(5-methyloxazol-2-yl)-1H-indazol-3-yl)-3-fluorobenzoic acid;
4-(1-(2-chloro-6-(trifluoromethyl)benzoyl)-6-(3-hydroxyprop-1-ynyl)-1H-indazol-3-yl)benzoic acid;
4-(1-(2-chloro-6-(trifluoromethyl)benzoyl)-6-(3-hydroxybut-1-ynyl)-1H-indazol-3-yl)-3-fluorobenzoic acid;
4-(6-(3-aminoprop-1-ynyl)-1-(2-chloro-6-(trifluoromethyl)benzoyl)-1H-indazol-3-yl)-3-fluorobenzoic acid;
4-(1-(2-chloro-6-(trifluoromethyl)benzoyl)-6-ethynyl-1H-indazol-3-yl)benzoic acid;
4-(1-(2-chloro-6-(trifluoromethyl)benzoyl)-6-(3-methyl-1,2,4-oxadiazol-5-yl)-1H-indazol-3-yl)-3-fluorobenzoic acid;
4-(1-(2-chloro-6-(trifluoromethyl)benzoyl)-6-(5-(hydroxymethyl)oxazol-2-yl)-1H-indazol-3-yl)-3-fluorobenzoic acid;
4-(1-(2-chloro-6-(trifluoromethyl)benzoyl)-6-(1-methyl-1H-imidazol-4-yl)-1H-indazol-3-yl)-3-fluorobenzoic acid;
4-(1-(2-chloro-6-(trifluoromethyl)benzoyl)-6-(oxazol-2-yl)-1H-indazol-3-yl)-3-fluorobenzoic acid;
4-(6-(5-bromooxazol-2-yl)-1-(2-chloro-6-(trifluoromethyl)benzoyl)-1H-indazol-3-yl)-3-fluorobenzoic acid;
(E)-4-(1-(2-chloro-6-(trifluoromethyl)benzoyl)-6-(N'-cyano-N,N-dimethylcarbamimidoyl)-1H-indazol-3-yl)-3-fluorobenzoic acid;

4-(1-(2-chloro-6-(trifluoromethyl)benzoyl)-6-(5-oxo-4,5-dihydro-1,3,4-oxadiazol-2-yl)-1H-indazol-3-yl)-3-fluorobenzoic acid;

4-(1-(2-chloro-6-(trifluoromethyl)benzoyl)-6-(4H-1,2,4-triazol-3-yl)-1H-indazol-3-yl)-3-fluorobenzoic acid;

4-(1-(2-chloro-6-(trifluoromethyl)benzoyl)-6-(5-methyl-1,3,4-oxadiazol-2-yl)-1H-indazol-3-yl)-3-fluorobenzoic acid;

4-(1-(2-chloro-6-(trifluoromethyl)benzoyl)-6-(1-methyl-1H-imidazol-2-yl)-1H-indazol-3-yl)-3-fluorobenzoic acid;

4-(1-(2-chloro-6-trifluorobenzoyl)-6-(thiazol-2-yl)-1H-indazol-3-yl)benzoic acid;

4-[1-{[2-chloro-6-(trifluoromethyl)phenyl]carbonyl}-6-(1-methyl-1H-imidazol-5-yl)-1H-indazol-3-yl]benzoic acid;

4-[1-{[2-chloro-6-(trifluoromethyl)phenyl]carbonyl}-6-(5-methylthiophen-3-yl)-1H-indazol-3-yl]benzoic acid;

4-(1-{[2-chloro-6-(trifluoromethyl)phenyl]carbonyl}-6-pyrimidin-2-yl-1H-indazol-3-yl)benzoic acid;

4-(1-{[2-chloro-6-(trifluoromethyl)phenyl]carbonyl}-6-pyrimidin-4-yl-1H-indazol-3-yl)benzoic acid;

4-[1-{[2-chloro-6-(trifluoromethyl)phenyl]carbonyl}-6-(1-methyl-1H-imidazol-4-yl)-1H-indazol-3-yl]benzoic acid;

4-[1-{[2-chloro-6-(trifluoromethyl)phenyl]carbonyl}-6-(1,3-thiazol-4-yl)-1H-indazol-3-yl]benzoic acid;

4-(6-[4-(aminomethyl)pyridin-2-yl]-1-{[2-chloro-6-(trifluoromethyl)phenyl]carbonyl}-1H-indazol-3-yl)benzoic acid;

4-(1-{[2-chloro-6-(trifluoromethyl)phenyl]carbonyl}-6-pyridin-2-yl-1H-indazol-3-yl)benzoic acid;

4-[1-{[2-chloro-6-(trifluoromethyl)phenyl]carbonyl}-6-(1,3-thiazol-5-yl)-1H-indazol-3-yl]benzoic acid;

4-(1-(2-chloro-6-trifluorobenzoyl)-6-(thiazol-2-yl)-1H-indazol-3-yl)benzoic acid;

4-(1-{[2-chloro-6-(trifluoromethyl)phenyl]carbonyl}-6-pyridin-4-yl-1H-indazol-3-yl)benzoic acid;

4-[1-{[2-chloro-6-(trifluoromethyl)phenyl]carbonyl}-6-(4-cyanophenyl)-1H-indazol-3-yl]benzoic acid;

4-[1-{[2-chloro-6-(trifluoromethyl)phenyl]carbonyl}-6-(3-cyanophenyl)-1H-indazol-3-yl]benzoic acid;

4-[1-{[2-chloro-6-(trifluoromethyl)phenyl]carbonyl}-6-(2-cyanophenyl)-1H-indazol-3-yl]benzoic acid;

4-[1-{[2-chloro-6-(trifluoromethyl)phenyl]carbonyl}-6-(2-fluorophenyl)-1H-indazol-3-yl]benzoic acid;

4-[1-{[2-chloro-6-(trifluoromethyl)phenyl]carbonyl}-6-(3-fluorophenyl)-1H-indazol-3-yl]benzoic acid;

4-[1-{[2-chloro-6-(trifluoromethyl)phenyl]carbonyl}-6-(4-fluorophenyl)-1H-indazol-3-yl]benzoic acid;

4-[1-{[2-chloro-6-(trifluoromethyl)phenyl]carbonyl}-6-(1-methyl-1H-pyrazol-5-yl)-1H-indazol-3-yl]benzoic acid;

methyl 4-(1-(2-chloro-6-trifluorobenzoyl)-6-(4-hydroxyphenyl)-1H-indazol-3-yl)benzoate;

4-(1-(2-chloro-6-(trifluoromethyl)benzoyl)-6-(methylsulfonamidomethyl)-1H-indazol-3-yl)benzoic acid;

4-(1-(2-chloro-6-(trifluoromethyl)benzoyl)-6-(2,5-dioxoimidazolidin-4-yl)-1H-indazol-3-yl)-3-fluorobenzoic acid;

4-(5-(tert-butoxycarbonylamino)-1-(2-chloro-6-(trifluoromethyl)benzoyl)-1H-pyrrolo[2,3-c]pyridin-3-yl)-3-fluorobenzoic acid;

4-(6-(tert-butoxycarbonylamino)-1-(2-chloro-6-(trifluoromethyl)benzoyl)-1H-pyrazolo[4,3-b]pyridin-3-yl)-3-fluorobenzoic acid;

4-(1-(2-chloro-6-(trifluoromethyl)benzoyl)-6-(methylamino)-1H-pyrazolo[4,3-b]pyridin-3-yl)-3-fluorobenzoic acid;

4-(5-acetamido-1-(2-chloro-6-(trifluoromethyl)-benzoyl)-1H-pyrrolo[2,3-c]pyridin-3-yl)-3-fluorobenzoic acid;

4-(1-(2-chloro-6-(trifluoromethyl)benzoyl)-5-(methylamino)-1H-pyrrolo[2,3-c]pyridin-3-yl)-3-fluorobenzoic acid;

4-(1-(2-chloro-6-cyclopropylbenzoyl)-1H-pyrazolo[4,3-b]pyridin-3-yl)-3-fluorobenzoic acid;

4-(1-(2-chloro-6-vinylbenzoyl)-1H-pyrazolo[4,3-b]pyridin-3-yl)-3-fluorobenzoic acid;

4-(1-(2-chloro-6-(prop-1-en-2-yl)benzoyl)-1H-pyrazolo[4,3-b]pyridin-3-yl)-3-fluorobenzoic acid;

4-(1-(6-chloro-2,3-dihydrobenzo[b][1,4]dioxine-5-carbonyl)-1H-pyrazolo[4,3-b]pyridin-3-yl)-3-fluorobenzoic acid;

4-(1-(2-(dimethylamino)-6-methylbenzoyl)-1H-pyrazolo[4,3-b]pyridin-3-yl)-3-fluorobenzoic acid;

4-(4-chloro-1-(2-chloro-6-cyclopropylbenzoyl)-1H-indazol-3-yl)-3-fluoro benzoic acid;

4-(1-(2-chloro-6-cyclopropylbenzoyl)-4-fluoro-1H-indazol-3-yl)-3-fluorobenzoic acid;

4-(1-(2-chloro-6-cyclobutylbenzoyl)-1H-pyrazolo[4,3-b]pyridin-3-yl)-3-fluorobenzoic acid;

4-(1-(2-chloro-6-cyclopropylbenzoyl)-1H-indazol-3-yl)-3-fluorobenzoic acid;

4-(1-(2-chloro-6-morpholinobenzoyl)-1H-pyrazolo[4,3-b]pyridin-3-yl)-3-fluorobenzoic acid;

4-(1-(2-chloro-6-(trifluoromethyl)benzoyl)-6-(3-methylmorpholine-4-carbonyl)-1H-pyrazolo[4,3-b]pyridin-3-yl)-3-fluorobenzoic acid;

4-(1-(2-chloro-6-(trifluoromethyl)benzoyl)-6-(3,5-dimethylmorpholine-4-carbonyl)-1H-pyrazolo[4,3-b]pyridin-3-yl)-3-fluorobenzoic acid;

4-(1-(2-chloro-6-(trifluoromethyl)benzoyl)-6-(2-methoxyethyl amino)-1H-pyrazolo[4,3-b]pyridin-3-yl)-3-fluorobenzoic acid;

4-(1-(2-chloro-6-(trifluoromethyl)benzoyl)-2-methyl-1H-indol-3-yl)-3-fluorobenzoic acid;

4-(2-methyl-1-(2-(trifluoromethyl)benzoyl)-1H-indol-3-yl)benzoic acid;

4-(1-(2-chloro-6-cyclopropylbenzoyl)-1H-pyrazolo[4,3-b]pyridin-3-yl)-3,5-difluorobenzoic acid;

4-(1-(2-chloro-6-cyclopropylbenzoyl)-1H-indazol-3-yl)-3,5-difluorobenzoic acid;

4-(1-(2-chloro-6-cyclopropylbenzoyl)-4-fluoro-1H-indazol-3-yl)-3,5-difluorobenzoic acid;

4-(1-(2-chloro-6-cyclopropylbenzoyl)-1H-pyrrolo[3,2-b]pyridin-3-yl)-3,5-difluorobenzoic acid;

4-(1-(2-chloro-6-cyclobutylbenzoyl)-1H-pyrazolo[4,3-b]pyridin-3-yl)-3,5-difluorobenzoic acid;

4-(1-(2-chloro-6-(trifluoromethyl)benzoyl)-6-(1,3-oxazinane-3-carbonyl)-1H-pyrazolo[4,3-b]pyridin-3-yl)-3-fluorobenzoic acid;

4-(1-(2-chloro-6-(trifluoromethyl)benzoyl)-6-(oxazolidine-3-carbonyl)-1H-pyrazolo[4,3-b]pyridin-3-yl)-3-fluorobenzoic acid;

4-(6-(azetidine-1-carbonyl)-1-(2-chloro-6-(trifluoromethyl)benzoyl)-1H-indol-3-yl)-3-fluorobenzoic acid;

4-(1-(2-chloro-6-(trifluoromethyl)benzoyl)-6-(3-methoxyazetidine-1-carbonyl)-1H-indol-3-yl)-3-fluorobenzoic acid;

4-(6-(2-amino-2-oxoethyl)-1-(2-chloro-6-(trifluoromethyl)benzoyl)-1H-pyrazolo[4,3-b]pyridin-3-yl)-3-fluorobenzoic acid;

4-(6-(2-(azetidin-1-yl)-2-oxoethyl)-1-(2-chloro-6-(trifluoromethyl)benzoyl)-1H-pyrazolo[4,3-b]pyridin-3-yl)-3-fluorobenzoic acid;

4-(1-(2-chloro-6-(trifluoromethyl)benzoyl)-6-(2-(methylamino)-2-oxoethyl)-1H-pyrazolo[4,3-b]pyridin-3-yl)-3-fluorobenzoic acid;

4-(1-(2-chloro-6-(trifluoromethyl)benzoyl)-6-(2-(dimethylamino)-2-oxoethyl)-1H-pyrazolo[4,3-b]pyridin-3-yl)-3-fluorobenzoic acid;

4-(1-(2-chloro-6-(trifluoromethyl)benzoyl)-6-(oxetan-3-yl)-1H-indazol-3-yl)-3-fluorobenzoic acid;

4-(1-(2-chloro-4-(2-methoxyethoxy)-6-methylbenzoyl)-1H-pyrazolo[4,3-b]pyridin-3-yl)-3-fluorobenzoic acid;

4-(1-(2-chloro-6-methyl-4-morpholinobenzoyl)-1H-pyrazolo[4,3-b]pyridin-3-yl)-3-fluorobenzoic acid;

4-(1-(2-chloro-6-(trifluoromethyl)benzoyl)-6-(dicyclopropylcarbamoyl)-1H-pyrazolo[4,3-b]pyridin-3-yl)-3-fluorobenzoic acid;

4-(1-(4-amino-2-chloro-6-methylbenzoyl)-1H-pyrazolo[4,3-b]pyridin-3-yl)-3-fluorobenzoic acid;

4-(1-(2-chloro-6-cyclopentylbenzoyl)-1H-pyrazolo[4,3-b]pyridin-3-yl)-3-fluorobenzoic acid; and 4-(1-(2-chloro-6-cyclobutylbenzoyl)-1H-pyrazolo[4,3-b]pyridin-3-yl)-3,5-difluorobenzoic acid.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "$C_{1-6}$ alkyl" (or "$C_1$-$C_6$ alkyl") includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-$C_4$alkylene-B" represents, for example, A-$CH_2$—$CH_2$—$CH_2$—$CH_2$—B, A-$CH_2$—$CH_2$—CH($CH_3$)—$CH_2$—B, A-$CH_2$—CH($CH_2CH_3$)—B, A-$CH_2$—C($CH_3$)($CH_3$)—B, and the like. "Alkoxy" represents a linear or branched alkyl group of indicated number of carbon atoms attached through an oxygen bridge; for example "$C_1$-$C_6$ alkoxy" includes —$OCH_3$, —$OCH_2CH_3$, —$OCH(CH_3)_2$, —$O(CH_2)_5CH_3$, and the like.

Unless otherwise specifically noted as only "unsubstituted" or only "substituted", alkyl groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, ($C_{3-7}$)cycloalkyl, ($C_{3-5}$)heterocycloalkyl, $C_2$-$C_6$ alkenyl, $C_2$-$C_6$ alkynyl, ($C_0$-$C_6$ alkyl) $S(O)_{0-2}$—, ($C_0$-$C_6$ alkyl)$S(O)_{0-2}(C_0$-$C_6$ alkyl)-, ($C_0$-$C_6$ alkyl)C(O)NH—, $H_2N$—C(NH)—, $H_2N$—C(O)(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl) OC(O)NH—, —NH($C_1$-$C_6$ alkyl)NHC(O)NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to, ethynyl, propargyl, 1-propynyl, 2-butynyl, and the like.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either attached via a bond to, or fused (including spirofused) to, the other ring, and each ring is saturated or unsaturated. The carbocycle may be attached to the rest of the molecule at any carbon atom that results in a stable compound.

Saturated carbocyclics form a subset of carbocycles in which the entire ring system (mono- or polycyclic) is saturated. Saturated monocyclic carbocyclic rings are also referred to as cycloalkyl rings, e.g., cyclopropyl, cyclobutyl, etc. The fused bicyclic carbocycles are a further subset of the carbocycles in which a $C_7$ to $C_{10}$ bicyclic ring system in which each ring is saturated or unsaturated and two adjacent carbon atoms (or in the case of spirofused, one carbon atom) are shared by each of the rings in the ring system. A saturated bicyclic carbocycle is one in which both rings are saturated. An unsaturated bicyclic carbocycle is one in which one ring is unsaturated and the other is unsaturated or saturated. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

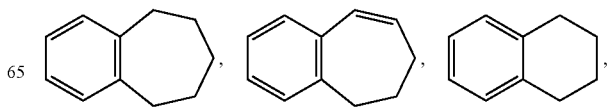

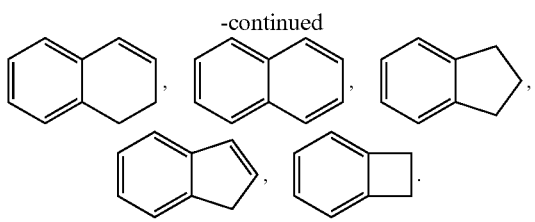

Aromatic carbocycles form another subset of the carbocycles. The term "aryl" refers to aromatic mono- and polycarbocyclic ring systems in which the individual carbocyclic rings in the polyring systems are fused or attached to each other via a single bond. Suitable aryl groups include phenyl, naphthyl, and biphenyl.

The term "cycloalkyl" means a cyclic ring of an alkane having the specified total ring carbon atoms; for example cyclopropyl, cyclobutyl, cyclopentyl, cyclohexyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is either attached via a bond to, or fused (including spirofused) to, the other ring, and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system that consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, 1,4-dioxanyl, 1,4-thioxanyl, tetrahydropyranyl, tetrahydrofuryl (or tetrahydrofuranyl), tetrahydrothienyl, and tetrahydrothiopyranyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic aromatic ring, and that consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of monocyclic heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isoxazolyl, oxadiazolyl, thiazolyl, isothiazolyl, and thiadiazolyl. Examples of bicyclic heteroaromatic rings include benzotriazolyl, indolyl, benzoxazolyl, benzofuranyl, benzothienyl, benzothiazolyl, benzimidazolyl, isoindolyl, indazolyl, quinoxalinyl, quinazolinyl, cinnolinyl, quinolinyl, isoquinolinyl, naphthyridinyl, pyrazolo[3,4-b]pyridine, imidazo[2,1-b](1,3)thiazole,

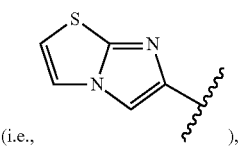

(i.e., ), 6-(1-pyrrolyl)-3-pyridyl, 4-(1-pyrrolyl)phenyl, 4-(pyrid-3-yl)phenyl, 4-(pyrid-4-yl)phenyl, and benzothiophenyl

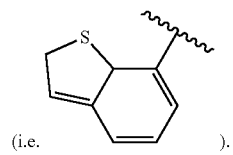 [SMILES: *C1=CC=CC2=CCSC12]

(i.e. ).

Another subset of heterocycles is unsaturated heterocycles in which one or both rings are unsaturated (provided the entire ring system is not aromatic). Representative examples of unsaturated heterocycles include dihydrofuranyl, dihydrothienyl, dihydropyranyl, dihydroimidazolyl, indolinyl, isoindolinyl, chromanyl, isochromanyl, tetrahydroquinolinyl, tetrahydroisoquinolinyl, tetrahydronaphthyridinyl, 2,3-dihydrobenzofuranyl, 1,4-benzoxazinyl, 1,3-benzoxazolinyl, 2,3-dihydrobenzo-1,4-dioxinyl

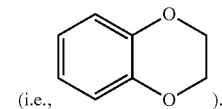

(i.e., ).

and benzo-1,3-dioxolyl

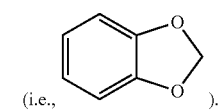

(i.e., ).

In certain contexts herein,

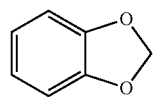

is alternatively referred to as phenyl having as a substituent methylenedioxy attached to two adjacent carbon atoms. Also included are groups such as chromone and coumarin.

Unless otherwise specifically noted as only unsubstituted or only substituted, cycloalkyl, cycloalkenyl, heterocycloalkyl, aryl (including phenyl) and heteroaryl groups are unsubstituted or substituted (also referred to as "optionally substituted"). Unless the substituents are specifically provided, substituents for substituted or optionally substituted cycloalkyl, heterocycloalkyl, cycloalkenyl, aryl (including phenyl, and as an isolated substituent or as part of a substituent such as in aryloxy and aralkyl), heteroaryl (as an isolated substituent or as part of a substituent such as in heteroaryloxy and heteroaralkyl) are one to three groups independently selected from halogen (or halo), $C_1$-$C_6$ alkyl optionally substituted with one to five fluorine, $NH_2$, $N(C_1$-$C_6$ alkyl$)_2$, $NO_2$, oxo, CN, $N_3$, —OH, —O($C_1$-$C_6$ alkyl) optionally substituted with one to five fluorine, $C_3$-$C_{10}$ cycloalkyl, ($C_{3-7}$)cycloalkyl, ($C_{3-5}$)heterocycloalkyl, $C_2$-$C_6$ alkenyl, $C_2$-$C_6$ alkynyl, ($C_0$-$C_6$ alkyl)S(O)$_{0-2}$—, aryl-S(O)$_{0-2}$—, ($C_0$-$C_6$ alkyl)S(O)$_{0-2}$($C_0$-$C_6$ alkylene)-, ($C_0$-$C_6$ alkyl)C(O)NH—, $H_2$N—C(NH)—, ($C_0$-$C_6$ alkyl)C(O)—, ($C_0$-$C_6$ alkyl)OC(O)—, ($C_0$-$C_6$alkyl)O($C_1$-$C_6$ alkylene)-, ($C_0$-$C_6$ alkyl)C(O)$_{1-2}$($C_0$-$C_6$ alkylene)-, ($C_0$-$C_6$ alkyl)$_2$NC(O)—, ($C_0$-$C_6$ alkyl)OC(O)NH—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

The term "halogen" (or "halo") refers to fluorine, chlorine, bromine and iodine (alternatively referred to as fluoro (F), chloro (Cl), bromo (Br), and iodo (I)).

The term "haloalkyl" means alkyl having the specified number of carbon atoms in which from one to all of the hydrogen atoms have been replaced by a halogen atom.

The terms "aralkyl" and "heteroaralkyl" refer to an aryl/heteroaryl linked to the rest of the molecule via a $C_1$ to $C_4$ alkylene.

The term "$C_0$" as employed in expressions such as "$C_{0-6}$ alkylene" means a direct covalent bond; or when employed in expressions such as "$C_{0-6}$ alkyl" means hydrogen. Similarly, when an integer defining the presence of a certain number of atoms in a group is equal to zero, it means that the atoms adjacent thereto are connected directly by a bond; for example, in the structure

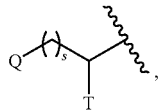

wherein s is an integer equal to zero, 1 or 2, the structure is

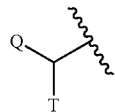

when s is zero; or it means that the indicated atom is absent; for example —S(O)$_0$— means —S—.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., (CRiRj)$_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)$_2$ can be

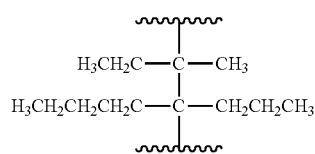

The term ($C_{1-6}$)alkyl as used hereinabove means a branched or unbranched alkyl group having 1-6 carbon atoms, for example methyl, ethyl, propyl, isopropyl, butyl, tert-butyl, n-pentyl and n-hexyl. Preferred is ($C_{1-4}$)alkyl.

The term ($C_{1-5}$)alkyl means a branched or unbranched alkyl group having 1-5 carbon atoms, for example methyl, ethyl, propyl, isopropyl, butyl, tert-butyl and n-pentyl.

The term ($C_{1-4}$)alkyl as used herein means a branched or unbranched alkyl group having 1-4 carbon atoms, being methyl, ethyl, n-propyl, isopropyl, n-butyl, isobutyl, sec-butyl and tert-butyl.

The term ($C_{1-3}$)alkoxy means an alkoxy group having 1-3 carbon atoms, the alkyl moiety being branched or unbranched.

The term ($C_{1-3}$)alkoxycarbonyl means an alkoxycarbonyl group having 1-3 carbon atoms in the alkoxy moiety, the alkoxy moiety having the same meaning as previously defined.

The term (di)($C_{1-6}$)alkylaminocarbonyl means an alkylaminocarbonyl group, the amino group of which is mono-substituted or disubstituted independently with an alkyl group which contains 1-6 carbon atoms and which has the same meaning as previously defined. Preferred alkyl group is ($C_{1-4}$)alkyl.

The term ($C_{3-7}$)cycloalkyl means a cycloalkyl group having 3-7 carbon atoms, such as cyclopropyl, cyclobutyl, cyclopentyl, cyclohexyl and cycloheptyl. 5-6 Carbon atoms are preferred.

The term ($C_{3-5}$)heterocycloalkyl means a heterocycloalkyl group having 3-5 carbon atoms, including 1-3 heteroatoms selected from N, O and/or S, which may be attached via a nitrogen if feasible, or a carbon atom. Preferred number of heteroatoms is one or two. Most preferred number is one. Preferred heteroatoms are N or O. Most preferred are piperazinyl, tetrahydropyranyl, morpholinyl and pyrrolidinyl.

A group having the formula

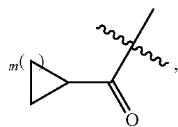

means a heterocyclocarbonyl group such as

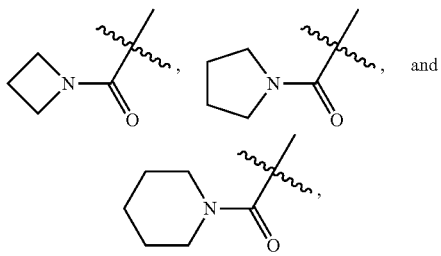

each optionally substituted with one or more $(C_{1-10})$alkyl, halogen, amino, cyano, hydroxy, and $(C_{1-3})$alkoxy.

The term $(C_{2-9})$heteroaryl means an aromatic group having 2-9 carbon atoms and 1-3 heteroatoms selected from N, O and S, like imidazolyl, thiadiazolyl, pyridinyl, pyrimidinyl, thiophenyl or furyl, pyrazolyl, isoxazolyl or quinolyl. Preferred number of heteroatoms is one or two. Preferred heteroaryl groups are pyrazolyl, thiophenyl, isoxazolyl, pyridyl and quinolyl. The $(C_{2-5})$heteroaryl group may be attached via a carbon atom or a nitrogen, if feasible.

The term $(C_{6-14})$aryl means an aromatic hydrocarbon group having 6-14 carbon atoms, such as phenyl, naphthyl, tetrahydronaphthyl, indenyl, anthracyl, More preferred are $(C_{6-10})$aryl groups. The most preferred aromatic hydrocarbon group is phenyl.

As used herein, the term "$X_a$-$X_b$", shall have the same meaning as the term "$X_{a-b}$", wherein X is any atom and a and b are any integers. For example, "$C_1$-$C_4$" shall have the same meaning as "$C_{1-4}$". Additionally, when referring to a functional group generically, "A" shall have the same meaning, and be interchangeable with, "AX", wherein "A" is any atom and "x" or "X" are any integer. For example, "$R^1$" shall have the same meaning, and be interchangeable with, "R1".

In the above definitions with multifunctional groups, the attachment point is at the last group. For example, the term $(C_{1-3})$alkoxycarbonyl refers to, e.g.

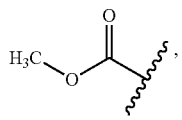

and the term (C1-4)alkylcarbonyloxy refers to, e.g.

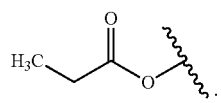 [SMILES: *OC(=O)CC]

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent. Accordingly, the term "one or more" when referring to a substituent and/or variable means that one or more hydrogens on the designated atom/atoms is/are replaced with a selection from the indicated group, provided that the designated atom's normal valency under the existing circumstances is not exceeded, and that the substitution results in a stable compound.

The term "optionally substituted" means that a substitution with the specified groups, radicals, or moieties may or may not be made on the specified group.

When, in the definition of a substituent, it is indicated that "all of the alkyl groups" of said substituent are optionally substituted, this also includes the alkyl moiety of an alkoxy group.

The use of the terms "salt", "solvate", "ester", "prodrug", and the like is intended to equally apply to the salt, solvate, ester, and prodrug of enantiomers, stereoisomers, rotamers, tautomers, positional isomers, racemates, or prodrugs of the inventive compounds.

The term "effective amount" as used herein refers to an amount of the compound of Formula (I) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human. In another embodiment, a subject is a chimpanzee.

It should be noted that any carbon as well as heteroatom with unsatisfied valences in the text, schemes, examples and tables herein is assumed to have the sufficient number of hydrogen atom(s) to satisfy the valences.

The compounds of this invention include the prodrugs, hydrates or solvates of the compounds.

Optical Isomers-Diastereomers-Geometric Isomers-Tautomers

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —$CH_2C(O)$— groups (keto forms) may undergo tautomerism to form hydroxyl —$CH$=$C(OH)$— groups (enol forms). Both keto and enol forms, individually as well as mixtures thereof, are included within the scope of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formula I can form salts which are also within the scope of this invention. Reference to a compound of Formula I herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound that may not be a compound of formula I, but that converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Prodrugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formula I, Ia, Ib, Ic, Id, Ie, If, Ig or Ih, or a pharmaceutically acceptable salt or solvate thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general formula I for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general formula I can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general formula I can be used for treatment of infectious diseases in which Th17 cells and/or non-Th17 cells, which express Th17 hallmark cytokines, play a prominent role, such as but not limited to mucosal leishmaniasis.

Compounds or a pharmaceutically acceptable salt thereof having the general formula I can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

This aspect of the present invention further includes the use of a compound of Formula I, Ia, Ib, Ic, Id, Ie, If, Ig or Ih, or a pharmaceutically acceptable salt or solvate thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula I or a pharmaceutically acceptable salt or solvate thereof and one or more pharmaceutically acceptable excipients. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of formula (I) may be combined with one or more other active agents such as: (1) TNF-α inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK1 and/or JAK2 and/or JAK3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula I, Ia, Ib, Ic, Id, Ie, If, Ig or Ih.

The invention further includes a compound of Formula I in combination with one or more other drug(s).
Methods of Synthesis Methods for preparing the compounds of this invention are illustrated in the following schemes and examples. Other synthetic protocols will be readily apparent to those skilled in the art in light of the present disclosure. The examples illustrate the preparation of the compounds of formula I and as such are not to be considered as limiting the invention set forth in the claims appended hereto. Unless otherwise indicated, all variables are as previously defined.

All the end products of the formula I were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloro methane; DMF: N,N-Dimethylformamide; Dppf: 1,1'-Bis(diphenylphosphino)ferrocene; AcOH: Acetic acid; DMAC: N,N-Dimethylacetamide; DMAP: N,N-dimethylpyridin-4-amine; TEA: Triethylamine; PYAOP: (7-Azabenzotriazol-1-yloxy)tripyrrolidinophosphonium hexafluorophosphate; Pd(PPh$_3$)$_4$:Tetrakis (Triphenylphosphine) Palladium(0); Pd(dppf)Cl$_2$: [1,1'-Bis(diphenylphosphino) ferrocene]dichloropalladium (II); Pd$_2$(dba)$_3$: Tris(dibenzylideneacetone)dipalladium(0); BnBr: Benzyl bromide; Ac$_2$O: Acetic an hydride; LiHMDS: Lithium bis(trimethylsilyl)amide; PhNTf$_2$: N-Phenyl-bis(trifluoromethane sulfonimide); S-Phos: 2-Dicyclohexylphosphino-2',6'-dimethoxybiphenyl; X-Phos: 2-Dicyclohexylphosphino-2',4',6'-triisopropylbiphenyl; CPME: Cyclopentyl methyl ether.

Scheme 1 illustrates a general method toward the preparation of compounds of formula I. Starting from halide A, N-acylation with either carboxylic acids or corresponding acid chloride in the presence of base led to the formation of compound B. Subsequent Suzuki coupling with pinacol boronic ester or acid followed by ester hydrolysis afforded the final compound. In certain cases, ester hydrolysis occurred under the Suzuki coupling condition and led to the formation of final product within one pot.

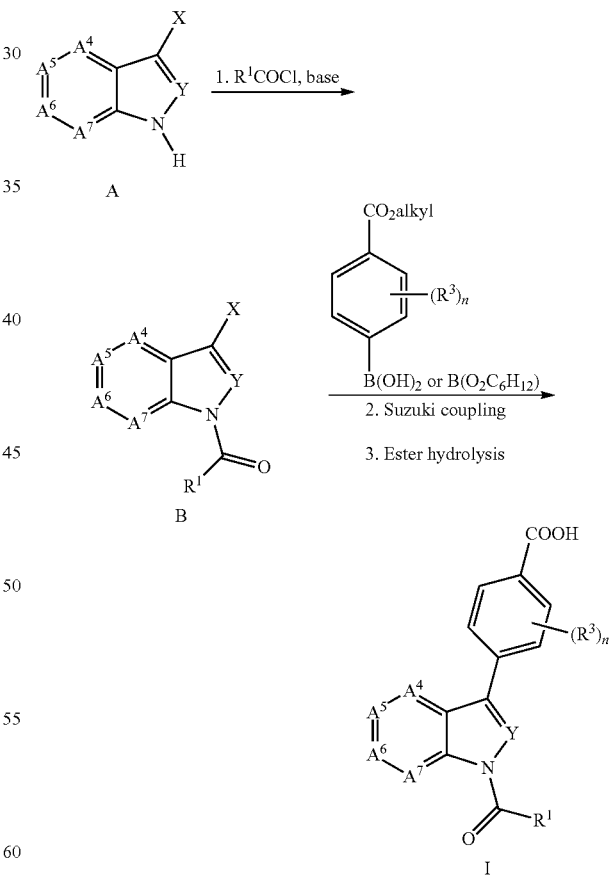

SCHEME 1

Alternatively the final compound I could also be prepared by switching the order of reaction sequence between acylation and Suzuki coupling (see Scheme 2). Suzuki coupling first by reacting halide A with pinacol boronic ester or acid gave intermediate B. Subsequent acylation in the presence of appropriate base, followed by hydrolysis, furnished final product. In some cases where the amide was unstable under hydrolysis conditions, the ester moiety could be hydrolyzed first followed by reacting with acid or acid chloride to give the final product.

SCHEME 2

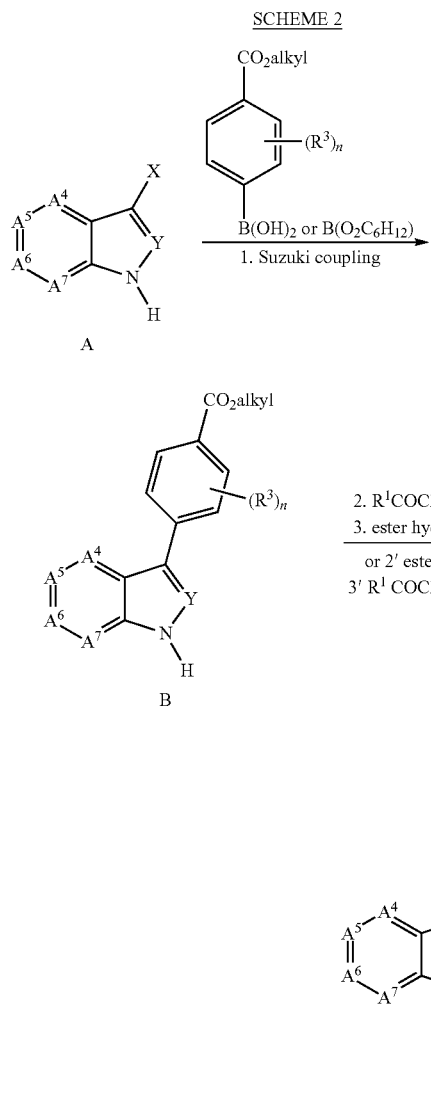

Scheme 3 illustrates a general method for the preparation of compounds of formula I that contain an amide moiety at $A^6$ position. Starting from halide A, acylation followed by ester hydrolysis gave intermediate B. Subsequent Suzuki coupling afforded acid C. Standard amide coupling followed by hydrolysis led to the formation of the final product.

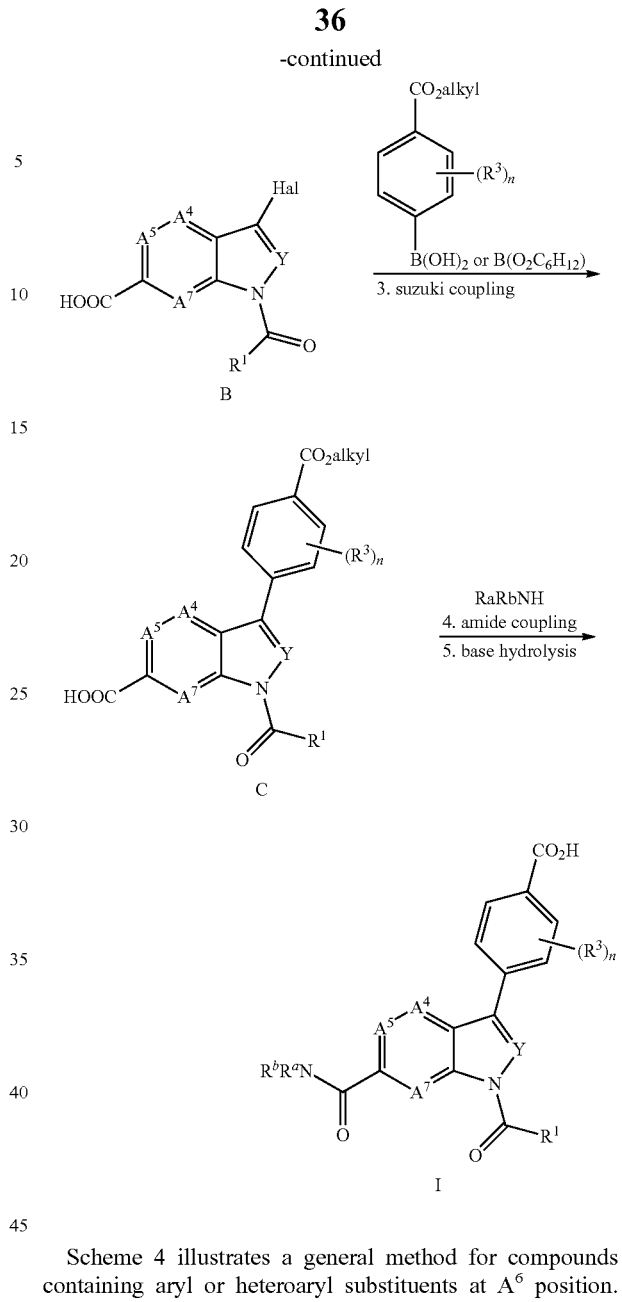

Scheme 4 illustrates a general method for compounds containing aryl or heteroaryl substituents at $A^6$ position. Starting from halide A, acylation followed by Suzuki compound furnished common intermediate B. Subsequent Suzuki coupling and ester hydrolysis gave the final product. Alternatively, Compound B could be converted into pinacol boronic ester or acid first, followed by subsequent Suzuki coupling with appropriate aryl or heteraryl halide and hydrolysis, delivered the final product.

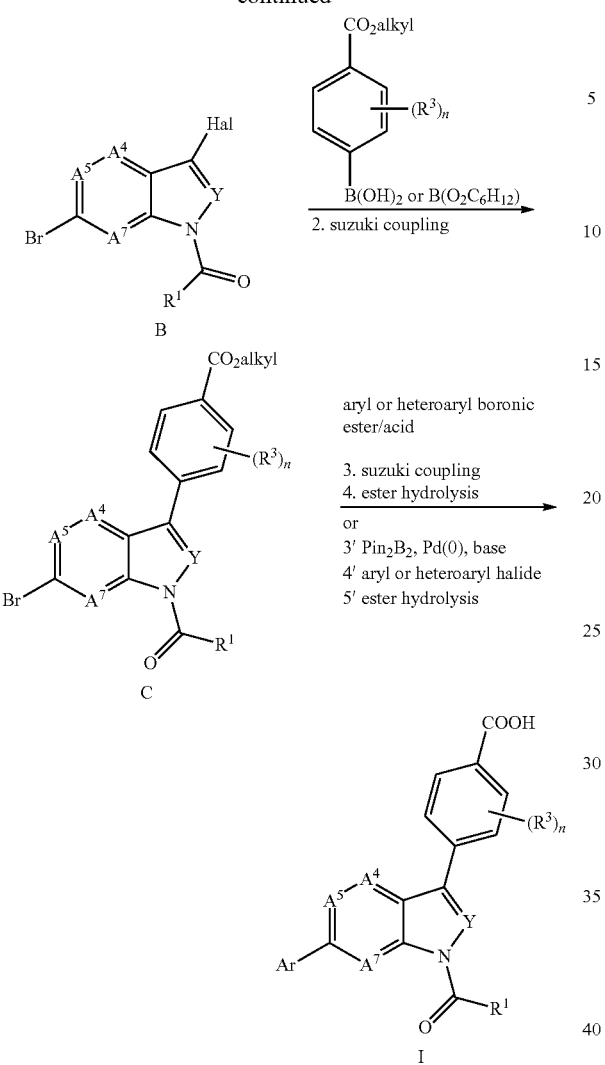

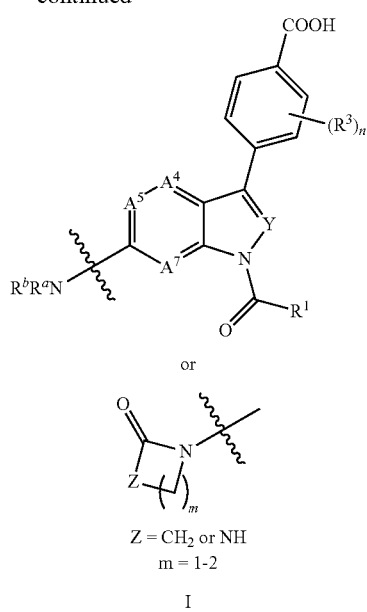

Scheme 5 illustrates a general method for the preparation of compounds containing amine or lactam moiety at $A^6$ position. Starting from common intermediate A (see Scheme 4 for its preparation), Pd-catalyzed reaction with primary or secondary amines or lactams followed by ester hydrolysis furnished the final product.

Scheme 6 illustrates a general method for the preparation of compounds that contain alcohol or ketone moiety at $A^6$ position. Starting with halide A, acylation followed by reduction of the ester moiety with reducing agent (such as DIBAL-H) afforded compound B. Suzuki coupling with boronic ester or acid gave compound C. Oxidation of the primary alcohol, followed by reacting with Grignard reagent and subsequent ester hydrolysis, gave the final compound I. Alternatively, oxidation of the product from Grignard addition, followed by ester hydrolysis, afforded ketone derivative I'.

SCHEME 6

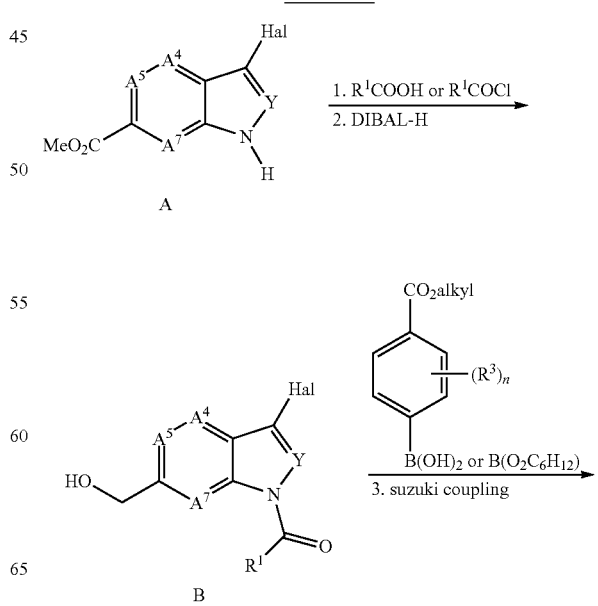

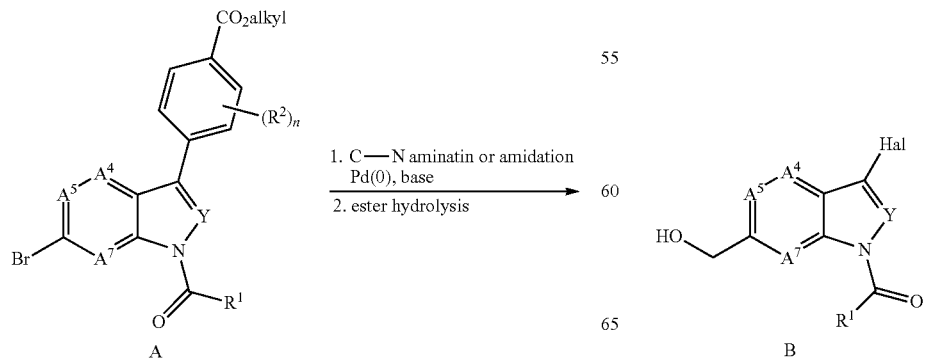

SCHEME 5

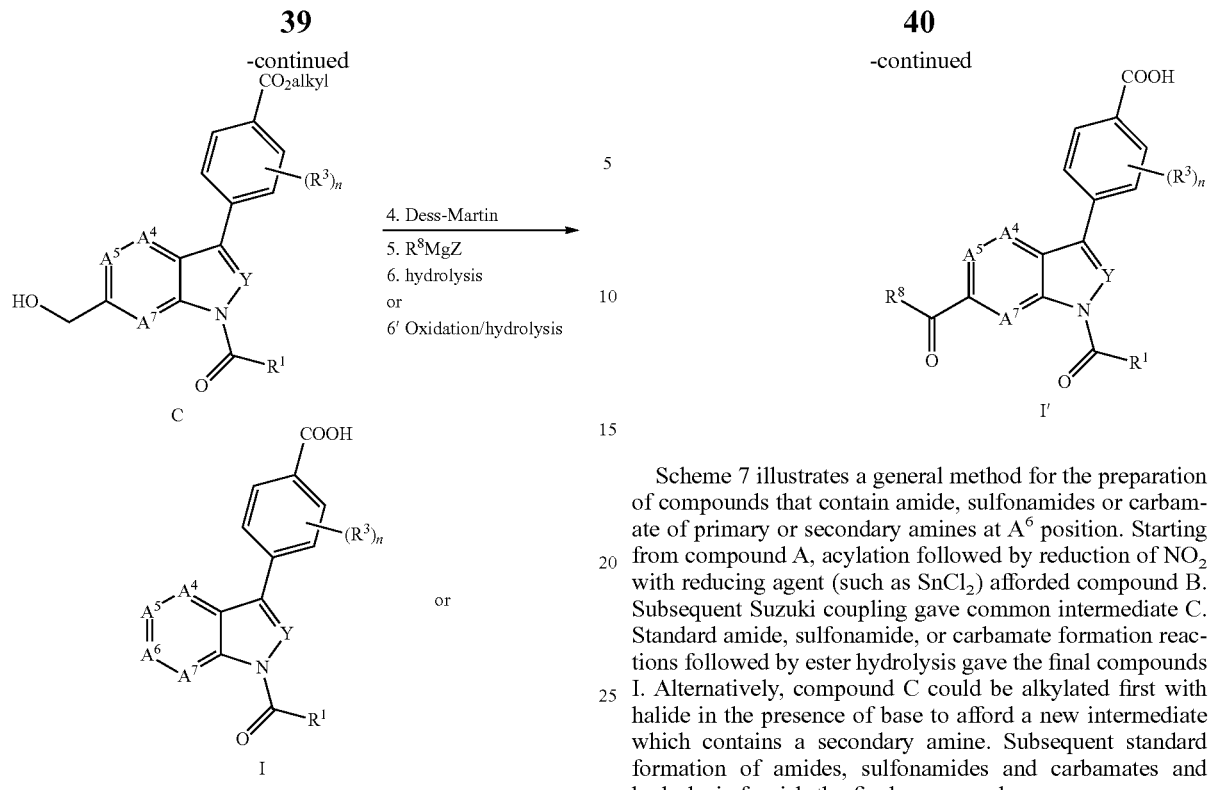

Scheme 7 illustrates a general method for the preparation of compounds that contain amide, sulfonamides or carbamate of primary or secondary amines at $A^6$ position. Starting from compound A, acylation followed by reduction of $NO_2$ with reducing agent (such as $SnCl_2$) afforded compound B. Subsequent Suzuki coupling gave common intermediate C. Standard amide, sulfonamide, or carbamate formation reactions followed by ester hydrolysis gave the final compounds I. Alternatively, compound C could be alkylated first with halide in the presence of base to afford a new intermediate which contains a secondary amine. Subsequent standard formation of amides, sulfonamides and carbamates and hydrolysis furnish the final compounds.

SCHEME 7

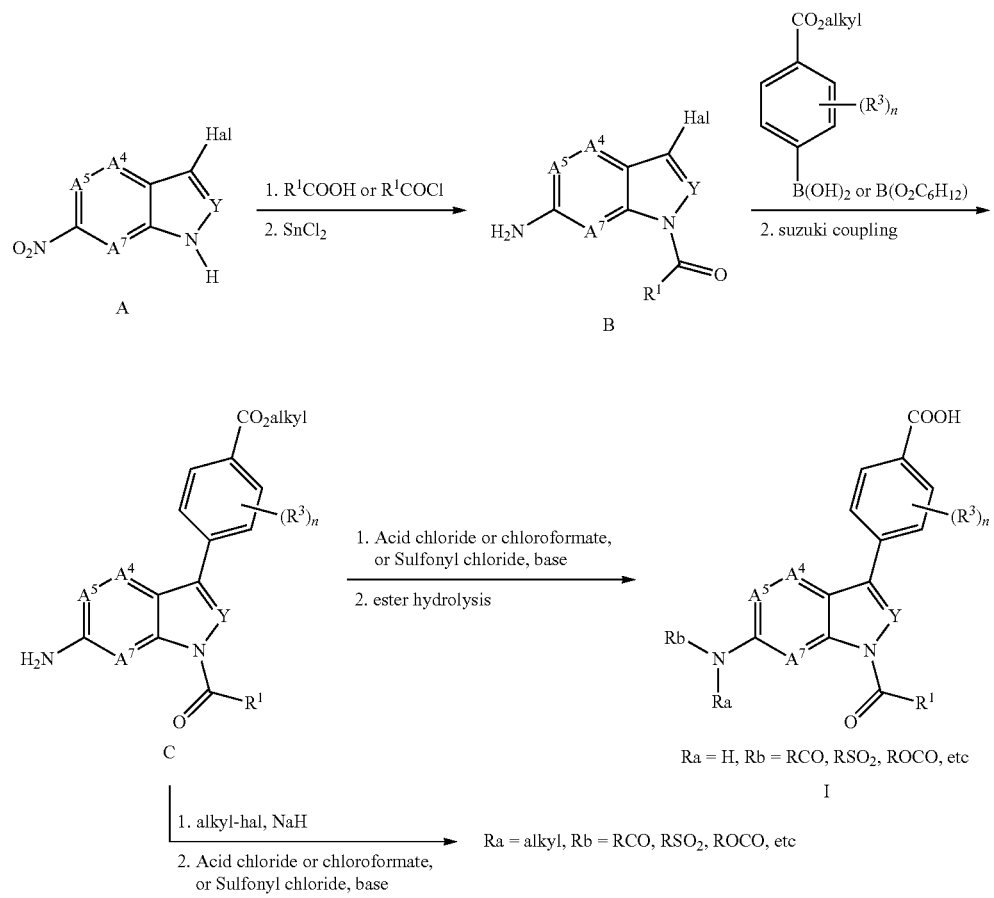

Scheme 8 illustrates a general strategy for the preparation of compounds that contain heteroaryl substituents at A⁶ position, but cannot be accessed through Suzuki coupling as shown in Scheme 4. Starting from carboxylic acid A (see scheme 4 for its synthesis), amide coupling afforded intermediate B. Subsequent cyclization by reacting with POCl₃ in the presence of pyridine, followed by ester hydrolysis, led to the formation of final product I, which contains an oxazole substituent at A⁶ position. The same strategy was also used for the synthesis of a number of other analogs containing different heterocycles at this position. Construction of those heterocycles can follow those well-known routes in the literature.

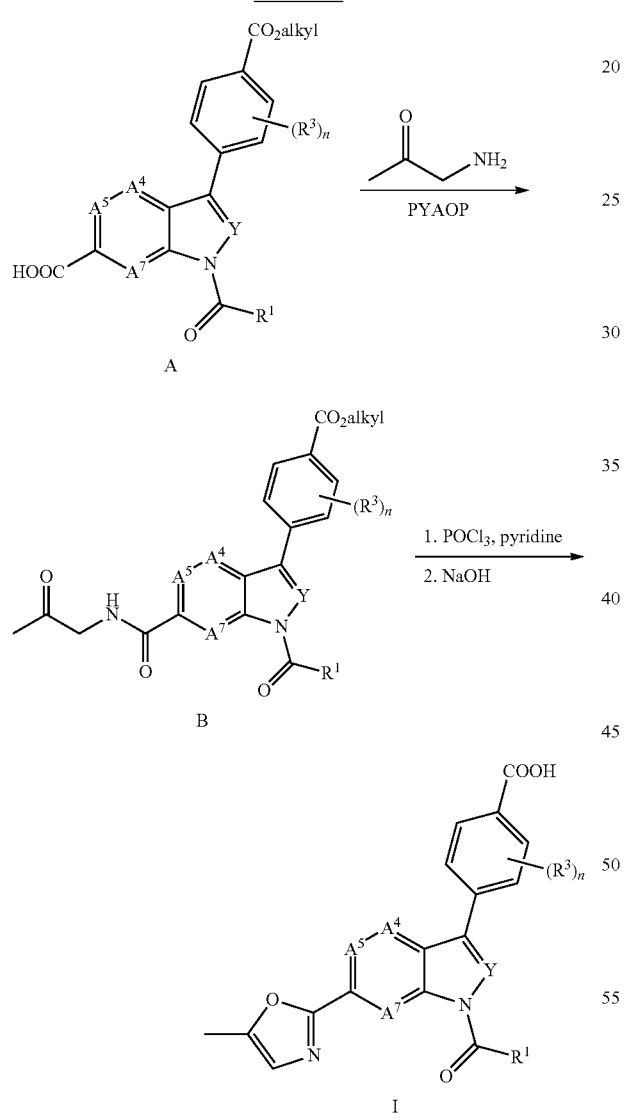

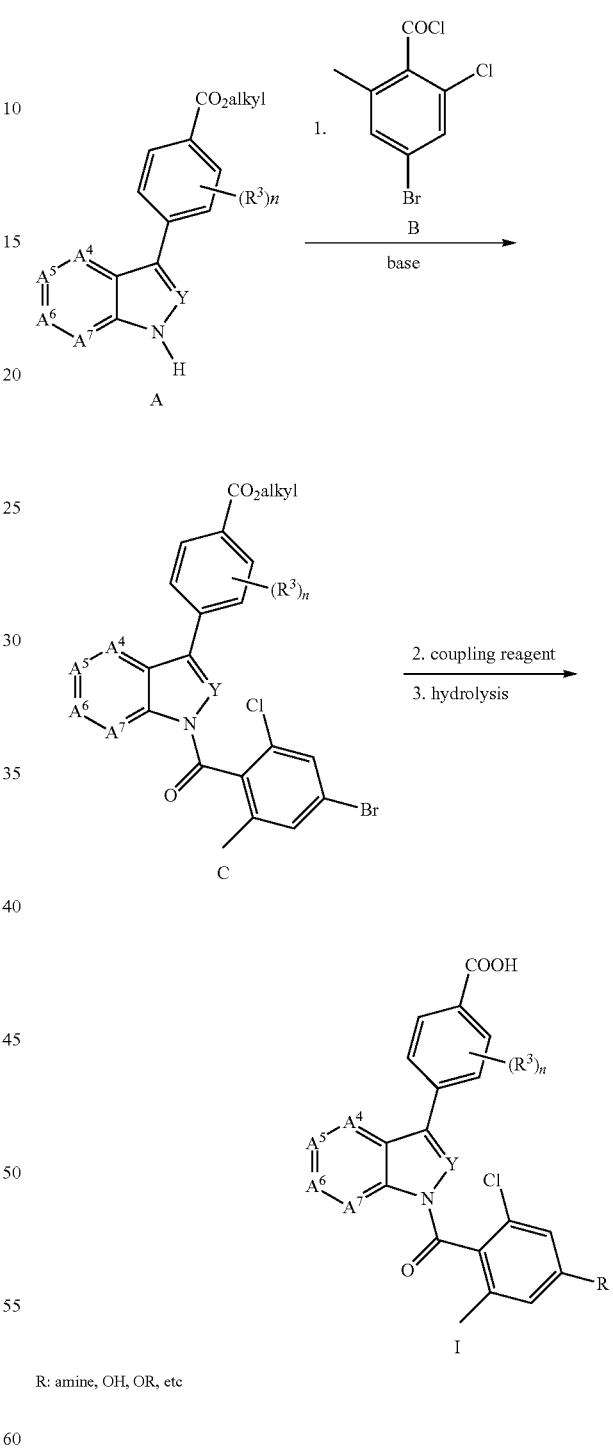

Scheme 9 illustrates a general strategy for the preparation of compounds that contain tri-substituted benzamide motif. Starting from unprotected indazole or indole A, acylation with bromo-substituted benzoic acid chloride B provided intermediate C. Subsequent coupling with various coupling reagents can convert bromine into a variety of substituents such as amine, hydroxyl, alkoxy etc. Final hydrolysis led to the formation of final product I.

Scheme 10 illustrates an alternative method to access intermediate B. Instead of direct Suzuki coupling to form B from A, which typically suffered from low to moderate yield, protection with THP first to give intermediate C, followed by Suzuki coupling and deprotection, could improve the overall yield significantly in some cases.

SCHEME 10

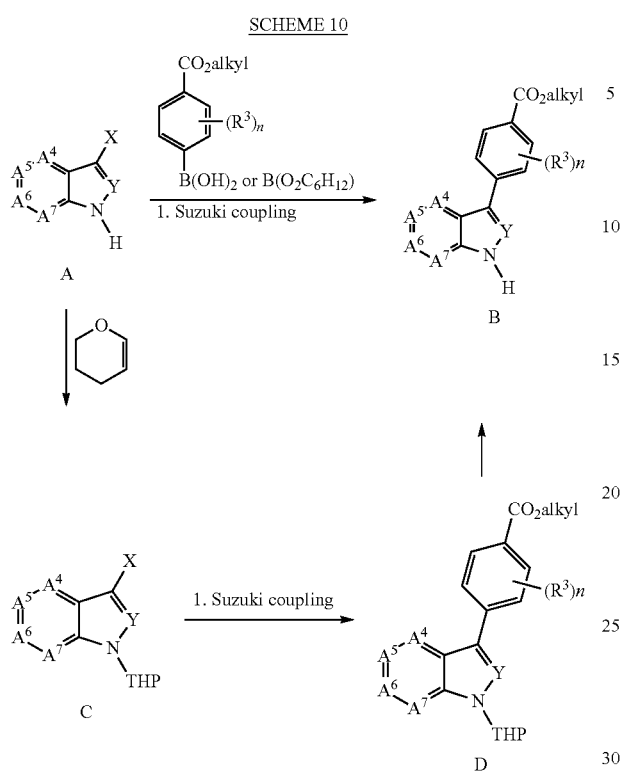

Commercially Available/Previously Described Materials

The following table lists commercial sources, and previously disclosed synthetic routes for chemical materials employed in the synthesis of intermediates and that can be used in the synthesis of examples of the instant invention. The list is not intended to be exhaustive, exclusive, or limiting in any way.

| Structure | Source |
|---|---|
| 3-bromo-1H-pyrazolo[4,3-b]pyridine | Frontier |
| 3-iodo-1H-pyrazolo[4,3-b]pyridine | Frontier |
| 6-bromo-1H-pyrazolo[4,3-b]pyridine | Alfa |
| 3-bromo-1H-pyrazolo[3,4-c]pyridine | Bellen |
| 6-bromo-1H-indazole | Aldrich |
| 3-bromo-4-fluoro-1H-pyrazolo[4,3-c]pyridine | Labpartner |
| 5-bromo-3-iodo-1H-pyrazolo[3,4-b]pyridine | Labpartner |
| 3-bromo-1H-pyrrolo[3,2-b]pyridine | Labpartner |
| 3-bromo-1H-pyrrolo[2,3-c]pyridine | Labpartner |
| 4-chloro-3-iodo-1H-pyrrolo[2,3-c]pyridine | Labpartner |
| 5-chloro-3-iodo-1H-pyrazolo[3,4-c]pyridine | Labpartner |
| 2-chloro-6-methylbenzoyl chloride | Alfa |
| 2-chloro-6-(difluoromethoxy)benzoyl chloride | WO2007/144327 A2 |

| Structure | Source |
|---|---|
| 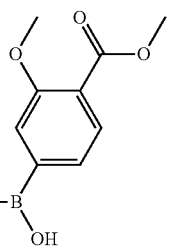 | Combi-blocks |
| 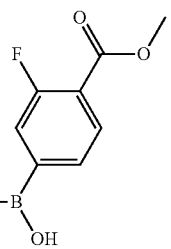 | Alfa |
| 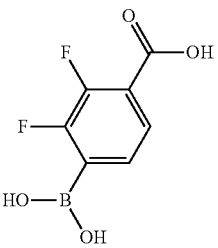 [SMILES: O=C(O)c1ccc(B(O)O)c(F)c1F] | Combi-blocks |
| 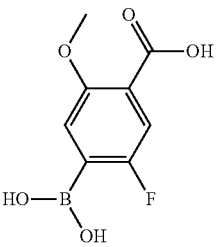 | Anisyn |
| 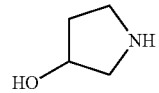 | Acros |
| 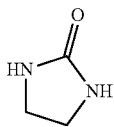 | Alfa Aesar |
| 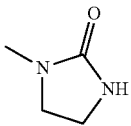 | ADAMAS |
| 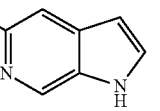 | Acros |
| Structure | Source |
|---|---|
| 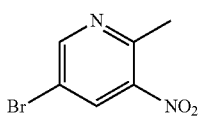 | Combi-blocks |
| 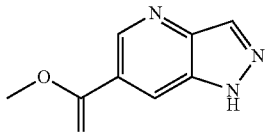 | Labpartner |
| 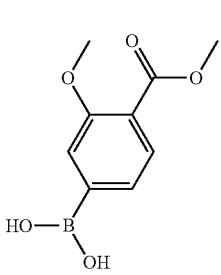 | Labpartner |
| 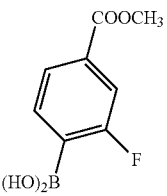 [SMILES: COC(=O)c1ccc(B(O)O)c(F)c1] | Combi-blocks |
| 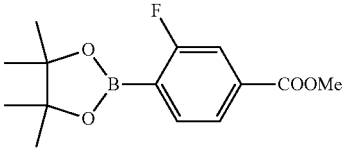 [SMILES: COC(=O)c1ccc(B2OC(C)(C)C(C)(C)O2)c(F)c1] | Combi-blocks |
| 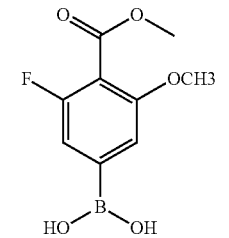 [SMILES: COC(=O)c1c(F)cc(B(O)O)cc1OC] | Combi-blocks |
| 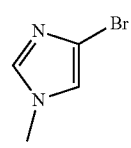 | Combi-blocks |
| 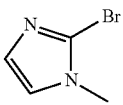 | Aldrich |
| | Aldrich |

| Structure | Source |
|---|---|
| (pinacol boronate with 2,6-difluoro-4-COOMe phenyl) | Combi-phos |

INTERMEDIATES

Preparation of (E)-2-chloro-6-(prop-1-enyl)benzoic acid (i-1)

SCHEME i-1

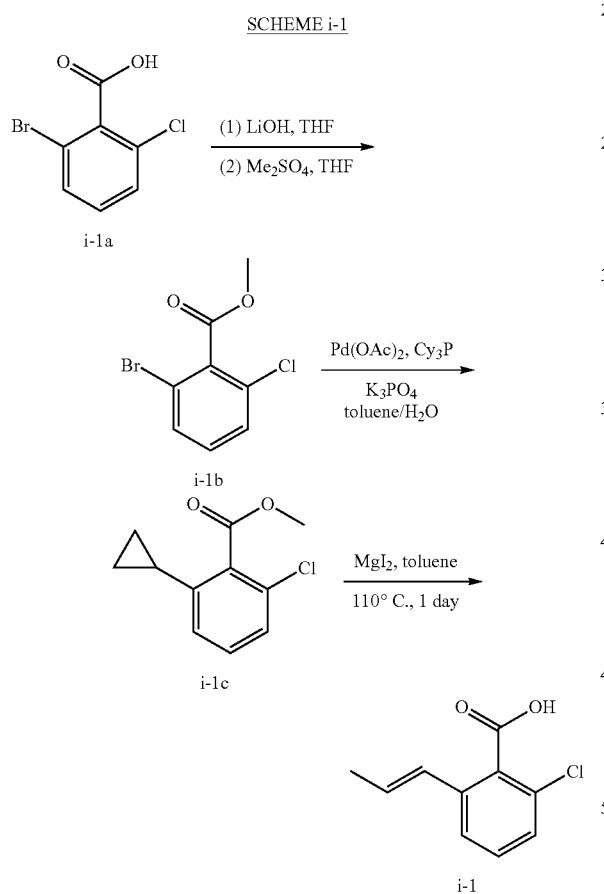

was extracted with EA (60 ml). The organic layer was dried over $Na_2SO_4$ and concentrated to obtain 800 mg (75%) of the title compound. LCMS (ESI): calc'd for $C_8H_6BrClO_2$ $[M+H]^+$: 251. found: 251.

Step 2. Preparation of methyl 2-chloro-6-cyclopropylbenzoate (i-1c)

Methyl 2-bromo-6-chlorobenzoate (i-1b) (0.8 g, 3.2 mmol), cyclopropylboronic acid (330 mg, 3.84 mmol), $Pd(OAc)_2$ (72 mg, 0.32 mmol), $Cy_3P$ (180 mg, 0.64 mmol) and $K_3PO_4$ (2.0 g, 9.6 mmol) were mixed in toluene (12 ml) and $H_2O$ (1.2 ml). The reaction mixture was stirred at 100° C. overnight under $N_2$ atmosphere. After cooling, the mixture was poured into water (30 ml) and extracted with EA (50 ml). The organic layer was dried over $Na_2SO_4$ and concentrated to obtain a residue. The residue was purified by chromatography on silica gel (PE/EA=10:1) to obtain 350 mg (52%) of the title compound. LCMS (ESI): calc'd for $C_{11}H_{11}ClO_2$ $[M+H]^+$: 211. found: 211.

Step 3. Preparation of (E)-2-chloro-6-(prop-1-enyl) benzoic acid (i-1)

To a suspension of anhydrous $MgI_2$ (880 mg, 3.18 mmol) in toluene (15 ml) was added a solution of methyl 2-chloro-6-cyclopropylbenzoate (i-1c) (400 mg, 1.9 mmol) in toluene (5 ml). The mixture was refluxed under exclusion of moisture, cooled and poured into 10% aqueous $NaHCO_3$ (20 ml). The acid was isolated by acidification of the aqueous phase with 15% HCl followed by extraction with EA. The combined organic layers were washed with water, dried over $Na_2SO_4$ and concentrated to obtain the crude product. The crude product was purified by chromatography on silica gel (PE/EA=3:1) to obtain 200 mg (54%) of the title compound. LCMS (ESI): calc'd for $C_{10}H_9ClO_2[M+H]^+$: 197. found: 197.

SCHEME i-2

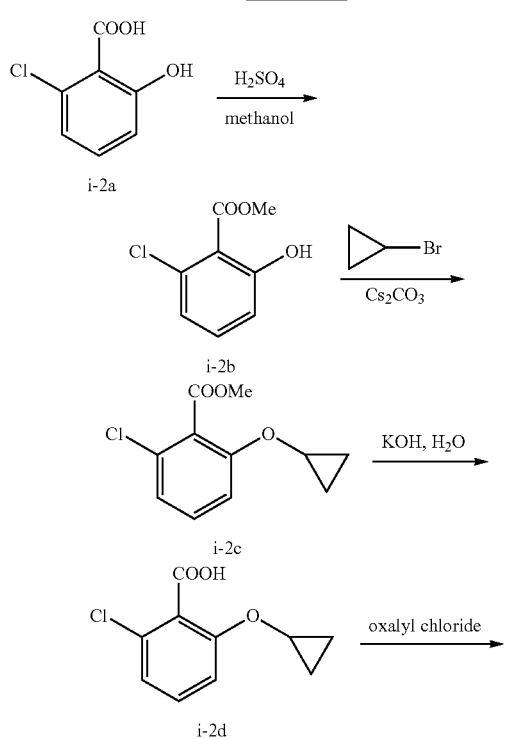

Step 1. Preparation of methyl 2-bromo-6-chlorobenzoate (i-1b)

$LiOH.H_2O$ (180 mg, 4.24 mmol) was added to a solution of 2-bromo-6-chlorobenzoic acid (i-1a) (1.0 g, 4.24 mmol) in THF (30 ml). The mixture was stirred at 25° C. for 1 h. Then the $Me_2SO_4$ (1.1 g, 8.48 mmol) was added to the reaction mixture. The mixture was warmed to 85° C. and stirred at 85° C. for 21 h. After cooling, $NH_3.H_2O$ was added dropwise to the mixture until pH=7-8. The solution was poured into water and THF was evaporated. The water layer

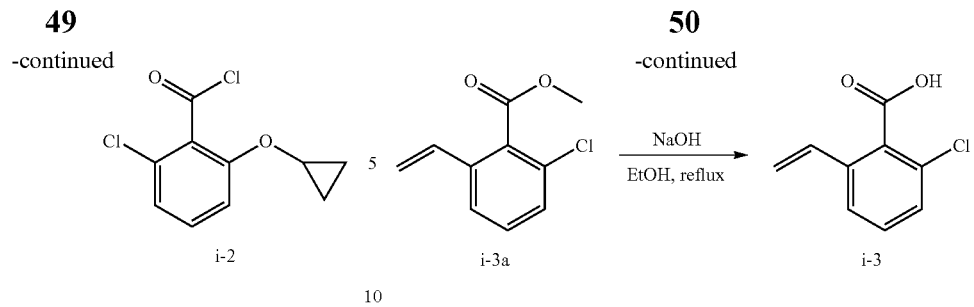

Preparation of methyl 2-chloro-6-hydroxybenzoate (i-2b)

To the solution of 2-chloro-6-hydroxybenzoic acid (i-2a) (1.71 g, 10 mmol) in $CH_3OH$ (100 ml) was added concentrated sulfuric acid (10 ml) drop wise. The mixture solution was protected by $N_2$ and stirred at 85° C. for 30 h. The solution was concentrated and purified by chromatography column (EA:PE=1:4) to afford 1.5 g product (81%). LCMS (ESI) calc'd [M+H]$^+$: 186.59. found: 187.0.

Step 2. Preparation of methyl 2-chloro-6-cyclopropoxybenzoate (i-2c)

The mixture of i-2b (186 mg, 1 mmol), bromocyclopropane (1.2 g, 10.0 mmol), $Cs_2CO_3$ (414 mg, 3.0 mmol), DMAC (15 ml) was protected by $N_2$ and stirred at 150° C. for 24 h. Then the reaction mixture was filtered, concentrated, and purified by chromatography column (EA:PE=1:4) to afford 198 mg product (87%). LCMS (ESI) calc'd [M+H]$^+$: 226.66. found: 227.1.

Step 3. Preparation of methyl 2-chloro-6-cyclopropoxybenzoic acid (i-2d)

To the solution of 2-chloro-6-cyclopropoxybenzoate (i-2c) (226 mg, 1.0 mmol) in $CH_3OH$ (10 ml) and $H_2O$ (10 ml) was added KOH (200 mg). The mixture solution was stirred at 85° C. for 12 h, the solution was acidified by aqueous HCl (1M) 50 ml, extracted with EA (30 ml×3), concentrated and purified by chromatography column (EA:PE=1:1) to afford 186 mg product (87%). LCMS (ESI) calc'd [M+H]$^+$: 212.63. found: 212.9.

Step 4. Preparation of 2-chloro-6-cyclopropoxybenzoyl chloride (i-2)

To the solution of methyl 2-chloro-6-cyclopropoxybenzoic acid (i-2d) (212 mg, 1 mmol) and DMF (0.1 ml) dissolved in anhydrous DCM (10 ml) was added oxalyl chloride (190 mg, 1.5 mmol) dropwise. The mixture solution was protected by $N_2$ and stirred at room temperature for 0.5 h. Then the solution was concentrated to afford 300 mg (crude) for the next step without further purification.

SCHEME i-3

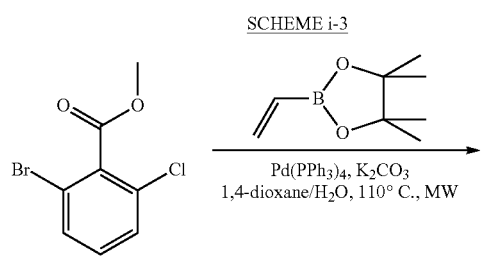

Step 1. Preparation of methyl 2-chloro-6-vinylbenzoate (i-3a)

To a mixture of 2-bromo-6-chlorobenzoate (1.0 g, 4.0 mmol), 4,4,5,5-tetramethyl-2-vinyl-1,3,2-dioxaborolane (0.92 g, 6 mmol), Pd(PPh$_3$)$_4$ (230 mg, 0.2 mmol) and $K_2CO_3$ (1.66 g, 12 mmol) was added dioxane (10 ml) and $H_2O$ (2.5 ml), and the mixture was heated at 100° C. under microwave for 3 h. The mixture was cooled down, and diluted with EtOAc (50 ml). The organic layer was separated, washed with brine, dried over $Na_2SO_4$ and concentrated. The residue was purified by flash chromatography (Petroleum/EtOAc 10/1) to give 0.4 g (51%) of the title compound. LCMS (ESI) calc'd for $C_{10}H_9ClO_2$ [M+H]$^+$: 197. found: 197.

Step 2. Preparation of 2-chloro-6-vinylbenzoic acid (i-3)

To a solution of methyl 2-chloro-6-vinylbenzoate (i-3a) (0.2 g, 1.02 mmol) in EtOH (15 ml) and $H_2O$ (7 ml) was added NaOH (0.4 g, 10 mmol). The resulting mixture was stirred at 80° C. for 2 h. The mixture was cooled down and acidified with 2N HCl to pH=2-3. Then the mixture was extracted with EA (30 ml). The organic layer was dried over $Na_2SO_4$ and concentrated to afford 160 mg (86%) of the title compound. LCMS (ESI) calc'd for $C_9H_7ClO_2$ [M+H]$^+$: 183. found: 183.

SCHEME i-5

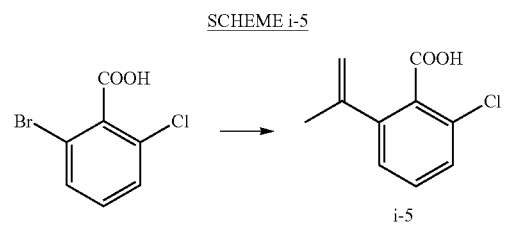

Step 1. Preparation of 2-chloro-6-(prop-1-en-2-yl)benzoic acid (i-5)

A mixture of 2-bromo-6-chlorobenzoic acid (472 mg, 2 mmol), 4,4,5,5-tetramethyl-2-(prop-1-en-2-yl)-1,3,2-dioxaborolane (400 mg, 2.4 mmol), Pd(PPh$_3$)$_4$ (115 mg, 0.1 mmol), $K_2CO_3$ (1238 mg, 9.0 mmol), dioxane (3 mL) and $H_2O$ (0.5 mL) was protected by $N_2$ and stirred at 100° C. for 1 h. Then the reaction mixture was filtered, concentrated and purified by chromatography column (EA:PE=1:5) to afford 200 mg of the title compound (yield: 51%). LCMS (ESI) calc'd $C_{10}H_9ClO_2$, [M+H]$^+$: 197. found: 197.

SCHEME i-6

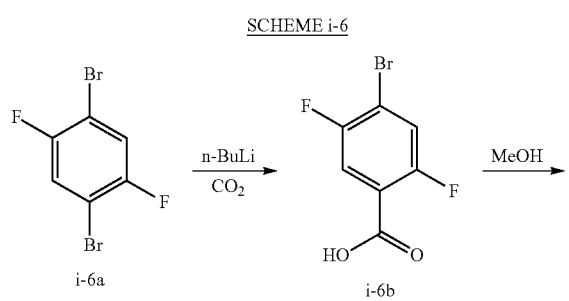

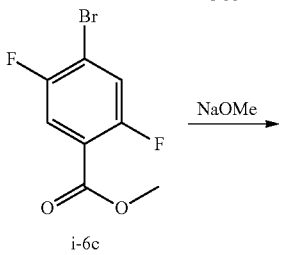

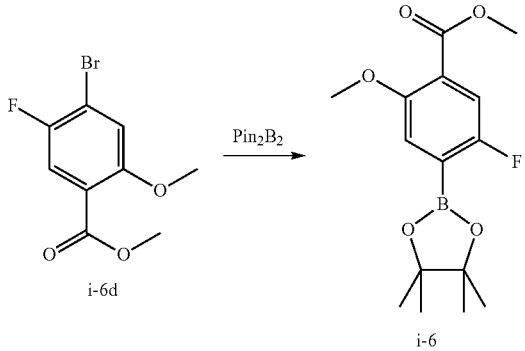

Step 1. Preparation of 4-bromo-2,5-difluorobenzoic acid (i-6b)

To the solution of 1,4-dibromo-2,5-difluorobenzene (i-6a) (27.0 g, 100 mmol) in THF (500 ml) was added n-BuLi (60 ml, 2M) dropwise at −78° C. and the reaction mixture was kept stirring for 3 h. Then excess dry ice was added into the reaction mixture portwise over 0.5 h. The reaction mixture was quenched with 300 ml water and extracted with EA (100 ml×3). The aqueous solution was acidified with HCl (2M), extracted with EA (150 ml×3), and the organic layer was dried and concentrated. The crude material was purified by chromatography column (EA:PE=1:10) to afford 18.24 g product (76%). LCMS (ESI) calc'd [M+H]+: 237.00. found: 237.1.

Step 2. Preparation of methyl 4-bromo-2,5-difluorobenzoate (i-6c)

To the solution of 4-bromo-2,5-difluorobenzoic acid (i-6b) (18.24 g, 77.3 mmol) in CH$_3$OH (200 ml) was added concentrated sulfuric acid (5 ml) dropwise. The mixture solution was protected by N$_2$ and stirred at 85° C. for 30 h. The solution was concentrated and purified by chromatography column (EA:PE=1:20) to afford 17.6 g product (91%). LCMS (ESI) calc'd [M+H]+: 251.01. found: 250.9.

Step 3. Preparation of methyl 4-bromo-5-fluoro-2-methoxybenzoate (i-6d)

To a solution of methyl 4-bromo-2,5-difluorobenzoate (i-6c) (17.6 g, 70.4 mmol) in anhydrous DMF (200 ml) was added CH$_3$ONa (4.56 g, 84.48 mmol). The mixture solution was protected by N$_2$ and stirred at room temperature for 16 h. The reaction was diluted with 500 ml EA and washed with water (100 ml×3). The organic layer was dried, concentrated, and purified by chromatography column (EA:PE=1:20) to afford 14.2 g product (77%). LCMS (ESI) calc'd [M+H]+: 263.06. found: 263.01.

Step 4. Preparation of 2 methyl 5-fluoro-2-methoxy-4-(4,4,5,5-tetramethyl-1,3,2-dioxaborolan-2-yl)benzoate (i-6)

The mixture of methyl 4-bromo-5-fluoro-2-methoxybenzoate (i-6d) (14.2 mg, 54.2 mmol), 4,4,4',4',5,5,5',5'-octamethyl-2,2'-bi(1,3,2-dioxaborolane) (13.8 g, 54.2 mmol), Pd(dppf)$_2$Cl$_2$ (224 mg, 0.2 mmol), dioxane (150 ml) was degassed and protected by N$_2$ and stirred at 80° C. for 4 h. Then the reaction mixture was filtered, concentrated, and purified by chromatography column (EA:PE=1:4) to afford 10.6 g product (63%). LCMS (ESI) calc'd [M+H]+: 310.13. found: 310.2.

SCHEME i-7

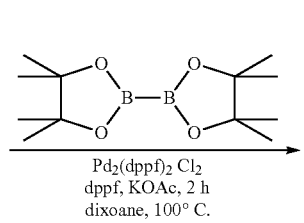

Step 1. Preparation of methyl 2-amino-4-(4,4,5,5-tetramethyl-1,3,2-dioxaborolan-2-yl)benzoate (i-7)

To a mixture of methyl 2-amino-4-bromobenzoate (i-7a) (1.15 g, 5 mmol), 4,4,4',4',5,5,5',5'-octamethyl-2,2'-bi(1,3,2-dioxaborolane) (1.27 g, 5 mmol), Pd(dppf)Cl$_2$ (204 mg, 0.25 mmol), dppf (138 mg, 0.25 mmol) and KOAc (1.47 g, 15 mmol) was added dioxane (20 ml), and the mixture was heated at 100° C. under argon for 2 h. The mixture was cooled down, and diluted with CH$_2$Cl$_2$ (50 mL). The organic layer was separated, washed with brine, dried over Na$_2$SO$_4$, and concentrated. The residue was purified by flash chromatography (Pentane/EtOAc 5/1) to give 1.5 g (89%) of the title compound. $^1$H NMR (500 MHz, CDCL3) δ7.84 (1H, d), 7.12 (1H, s), 7.05 (1H, d), 5.68 (2H, bs), 3.86 (3H, s), 1.33 (12H, s).

SCHEME i-8

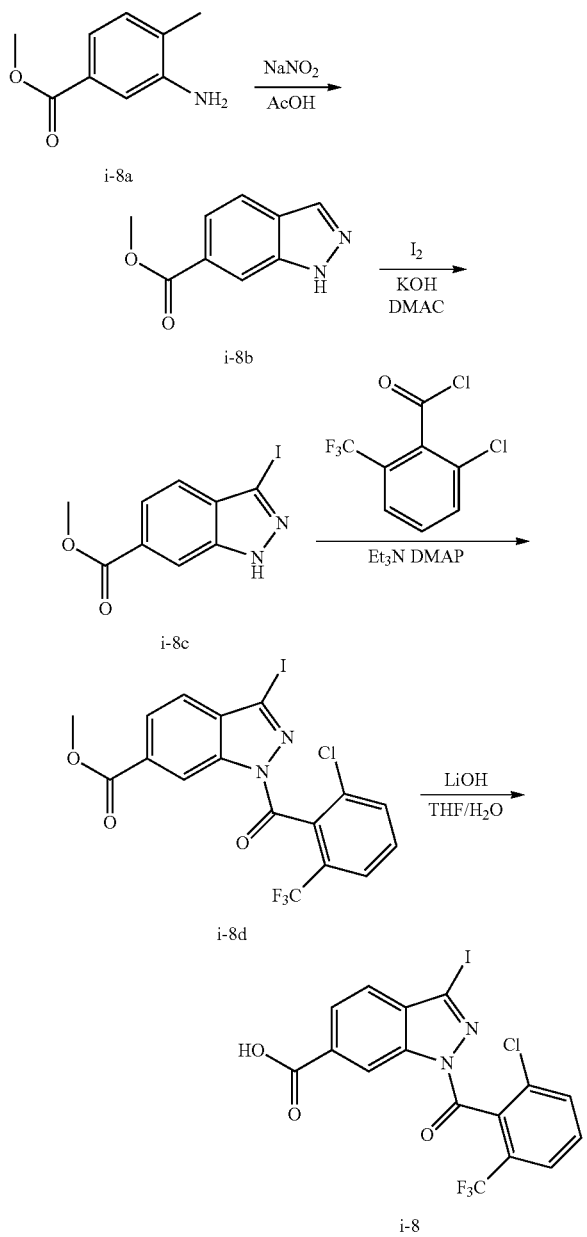

Step 1. Preparation of methyl 1H-indazole-6-carboxylate (i-8b)

Methyl 3-amino-4-methylbenzoate (i-8a) (5.0 g, 30.2 mmol) was dissolved in AcOH (140 mL). Sodium nitrite (2.1 g, 30.2 mmol) in water (3.5 mL) was added dropwise to the solution of starting material under ice-cooling at room temperature. The icebath was removed and the mixture was stirred overnight. Half of the solvents were then evaporated, and the mixture was diluted with water (80 mL) and extracted with EtOAc (3×30 mL). The collected organic phase was washed with water and brine (2×200 mL), dried and evaporated to afford i-8b (4.4 g, 83%). LCMS (ESI): calc'd for $C_9H_8N_2O_2$, [M+H]$^+$: 177. found: 177.

Step 2. Preparation of methyl 3-iodo-1H-indazole-6-carboxylate (i-8c)

Methyl 1H-indazole-6-carboxylate (i-8b) (5.0 g, 28.3 mmol) was dissolved in anhydrous DMAC (50 mL). Iodine (14.4 g, 56.7 mmol) and potassium hydroxide (6.3 g, 113.5 mmol) were added in portions under ice-cooling at room temperature. The ice bath was removed and the mixture was stirred at room temperature for 1 h. The reaction was monitored by TLC (25% MeOH in chloroform) then it was slowly quenched with sat. $Na_2S_2O_3$ aqueous (100 mL), diluted with water (50 mL) and extracted with EtOAc (3×100 mL). The organic phase was evaporated and triturated with n-hexane. The precipitated material was filtered and dried to afford a brown solid i-8c (5.3 g, 62%). LCMS (ESI): calc'd for C9H7IN2O2, [M+H]+: 303. found: 303.

Step 3. Preparation of methyl 1-(2-chloro-6-(trifluoromethyl)benzoyl)-3-iodo-1H-indazole-6-carboxylate (i-8d)

To a 250 mL round-bottomed flask, was added Methyl 3-iodo-1H-indazole-6-carboxylate (i-8c) (11.7 g, 38.7 mmol), 2-chloro-6-(trifluoromethyl)benzoyl chloride (9.1 g, 38.7 mmol), DMAP (4.72 g, 38.7 mmol) and $CH_2Cl_2$ (30 mL). After stirring at room temperature for 3 minutes, TEA (11.2 mL, 77 mmol) was added slowly. The reaction mixture was stirred at room temperature overnight. LCMS showed that no starting materials remained. Then the mixture was poured into 30 mL water, and the lower (organic) and upper (aqueous) phases were separated. The aqueous phase was extracted twice with 20 mL $CH_2Cl_2$. The combined organic phases were washed successively with two 20 mL portions of water and 10 mL of brine. The resulting organic phase was dried over anhydrous sodium sulfate, filtered and concentrated at reduced pressure to give a yellow solid. The residue was purified by column chromatography on 60 g of silica gel eluting with petroleum ether/EtOAc from 50/1 to 10/1, to give a fawn solid i-8d (16.5 g, 84%). LCMS (ESI): calc'd for $C_{17}H_9ClF_3IN_2O_3$, [M+H]+: 509. found: 509.

Step 4. Preparation of 1-(2-chloro-6-(trifluoromethyl)benzoyl)-3-iodo-1H-indazole-6-carboxylic acid (i-8)

A mixture of methyl 1-(2-chloro-6-(trifluoromethyl)benzoyl)-3-iodo-1H-indazole-6-carboxylate (i-8d) (16.5 g, 32.5 mmol) and LiOH (3.40 g, 162.40 mmol) in 10 ml THF and 50 ml $H_2O$ was stirred at room temperature overnight. The solvent was evaporated and the residue was dissolved in water. 5% HCl aqueous was added until pH was ~4-5. The precipitated solid was filtered, washed with water and n-hexane, and dried to afford an off-white solid i-8 (16.0 g, 83%). LCMS (ESI): calc'd for $C_{16}H_7ClF_3IN_2O_3$, [M+H]$^+$: 495. found: 495.

SCHEME i-9

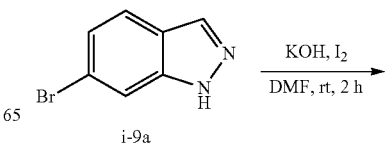

Step 2. Preparation of (6-bromo-3-iodo-1H-indazol-1-yl)(2-chloro-6-(trifluoromethyl)phenyl)methanone (i-9c)

To a flask was added 6-bromo-3-iodo-1H-indazole (i-9b) (3.22 g, 10 mmol), DMAP (1.22 g, 10 mmol), TEA (2.77 mL, 20 mmol) and DCM (50 mL), followed by the addition of 2-chloro-6-(trifluoromethyl)benzoyl chloride (2.61 g, 10 mmol) slowly. The reaction mixture was stirred at room temperature for 5 h. The mixture was diluted with H₂O, and the organic layer was separated. The aqueous layer was extracted with CH₂Cl₂ (3×50 mL), The combined organics were washed with H₂O, brine, dried over Na₂SO₄, and concentrated. The residue was purified by column chromatography (PE/EA=10/1) to afford 4.9 g (82%) of the title compound. LCMS (ESI) calc'd for $C_{15}H_6BrClF_3IN_2O$ [M+H]⁺: 528.83. found: 529.

Step 3. Preparation of methyl 4-(6-bromo-1-(2-chloro-6-(trifluoromethyl)benzo-yl)-1H-indazol-3-yl)benzoate (i-9)

To a mixture of (6-bromo-3-iodo-1H-indazol-1-yl)(2-chloro-6-(trifluoromethyl)phenyl)methanone (i-9c) (1.058 g, 2 mmol), 4-(methoxycarbonyl)phenylboronic acid (360 mg, 2 mmol), PdCl₂(dppf)₂ (82 mg, 0.1 mmol) and KF (290 mg, 5 mmol) was added dioxane (25 ml) and H₂O (0.5 ml), and the mixture was heated at 90° C. under argon for 6 h. The mixture was cooled down, and diluted with CH₂Cl₂ (180 ml). The organic layer was separated, washed with brine, dried over Na₂SO₄, and concentrated. The residue was purified by SiO₂ (PE/EA from 10/1 to 20/1) to give 850 mg (81%) of the title compound. LCMS (ESI) calc'd for $C_{23}H_{13}BrClF_3N_2O_3$ [M+H]⁺: 536.98. found: 537.

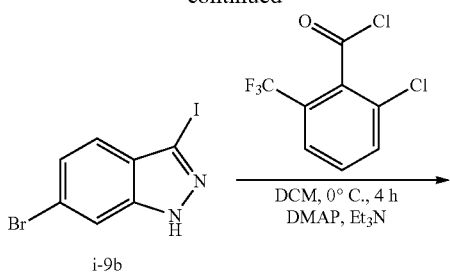

i-9b

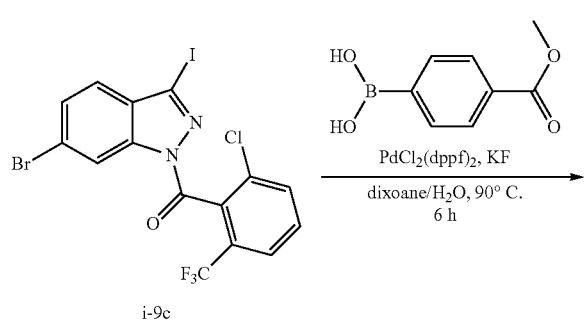

i-9c

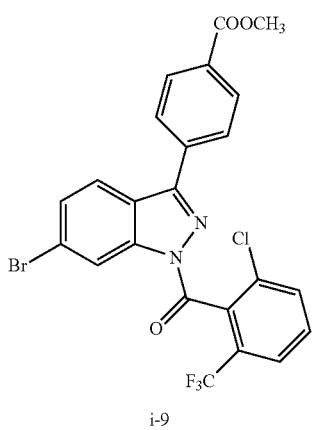

i-9

SCHEME i-10

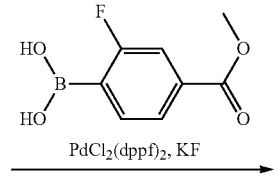

i-9c

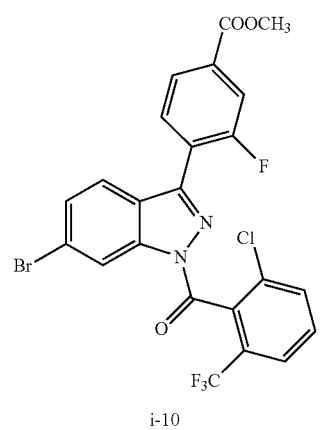

i-10

Step 1. Preparation of 6-bromo-3-iodo-1H-indazole (i-9b)

To a flask was added 6-bromo-1H-indazole (i-9a) (1.96 g, 10 mmol), KOH (1.68 g, 30 mmol) and DMF (60 mL), followed by the addition of I₂ (5.08 g, 20 mmol) in portions. The reaction mixture was stirred at room temperature for 1 h. The mixture was diluted with H₂O, and the organic layer was separated. The aqueous layer was extracted with CH₂Cl₂ (3*50 mL). The combined organics were washed with H₂O, brine, dried over Na₂SO₄, and concentrated. The residue was purified by column chromatography (PE/EA=10/1) to afford 2.84 g (88%) of the title compound. LCMS (ESI) calc'd for $C_7H_4BrIN_2$ [M+H]⁺: 322.86. found: 323.

Preparation of Methyl 4-(6-bromo-1-(2-chloro-6-(trifluoromethyl)benzo-yl)-1H-indazol-3-yl)benzoate (i-10)

Synthesized according to the method shown in Scheme i-9

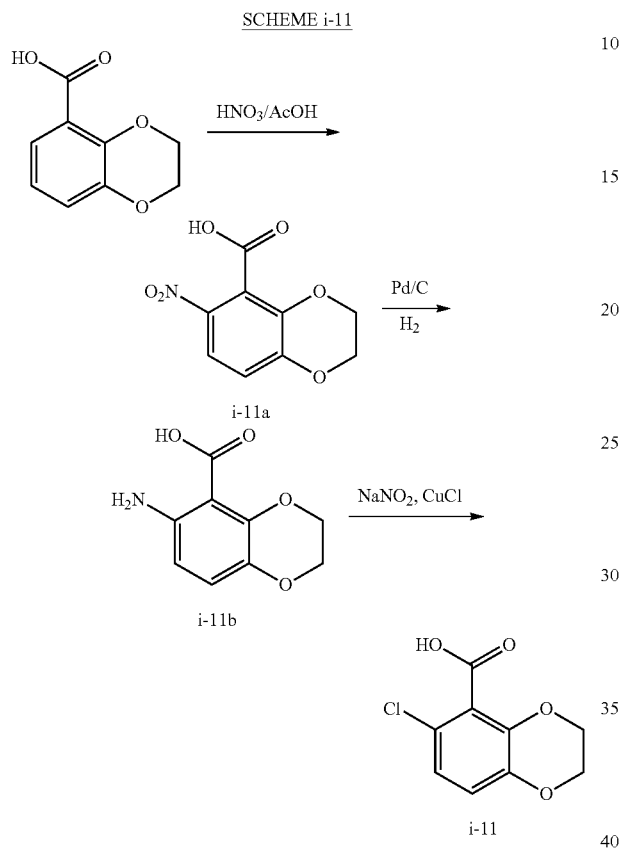

Step 1. Preparation of 6-nitro-2,3-dihydrobenzo[b][1,4]dioxine-5-carbonylic acid (i-11a)

A solution of 2,3-dihydrobenzo[b][1,4]dioxine-5-carbonylic acid (1 g, 5.56 mmol) in 4 ml of acetic acid and 4 ml of acetic anhydride was heated to 40° C., and a solution 0.6 ml nitric acid in 0.6 ml acetic acid was added. The mixture was stirred at 40-45° C. for 2 h and then cooled to 5° C. The precipitate was filtered with suction filter, washed with 10 ml water, collected and dried to afford 700 mg of the title compound as white solid, which was used in the next step without further purification. LCMS (ESI) calc'd for $C_9H_7NO_6$, [M+H]$^+$: 226. found: 226.

Step 2. Preparation of 6-amino-2,3-dihydrobenzo[b][1,4]dioxine-5-carbonylic acid (i-11b)

To a solution of 6-nitro-2,3-dihydrobenzo[b][1,4]dioxine-5-carbonylic acid (i-11a) (700 mg, 3.11 mmol) in MeOH (30 ml) was added Pd/C (33 mg, 0.311 mmol), and the mixture was placed under an atmosphere of $H_2$ (g). Then the reaction mixture was stirred at room temperature for 4 h. The mixture was filtered over celite and concentrated to give the title compound as a brown oil (500 mg), which was used in the next step without further purification. LCMS (ESI) calc'd for $C_9H_9NO_4$, [M+H]$^+$: 196. found: 196.

Step 3. Preparation of 6-chloro-2,3-dihydrobenzo[b][1,4]dioxine-5-carbonylic acid (i-11)

A solution of 6-amino-2,3-dihydrobenzo[b][1,4]dioxine-5-carbonylic acid (i-11b) (500 mg, 2.56 mmol) in HCl (5 ml, 6M) was cooled to 0° C. and treated slowly with a solution of NaNO$_2$ (177 mg, 2.56 mmol) in 5 ml water. The mixture was stirred for 1 h. In the meantime, a mixture of CuCl (506.9 mg, 5.12 mmol) and 4 ml of HCl was heated to 80° C. Then, the solution of the first step was added slowly into the heated solution, followed by refluxing for 5 h. After filtration, the filtrate was extracted with EA (4*10 ml), and then the solvent was removed to give a crude product of the title compound (400 mg, brown solid), which was used in the next step without further purification. LCMS (ESI) calc'd for $C_9H_7ClO_4$, [M+H]$^+$: 215. found: 215.

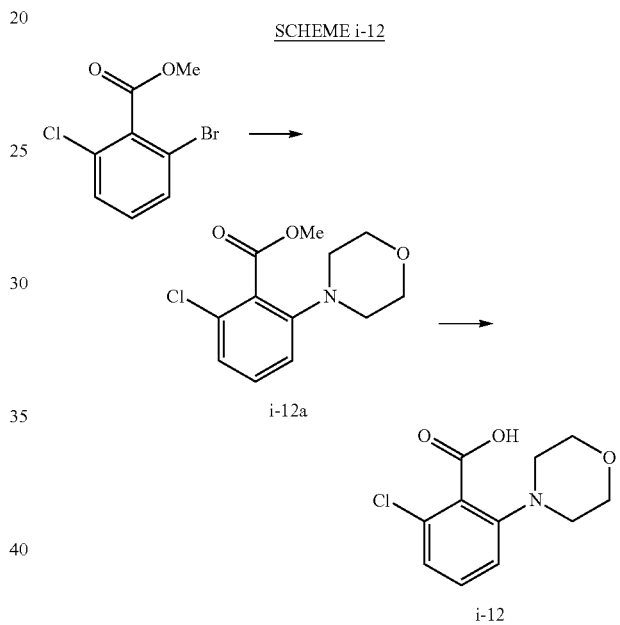

Step 1: methyl 2-chloro-6-morpholinobenzoate (i-12a)

To a vial were added methyl 2-bromo-6-chlorobenzoate (430 mg, 1.724 mmol), morpholine (180 μl, 2.068 mmol), Pd$_2$(dba)$_3$ (158 mg, 0.172 mmol), Xantphos (150 mg, 0.259 mmol), cesium carbonate (1123 mg, 3.45 mmol) and dioxane (5.7 mL), and the reaction was heated to 80° C. overnight. The mixture was cooled, diluted with ethyl acetate, washed twice with aqueous sodium hydrogen carbonate, and washed once with brine. Aqueous layers were back extracted once with ethyl acetate, combined organic layers were dried with Na$_2$SO$_4$ and filtered, and the solvent was evaporated under reduced pressure. The residue was purified by flash chromatography (EtOAc/Hexane 10-75%) to give the title compound as yellow oil. (156 mg, 35%) LCMS (ESI) calc'd for $C_{12}H_{14}ClNO_3$ [M+H]$^+$: 256. found: 256.

Step 2: 2-chloro-6-morpholinobenzoic acid (i-12)

To a vial were added methyl 2-chloro-6-morpholinobenzoate (i-12a) (150 mg, 0.587 mmol), potassium hydroxide (2933 μl, 5.87 mmol), THF (1.5 ml) and water (1.5 ml), and the reaction was heated to 100° C. over the weekend. The reaction was acidified with 2N HCl and then extracted twice with 3:1 CHCl$_3$:IPA. The combined organic layers were dried with sodium sulfate, filtered and concentrated to give the title compound. (140 mg, 99%) LCMS (ESI) calc'd for C$_{11}$H$_{12}$ClNO$_3$ [M+H]$^+$: 242. found: 242.

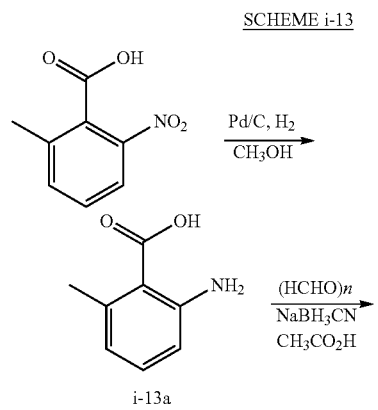

Step 1. Preparation of 2-amino-6-methylbenzoic acid (i-13a)

Pd/C (150 mg) was added to a solution of 2-methyl-6-nitrobenzoic acid (1.5 g, 8.29 mmol) in CH$_3$OH (35 ml). The mixture was stirred at room temperature under H$_2$ atmosphere for 2 h. Then the mixture was filtered and concentrated to afford 1.2 g of the title compound as yellow solid. LCMS (ESI): calc'd for C$_8$H$_9$NO$_2$[M+H]$^+$: 152. found: 152.

Step 2. Preparation of 2-(dimethylamino)-6-methylbenzoic acid (i-13)

2-amino-6-methylbenzoic acid (i-13a) (1.2 g, 8.0 mmol) was dissolved in CH$_3$COOH (50 ml) and heated to 40° C. To this stirring solution was added (HCHO)$_n$ (0.72 g, 24 mmol), followed by NaBH$_3$CN (1.51 g, 24 mmol). The reaction mixture was stirred for 1 h at 40° C., then additional (HCHO)$_n$ (0.72 g, 24 mmol) and NaBH$_3$CN (1.51 g, 24 mmol) were added. The mixture was stirred for 16 h at 40° C. The solvent was removed under reduced pressure. The residues were partitioned between EA and water. The organic layer was dried over Na$_2$SO$_4$, filtered and concentrated to obtain a residue. The residue was purified by chromatography on silica gel (PE/EA=3/1) to afford 700 mg (50%) of the title compound. LCMS (ESI) calc'd for C$_{10}$H$_{13}$NO$_2$ [M+H]$^+$: 180. found: 180.

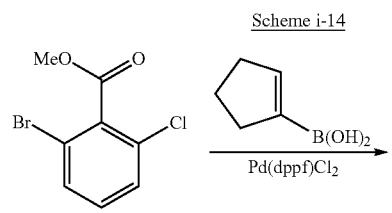

Step 1. Preparation of methyl 2-chloro-6-cyclopentylbenzoate (i-14a)

To a stirred solution of methyl 2-bromo-6-chlorobenzoate (500 mg, 2.0 mmol) and 1-cyclopentenylboronic acid pinacol ester (429 mg, 2.2 mmol) in dioxane (20 mL) was added Pd(dppf)Cl$_2$ (50 mg, 0.021 mmol), Na$_2$CO$_3$ (430 mg, 4.0 mmol) and dioxane/H$_2$O (10 mL/2 mL) at room temperature. The mixture was stirred at 110° C. under N$_2$ for 8 h. The mixture was washed with H$_2$O (30 mL*3) and then dried over anhydrous sodium sulfate. After filtration and concentration, the residue was purified by prep-TLC (PE: EtOAc=10:1) to give the title compound (300 mg, yield: 56%) as a white solid. LCMS (ESI): calc'd for C$_{13}$H$_{13}$ClO$_2$ [M+H]$^+$: 237. found: 237.

Step 2. Preparation of methyl 2-chloro-6-cyclopentylbenzoate (i-14b)

A solution of methyl 2-chloro-6-cyclopentylbenzoate (i-14a) (300 mg, 1.02 mmol) and Pd/C (30 mg, 1.53 mol) in EtOAc (10 mL) was stirred at 15° C. under 15 psi H$_2$ (g) for 2 h. The reaction mixture was filtered, and the filtrate was concentrated in vacuo to obtain the title compound (200 mg, 75%) as yellow oil. LCMS (ESI): calc'd for C$_{13}$H$_{15}$ClO$_2$ [M+H]$^+$: 239 found: 239.

Step 3. Preparation of 2-chloro-6-cyclopentylbenzoic acid (i-14c)

A solution of methyl 2-chloro-6-cyclopentylbenzoate (i-14b) (200 mg, 0.61 mmol) in EtOH (10 mL) and aq. NaOH (10 mL, 30%) was refluxed over 3 days. Then the mixture was acidified by aq.HCl (1M) to pH=3~4 and extracted with ethyl acetate. The combined extracts were washed with brine, dried over anhydrous Na$_2$SO$_4$ and concentrated to give the title compound (100 mg, yield: 39%) as a white solid. LCMS (ESI): calc'd for C$_{12}$H$_{13}$ClO$_2$ [M+H]$^+$: 225. found: 225.

Step 4. Preparation of 2-chloro-6-cyclopentylbenzoyl chloride (i-14)

A mixture of 2-chloro-6-cyclopentylbenzoic acid (i-14c) (80 mg, 0.36 mmol) and 5 mL of $SOCl_2$ was heated to reflux for 24 h under $N_2$. After the reaction finished, the mixture was cooled to 15° C. and evaporated to afford the title compound (100 mg, 100%) as yellow oil. LCMS (ESI): calc'd for $C_{12}H_{12}Cl_2O$ [M+H]$^+$: 243. found: 243.

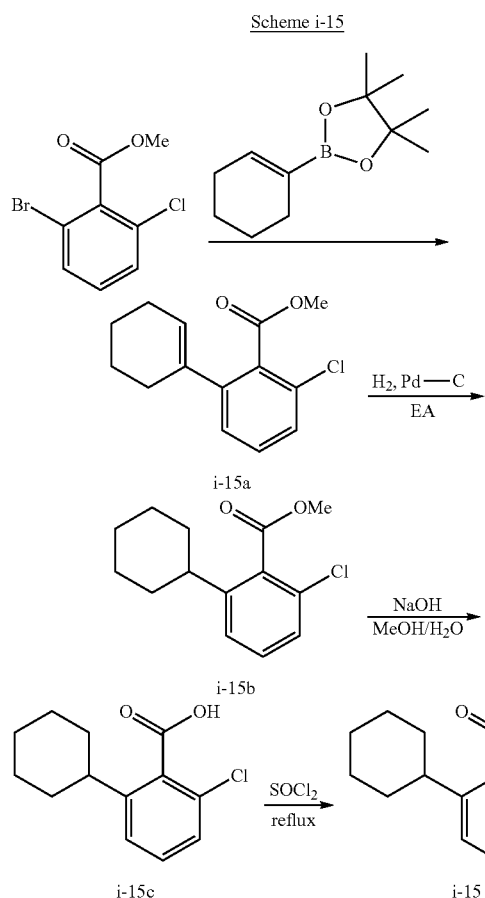

i-15a i-15b i-15c i-15

Step 1. Preparation of methyl 3-chloro-2',3',4',5'-tetrahydro-[1,1'-biphenyl]-2-carboxylate (i-15a)

To a solution of methyl 2-bromo-6-chlorobenzoate (520 mg, 2.00 mmol) and 1-cyclohexenylboronic acid pinacol ester (500 mg, 2.40 mmol) in 10 mL of dioxane and 2 mL of water under nitrogen was added sodium carbonate (500 mg, 4.60 mmol) and Pd(dppf)$Cl_2$ (10 mg), and the resulting mixture was stirred at 90° C. for 3 hrs. The mixture was concentrated and the residue was purified on silica gel by column chromatography (petroleum as eluent) to give the title compound (520 mg, 100%) as colorless oil. LCMS (ESI) calc'd for $C_{14}H_{15}ClO_2$ [M+H]$^+$: 251. found: 251.

Step 2. Preparation of methyl 2-chloro-6-cyclohexylbenzoate (i-15b)

A mixture of methyl 3-chloro-2',3',4',5'-tetrahydro-[1,1'-biphenyl]-2-carboxylate (i-15a) (520 mg, 2 mmol) and Pd/C (100 mg, 10% wet) in 10 mL of ethyl acetate was stirred at room temperature under $H_2$ (1 atm) for 4 hours. The reaction mixture was filtered. The filtrate was concentrated to afford the title compound in crude form (500 mg, 70% purity, along with 30% of de-chloro by-product), which was used without further purification. LCMS (ESI) calc'd for $C_{14}H_{17}ClO_2$ [M+H]$^+$: 253. found: 253.

Step 3. Preparation of 2-chloro-6-cyclohexylbenzoic acid (i-15c)

To a solution of methyl 2-chloro-6-cyclohexylbenzoate (i-15b) (500 mg, 1.04 mmol) in 10 mL of MeOH/$H_2O$ (1:1) was added sodium hydroxide (175 mg, 4.16 mmol), and the reaction mixture was then stirred for 48 h at 80° C. The mixture was diluted with 10 mL of water and extracted with PE (200 mL*2). The aqueous layer was acidified by 2 M HCl to pH=3 and then extracted with EtOAc (300 mL*3). The combined organic layers were washed with brine (200 mL*2), dried over $Na_2SO_4$ and concentrated to afford the title compound (300 mg, 64%) as a yellow solid. LCMS (ESI) calc'd for $C_{13}H_{15}ClO_2$ [M+H]$^+$: 239. found: 239.

Step 4. Preparation of 2-chloro-6-cyclohexylbenzoyl chloride (i-15)

A mixture of 2-chloro-6-cyclohexylbenzoic acid (i-15c) (150 mg, 0.63 mmol) and 5 mL of $SOCl_2$ was heated to reflux for 24 h under $N_2$. The mixture was cooled to 15° C. and evaporated to afford the title compound (150 mg, 93%) as yellow oil. LCMS (ESI) calc'd for $C_{13}H_{14}Cl_2O$ [M+H]$^+$: 257. found: 257.

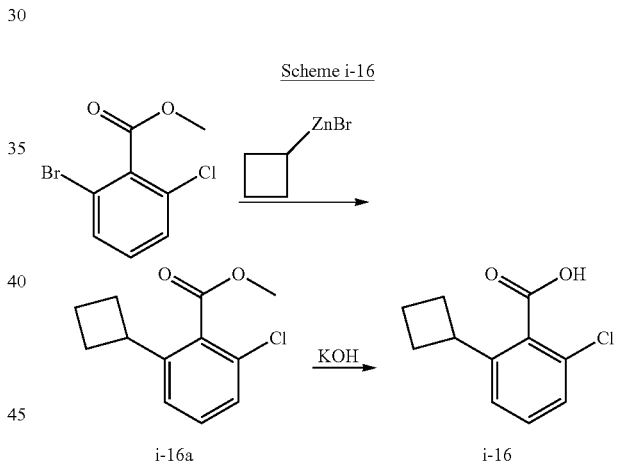

i-16a i-16

Step 1. Preparation of methyl 2-chloro-6-cyclobutylbenzoate (i-16a)

A mixture of methyl 2-bromo-6-chlorobenzoate (750 mg g, 3 mmol), (PPh$_3$)$_4$Pd (345 mg, 0.3 mmol) and cyclobutylzinc bromide (12 ml in THF, 6 mmol) was stirred at 70° C. for 12 h under $N_2$. The mixture was extracted with EA and water. The organic phase was washed with brine, dried over $Na_2SO_4$, filtered, and concentrated. Purification by flash chromatography (PE: EtOAc=50:1) afforded 350 mg (61% in LCMS, contained some PPh$_3$) of the title compound. LCMS (ESI) calc'd for $C_{12}H_{13}ClO_2$ [M+H]$^+$: 225. found: 225.

Step 2. Preparation of 2-chloro-6-cyclobutylbenzoic acid (i-16)

To a solution of methyl 2-chloro-6-cyclobutylbenzoate (i-16a) (350 mg, 1 mmol) in EtOH (2 ml), was added KOH (2M in H₂O, 1.5 ml, 3 mmol). The mixture was stirred at 100° C. for 12 h, acidified with 3N HCl and extracted with EA. The organic phase was washed with brine, dried over Na₂SO₄, filtered and concentrated. Purification by prep-HPLC (ACN: H₂O) afforded 125 mg of the title compound. LCMS (ESI) calc'd for C₁₁H₁₁ClO₂ [M+H]⁺: 211. found: 211.

Scheme i-17

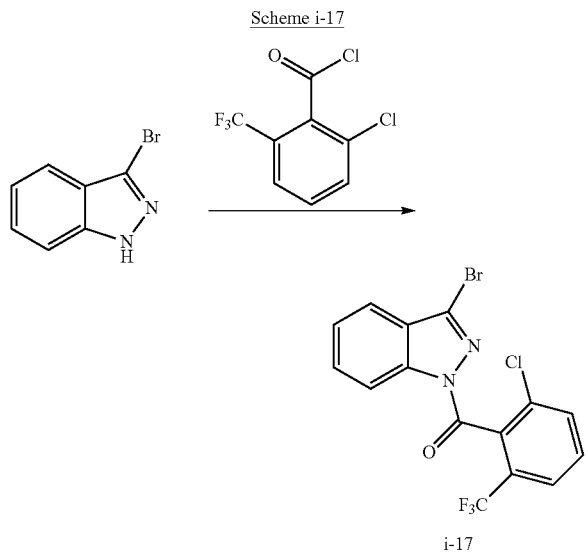

Step 1. Preparation of (3-bromo-1H-indazol-1-yl) (2-chloro-6-(trifluoromethyl)phenyl) methanone (i-17)

To a solution of 3-bromo-1H-indazole (500 mg, 2.55 mmol) in DCM (15 mL) was added 2-chloro-6-(trifluoromethyl)benzoyl chloride (678 mg, 2.8 mmol). Then Et₃N (386 mg, 3.825 mmol) and DMAP (93 mg, 0.765 mmol) were added. The mixture was stirred at room temperature for 4 h. Water was added, and the aqueous phase was extracted with DCM. The organic phase was collected, washed with brine, dried over anhydrous Na₂SO₄, and concentrated to obtain the title compound as a crude solid (812 mg). LCMS (ESI): calc'd for C₁₅H₇BrClF₃N₂O [M+H]⁺: 403. found: 403.

SCHEME i-18

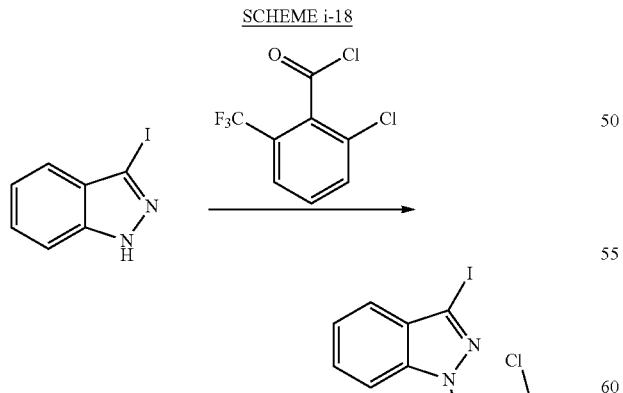

Step 1. Preparation of (2-chloro-6-(trifluoromethyl)phenyl)(3-iodo-1H-indazol-1-yl)methanone (i-18)

To a solution of 3-iodo-1H-indazole (500 mg, 2.05 mmol) in DCM (20 mL), was added 2-chloro-6-(trifluoromethyl)benzoyl chloride (547 mg, 2.25 mmol). Then Et₃N (311 mg, 3.1 mmol) and DMAP (75 mg, 0.615 mmol) were added. The mixture was stirred at room temperature overnight. Water was added, and the aqueous phase was extracted with DCM. The organic phase was collected, washed with brine, dried over anhydrous Na₂SO₄ and concentrated to obtain the title compound as a solid product (750 mg). LCMS (ESI): calc'd for C₁₅H₇ClF₃N₂O [M+H]⁺: 451. found: 451.

SCHEME i-19

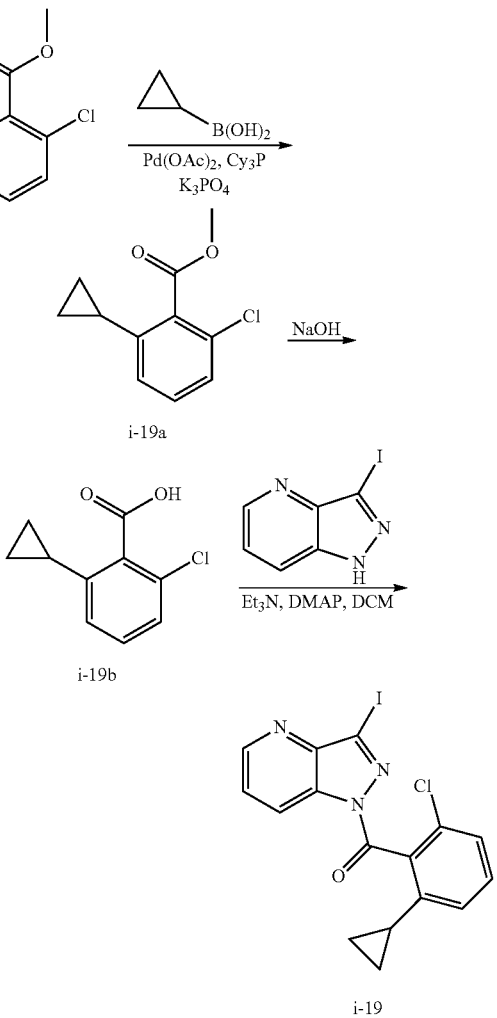

Step 1. Preparation of methyl 2-chloro-6-cyclopropylbenzoate (i-19a)

Methyl 2-bromo-6-chlorobenzoate (1.0 g, 4.0 mmol), cyclopropylboronic acid (516 mg, 6.0 mmol), Pd(OAc)₂ (90 mg, 0.4 mmol), Cy₃P (224 mg, 0.8 mmol) and K₃PO₄ (2.5 g, 12.0 mmol) were stirred overnight in toluene (20 ml) and H₂O (2.5 ml) under an atmosphere of N₂ (g). The mixture was cooled to room temperature and poured into water (50 ml). The mixture was then extracted with EA (50 ml). The organic layer was dried over Na₂SO₄ and concentrated. The residue was purified by flash chromatography (Petroleum/EtOAc 15/1) to give 0.6 g (71%) of the title compound. LCMS (ESI) calc'd for $C_{11}H_{11}ClO_2$ [M+H]⁺: 211. found: 211.

Step 2. Preparation of 2-chloro-6-cyclopropylbenzoic acid (i-19b)

NaOH (380 mg, 9.5 mmol) was added to a solution of methyl 2-chloro-6-cyclopropylbenzoate (i-19a) (200 mg, 0.95 mmol) in EtOH (15 ml) and H₂O (6 ml). The resulting solution was stirred at 80° C. for 14 h. The mixture was cooled down and acidified with 2N HCl to pH=2-3. Then the mixture was extracted with EA (50 ml). The organic layer was dried over Na₂SO₄ and concentrated to afford 160 mg (86%) of the title compound. LCMS (ESI) calc'd for $C_{10}H_9ClO_2$ [M+H]⁺: 197. found: 197.

Step 3. Preparation of methyl 4-(1-(2-chloro-6-cyclopropylbenzoyl)-1H-pyrazolo[4,3-b]pyridin-3-yl)-3-fluorobenzoate (i-19)

To a solution of 2-chloro-6-cyclopropylbenzoic acid (i-19b) (160 mg, 0.816 mmol) in DCM (20 mL) was added two drops of DMF. Oxalyl dichloride (207 mg, 1.63 mmol) was added, and the solution was stirred at room temperature for 30 min. The reaction mixture was evaporated to dryness. The residue was dissolved in DCM (15 mL) and next added to a mixture of 3-iodo-1H-pyrazolo[4,3-b]pyridine (200 mg, 0.816 mmol), DMAP (100 mg, 0.816 mmol) and TEA (123 mg, 1.22 mmol) in DCM (30 ml). The reaction mixture was stirred at 40° C. for 3 h. The mixture was diluted with H₂O, and the organic layer was separated. The aqueous layer was extracted with CH₂Cl₂. The combined organic extracts were dried over Na₂SO₄ and concentrated. The residue was purified by flash chromatography (Petroleum/EtOAc, 6/1) to afford 208 mg (60%) of the title compound. LCMS (ESI) calc'd for $C_{16}H_{11}ClIN_3O$ [M+H]⁺: 424. found: 424.

SCHEME i-20 i-20

Step 1. Preparation of (3-bromo-1H-indazol-1-yl)(2-chloro-6-cyclopropylphenyl) methanone (i-20)

A mixture of 2-chloro-6-cyclopropylbenzoic acid (0.23 g, 1.17 mol) and (COCl)₂ (0.2 mL, 2.34 mol) in DCM (10 mL) and DMF (5 drops) was stirred at room temperature for 1.5 h. The solvent was removed and the residue was dissolved in DCM (10 mL)

To a mixture of 3-bromo-1H-indazole (0.23 g, 1.17 mol), DMAP (74 mg, 0.59 mol) and Et₃N (0.32 mL, 2.34 mol) in DCM (10 mL) was added the above DCM solution dropwise, and the reaction mixture was stirred at room temperature overnight. The resulting solution was diluted with H₂O (50 mL), and the aqueous layer was extracted with DCM (30 mL×3). The combined organic layers were washed with brine (30 mL), dried over anhydrous Na₂SO₄ and concentrated. The residue was chromatographed on silica gel (PE:EA 10:1) to obtain the title compound as a white solid. LCMS (ESI) calc'd for $C_{17}H_{12}BrClN_2O$ [M+H]⁺: 375. found: 375.

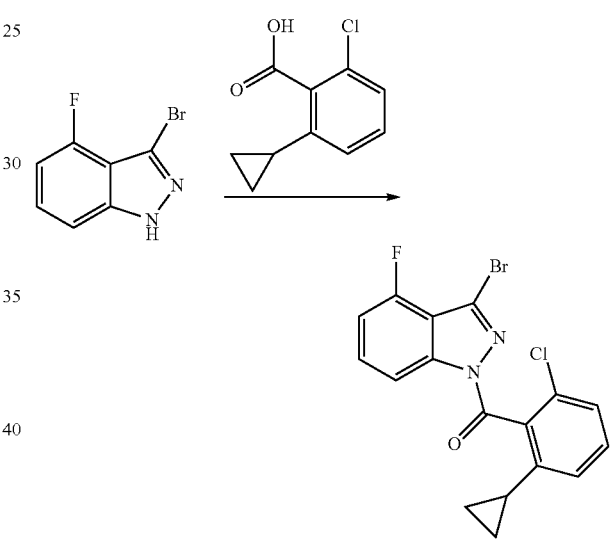

SCHEME i-21 i-21

Step 1. Preparation of (3-bromo-4-fluoro-1H-indazol-1-yl)(2-chloro-6-cyclopropyl phenyl)methanone (i-21)

A mixture of 2-chloro-6-cyclopropylbenzoic acid (0.23 g, 1.17 mol) and (COCl)₂ (0.2 mL, 2.34 mol) in DCM (10 mL) and DMF (5 drops) was stirred at room temperature for 1.5 h. The solvent was removed and the residue was dissolved in DCM (10 mL).

To a mixture of 3-bromo-4-fluoro-1H-indazole (0.25 g, 1.17 mol), DMAP (74 mg, 0.59 mol) and Et₃N (0.32 mL, 2.34 mol) in DCM (10 mL) was added the above DCM solution dropwise, and the reaction mixture was stirred at room temperature overnight. The resulting solution was diluted with H₂O (50 mL), and the aqueous layer was extracted with DCM (30 mL×3). The combined organic layers were washed with brine (30 mL), dried over anhydrous Na₂SO₄ and concentrated. The residue was chromatographed on silica gel (PE:EA 10:1) to obtain the title compound as a white solid. LCMS (ESI) calc'd for C$_{17}$H$_{11}$BrClFN$_2$O [M+H]$^+$: 393. found: 393.

SCHEME i-22

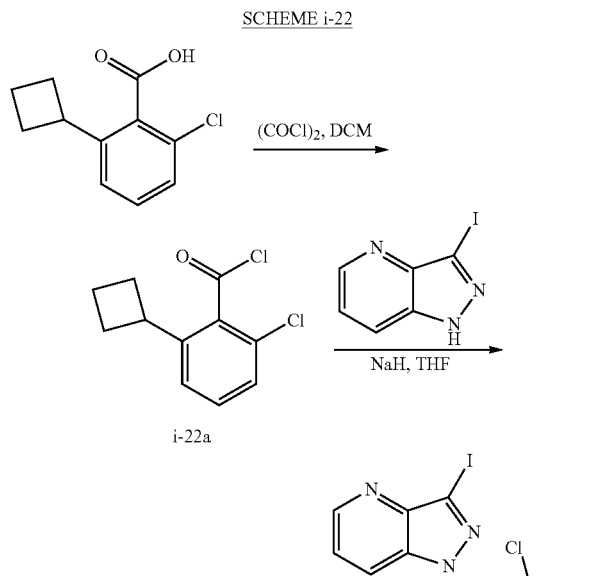

i-22a i-22

SCHEME i-23

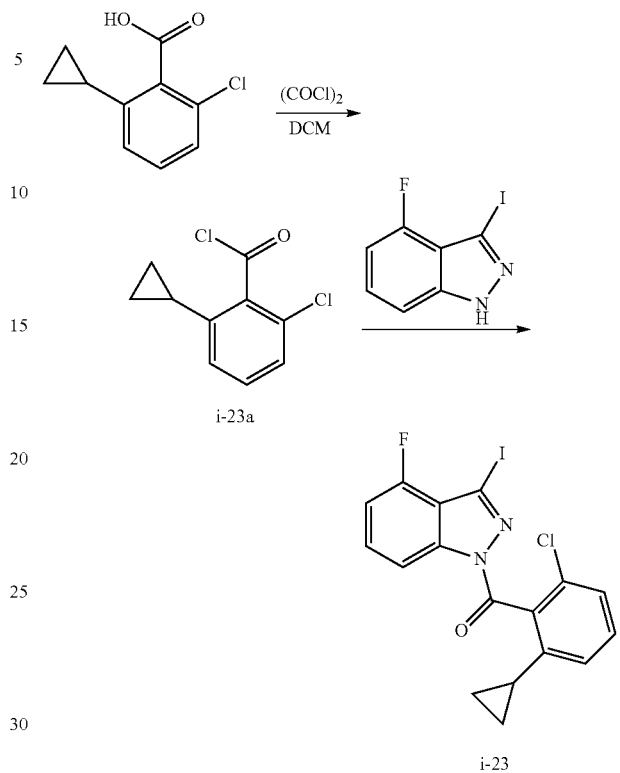

i-23a i-23

Step 1. Preparation of 2-chloro-6-cyclobutylbenzoyl chloride (i-22a)

To a solution of 2-chloro-6-cyclobutylbenzoic acid (300 mg, 1.43 mmol) and oxalyl dichloride (301 mg, 2.37 mmol) in DCM (5 mL) was added one drop of DMF, and the mixture was stirred at 10° C. for 3 hours. The reaction mixture was concentrated in vacuo to give the crude title compound (350 mg crude) as a yellowish solid, which was used in the next step without further purification.

Step 2. Preparation of (2-chloro-6-cyclobutylphenyl)(3-iodo-1H-pyrazolo[4,3-b]pyridin-1-yl)methanone (i-22)

To a stirred solution of 3-iodo-1H-pyrazolo[4,3-b]pyridine (300 mg, 1.224 mmol) in THF (3 mL) at 0° C. was added NaH (59 mg, 2.45 mmol, 60% in mineral oil), and the mixture was stirred at this temperature for 30 min. A solution of 2-chloro-6-cyclobutylbenzoyl chloride (i-22a) (350 mg crude) in THF (1 mL) was added, and the resulting mixture was stirred at 10° C. for an additional 2 hours, after which time LCMS showed that the reaction was completed. The reaction mixture was poured into water (20 mL) and extracted with DCM (20 mL*2). The combined organic layers were washed with brine (30 mL), dried over Na$_2$SO$_4$ and concentrated in vacuo. The crude product was purified by prep-TLC (PE: EtOAc=3:1) to give the title compound (380 mg, 70.9% yield) as a white solid. LCMS (ESI) calc'd for C$_{17}$H$_{13}$ClIN$_3$O [M+H]$^+$: 438. found: 438.

Step 1. Preparation of 2-chloro-6-cyclopropylbenzoyl chloride (i-23a)

To a solution of 2-chloro-6-cyclopropylbenzoic acid (1 g, 7.19 mmol) in 50 mL of DCM at 0° C. was added oxalyl dichloride (13 mL) dropwise, and then the mixture was stirred at 25° C. for 12 h. The mixture was evaporated to dryness. The residue was next concentrated under reduced pressure to afford 12 g (86%) of the title compound as a yellow oil. LCMS (ESI) calc'd for C$_{10}$H$_8$Cl$_2$O [M+H]$^+$: 215. found: 215.

Step 2. Preparation of (2-chloro-6-cyclopropylphenyl)(4-fluoro-3-iodo-1H-indazol-1-yl)methanone (i-23)

To a suspension of 4-fluoro-3-iodo-1H-indazole (1.14 g, 4.65 mmol) in 20 mL of THF at 0° C. was added NaH (279 mg, 6.9 mmol) dropwise. The mixture was stirred at 0° C. for 30 mins, and a solution of 2-chloro-6-cyclopropylbenzoyl chloride (i-23a) (1 g, 4.65 mol) in anhydrous THF (20 mL) was then added dropwise to the mixture. The mixture was stirred at 25° C. for another 30 mins. Then the reaction mixture was quenched by sat. NH$_4$Cl solution, diluted with water (100 mL) and extracted with EtOAc (150 mL*3). The combined organic layers were washed with brine (50 mL*2), dried over Na$_2$SO$_4$ and evaporated to dryness. The residue was purified by column chromatography on silica gel (PE: EtOAc=5:1) to give 1.7 g (86.3%) of the title compound as a yellow solid. LCMS (ESI) calc'd for C$_{17}$H$_{11}$ClFIN$_2$O [M+H]$^+$: 441. found: 441.

SCHEME i-24

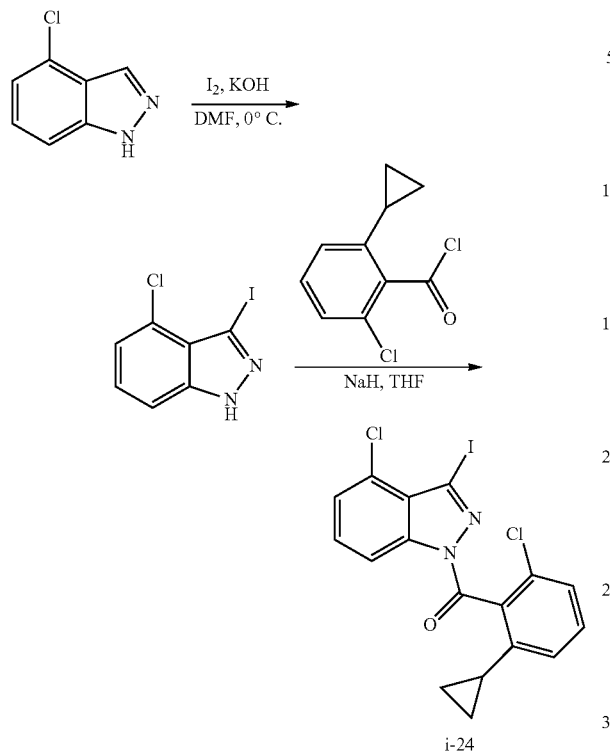

Step 1. Preparation of 4-chloro-3-iodo-1H-indazole (i-24a)

To a solution of 4-chloro-1H-indazole (3.0 g, 20 mmol) in dry DMF (20 mL) was added KOH (4.5 g, 80 mmol). After stirring at 25° C. for 30 minutes, I$_2$ (10.0 g, 40 mmol) was added at 0° C. The mixture was stirred at 25° C. for an additional 12 hours. The resulting mixture was poured into saturated aq.Na$_2$S$_2$O$_3$ solution (200 mL). The solid was collected by filtration and dried to afford the title compound (6.0 g, crude) as a gray solid. LCMS (ESI) calc'd for C$_7$H$_4$ClIN$_2$ [M+H]$^+$: 279. found: 279.

Step 2. Preparation of (4-chloro-3-iodo-1H-indazol-1-yl)(2-chloro-6-cyclopropylphenyl) methanone (i-24)

To a suspension of NaH (48 mg, 2 mmol, 60% in mineral oil) in dry THF (20 mL) at 0° C. was added 4-chloro-3-iodo-1H-indazole (i-24a) (280 mg, 1 mmol). After stirring this at 0° C. for 1 h, 2-chloro-6-cyclopropylbenzoyl chloride (260 mg, 1.2 mmol) was added dropwise. The mixture was stirred at 25° C. for an additional 2 h. After the reaction was completed, the mixture was quenched with water (10 mL) and concentrated in vacuo. The residue was partitioned between ethyl acetate (100 mL) and water (100 mL). The aqueous layer was extracted with ethyl acetate (50 mL*3). The combined organic layers were dried over anhydrous Na$_2$SO$_4$, and concentrated under reduced pressure to give the crude title compound (500 mg, crude) as a brown solid. LCMS (ESI) calc'd for C$_{17}$H$_{11}$Cl$_2$IN$_2$O [M+H]$^+$: 457. found: 457.

SCHEME i-25

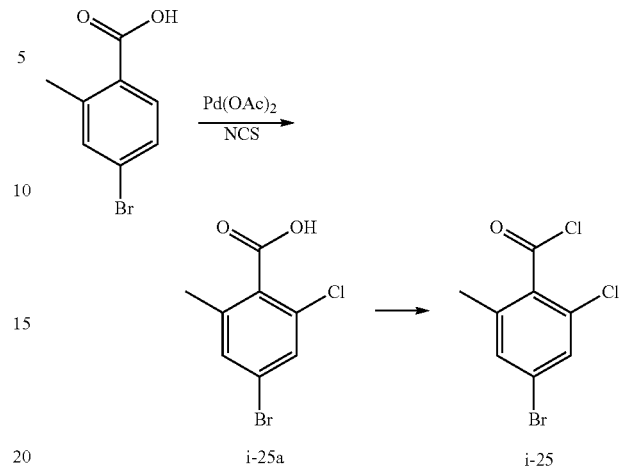

Step 1. Preparation of 4-bromo-2-chloro-6-methylbenzoic acid (i-25a)

A mixture of 4-bromo-2-methylbenzoic acid (4.3 g, 20 mmol), Pd(OAc)$_2$ (223 mg, 1 mmol) and NCS (2.7 g, 20 mmol) in anhydrous DMF (17 mL) was stirred at 100° C. for 12 h under argon. The mixture was extracted with EtOAc and water. The organic phase was washed with brine, dried over Na$_2$SO$_4$, filtered, and concentrated. The residue was purified by flash chromatography (PE: EA=1:1) to give 2.3 g (yield: 46%) of the title compound. LCMS (ESI) calc'd for C$_8$H$_6$BrClO$_2$ [M+H]$^+$: 249. found: 249.

Step 2. Preparation of 4-bromo-2-chloro-6-methylbenzoyl chloride (i-25)

To a solution of 4-bromo-2-chloro-6-methylbenzoic acid (i-25a) (250 mg, 1 mmol) in DCM (10 ml), (COCl)$_2$ (630 mg, 5 mmol) was added, as well as a drop of DMF. The solution was stirred at room temperature for 1 h and concentrated to afford the title compound, which was used without further purification.

SCHEME i-26

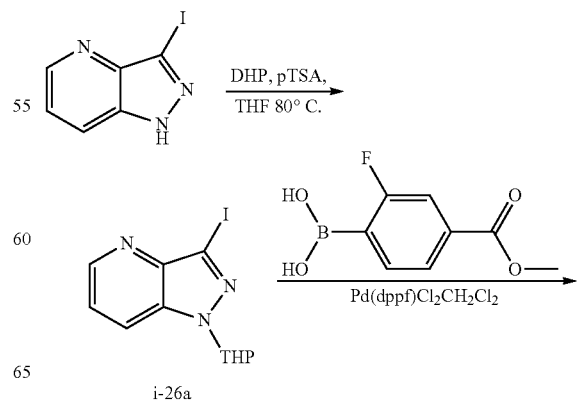

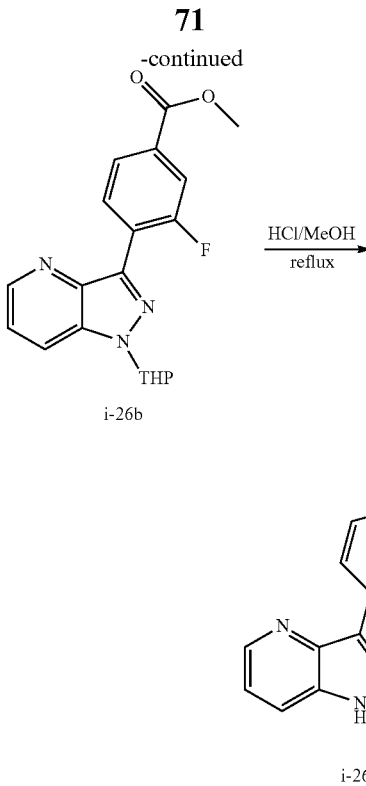

i-26b

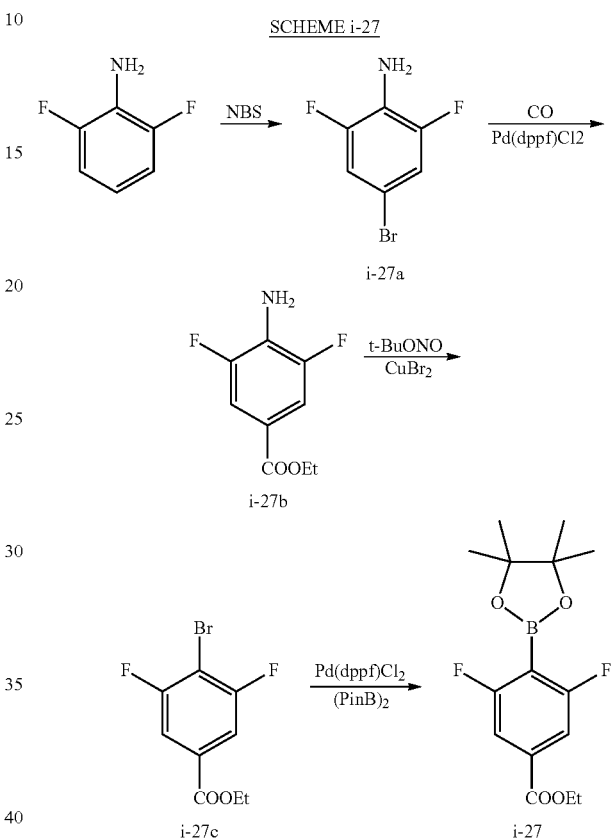

i-26

Step 1. Preparation of 3-iodo-1-(tetrahydro-2H-pyran-2-yl)-1H-pyrazolo[4,3-b]pyridine (i-26a)

To a solution of 3-iodo-1H-pyrazolo[4,3-b]pyridine (10 g, 40.1 mmol) in 150 mL of THF was added DHP (10.3 g, 122.4 mmol) and p-TSA (776 mg, 4 mmol). The reaction mixture was heated to reflux for 6 h. The mixture was poured into water and extracted with EtOAc (300 mL*3). The combined organic layers were washed with brine, dried over $Na_2SO_4$ and concentrated. The residue was purified by silica gel chromatography, eluting with PE:EA=50:1 to PE:EA=5:1 to afford the title compound (7 g, 54%) as a yellow solid. LCMS (ESI): calc'd for $C_{11}H_{12}IN_3O$ [M+H]$^+$: 330. found: 330.

Step 2. Preparation of methyl 3-fluoro-4-(1-(tetrahydro-2H-pyran-2-yl)-1H-pyrazolo[4,3-b]pyridin-3-yl)benzoate (i-26b)

To a solution of 3-iodo-1-(tetrahydro-2H-pyran-2-yl)-1H-pyrazolo[4,3-b]pyridine (i-26a) (3.5 g, 10.6 mmol) and (2-fluoro-4-(methoxycarbonyl)phenyl)boronic acid (3.2 g, 15.9 mmol) in 70 mL of toluene/EtOH (1:1) was added 7.35 mL of sat. $Na_2CO_3$ solution and Pd(dppf)Cl$_2$·CH$_2$Cl$_2$ (867 mg, 1.06 mmol). The reaction mixture was heated to 120° C. for 6 h under an atmosphere of $N_2$ (g). The mixture was filtered and concentrated in vacuo. The crude title compound was used directly for the next reaction without further purification. LCMS (ESI): calc'd for $C_{19}H_{18}FN_3O_3$ [M+H]$^+$: 356. found: 356.

Step 3. Preparation of methyl 3-fluoro-4-(1H-pyrazolo[4,3-b]pyridin-3-yl)benzoate (i-26)

Crude methyl 3-fluoro-4-(1-(tetrahydro-2H-pyran-2-yl)-1H-pyrazolo[4,3-b]pyridin-3-yl)benzoate (i-26b) (5 g, 12.9 mmol) was added to 100 mL of 4N HCl/MeOH, and the reaction mixture was heated to reflux for 14 h. The mixture was basified with sat. NaOH solution to pH=7. The white solid precipitates were collected, washed with PE (100 mL) and dried in vacuum to afford the title compound (2 g, 68%) as a light yellow solid. LCMS (ESI): calc'd for $C_{14}H_{10}FN_3O_2$ [M+H]$^+$: 272. found: 272.

SCHEME i-27

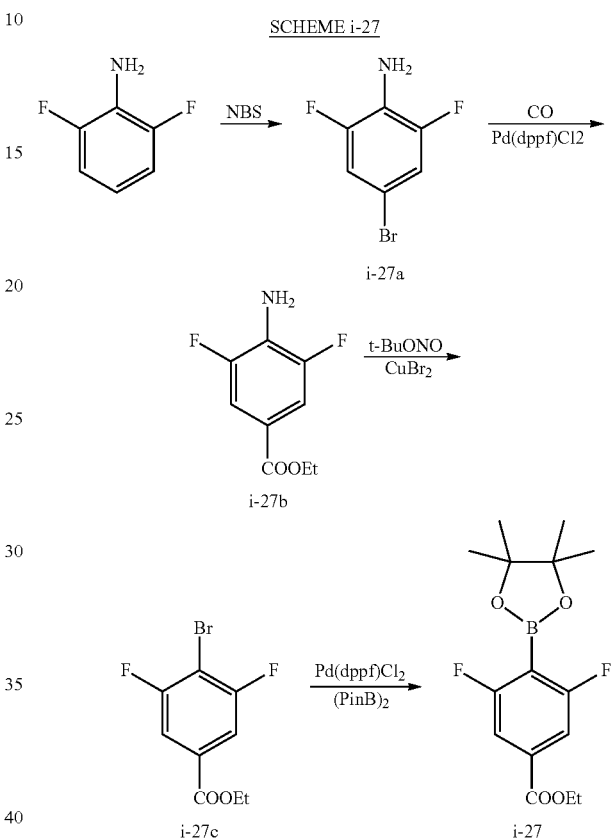

Step 1. Preparation of 4-bromo-2,6-difluoroaniline (i-27a)

To a solution of 2,6-difluoroaniline (1 g, 7.75 mmol) in 20 mL of dry DCM was added NBS (1.96 g, 9.29 mmol). The mixture was stirred at room temperature for 3 hours. The mixture was filtered and concentrated under reduced pressure. The residue was purified by column chromatography on silica gel (PE/EA=50/1 to 20/1) to afford the title compound (1.61 g, 80.7% yield) as a yellow solid. LCMS (ESI) calc'd for $C_6H_4BrF_2N$ [M+H]$^+$: 208. found: 208.

Step 2. Preparation of ethyl 4-amino-3,5-difluorobenzoate (i-27b)

To a solution of 4-bromo-2,6-difluoroaniline (i-27a) (10 g, 48.1 mmol) in EtOH (100 mL) was added Et$_3$N (14.6 g, 144 mmol) and Pd(dppf)Cl$_2$ (1 g). The mixture was stirred at 80° C. for 24 hours under CO (2 MPa) atmosphere, after which LCMS showed 15% conversion. The resulting mixture was filtered and concentrated. The residue was purified by column chromatography on silica gel (PE/EA=50:1 to 40:1) to afford the title compound (1 g, 10% yield). LCMS (ESI) calc'd for $C_9H_9F_2NO_2$ [M+H]$^+$: 202. found: 202.

Step 3. Preparation of ethyl 4-bromo-3,5-difluorobenzoate (i-27c)

To a solution of ethyl 4-amino-3,5-difluorobenzoate (i-27b) (1 g, 4.98 mmol), t-BuONO (3769 mg, 7.46 mmol) in 20 mL CH₃CN at room temperature was added CuBr₂ (1.66 g, 7.46 mmol). The mixture was stirred at room temperature for 1 hour, diluted with water (40 mL), and extracted with EtOAc (40 mL*2). The combined organic layers were washed with brine, dried over Na₂SO₄, filtered and concentrated. The residue was purified by column chromatography on silica gel (PE/EA=100/1 to 20/1) to afford the title compound (0.9 g, 68% yield). LCMS (ESI) calc'd for $C_9H_7BrF_2O_2$ [M+H]⁺: 265. found: 265.

Step 4. Preparation of ethyl 3,5-difluoro-4-(4,4,5,5-tetramethyl-1,3,2-dioxaborolan-2-yl)benzoate (i-27)

To a solution of ethyl 4-bromo-3,5-difluorobenzoate (i-27c) (600 mg, 2.26 mmol), 4,4,4',4',5,5,5',5'-octamethyl-2,2'-bi(1,3,2-dioxaborolane) (1.73 g, 6.79 mmol) and KOAc (666 mg, 6.79 mmol) in toluene (20 mL) was added Pd(dppf)Cl₂ (60 mg). The mixture was stirred at 110° C. for 4 hours under an atmosphere of N₂ (g). After cooling to room temperature, the mixture was diluted with water (60 mL) and extracted with EtOAc (60 mL*3). The combined organic layers were washed with brine, dried over anhydrous Na₂SO₄, and filtered and concentrated under reduced pressure. The residue was purified by column chromatography on silica gel (PE/EA=100:1 to 8:1) to afford the title compound (340 mg, 48% yield) as a white solid. LCMS (ESI) calc'd for $C_{15}H_{19}BF_2O_4$ [M+H]⁺: 313. found: 313.

EXAMPLES

Example 1A: Preparation of (E)-4-(1-(2-chloro-6-(prop-1-enyl)benzoyl)-1H-pyrazolo[4,3-b]pyridin-3-yl)-3-fluorobenzoic acid (1A)

SCHEME A.

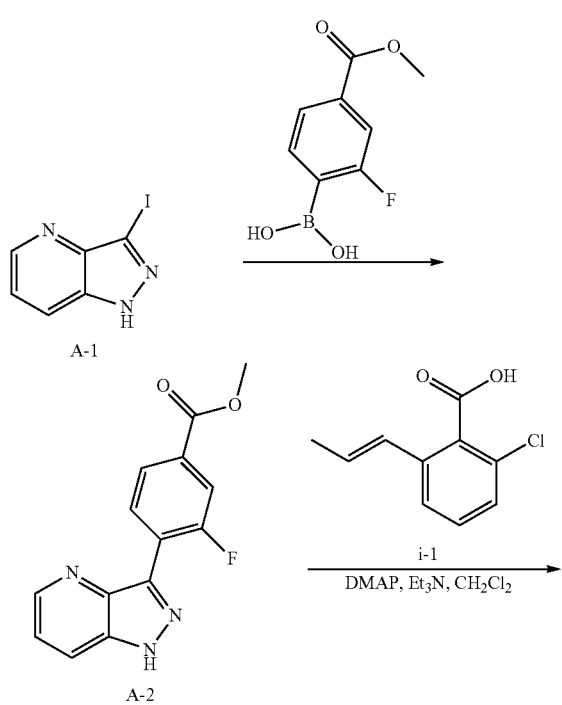

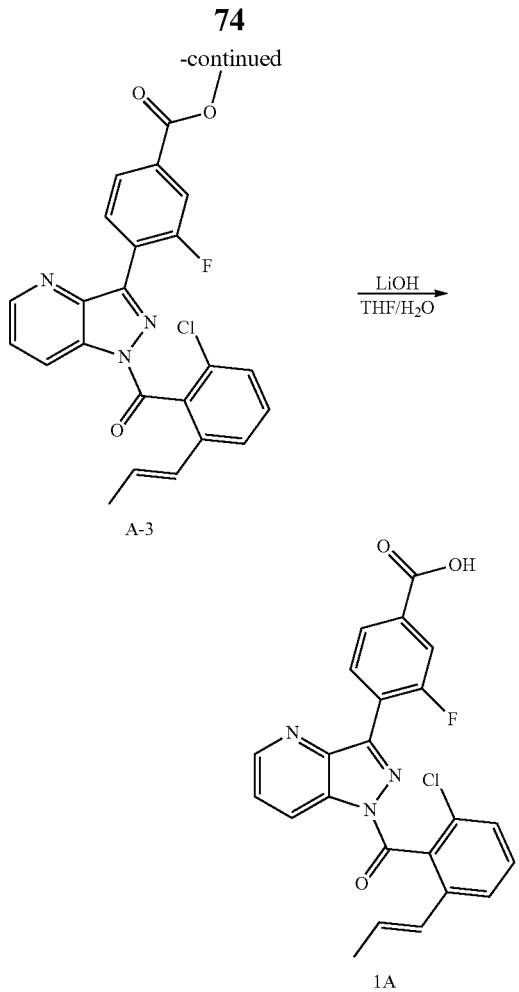

Step 1. Preparation of methyl 3-fluoro-4-(1H-pyrazolo[4,3-b]pyridin-3-yl)benzoate (A-2)

A mixture of 3-bromo-1H-pyrazolo[4,3-b]pyridine (A-1) (196.9 mg, 1 mol), 4-(methoxycarbonyl)phenylboronic acid (198 mg, 1 mol), Pd(PPh3)4 (115 mg, 0.1 mol) and K₂CO₃ (420 mg, 3 mol) was suspended in 1,4-dioxane (5 ml) and H₂O (1 ml). The reaction mixture was heated at 110° C. in a microwave reactor for 2 h. The resulting mixture was diluted with H₂O (30 ml) and the aqueous layer was extracted with ethyl acetate (30 ml×2). The combined organic layers were washed with brine (30 ml×1), dried over anhydrous Na₂SO₄ and concentrated to obtain the crude product A-2 as a brown oil. LCMS (ESI) calc'd for $C_{14}H_{10}FN_3O_2$ [M+H]+: 272.08. found: 272.

Step 2. Preparation of (E)-methyl 4-(1-(2-chloro-6-(prop-1-enyl)benzoyl)-1H-pyrazolo[4,3-b]pyridin-3-yl)-3-fluorobenzoate (A-3)

(COCl)₂ (907 mg, 7.14 mmol) was added dropwise to a solution of (E)-2-chloro-6-(prop-1-enyl)benzoic acid (i-1) (700 mg, 3.57 mmol) and 3 drops of DMF in DCM (20 ml). The resulting solution was stirred at room temperature for 30 min. Then the solution was added to a solution of methyl 3-fluoro-4-(1H-pyrazolo[4,3-b]pyridin-3-yl)benzoate (A-2) (968 mg, 3.57 mmol), Et₃N (720 mg, 7.14 mmol) and DMAP (436 mg, 3.57 mmol) in DCM (20 ml). The solution was stirred at room temperature for 3 h. Then the reaction mixture was poured into water and separated. The organic layer was dried over $Na_2SO_4$ and concentrated to obtain a crude product. The crude product was purified by chromatography on silica gel (PE/EA=6:1) to afford 133 mg of the title compound. LCMS (ESI) calc'd for $C_{24}H_{17}ClFN_3O_3$ [M+H]$^+$: 450. found: 450.

Step 3. Preparation of (E)-4-(1-(2-chloro-6-(prop-1-enyl)benzoyl)-1H-pyrazolo[4,3-b]pyridin-3-yl)-3-fluorobenzoic acid (1A)

To a solution of (E)-methyl 4-(1-(2-chloro-6-(prop-1-enyl)benzoyl)-1H-pyrazolo[4,3-b]pyridin-3-yl)-3-fluorobenzoate (A-3) (120 mg, 2.67 mmol) in THF (15 mL) and $H_2O$ (15 mL) was added $LiOH \cdot H_2O$ (112 mg, 2.67 mmol), and the mixture was stirred at 30° C. for 2 h. The mixture was neutralized with 2N HCl to pH=3-4. The mixture was extracted with EA (50 ml). The organic layer was dried over $Na_2SO_4$ and concentrated to obtain a crude product. The crude product was purified by prep-HPLC to afford 17 mg (15%) of the title compound as a white solid. LCMS (ESI): calc'd for $C_{23}H_{15}ClFN_3O_3[M+H]^+$: 436. found: 436; $^1$HNMR (400 MHz, DMSO) δ 8.94 (2H, m), 8.26-8.23 (1H, t), 7.91-7.72 (4H, m), 7.57-7.48 (2H, m), 6.45-6.43 (1H, m), 6.34-6.30 (1H, d), 1.75-1.74 (3H, d).

Example 1B: Preparation of 4-(1-(2-chloro-6-(trifluoromethyl)benzoyl)-4-formyl-1H-indazol-3-yl)benzoic acid (1B)

SCHEME B.

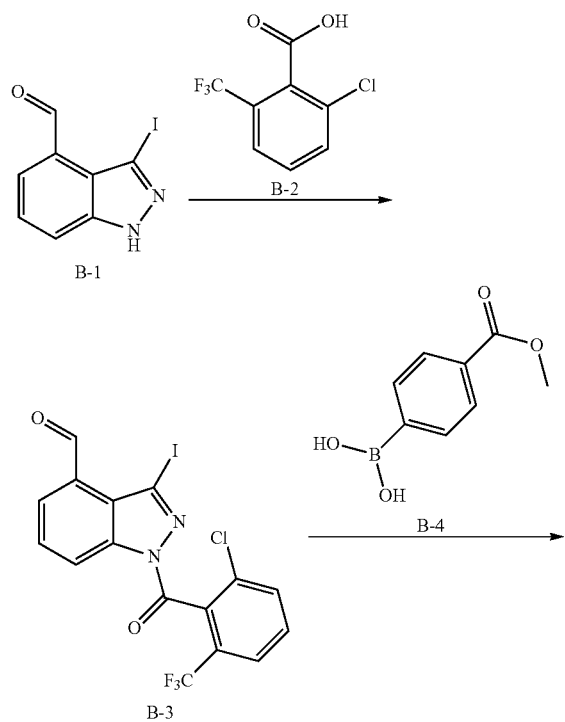

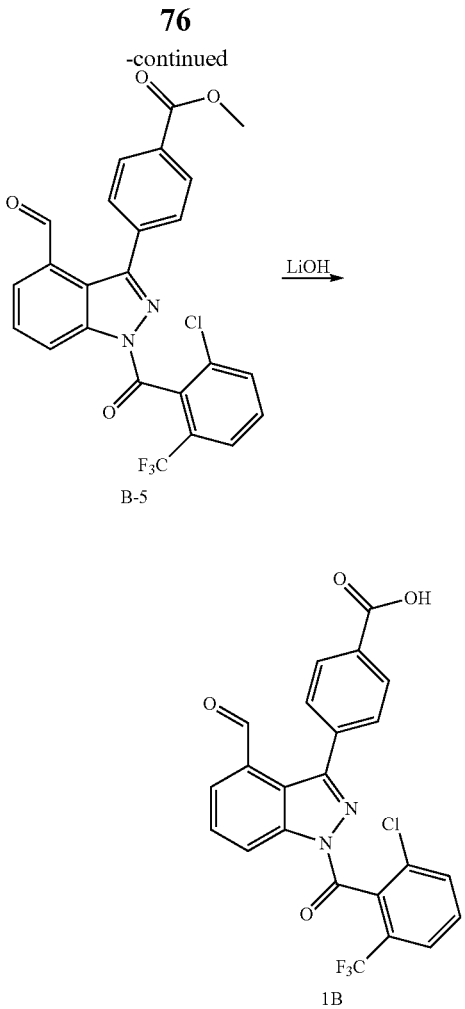

Step 1. Preparation of 1-(2-chloro-6-(trifluoromethyl)benzoyl)-3-iodo-1H-indazole-4-carbaldehyde (B-3)

The mixture of 2-chloro-6-(trifluoromethyl)benzoic acid (B-2) (0.46 g, 2.07 mol) and (COCl)$_2$ (0.32 mL, 3.76 mol) in DCM (10 mL) and DMF (5 drops) was stirred at room temperature for 1 h. The solvent was removed and the residue was dissolved in DCM (10 mL). To the mixture of 3-iodo-1H-indazole-4-carbaldehyde (B–1) (0.51 g, 1.88 mol), DMAP (23 mg, 0.19 mol) and Et$_3$N (0.52 mL, 3.76 mol) in DCM (10 mL) was added the above DCM solution dropwise and the reaction mixture was stirred at room temperature overnight. The resulting solution was diluted with $H_2O$ (50 mL) and the aqueous layer was extracted with DCM (30 mL×3). The combined organic layers were washed with brine (30 mL×1), dried over anhydrous $Na_2SO_4$ and concentrated. The residue was chromatographed on silica gel (PE:EA 8:1 to 4:1) to obtain the desired product B-3 as a white solid. LCMS (ESI) calc'd for $C_{16}H_7ClF_3IN_2O_2$ [M+H]$^+$: 479. found: 479.

Step 2. Preparation of methyl 4-(1-(2-chloro-6-(trifluoromethyl)benzoyl)-4-formyl-1H-indazol-3-yl)benzoate (B-5)

A mixture of 1-(2-chloro-6-(trifluoromethyl)benzoyl)-3-iodo-1H-indazole-4-carbaldehyde (B-3) (0.5 g, 1.05 mol), 4-(methoxycarbonyl)phenylboronic acid (B-4) (0.28 g, 1.57 mol), Pd(PPh$_3$)$_4$ (0.13 g, 0.11 mol) and K$_2$CO$_3$ (0.43 g, 3.15 mol) were suspended in 1,4-dioxane (10 mL) and H$_2$O (2 mL). The reaction mixture was heated at 100° C. in a microwave reactor for 1.5 h. The resulting mixture was diluted with H$_2$O (50 mL) and the aqueous layer was extracted with ethyl acetate (50 mL×3). The combined organic layers were washed with brine (50 mL), dried over anhydrous Na$_2$SO$_4$ and concentrated. The residue was chromatographed on silica gel (PE:EA=4:1) to obtain the desired product B-5 as a pale yellow solid. LCMS (ESI) calc'd for C$_{24}$H$_{14}$ClF$_3$N$_2$O$_4$ [M+H]$^+$: 487. found: 487.

Step 3. Preparation of 4-(1-(2-chloro-6-(trifluoromethyl)benzoyl)-4-formyl-1H-indazol-3-yl)benzoic acid (1B)

The mixture of methyl 4-(1-(2-chloro-6-(trifluoromethyl)benzoyl)-4-formyl-1H-indazol-3-yl)benzoate (B-5) (40 mg, 0.08 mol) and LiOH (17 mg, 0.41 mol) in THF (4 mL) and H$_2$O (2 mL) was stirred at room temperature for 4 h. The reaction mixture was diluted with H$_2$O (20 mL). 2M HCl solution was added to adjust the pH to 3, and the aqueous layer was extracted with ethyl acetate (20 mL×3). The combined organic layers were washed with brine (20 mL×1), dried over anhydrous Na$_2$SO$_4$ and concentrated. The residue was purified with Prep-HPLC to obtain the desired product 1B as a white solid. LCMS (ESI): calc'd for C$_{23}$H$_{12}$ClF$_3$N$_2$O$_4$ [M+H]$^+$: 473. found: 473; $^1$HNMR (400 MHz, DMSO) δ 10.07 (1H, s), 8.89 (1H, d, J=8.4 Hz), 8.13 (1H, d, J=7.2 Hz), 8.03-8.07 (4H, m), 7.99 (1H, d, J=8.0 Hz), 7.83-7.87 (1H, m), 7.70 (2H, d, J=8.4 Hz).

Preparation of 4-(1-(2-chloro-6-cyclopropylbenzoyl)-1H-pyrazolo[4,3-b]pyridin-3-yl)-3-fluorobenzoic acid (1C)

SCHEME C.

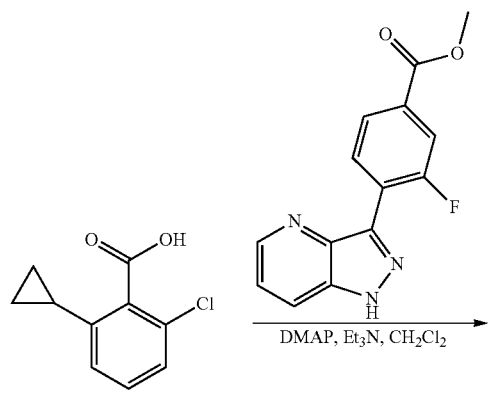

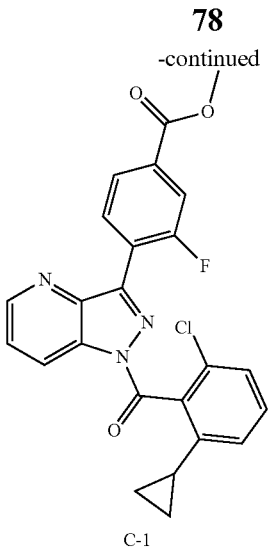

C-1

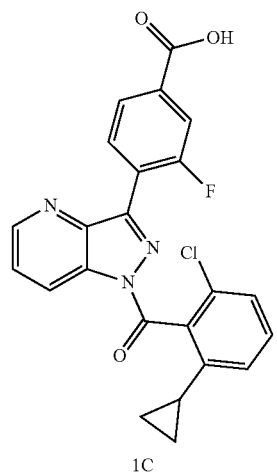

1C

Step 1. Preparation of methyl 4-(1-(2-chloro-6-cyclopropylbenzoyl)-1H-pyrazolo[4,3-b]pyridin-3-yl)-3-fluorobenzoate (C-1)

To a solution of 2-chloro-6-cyclopropylbenzoic acid (160 mg, 0.82 mmol) in DCM (2 mL) was added two drops of DMF. Then oxalyl dichloride (207 mg, 1.63 mmol) was added, and the solution was stirred at room temperature for 30 min. The reaction mixture was concentrated and the residue was taken up in DCM (2 mL), and added to a mixture of methyl 3-fluoro-4-(1H-pyrazolo[4,3-b]pyridin-3-yl)benzoate (221 mg, 0.816 mmol), DMAP (100 mg, 0.816 mmol) and TEA (123 mg, 1.22 mmol) in DCM (5 mL). The reaction mixture was stirred at 40° C. for 3 h. The mixture was diluted with H$_2$O, and the organic layer was separated. The aqueous layer was extracted with CH$_2$Cl$_2$. The combined organics were dried over Na$_2$SO$_4$ and concentrated.

The residue was purified by flash chromatography (Petroleum/EtOAc, 6/1) to afford the title compound. LCMS (ESI) calc'd for $C_{24}H_{17}ClFN_3O_3$ [M+H]+: 450. found: 450.

Step 2. Preparation of 4-(1-(2-chloro-6-cyclopropyl-benzoyl)-1H-pyrazolo[4,3-b]pyridin-3-yl)-3-fluorobenzoic acid (1C)

To a solution of C-1 (110 mg, 0.245 mmol) in THF (2 mL) and H$_2$O (2 mL) was added LiOH (103 mg, 2.5 mmol), and the mixture was stirred at 30° C. for 2 h. The mixture was neutralized with 2N HCl to PH=3~4. The mixture was extracted with EtOAc. The organic layer was dried over Na$_2$SO$_4$ and concentrated. The residue was purified by prep-HPLC (CH$_3$CN/H$_2$O) to afford the title compound as a white solid. LCMS (ESI): calc'd for $C_{23}H_{15}ClFN_3O_3$ [M+H]+: 436. found: 436; $^1$HNMR (400 MHz, DMSO) δ 13.51 (1H, s), 8.96-8.94 (2H, m), 8.36-8.32 (1H, t), 7.98-7.96 (1H, d), 7.88-7.82 (2H, m), 7.52-7.43 (2H, m), 7.14-7.13 (1H, d), 1.82-1.78 (1H, m), 0.87-0.83 (1H, m), 0.79-0.70 (2H, m), 0.67-0.62 (1H, m).

Example 1D: Preparation of 3 fluoro-4-[1-(pyridin-2-ylcarbonyl)-1H-indazol-3-yl]benzoic acid (1D)

SCHEME D.

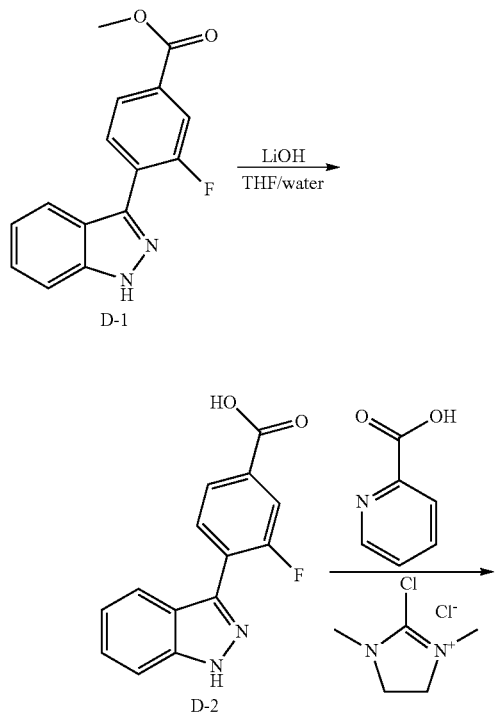

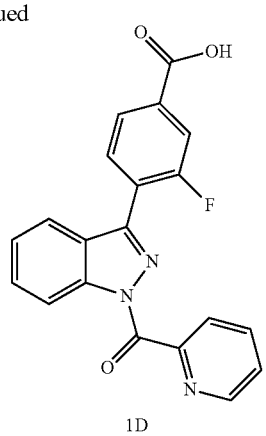

Step 1. Preparation of 3-fluoro-4-[1-(pyridin-2-yl-carbonyl)-1H-indazol-3-yl]benzoic acid (1D)

To a vial was added methyl 3-fluoro-4-(1H-indazol-3-yl) benzoate (D-1) (30 mg, 0.11 mmol), LiOH (1M, 0.33 ml), methanol (0.25 ml) and THF (0.5 ml), The reaction mixture was stirred at room temperature for 2 hours. The mixture was then evaporated under reduced pressure. The remaining residue was dissolved in DCM (0.5 ml) and was added to a mixture of picolinic acid (27 mg, 0.22 mmol), 2-chloro-1,3-dimethylimidazolinium chloride (37.5 mg, 0.22 mmol), and DCM (1 ml). The resulting mixture was stirred at room temperature for 4 h. The combined mixture was stirred overnight at room temperature and then evaporated under reduced pressure. The residue was diluted with 1.0 mL DMSO, filtered, and purified by reverse phase HPLC, eluting with a 1% ammonium hydroxide buffered water/acetonitrile gradient over a Waters X-Bridge C-18 column, to afford the desired products D-1. LCMS (ESI) calc'd for $C_{20}H_{12}FN_3O_3$ [M+H]+: 362.1. found: 362.1.

The following examples shown in TABLE 1 were prepared following similar procedures described for Examples A, B, C, D in Schemes A-D, which can be achieved by those of ordinary skill in the art of organic synthesis in light of the present disclosure.

TABLE 1

| Ex. | Chemical Name | A ring | P | Q | LCMS [M + H]+ Found |
|---|---|---|---|---|---|
| 1H | 4-(1-(2-chloro-6-cyclypropoxybenzoyl)-1H-indazol-3-yl)benzoic acid | benzene | 2-chloro-6-cyclopropoxybenzoyl | 4-carboxyphenyl | 434 |
| 1I | 3-fluoro-4-(1-(2-phenylpropanoyl)-1H-indazol-3-yl)benzoic acid | benzene | 2-phenylpropanoyl | 4-carboxy-2-fluorophenyl | 389 |
| 1J | 3-fluoro-4-[1-(methoxy-acetyl)-1H-indazol-3-yl]benzoic acid | benzene | methoxyacetyl | 4-carboxy-2-fluorophenyl | 329 |
| 1K | 3-fluoro-4-[1-(pyridin-3-ylcarbonyl)-1H-indazol-3-yl]benzoic acid | benzene | pyridin-3-ylcarbonyl | 4-carboxy-2-fluorophenyl | 362 |

TABLE 1-continued
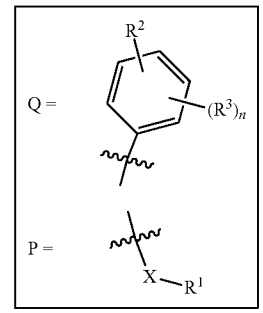
| Ex. | Chemical Name | A ring | P | Q | LCMS [M + H]+ Found |
|---|---|---|---|---|---|
| 1L | 3-fluoro-4-{1-[(2-oxo-pyrrolidin-1-yl)acetyl]-1H-indazol-3-yl}benzoic acid | | | | 382 |
| 1M | 3-fluoro-4-[1-(naphthalen-1-ylcarbonyl)-1H-indazol-3-yl]benzoic acid | | | | 411 |
| 1N | 3-fluoro-4-{1-[(1-methyl-1H-indol-2-yl)carbonyl]-1H-indazol-3-yl}benzoic acid | | | | 414 |
| 1O | 4-{1-[(2-bromo-3-methyl-phenyl)carbonyl]-1H-indazol-3-yl}-3-fluorobenzoic acid | | | | 454 |

TABLE 1-continued
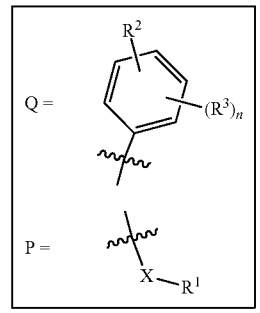
| Ex. | Chemical Name | A ring | P | Q | LCMS [M + H]+ Found |
|---|---|---|---|---|---|
| 1P | 4-[1-(2,3-dihydro-1H-inden-4-ylcarbonyl)-1H-indazol-3-yl]-3-fluorobenzoic acid | | | | 401 |
| 1Q | 4-(1-{[3-(tertbutoxycarbonyl)-3-azabicyclo[3.1.0]hex-6-yl]carbonyl}-1H-indazol-3-yl)-3-fluorobenzoic acid | | | | 465 |
| 1R | 4-[1-(2,3-dihydro-1-benzofuran-7-ylcarbonyl)-1H-indazol-3-yl]-3-fluorobenzoic acid | | | | 403 |
| 1S | 4-[1-(1-benzofuran-7-ylcarbonyl)-1H-indazol-3-yl]-3-fluorobenzoic acid | | | | 401 |

TABLE 1-continued
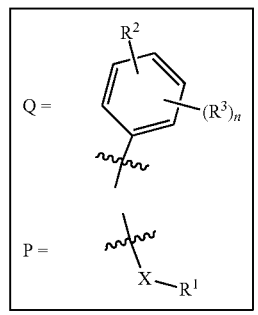
| Ex. | Chemical Name | A ring | P | Q | LCMS [M + H]+ Found |
|---|---|---|---|---|---|
| 1T | 4-{1-[(2-bromo-3-chloro-phenyl)carbonyl]-1H-indazol-3-yl}-3-fluorobenzoic acid | | | | 474 |
| 1U | 3-fluoro-4-(1-(tetrahydro-furan-2-carbonyl)-1H-indazol-3-yl)benzoic acid | | | | 355 |
| 1V | 4-(1-(2-chloro-6-vinyl-benzoyl)-1H-pyrazolo-[4,3-b]pyridin-3-yl)-3-fluorobenzoic acid | | | | 422 |
| 1W | 4-(1-(2-chloro-6-(prop-1-en-2-yl)benzoyl)-1H-pyrazolo[4,3-b]pyridin-3-yl)-3-fluorobenzoic acid | | | | 436 |

TABLE 1-continued
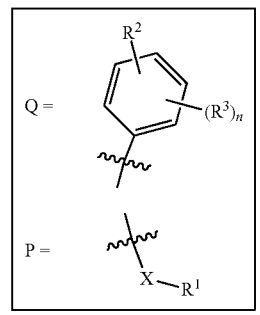
| Ex. | Chemical Name | A ring | P | Q | LCMS [M + H]+ Found |
|---|---|---|---|---|---|
| 1X | 4-(1-(6-chloro-2,3-dihydrobenzo[b]-[1,4]dioxine-5-carbonyl)-1H-pyrazolo[4,3-b]pyridin-3-yl)-3-fluorobenzoic acid | | | | 454 |
| 1Y | 4-(1-(2-(dimethylamino)-6-methylbenzoyl)-1H-pyrazolo[4,3-b]pyridin-3-yl)-3-fluorobenzoic acid | | | | 418 |
| 1Z | 4-(4-chloro-1-(2-chloro-6-cyclopropylbenzoyl)-1H-indazol-3-yl)-3-fluorobenzoic acid | | | | 469 |
| 1AA | 4-(1-(2-chloro-6-cyclopropylbenzoyl)-4-fluoro-1H-indazol-3-yl)-3-fluorobenzoic acid | | | | 453 |

TABLE 1-continued
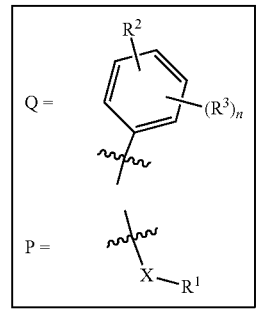
| Ex. | Chemical Name | A ring | P | Q | LCMS [M + H]+ Found |
|---|---|---|---|---|---|
| 1AB | 4-(1-(2-chloro-6-cyclobutylbenzoyl)-1H-pyrazolo[4,3-b]pyridin-3-yl)-3-fluorobenzoic acid | | | | 450 |
| 1AC | 4-(1-(2-chloro-6-cyclopropylbenzoyl)-1H-indazol-3-yl)-3-fluorobenzoic acid | | | | 435 |
| 1AD | 4-(1-(2-chloro-6-morpholinobenzoyl)-1H-pyrazolo[4,3-b]pyridin-3-yl)-3-fluorobenzoic acid | | | | 481 |

Example 2A: Preparation of 4-(1-(2-chloro-6-(trifluoromethyl)benzoyl)-6-(morpholine-4-carbonyl)-1H-indazol-3-yl)benzoic acid (2A)

SCHEME E

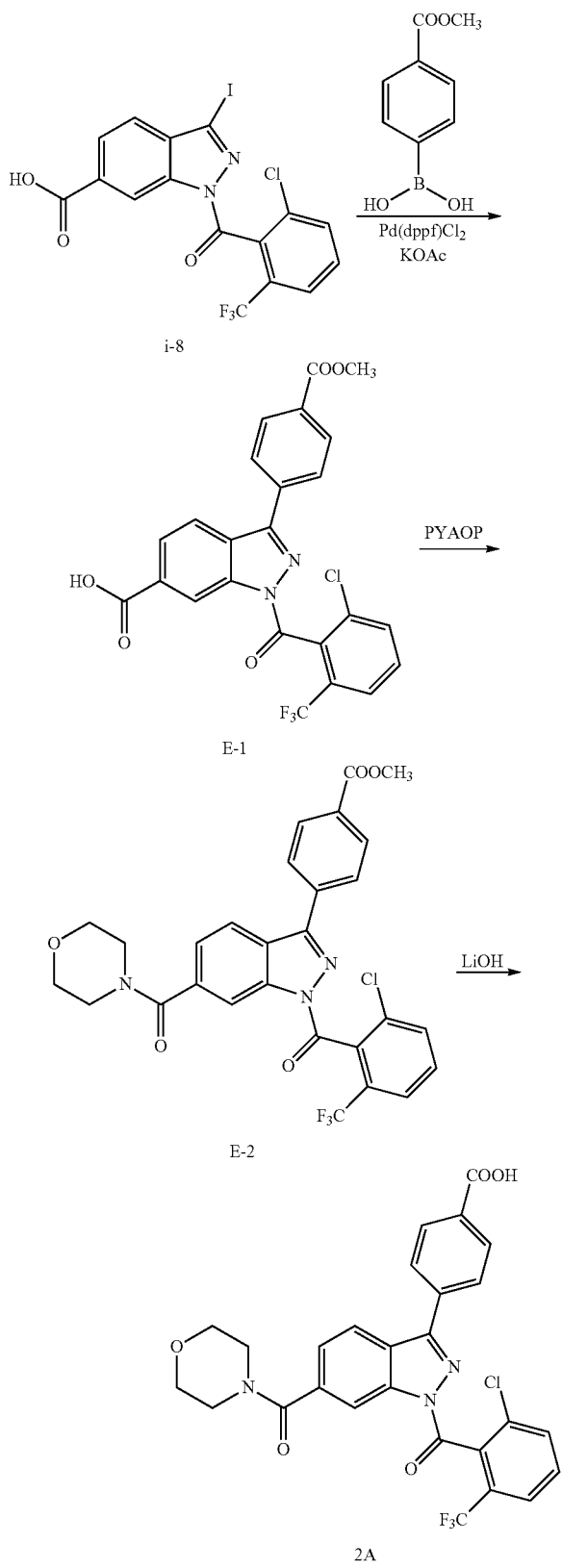

Step 1. Preparation of 1-(2-chloro-6-(trifluoromethyl)benzoyl)-3-(4-(methoxycarbonyl)phenyl)-1H-indazole-6-carboxylic acid (E-1)

A mixture of i-8 (300 mg, 0.61 mmol), 4-(methoxycarbonyl)phenylboronic acid (165 mg, 0.92 mmol), Pd(dppf)Cl$_2$ (50 mg, 0.061 mmol) and KOAc (181 mg, 1.83 mmol) in 10 ml dioxane and 2 ml pure H$_2$O was heated to 95° C. for 2 h under microwave. Then the reaction mixture was diluted with EtOAC (50 ml), washed with brine (50 ml×2), dried over anhydrous Na$_2$SO$_4$, concentrated, and purified by silica gel column (Petroleum ether/EtOAc=20/1) to obtain E-1 as a white solid (180 mg, 59%). LCMS (ESI): calc'd for C$_{24}$H$_{14}$ClF$_3$N$_2$O$_5$, [M+H]$^+$: 503.1. found: 503.1.

Step 2. Preparation of methyl 4-(1-(2-chloro-6-(trifluoromethyl)benzoyl)-6-(morpholine-4-carbonyl)-1H-indazol-3-yl)benzoate (E-2)

The compound E-1 (180 mg, 0.36 mmol) was dissolved in CH$_2$Cl$_2$ (15 mL). Morpholine (37 mg, 0.43 mmol) and PYAOP (374 mg, 0.72 mmol) were added and the mixture was stirred at room temperature for 2 mins. TEA (0.16 mL, 1.08 mmol) was added and the mixture was stirred at room temperature for 2 h. Then the mixture was diluted with EtOAC (20 ml), washed with brine (2×20 ml), dried over anhydrous Na$_2$SO$_4$, and concentrated to obtain E-2 as a white solid (195 mg, 95%). LCMS (ESI): calc'd for C$_{28}$H$_{21}$ClF$_3$N$_3$O$_5$, [M+H]$^+$: 572. found: 572.

Step 3. Preparation of 4-(1-(2-chloro-6-(trifluoromethyl)benzoyl)-6-(morpholine-4-carbonyl)-1H-indazol-3-yl)benzoic acid (2A)

A mixture of E-2 (195 mg, 0.34 mmol) and LiOH.H$_2$O (72 mg, 1.7 mmol) in 10 ml THF and 10 ml pure H$_2$O was stirred at room temperature for 2 hours. The solvent was evaporated and the residue was dissolved in water. HCl (5% sol in water) was added until pH=4-5. The precipitated solid was filtered, washed with water and n-hexane, and dried to afford an off-white solid 2A (184 mg, 97%). LCMS (ESI): calc'd for C$_{27}$H$_{19}$ClF$_3$N$_3$O$_5$, [M+H]$^+$: 558.1 found: 558.1. 1HNMR (400 MHz, DMSO) δ 8.55 (1H, s), 8.32-8.34 (1H, d, J=8 Hz), 8.05-8.11 (3H, m), 8.01-8.03 (1H, d, J=8 Hz), 7.95-7.97 (2H, d, J=8 Hz), 7.87-7.91 (1H, m), 7.69-7.71 (1H, d, J=8 Hz), 3.52-3.72 (8H, m).

The following examples shown in TABLE 2 were prepared following similar procedures described for Examples E in Schemes E, which can be achieved by those of ordinary skill in the art of organic synthesis in light of the present disclosure.

TABLE 2
| Ex. | Chemical Name | P | Q | LCMS [M + H]+ Found |
|---|---|---|---|---|
| 2B | 4-(1-(2-chloro-6-(trifluoromethyl)benzoyl)-6-((2S,6R)-2,6-dimethylmorpholine-4-carbonyl)-1H-indazol-3-yl)-3-fluorobenzoic acid | | | 604 |
| 2C | 4-(1-(2-chloro-6-(trifluoromethyl)benzoyl)-6-(4-oxopiperidine-1-carbonyl)-1H-indazol-3-yl)-3-fluorobenzoic acid | | | 588 |
Example 3A: Preparation of 2-acetamido-4-(1-(2-chloro-6-(trifluoromethyl)benzoyl)-1H-indazol-3-yl)benzoic acid (3A)
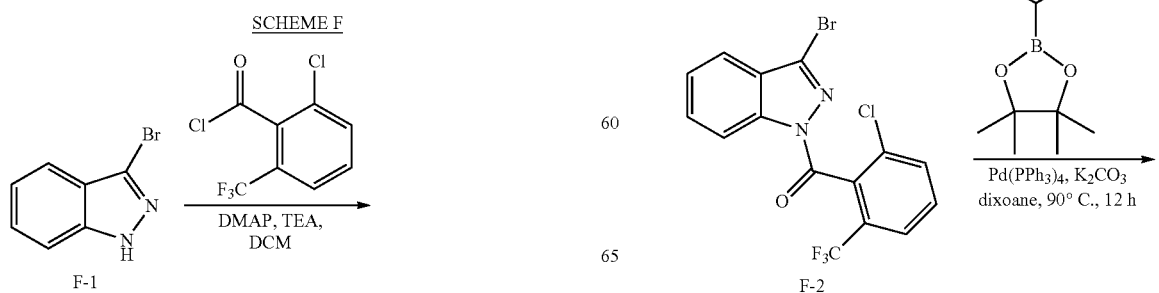

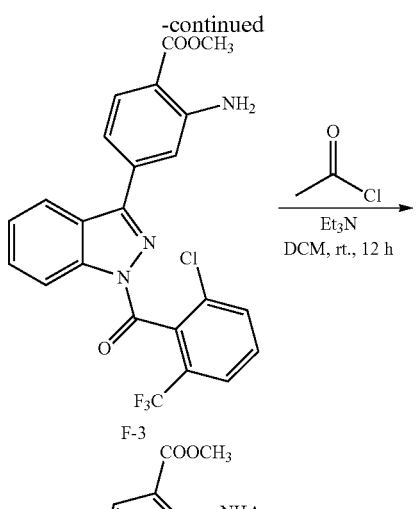

Step 1. Preparation of (3-bromo-1H-indazol-1-yl) (2-chloro-6-(trifluoromethyl)phenyl) methanone. (F-2)

To a solution of 3-bromo-1H-indazole (F-1) (200 mg, 1.02 mmol) in DCM (20 mL) was added DMAP (12.5 mg, 0.1 mmol), TEA (0.3 mL, 2 mmol), followed by the addition of 2-chloro-6-(trifluoromethyl)benzoyl chloride (370 mg, 1.53 mmol) in DCM (5 mL) slowly. The reaction mixture was stirred at room temperature for 3 h, then diluted with EA (100 mL), washed with sat. $NaHCO_3$ aqueous, water and brine, concentrated, and purified with flash chromatography (PE:EA=10:1) to give 400 mg (99%) of the title compound as a yellow solid. LCMS (ESI) calc'd for $C_{15}H_7BrClF_3N_2O$ $[M+H]^+$, 402.9. found: 403, 405.

Step 2. Preparation of methyl 2-amino-4-(1-(2-chloro-6-(trifluoromethyl)benzoyl)-1H-indazol-3-yl) benzoate (F-3)

To a mixture of F-2 (110 mg, 0.4 mmol), methyl 2-amino-4-(4,4,5,5-tetramethyl-1,3,2-dioxaborolan-2-yl)benzoate (168 mg, 0.4 mmol), $Pd(PPh_3)_4$ (46 mg, 0.04 mmol) and $K_2CO_3$ (138 mg, 1 mmol) was added dioxane (15 ml) and $H_2O$ (1 ml), and the mixture was heated at 90° C. under argon for 6 h. The mixture was cooled down, and diluted with $CH_2Cl_2$ (50 mL). The organic layer was separated, washed with brine, dried over $Na_2SO_4$, and concentrated. The residue was purified by Prep-TLC (Pentane/EtOAc 10/1) to give 155 mg (71%) of the title compound. LCMS (ESI) calc'd for $C_{23}H_{15}ClF_3N_3O_3$ $[M+H]^+$, 474. found: 474.

Step 2. Preparation of methyl 2-acetamido-4-(1-(2-chloro-6-(trifluoromethyl)benzoyl)-1H-indazol-3-yl) benzoate (F-4)

To a flask was added compound F-3 (180 mg, 0.38 mmol), acetyl chloride (36 mg, 0.46 mmol), and DCM (30 mL), followed by the addition of TEA (1.3 mL, 0.95 mmol) slowly. The reaction mixture was stirred at room temperature for 2 h. The mixture was diluted with $H_2O$, and the organic layer was separated. The aqueous layer was extracted with $CH_2Cl_2$. The combined organics were washed with $H_2O$, brine, dried over $Na_2SO_4$, and concentrated. The residue was purified by Prep-TLC (Pentane/EtOAc, 10/1) to afford 210 g (97%) of the title compound. LCMS (ESI) calc'd for $C_{25}H_{17}ClF_3N_3O_4$ $[M+H]^+$: 516. found: 516.

Step 3. Preparation of 2-acetamido-4-(1-(2-chloro-6-(trifluoromethyl)benzoyl)-1H-indazol 3-yl)benzoic acid (3A)

To a stirred solution of compound F-4 (210 mg, 0.41 mmol) was added THF (8.0 mL), $H_2O$ (2.0 mL) and $LiOH \cdot H_2O$ (172 mg, 4.1 mmol) and the solution was stirred at room temperature overnight. LCMS showed disappearance of starting material. The solution was adjusted to pH 4.0 using 1N HCl and poured into THF (30 mL), and washed with brine (20 mL). The organic layer was dried over $Na_2SO_4$, and the organic layer was evaporated and submitted for Prep-HPLC. 45 mg product was collected (23%). LCMS (ESI) calc'd for $C_{24}H_{15}ClF_3N_3O_4$ $[M+H]^+$: 502. found: 502. $^1$HNMR (500 MHz, DMSO) δ1.72 (1H, bs), 9.09 (1H, s), 8.59 (1H, d), 8.23 (1H, d), 8.06 (3H, m), 7.88 (2H, m), 7.07 (1H, s), 7.49 (1H, d), 2.15 (3H, s).

The following example shown in TABLE 3 was prepared following similar procedures described for Example 3A in Scheme F, which can be achieved by those of ordinary skill in the art of organic synthesis in light of the present disclosure.

TABLE 3

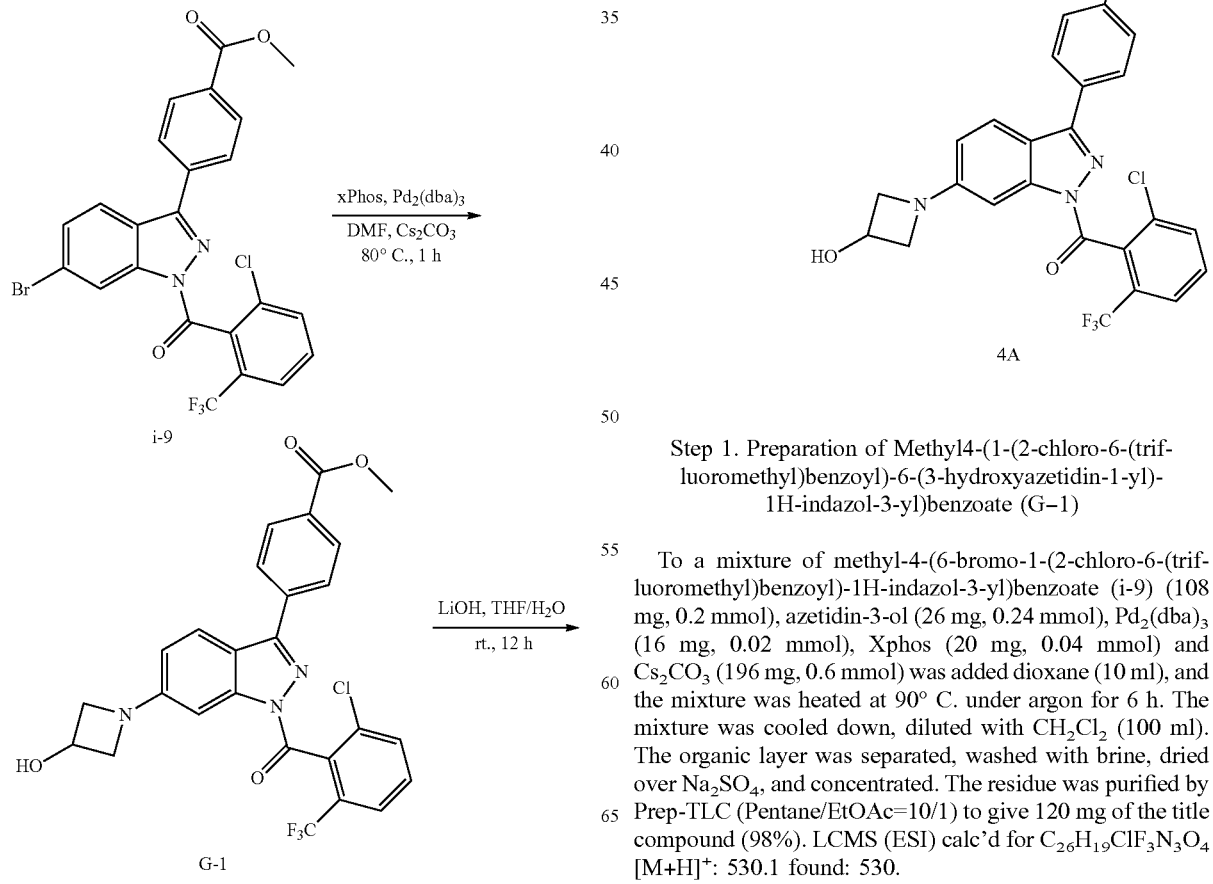

| Ex. | Chemical Name | A ring | P | Q | LCMS [M + H]+ Found |
|---|---|---|---|---|---|
| 3B | 4-(1-(2-chloro-6-(trifluoromethyl)benzoyl)-1H-pyrazolo[4,3-b]pyridin-3-yl)-2-(methylsulfonamido)benzoic acid | | | | 539 |

Example 4A: Preparation of 4-(1-(2-chloro-6-(trifluoromethyl)benzoyl)-6-(3-hydroxyazetidin-1-yl)-1H-indazol-3-yl)benzoic acid (4A)

SCHEME G

Step 1. Preparation of Methyl4-(1-(2-chloro-6-(trifluoromethyl)benzoyl)-6-(3-hydroxyazetidin-1-yl)-1H-indazol-3-yl)benzoate (G-1)

To a mixture of methyl-4-(6-bromo-1-(2-chloro-6-(trifluoromethyl)benzoyl)-1H-indazol-3-yl)benzoate (i-9) (108 mg, 0.2 mmol), azetidin-3-ol (26 mg, 0.24 mmol), Pd$_2$(dba)$_3$ (16 mg, 0.02 mmol), Xphos (20 mg, 0.04 mmol) and Cs$_2$CO$_3$ (196 mg, 0.6 mmol) was added dioxane (10 ml), and the mixture was heated at 90° C. under argon for 6 h. The mixture was cooled down, diluted with CH$_2$Cl$_2$ (100 ml). The organic layer was separated, washed with brine, dried over Na$_2$SO$_4$, and concentrated. The residue was purified by Prep-TLC (Pentane/EtOAc=10/1) to give 120 mg of the title compound (98%). LCMS (ESI) calc'd for C$_{26}$H$_{19}$ClF$_3$N$_3$O$_4$ [M+H]+: 530.1 found: 530.

Step 2. Preparation of 4-(1-(2-chloro-6-(trifluoromethyl)benzoyl)-6-(3-hydroxyazetidin-1-yl)-1H-indazol-3-yl)benzoic acid (4A)

To a stirred solution of Methyl 4-(1-(2-chloro-6-(trifluoromethyl)benzoyl)-6-(3-hydroxyazetidin-1-yl)-1H-indazol-3-yl)benzoate (G-1) (159 mg, 0.3 mmol) was added THF (8.0 ml), $H_2O$ (2.0 ml) and $LiOH.H_2O$ (126 mg, 3 mmol) and the solution was stirred at room temperature overnight. LCMS showed disappearance of starting material. The solution was adjusted to pH 4.0 using 1N HCl and poured into THF (30 ml), and washed with brine (20 mL). The organic layer was dried over $Na_2SO_4$, and the organic layer was evaporated and submitted for Prep-HPLC (ACN/$H_2O$). 55 mg product was collected (68%). LCMS (ESI) calc'd for $C_{25}H_{17}ClF_3N_3O_4$ [M+H]$^+$: 516.09. found: 516; $^1$HNMR (500 MHz, DMSO) δ13.24 (1H, s), 8.05 (3H, d), 8.03 (2H, d), 7.87 (3H, t), 7.36 (1H, s), 6.73 (1H, d), 5.72 (1H, bs), 4.67 (1H, m), 4.30 (2H, d), 3.76 (2H, d).

The following examples shown in TABLE 4 were prepared following similar procedures described for Examples 4A in Scheme G, which can be achieved by those of ordinary skill in the art of organic synthesis in light of the present disclosure.

TABLE 4

| Example | Chemical Name | R | LCMS [M + H]$^+$ Found |
|---|---|---|---|
| 4B | 4-(6-(azetidin-1-yl)-1-(2-chloro-6-(trifluoromethyl)benzoyl)-1H-indazol-3-yl)-3-fluorobenzoic acid | azetidinyl | 518 |
| 4D | 4-(1-(2-chloro-6-(trifluoromethyl)benzoyl)-6-(cyclopropylamino)-1H-indazol-3-yl)-3-fluorobenzoic acid | cyclopropylamino | 518 |
| 4F | 4-(1-(2-chloro-6-(trifluoromethyl)benzoyl)-6-(oxetan-3-ylamino)-1H-indazol-3-yl)-3-fluorobenzoic acid | oxetan-3-ylamino | 534 |
| 4G | 4-(1-(2-chloro-6-(trifluoromethyl)benzoyl)-6-(3-hydroxypyrrolidin-1-yl)-1H-indazol-3-yl)-3-fluorobenzoic acid | 3-hydroxypyrrolidinyl | 548 |
| 4H | 4-(1-(2-chloro-6-(trifluoromethyl)benzoyl)-6-morpholino-1H-indazol-3-yl)benzoic acid | morpholino | 530 |

Example 5A: Preparation of 4-(1-(2-chloro-6-(trifluoromethyl)benzoyl)-6-(methoxycarbonylamino)-1H-indazol-3-yl)-3-fluorobenzoic acid (5A)

Scheme H.

-continued

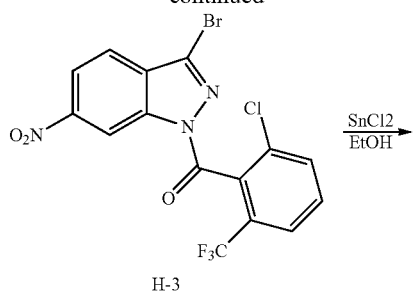
H-3

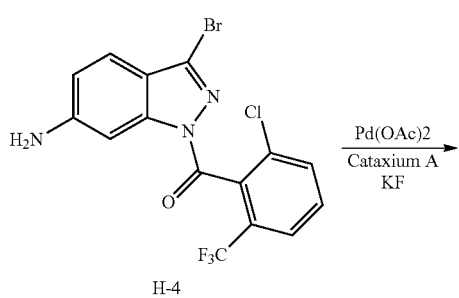
H-4

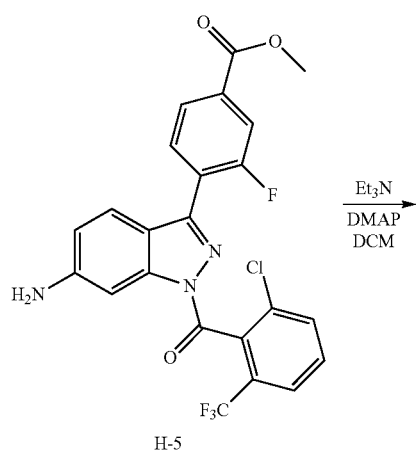
H-5

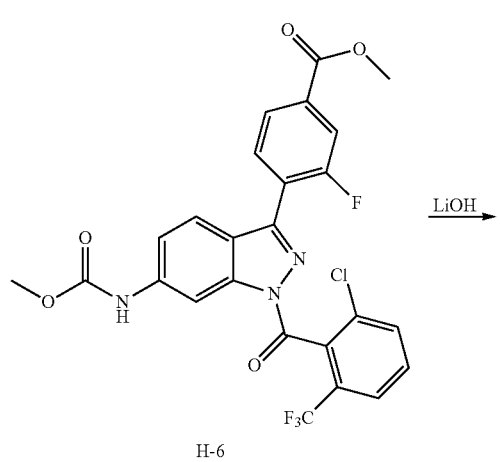
H-6

-continued

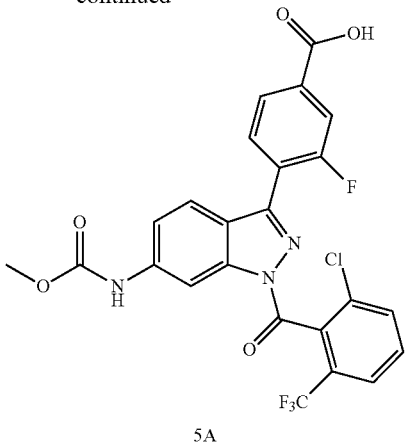
5A

Step 1. Preparation of 3-bromo-6-nitro-1H-indazole (H-2)

A mixture of 6-nitro-1H-indazole (H-1) (5 g, 30 mmol) and NaOH (2 M, 20 ml) in 20 ml THF was made, $Br_2$ (9.5 g, 60 mmol) dissolved in NaOH (2 M, 100 ml) was added, and the mixture was stirred at room temperature for 1 night. The solvent was evaporated, and the precipitated solid was filtered, washed with water (30 ml) and n-hexane (50 ml), and dried to afford an off-white solid H-2. LCMS (ESI): calc'd for $C_7H_4BrN_3O_2$ [M+H]$^+$: 242 found: 242.

Step 2. Preparation of (3-bromo-6-nitro-1H-indazol-1-yl)(2-chloro-6-(trifluoro methyl)phenyl)methanone (H-3)

To a 250 mL round-bottomed flask, was added 3-bromo-6-nitro-1H-indazole (H-2) (9.4 g, 38.7 mmol), (2-chloro-6-(trifluoromethyl)benzoyl chloride) (10.3 g, 42.6 mmol), DMAP (472 mg, 3.87 mmol) and $CH_2Cl_2$ (100 mL); after stirring at room temperature for 3 minutes, TEA (11.2 mL, 77 mmol) was added slowly. The reaction mixture was stirred at room temperature overnight. LCMS showed that no starting materials remained. Then the mixture was poured into 30 mL water, and the lower (organic) and upper (aqueous) phases were separated. The aqueous phase was extracted twice with 50 ml $CH_2Cl_2$. The combined organic phases were washed successively with two 20 ml portions of water and 10 ml of brine. The resulting organic phase was dried over anhydrous sodium sulfate, filtered and concentrated at reduced pressure to give a yellow solid. The residue was purified by column chromatography (PE/EA from 50/1 to 10/1), to give a solid H-3. LCMS (ESI): calc'd for $C_{15}H_6BrClF_3N_3O_3$ [M+H]$^+$: 448. found: 448.

Step 3. Preparation of (6-amino-3-bromo-1H-indazol-1-yl)(2-chloro-6-(trifluoro methyl)phenyl)methanone (H-4)

A mixture of (3-bromo-6-nitro-1H-indazol-1-yl)(2-chloro-6-(trifluoromethyl)phenyl)methanone (H-3) (10 g, 20 mmol) and $SnCl_2$ (21 g, 10 mmol) in 100 ml EtOH was made, and stirred at 80° C. for 4 hours. The solvent was evaporated with EtOAc (100 ml×3) and water (200 ml). The organic phase was collected and evaporation-dried to afford an off-white solid H-4. LCMS (ESI): calc'd for $C_{15}H_8BrClF_3N_3O$, [M+H]$^+$: 418 found: 418.

Step 4. Preparation of methyl 4-(6-amino-1-(2-chloro-6-(trifluoromethyl)ben-zoyl)-1H-indazol-3-yl)-3-fluorobenzoate (H-5)

A 30 ml microwave vial was charged with (6-amino-3-bromo-1H-indazol-1-yl)(2-chloro-6-(trifluoromethyl)phenyl)methanone (H-4) (2 g, 4.8 mmol), 2-fluoro-4-(methoxycarbonyl)phenylboronic acid (1 g, 5.2 mmol), Pd(OAc)$_2$ (54 mg, 0.24 mmol), Catacxium A (86 mg, 0.24 mmol) and KF (835 mg, 14.4 mmol) dissolved in anhydrous THF (5 ml). A stir bar was added, the vial was sealed, and the reaction was heated for 2 hours at a constant temperature of 80° C. The mixture was filtered and the filtrate was collected, then purified by column chromatography (DCM) to obtain the desired product H-5. LCMS (ESI): calc'd for $C_{23}H_{14}ClF_4N_3O_3$ [M+H]$^+$: 492 found: 492.

Step 5. Preparation of methyl 4-(1-(2-chloro-6-(trifluoromethyl)benzoyl)-6-(methoxycarbonylamino)-1H-indazol-3-yl)-3-fluorobenzoate (H-6)

Methyl 4-(6-amino-1-(2-chloro-6-(trifluoromethyl)benzoyl)-1H-indazol-3-yl)-3-fluorobenzoate (H-5)(186 mg, 0.38 mmol), methyl carbonochloridate (40 mg, 0.43 mmol), DMAP (5 mg, 0.04 mmol) and CH$_2$Cl$_2$ (100 mL) were combined, and after stirring at room temperature for 3 minutes, TEA (0.1 mL, 0.77 mmol) was added slowly. The reaction mixture was stirred at room temperature overnight. The reaction mixture was concentrated at reduced pressure to give a yellow solid H-6. LCMS (ESI): calc'd for $C_{25}H_{16}ClF_4N_3O_5$ [M+H]$^+$: 550. found: 550.

Step 6. Preparation of 4-(1-(2-chloro-6-(trifluoromethyl)benzoyl)-6-(methoxycarbonylamino)-1H-indazol-3-yl)-3-fluorobenzoic acid (5A)

A mixture of methyl 4-(1-(2-chloro-6-(trifluoromethyl)benzoyl)-6-(methoxycarbonylamino)-1H-indazol-3-yl)-3-fluoro benzoate (H-6) (38 mg, 0.07 mmol) and LiOH.H$_2$O (16 mg, 0.37 mmol) in 10 ml THF and 10 ml pure H$_2$O was stirred at room temperature for 2 hours. The solvent was evaporated and the residue was dissolved in water. HCl (5% sol in water) was added until pH=4-5. The precipitated solid was filtered, washed with water (10 ml) and n-hexane (10 ml), and dried to afford an off-white solid 5A. LCMS (ESI): calc'd for $C_{24}H_{14}ClF_4N_3O_5$ [M+H]$^+$: 536 found: 536; 1HNMR (400 MHz, DMSO) δ 13.54 (1H, s), 10.32 (1H, s), 8.93 (1H, s), 7.97-8.03 (2H, m), 7.83-7.91 (4H, m), 7.70-7.75 (1H, m), 7.61-7.63 (1H, d, J=8 Hz), 3.76 (3H, s).

Example 5B: Preparation of 4-(1-(2-chloro-6-(trifluoromethyl)benzoyl)-6-(N-methylacetamido)-1H-indazol-3-yl)-3-fluorobenzoic acid (5B)

Scheme I

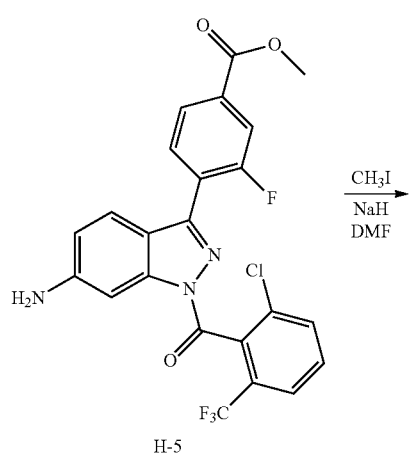

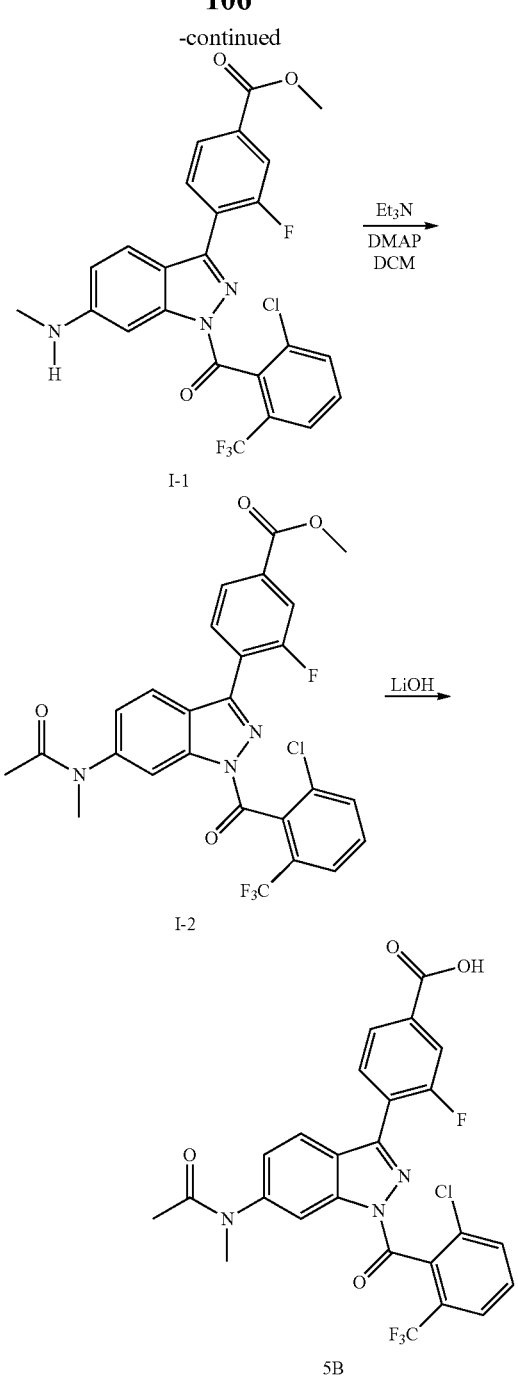

Step 1. Preparation of methyl 4-(1-(2-chloro-6-(trifluoromethyl)benzoyl)-6-(methylamino)-1H-indazol-3-yl)-3-fluorobenzoate (I-1)

A mixture was made of Methyl 4-(6-amino-1-(2-chloro-6-(trifluoromethyl)benzoyl)-1H-indazol-3-yl)-3-fluorobenzoate (H-5) (344 mg, 0.7 mmol) in 10 ml DMF under ice bath, CH$_3$I (0.07 ml, 0.14 mmol) was added, and then the icebath was removed and stirring occurred at room temperature for 5 hours. The solvent was extracted with EtOAc (30 ml) and water (3×20 ml), the organic phase was collected, and the residue purified by column chromatography on silica gel eluting with (PE/DCM=2:1) to obtain the desired product I-1. LCMS (ESI) calc'd for $C_{24}H_{16}ClF_4N_3O_3$ $[M+H]^+$: 506. found: 506.

Step 2. Preparation of 4-(1-(2-chloro-6-(trifluoromethyl)benzoyl)-6-(N-methylacetamido)-1H-indazol-3-yl)-3-fluorobenzoate (I-2)

Methyl 4-(1-(2-chloro-6-(tri-fluoromethyl)benzoyl)-6-(methylamino)-1H-indazol-3-yl)-3-fluorobenzoate (I-1) (19 2 mg, 0.38 mmol), acetyl chloride (33 mg, 0.43 mmol), DMAP (5 mg, 0.04 mmol) and $CH_2Cl_2$ (100 mL) were combined, and after stirring at room temperature for 3 minutes, TEA (0.1 ml, 0.77 mmol) was added slowly. The reaction mixture was stirred at room temperature overnight. The reaction mixture was concentrated at reduced pressure to give a yellow solid I-3. LCMS (ESI): calc'd for $C_{26}H_{18}ClF_4N_3O_4$ $[M+H]^+$: 548. found: 548.

Step 3. Preparation of 4-(1-(2-chloro-6-(trifluoromethyl)benzoyl)-6-(N-methylacetamido)-1H-indazol-3-yl)-3-fluorobenzoic acid (5B)

A mixture of 4-(1-(2-chloro-6-(trifluoromethyl)benzoyl)-6-(N-methylacetamido)-1H-indazol-3-yl)-3-fluorobenzoate (I-2) (38 mg, 0.07 mmol) and $LiOH \cdot H_2O$ (16 mg, 0.37 mmol) in 10 ml THF and 10 ml pure $H_2O$ was stirred at room temperature for 2 hours. The solvent was evaporated and the residue was dissolved in water. HCl (5% in water) was added until pH=4-5. The precipitated solid was filtered, washed with water (10 ml) and n-hexane (10 ml), and dried to afford an off-white solid 5B. LCMS (ESI): calc'd for $C_{25}H_{16}ClF_4N_3O_4[M+H]^+$: 534. found: 534; 1HNMR (400 MHz, DMSO) δ 8.46 (1H, s), 7.98-8.05 (3H, m), 7.87-7.93 (3H, s), 7.76 (1H, s), 7.61-7.63 (1H, d, J=8 Hz), 3.36 (3H, s), 2.01 (3H, s).

The following examples shown in TABLE 5 were prepared following similar procedures described for Examples #5A, 5B in Schemes H, I, which can be achieved by those of ordinary skill in the art of organic synthesis in light of the present disclosure.

TABLE 5

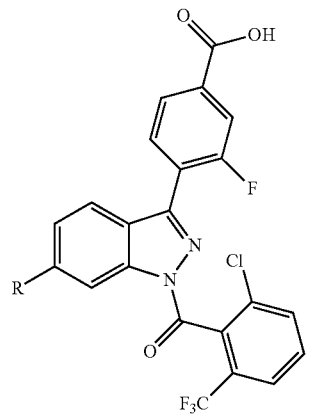

| Example | Chemical Name | R | LCMS [M + H]+ Found |
|---|---|---|---|
| 5C | 4-(1-(2-chloro-6-(trifluoromethyl)benzoyl)-6-(cyclopropanecarboxamido)-1H-indazol-3-yl)-3-fluorobenzoic acid | cyclopropyl-C(=O)-NH- | 546 |
| 5D | 4-(1-(2-chloro-6-(trifluoromethyl)benzoyl)-6-(methylsulfonamido)-1H-indazol-3-yl)-3-fluorobenzoic acid | CH3-S(=O)2-NH- | 556 |
| 5E | 4-(1-(2-chloro-6-(trifluoromethyl)benzoyl)-6-(3-methylureido)-1H-indazol-3-yl)-3-fluorobenzoic acid | CH3-NH-C(=O)-NH- | 535 |
| 5F | 4-(6-acetamido-1-(2-chloro-6-(trifluoromethyl)benzoyl)-1H-indazol-3-yl)-3-fluorobenzoic acid | CH3-C(=O)-NH- | 520 |
| 5G | 4-(1-(2-chloro-6-(trifluoromethyl)benzoyl)-6-(N-methylmethylsulfonamido)-1H-indazol-3-yl)-3-fluorobenzoic acid | CH3-S(=O)2-N(CH3)- | 570 |
| 5H | 4-(1-(2-chloro-6-(trifluoromethyl)benzoyl)-6-(1,3-dimethylureido)-1H-indazol-3-yl)-3-fluorobenzoic acid | CH3-NH-C(=O)-N(CH3)- | 549 |

Example 6A: Preparation of 4-(1-(2-chloro-6-(trifluoromethyl)benzoyl)-6-(2-oxo-imidazolidin-1-yl)-1H-indazol-3-yl)-3-fluorobenzoic acid (6A)

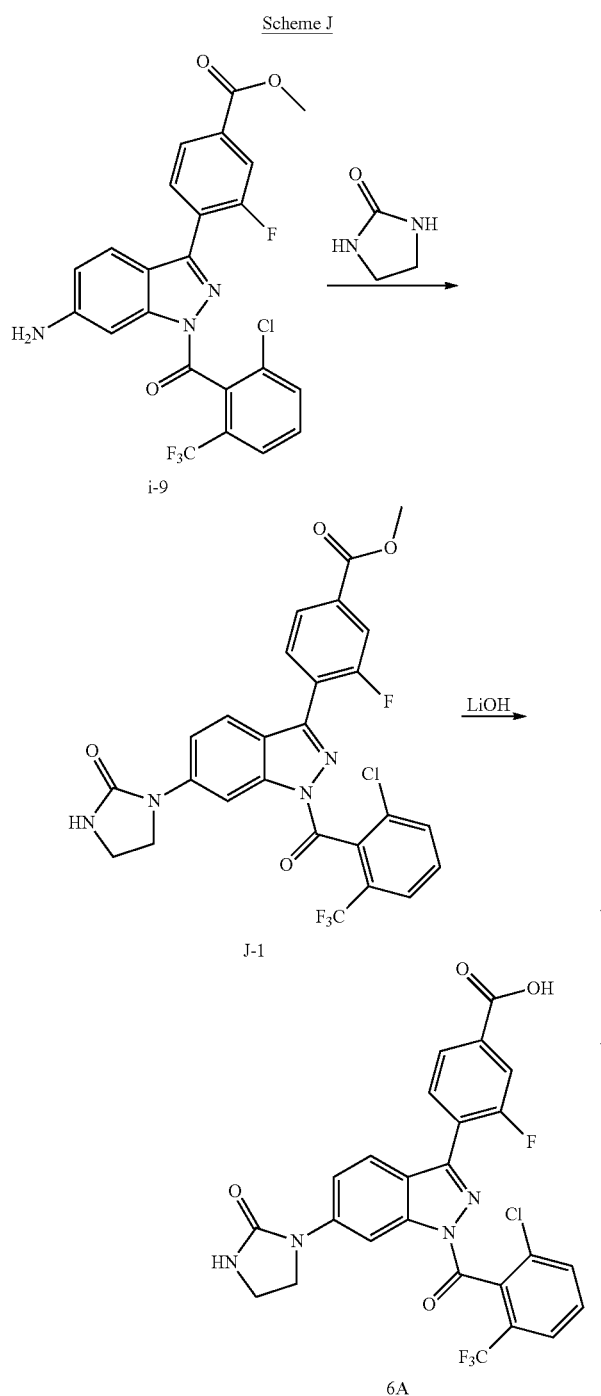

Step 1. Preparation of methyl-4-(1-(2-chloro-6-(trifluoromethyl)benzoyl)-6-(2-oxoimidazolidin-1-yl)-1H-indazol-3-yl)-3-fluorobenzoate (J-1)

To a microwave tube was added methyl-4-(6-bromo-1-(2-chloro-6-(trifluoromethyl)benzoyl)-1H-ind-azol-3-yl)-3-fluorobenzoate (i-9) (70 mg, 0.14 mmol), dioxane (1.5 ml), imidazolidin-2-one (17 mg, 0.21 mmol), Pd$_2$(dba)$_3$ (6.3 mg, 0.007 mmol), xant-phos (11.7 mg, 0.021 mmol), Cs$_2$CO$_3$ (86 mg, 0.28 mmol). The solution was microwaved at 100° C. for 2 hours and the organic layer was evaporated for use in the next step without purification. LCMS (ESI) calc'd for C$_{26}$H$_{17}$ClF$_4$N$_4$O$_4$ [M+H]$^+$: 561. found: 561.

Step 2. Preparation of 4-(1-(2-chloro-6-(trifluoromethyl)benzoyl)-6-(2-oxoimidazolidin-1-yl)-1H-indazol-3-yl)-3-fluorobenzoic acid (6A)

To a stirred solution of methyl 4-(1-(2-chloro-6-(trifluoromethyl)benzoyl)-6-(2-oxoimidazolidin-1-yl)-1H-indazol-3-yl)-3-fluorobenzoate (J-1) in dioxane (1.5 ml) from the previous step was added LiOH.H$_2$O (59 mg, 1.4 mmol) and H$_2$O (0.5 ml). The solution was stirred overnight and LCMS showed major product peak. The solution was adjusted to pH=3 using 1 N HCl. The upper organic layer was collected and the aqueous layer was extracted with THF (2×1 mL). To the combined organic layer was added 0.5 mL MeOH, and submitting for Prep-HPLC (H$_2$O/ACN) gave 10 mg of product, the yield for two steps being 26%. LCMS (ESI) calc'd for C25H15ClF4N4O4 [M+H]$^+$: 547. found: 547; $^1$HNMR (400 MHz, DMSO) δ 13.44 (1H, s), 8.75 (1H, s), 8.01 (2H, m), 7.98-7.89 (5H, m), 7.71 (1H, d), 4.08-4.05 (2H, d), 3.52-3.33 (2H, d).

Example 6B: Preparation of 4-(1-(2-chloro-6-(trifluoromethyl)benzoyl)-6-(2-oxoazetidin-1-yl)-1H-indazol-3-yl)-3-fluorobenzoic acid (6B)

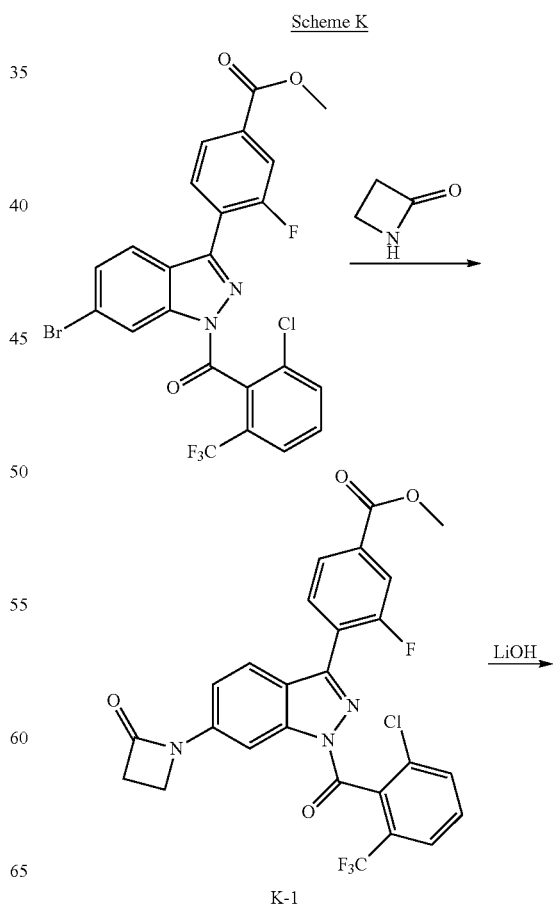

111
-continued

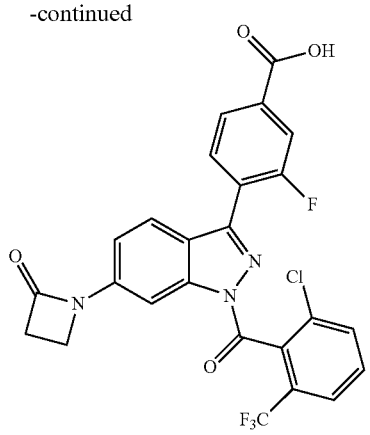

6B

Step 1. Preparation of methyl 4-(1-(2-chloro-6-(trifluoromethyl)benzoyl)-6-(2-oxoazetidin-1-yl)-1H-indazol-3-yl)-3-fluorobenzoate (K-1)

The mixture of methyl 4-(6-bromo-1-(2-chloro-6-(trifluoromethyl)benzoyl)-1H-indazol-3-yl)-3-fluorobenzoate (554 mg, 1.0 mmol), Pd(dppf)$_2$Cl$_2$ (79 mg, 0.1 mmol), azetidin-2-one (114 mg, 2.0 mmol), TEA (20 ml) and DMF (20 ml) was purged with N$_2$ and stirred at 90° C. overnight. LCMS showed the starting material was completely consumed, and the expected product appeared. The resulting solution was filtered, concentrated, and purified by column chromatography (PE/EA) to give 248 mg product as a white solid (45%). LCMS (ESI) calc'd for C$_{26}$H$_{16}$ClF$_4$N$_3$O$_4$ [M+H]$^+$: 545.87. found: 546.2.

Step 2. Preparation of 4-(1-(2-chloro-6-(trifluoromethyl)benzoyl)-6-(2-oxoazeti-din-1-yl)-1H-indazol-3-yl)-3-fluorobenzoic acid (6B)

To the solution of methyl 4-(1-(2-chloro-6-(trifluoromethyl)benzoyl)-6-(2-oxoazetidin-1-yl)-1H-indazol-3-yl)-3-fluorobenzoate (K-1) (53.1 mg, 0.1 mmol) in THF (30 ml) and water (10 ml) was added LiOH (240 mg, 10 mmol). The mixture solution was stirred at 0° C. for 2 h. 100 ml HCl aqueous was added, followed by extracting with EA (30 ml×3), and the organic layer was concentrated and purified by chromatography column (EA:PE=1:1) to afford 27 mg product (51%). LCMS (ESI) calc'd for C$_{25}$H$_{14}$ClF$_4$N$_3$O$_4$ [M+H]$^+$: 531.84. found: 532.1; $^1$HNMR (400 MHz, CDCl$_3$) δ:13.5 (1H, w), 8.46 (1H, s), 7.98 (6H, m), 7.72 (1H, t), 7.61 (1H, d), 3.85 (2H, m), 3.21 (2H, m).

Example 6C: Preparation of 4-(6-(2-carboxyethylamino)-1-(2-chloro-6-(trifluoromethyl)benzoyl)-1H-indazol-3-yl)-3-fluorobenzoic acid (6C)

Scheme L

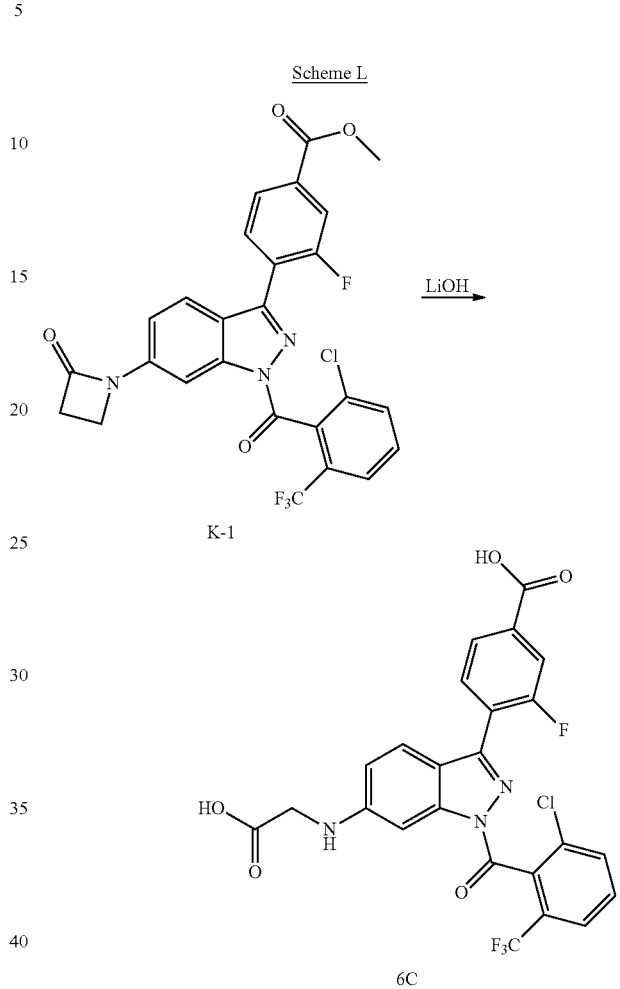

Step 1. Preparation of 4-(6-(2-carboxyethylamino)-1-(2-chloro-6-(trifluoromethyl)benzoyl)-1H-indazol-3-yl)-3-fluorobenzoic acid (6C)

To the solution of methyl 4-(1-(2-chloro-6-(trifluoromethyl)benzoyl)-6-(2-oxoazetidin-1-yl)-1H-indazol-3-yl)-3-fluorobenzoate (K-1) (53.1 mg, 0.1 mmol) in THF (30 ml) and water (10 ml) was added LiOH (240 mg, 10 mmol). The mixture solution was stirred at room temperature for 12 h. 100 ml HCl aqueous was added, followed by extracting with EA (30 ml×3), and then the organic layer was concentrated and purified by chromatography column (EA:PE=1:1) to afford 39 mg product (yield: 72%). LCMS (ESI) calc'd for C$_{24}$H$_{14}$ClF$_4$N$_3$O$_5$ [M+H]$^+$: 549.86. found: 550.1. $^1$HNMR (400 MHz, CDCl$_3$) δ:13.1 (2H, w), 7.9 (5H, m), 7.66 (1H, t), 7.541 (2H, m), 6.91 (1H, m), 3.41 (2H, m), 2.62 (2H, m).

The following examples shown in TABLE 6 were prepared following similar procedures described for Examples #6A, 6B, 6C in Schemes J, K, L, which can be achieved by those of ordinary skill in the art of organic synthesis in light of the present disclosure.

TABLE 6
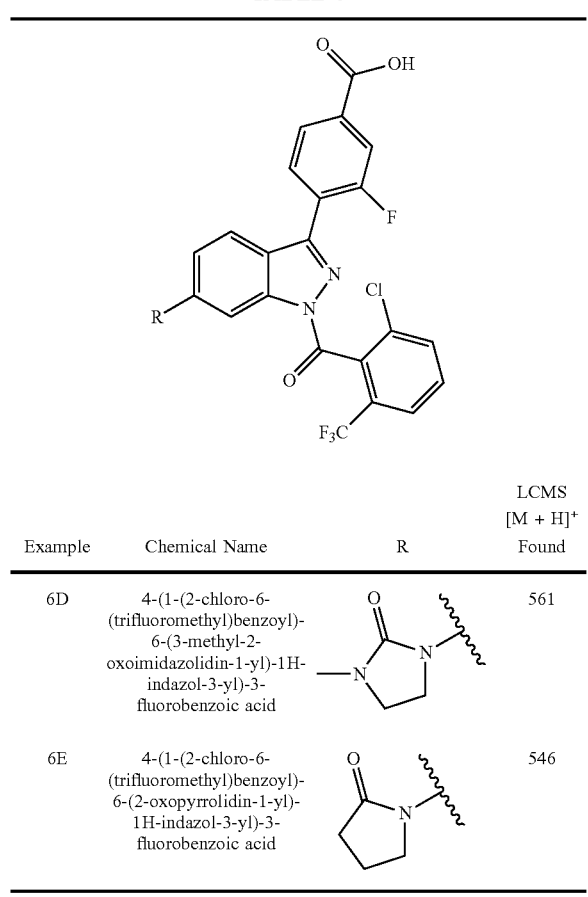
| Example | Chemical Name | R | LCMS [M + H]+ Found |
|---|---|---|---|
| 6D | 4-(1-(2-chloro-6-(trifluoromethyl)benzoyl)-6-(3-methyl-2-oxoimidazolidin-1-yl)-1H-indazol-3-yl)-3-fluorobenzoic acid | | 561 |
| 6E | 4-(1-(2-chloro-6-(trifluoromethyl)benzoyl)-6-(2-oxopyrrolidin-1-yl)-1H-indazol-3-yl)-3-fluorobenzoic acid | | 546 |
Example 7A: Preparation of 4-(1-(2-chloro-6-(trifluoromethyl)benzoyl)-6-(morpholine-4-carbonyl)-1H-indazol-3-yl)benzoic acid (7A)
Scheme M
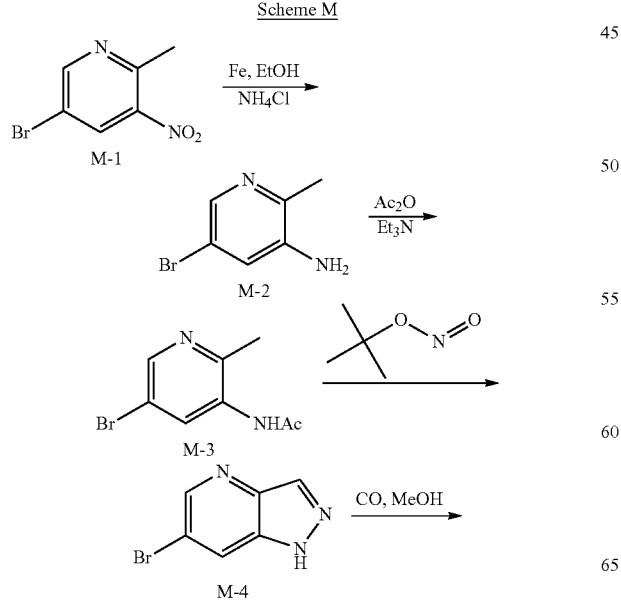
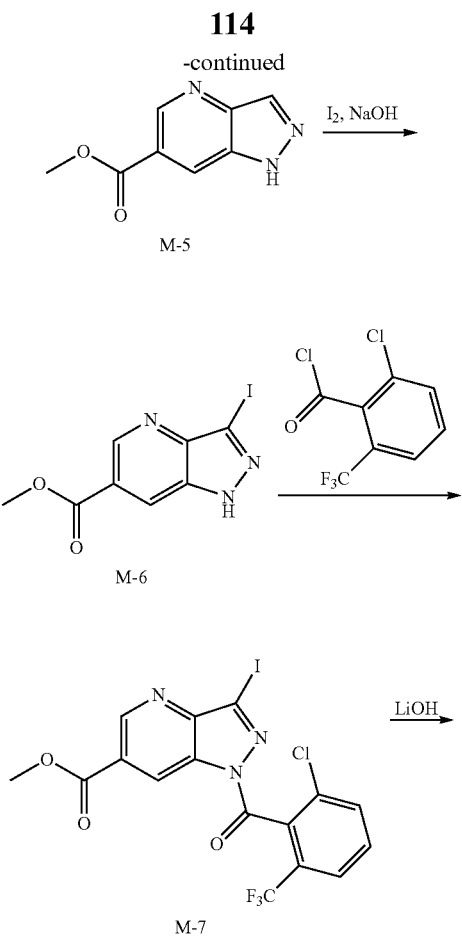
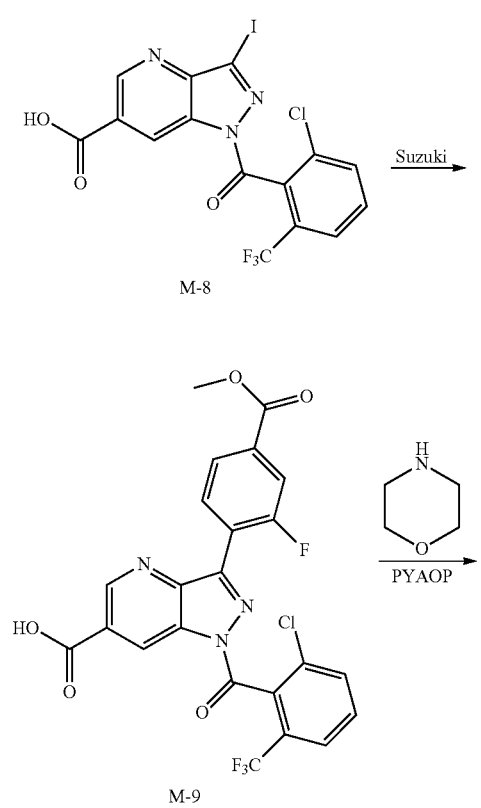

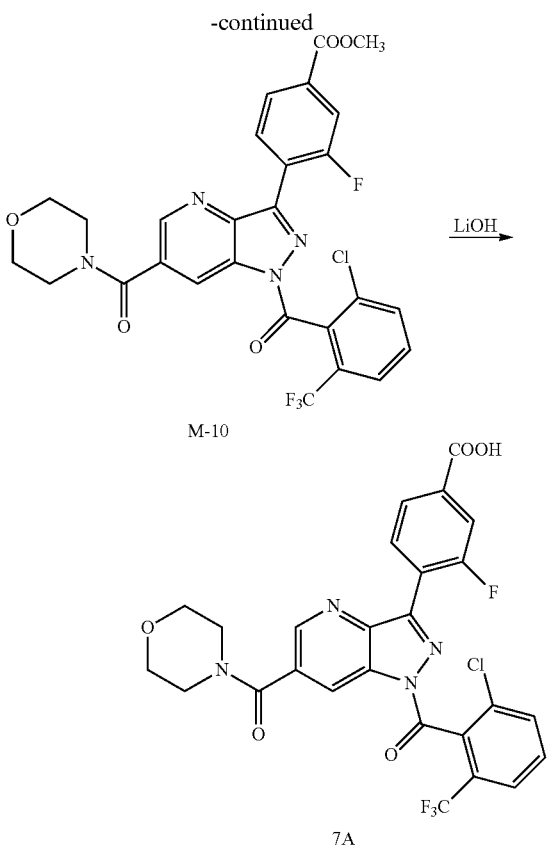

Step 1. Preparation of 5-bromo-2-methylpyridin-3-amine (M-2)

To a solution of 5-bromo-2-methyl-3-nitropyridine (1) (15 g, 69.4 mmol) in EtOH (300 mL) and water (70 ml), was added iron powder (46.7 g, 833 mmol) and ammonium chloride (4.5 g, 83.4 mmol) successively at room temperature. The reaction mixture was heated to 90° C. for 40 min. The reaction was filtered hot and rinsed with EtOAc. The filtrate was washed with a saturated aqueous solution of sodium bicarbonate (200 mL), washed with brine, dried over magnesium sulfate and solvent removed in vacuo to give the title compound as an orange solid, (11.7 g, 62.9 mmol, 90%). LCMS (ESI) calc'd for $C_6H_7BrN_2$ [M+H]$^+$: 187. found: 187, 188.

Step 2. Preparation of N-(5-bromo-2-methylpyridin-3-yl)acetamide (M-3)

To a solution of 5-bromo-2-methylpyridin-3-amine (M-2) (10.7 g, 57.5 mmol) in dichloromethane (575 mL) was added acetic anhydride (12 mL, 126.5 mmol) at 0° C., followed by triethylamine (22 mL, 158 mmol). The mixture was allowed to warm to ambient temperature and stirred for 18 hours at which point a further equivalent of acetic anhydride (6 mL, 63 mmol) was added. The mixture was stirred at ambient temperature for a further 18 hours. The reaction mixture was quenched with a saturated aqueous solution of sodium bicarbonate (500 mL) and the organic phase washed with saturated aqueous sodium chloride (500 mL), dried over magnesium sulfate and concentrated in vacuo to give a brown solid. This solid was triturated with 30% ethyl acetate in hexanes to yield the title compound as an off-white solid, (8.28 g, 36 mmol, 63%). $^1$HNMR (400 MHz, CD$_3$OD): δ ppm 8.31 (s, 1H), 8.18 (s, 1H), 2.43 (s, 3H), 2.18 (s, 3H). LCMS (ESI) calc'd for $C_8H_9BrN_2O$ [M+H]$^+$: 228.99. found: 229, 230.

Step 3. Preparation of 6-bromo-1H-pyrazolo[4,3-b]pyridine (M-4)

To a solution of N-(5-bromo-2-methylpyridin-3-yl)acetamide (M-3) (8.3 g, 36 mmol) in chloroform (550 mL) at ambient temperature was added potassium acetate (4.3 g, 43.6 mmol), acetic acid (2.5 mL, 43.6 mmol) and followed by acetic anhydride (6.9 mL, 72.6 mmol). The mixture was stirred at ambient temperature for 15 minutes before being heated to 40° C. Tert-butyl nitrite (6.5 mL, 54 mmol) was then added dropwise. The reaction was then stirred at 60° C. for 48 hours. The reaction mixture was poured slowly into a saturated solution of sodium bicarbonate (500 mL) at 0° C. The organic phase was retained and the aqueous phase extracted with dichloromethane (500 mL). The combined organics were then concentrated to a brown oil which was dissolved in methanol (500 mL). Aqueous sodium hydroxide (2 M, 500 mL) was added at 0° C. and the mixture stirred at ambient temperature for 1 hour before the methanol was removed in vacuo. The aqueous mixture was then extracted with ethyl acetate (3×500 mL). The combined organics were dried over magnesium sulfate, and the solvent removed in vacuo to give the title compound as a light brown solid (5.5 g, 27.9 mmol, 77%). $^1$HNMR (400, CD$_3$OD): δ ppm 8.55 (s, 1H), 8.24 (s, 1H), 8.21 (s, 1H). LCMS (ESI) calc'd for $C_6H_4BrN_3$ [M+H]$^+$: 197.96. found: 198, 199.

Step 4. Preparation of methyl 1H-pyrazolo[4,3-b]pyridine-6-carboxylate (M-5)

To a solution of 6-bromo-1H-pyrazolo[4,3-b]pyridine (M-4) (0.5 g, 2.5 mmol) in methanol (15 ml) and acetonitrile (7 ml) was added Et$_3$N (2.2 ml, 5.6 mmol), Binap (0.17 g, 0.63 mmol) and palladium dichloride (0.17 g, 0.27 mmol). The mixture was placed under 20 bar of carbon monoxide, and stirred at 100° C. for 18 h. The mixture was cooled, filtered and purified by Prep-TLC to give 310 mg of a white solid. (69%). LCMS (ESI) calc'd for [M+H]$^+$: 178.1. found: 178.1.

Step 5. Preparation of methyl 3-iodo-1H-pyrazolo[4,3-b]pyridine-6-carboxyl-ate (M-6)

To a solution of methyl 1H-pyrazolo[4,3-b]pyridine-6-carboxylate (M-5) (316 mg, 1.8 mmol) in DMAC (30 ml) was added KOH (40 mg, 7.18 mmol). The vigorously stirred mixture was treated with iodine (550 mg, 2.15 mmol) and added portionwise over 5 minutes then stirred for 60 minutes. The reaction was quenched with 20 ml of 20% citric acid solution, followed by 16 ml of saturated NaHSO$_3$ solution, then adjusted to pH=8 with solid NaHCO$_3$ and partitioned between ethyl acetate and water. The organic extract was dried and concentrated to a dark-red oil containing DMAC for use in the next step directly. LCMS (ESI) calc'd for [M+H]$^+$: 304.1. found: 304.1.

Step 6. Preparation of methyl 1-(2-chloro-6-(trifluoromethyl)benzoyl)-3-iodo-1H-pyrazolo[4,3-b]pyridine-6-carboxylate (M-7)

To the solution of methyl 3-iodo-1H-pyrazolo[4,3-b]pyridine-6-carboxylate (M-6) (400 mg, 1.32 mmol), Et$_3$N (290 mg) and DMAP (32 mg, 0.26 mmol) dissolved in anhydrous DCM (10 ml) was added 2-chloro-6-(trifluoromethyl)benzoyl chloride (630 mg, 2.64 mmol) in anhydrous DCM (10 ml) dropwise. The mixture solution was protected by $N_2$ and stirred at room temperature for 20 h. Then the solution was concentrated to afford 500 mg product (78%). LCMS (ESI) calc'd [M+H]$^+$: 510.1. found: 510.1.

Step 7. Preparation of 1-(2-chloro-6-(trifluoromethyl)benzoyl)-3-iodo-1H-pyrazolo[4,3-b]pyridine-6-carboxylic acid (M-8)

To the solution of methyl 1-(2-chloro-6-(trifluoromethyl)benzoyl)-3-iodo-1H-pyrazolo[4,3-b]pyridine-6-carboxylate (M-7) (700 mg, 1.37 mmol) in THF (15 mL) and $H_2O$ (5 mL) was added LiOH (242 mg, 10.9 mmol). The mixture solution was stirred at room temperature for 24 h. Water (10 ml) was added, then the solution was acidified by HCl (2 M) and extracted with EtOAc (20 ml×3). The combined organic layer was dried, filtered, concentrated, and purified by Prep-HPLC to afford 670 mg (99%). LCMS (ESI) calc'd [M+H]$^+$: 496.1. found: 496.1.

Step 8. Preparation of 1-(2-chloro-6-(trifluoromethyl)benzoyl)-3-(2-fluoro-4-(methoxycarbonyl)phenyl)-1H-pyrazolo[4,3-b]pyridine-6-carboxylic acid (M-9)

The mixture of 1-(2-chloro-6-(trifluoromethyl)benzoyl)-3-iodo-1H-pyrazolo[4,3-b]pyridine-6-carboxylic acid (M-8) (100 mg, 0.20 mmol), 2-fluoro-4-(methoxycarbonyl phenyl-boronic acid (100 mg, 0.5 mmol), Pd(dppf)Cl$_2$ (44 mg, 0.06 mmol), Na$_2$CO$_3$ (50 mg, 0.6 mmol) in dioxane (4 ml) and H$_2$O (0.5 mL) was stirred at 100° C. under microwave for 1 h. Then the reaction mixture was filtered, concentrated, and purified by Prep-HPLC to afford 60 mg product (58%). LCMS (ESI) calc'd [M+H]$^+$: 522.0. found: 522.0.

Step 9. Preparation of methyl 4-(1-(2-chloro-6-(trifluoromethyl)benzoyl)-6-(morpholine-4-carbonyl)-1H-indazol-3-yl)benzoate (M-10)

1-(2-Chloro-6-(trifluoromethyl)benzoyl)-3-(2-fluoro-4-(methoxycarbonyl)phenyl)-1H-pyrazolo[4,3-b]pyridine-6-carboxylic acid (M-9) (180 mg, 0.36 mmol) was dissolved in CH$_2$Cl$_2$ (15 mL). Morpholine (37 mg, 0.43 mmol) and PYAOP (374 mg, 0.72 mmol) were added and the mixture was stirred at room temperature for 2 min. TEA (0.16 mL, 1.08 mmol) was added and the mixture was stirred at room temperature for 2 h. Then the reaction mixture was diluted with EtOAc (20 ml), washed with brine (20 ml×2), dried with anhydrous Na$_2$SO$_4$, and concentrated to obtain a white solid 195 mg (95%). LCMS (ESI): calc'd for C$_{28}$H$_{21}$ClF$_3$N$_3$O$_5$, [M+H]$^+$: 572. found: 572.

Step 10. Preparation of 4-(1-(2-chloro-6-(trifluoromethyl)benzoyl)-6-(morphol-ine-4-carbonyl)-1H-indazol-3-yl)benzoic acid (7A)

A mixture of methyl 4-(1-(2-ch-loro-6-(trifluoromethyl)benzoyl)-6-(morpholine-4-carbonyl)-1H-indazol-3-yl)benzoate (M-10) (195 mg, 0.34 mmol) and LiOH (72 mg, 1.7 mmol) in 10 ml THF and 10 ml H$_2$O was stirred at room temperature for 2 hours. The solvent was evaporated and the residue was dissolved in water. HCl (5% sol. in water) was added until pH was 4-5. The precipitated solid was filtered, washed with water and n-hexane, and dried to afford an off-white solid 184 mg (97%). LCMS (ESI): calc'd for C$_{27}$H$_{19}$ClF$_3$N$_3$O$_5$, [M+H]$^+$: 558.1 found: 558.1. 1HNMR (400 MHz, DMSO) δ 8.55 (1H, s), 8.32-8.34 (1H, d, J=8 Hz), 8.05-8.11 (3H, m), 8.01-8.03 (1H, d, J=8 Hz), 7.95-7.97 (2H, d, J=8 Hz), 7.87-7.91 (1H, m), 7.69-7.71 (1H, d, J=8 Hz), 3.52-3.72 (8H, m).

Example 7B: Preparation of 3-(4-carboxyphenyl)-1-(2-chloro-6-(trifluoromethyl)benzoyl)-1H-indazole-6-carboxylic acid (7B)

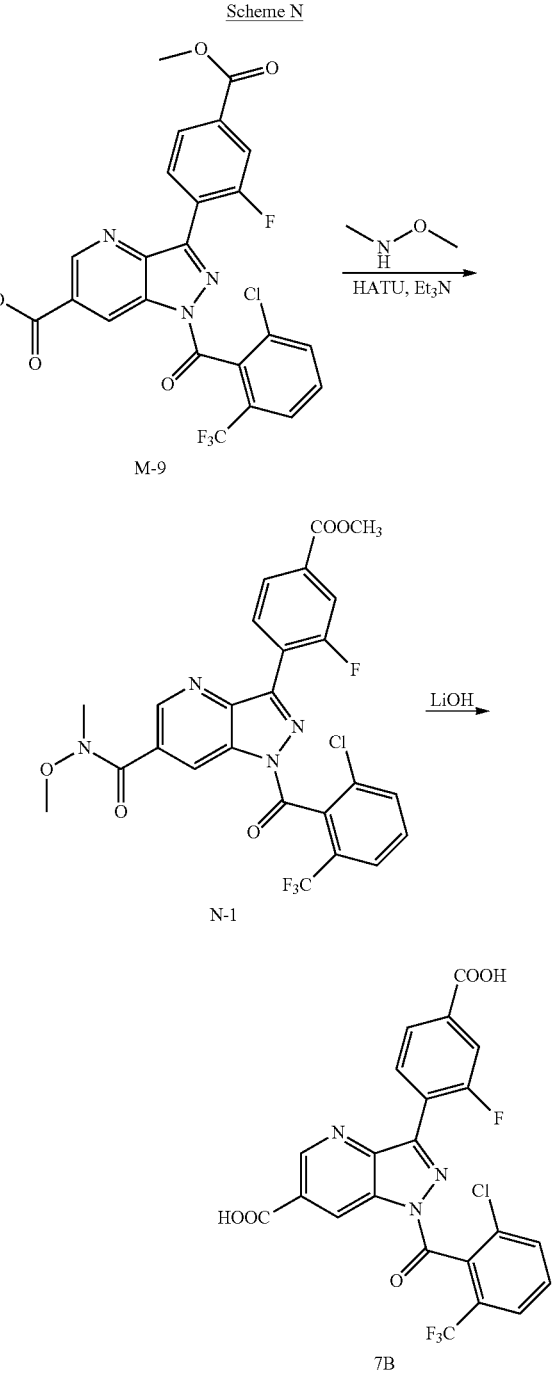

Step 1. Preparation of methyl 4-(1-(2-chloro-6-(trifluoromethyl)benzoyl)-6-(methoxy(methyl)carbamoyl)-1H-pyrazolo[4,3-b]pyridin-3-yl)-3-fluorobenzoate (N-2)

1-(2-Chloro-6-(trifluoromethyl)benzoyl)-3-(2-fluoro-4-(methoxycarbonyl)phenyl)-1H-pyrazolo[4,3-b]pyridine-6-carboxylic acid (M-9) (100 mg, 0.19 mmol) was dissolved in CH$_2$Cl$_2$ (10 mL). O,N-dimethylhydroxylamine (22 mg, 0.23 mmol) and HATU (94 mg, 0.25 mmol) were added and the resulting reaction mixture was stirred at room temperature for 2 min, followed by the addition of TEA (23 mg, 0.23 mmol). The reaction mixture was stirred at room temperature overnight. Then the reaction mixture was diluted with EtOAc (15 ml), washed with brine (15 ml×2), dried over anhydrous Na$_2$SO$_4$, and concentrated to obtain a crude solid N-2 (80 mg). LCMS (ESI): calc'd for C$_{25}$H$_{17}$ClF$_4$N$_4$O$_5$, [M+H]$^+$: 564.7. found: 564.7.

Step 2. Preparation of 3-(4-carboxy-2-fluorophenyl)-1-(2-chloro-6-(trifluoromethyl)benzoyl)-1H-pyrazolo[4,3-b]pyridine-6-carboxylic acid (7B)

A mixture of methyl 4-(1-(2-chloro-6-(trifluoromethyl)benzoyl)-6-(methoxy(methyl)carbamoyl)-1H-pyrazolo[4,3-b]pyridin-3-yl)-3-fluorobenzoate (N-1) (80 mg, 0.14 mmol) and LiOH.H$_2$O (30 mg, 0.7 mmol) in 5 ml THF and 5 ml H$_2$O was stirred at room temperature for 2 hours. The solvent was evaporated and the residue was dissolved in water. HCl (5% sol. in water) was added until pH was 4-5. The product was extracted by EtOAc, and concentrated to obtain a crude solid. The product was purified by prep-HPLC to obtain 7B (10 mg), yield 14.1%. Physical characterization data for 7B was as follows: LCMS (ESI): calc'd for C$_{22}$H$_{10}$ClF$_4$N$_3$O$_5$, [M+H]$^+$: 508. found: 508. $^1$HNMR (400 MHz, MeOD) δ 9.43-9.47 (2H, d, J=13.6 Hz), 8.35-8.38 (1H, m), 7.99-8.02 (1H, d, J=8 Hz), 7.89-7.93 (2H, m), 7.80-7.88 (2H, m).

The following examples shown in TABLE 7 were prepared following similar procedures described for Examples 7A, 7B in Schemes M, N, which can be achieved by those of ordinary skill in the art of organic synthesis in light of the present disclosure.

TABLE 7

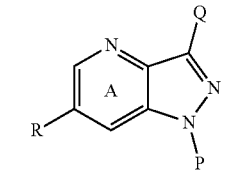

| Ex. | Chemical Name | A ring | P | Q | LCMS [M + H]$^+$ Found |
|---|---|---|---|---|---|
| 7C | 4-(1-(2-chloro-6-(trifluoromethyl)benzoyl)-6-(cyclopropylcarbamoyl)-1H-pyrazolo[4,3-b]pyridin-3-yl)-3-fluorobenzoic acid | 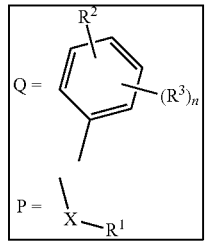 |  |  | 547 |
| 7D | 4-(1-(2-chloro-6-(trifluoromethyl)benzoyl)-6-(cyclopropyl(methyl)carbamoyl)-1H-pyrazolo[4,3-b]pyridin-3-yl)-3-fluorobenzoic acid | 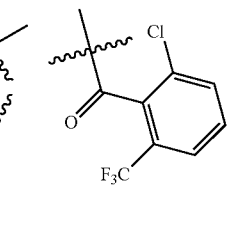 |  | 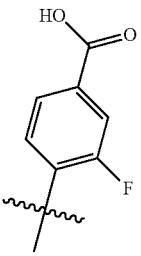 [SMILES: *c1ccc(C(=O)O)cc1F] | 561 |

TABLE 7-continued

| Ex. | Chemical Name | A ring | P | Q | LCMS [M + H]+ Found |
|---|---|---|---|---|---|
| 7E | 4-(1-(2-chloro-6-(trifluoromethyl)benzoyl)-6-(3-methylmorpholine-4-carbonyl)-1H-pyrazolo[4,3-b]pyridin-3-yl)-3-fluorobenzoic acid | | | | 591 |
| 7F | 4-(1-(2-chloro-6-(trifluoromethyl)benzoyl)-6-(3,5-dimethylmorpholine-4-carbonyl)-1H-pyrazolo[4,3-b]pyridin-3-yl)-3-fluorobenzoic acid | | | | 605 |

Example 8A: Preparation of 4-(1-(2-chloro-6-(trifluoromethyl)benzoyl)-6-(cyclopropyl(hydroxy)methyl)-1H-pyrazolo[4,3-b]pyridin-3-yl)-3-fluorobenzoic acid (8A)

SCHEME O

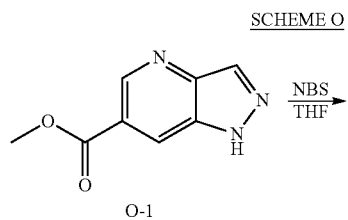

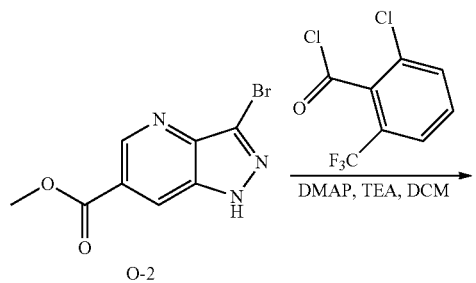

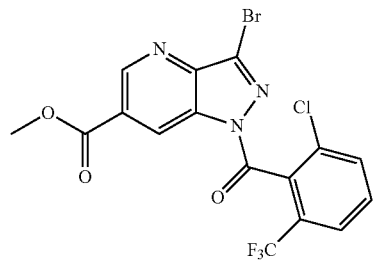

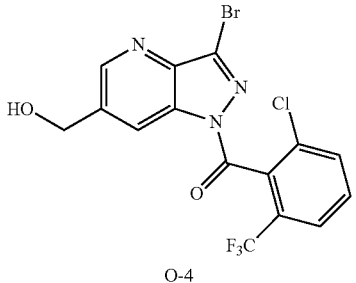

123
-continued

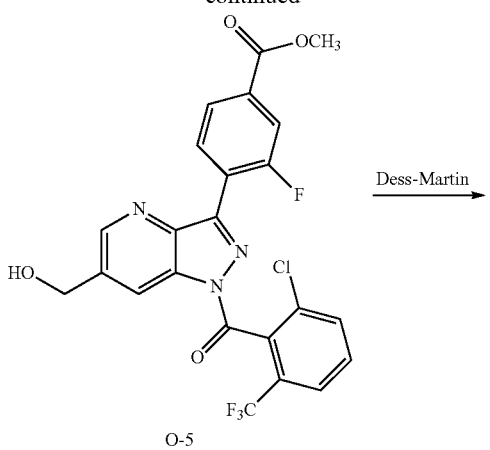

O-5

Dess-Martin →

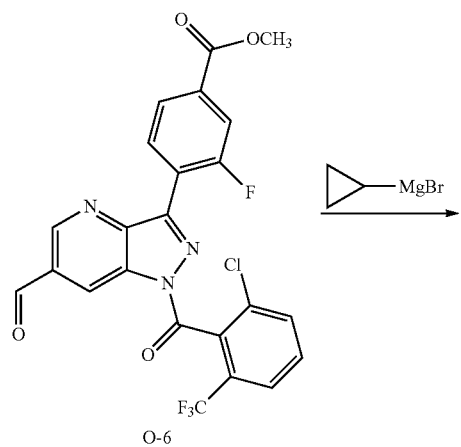

O-6

⊳—MgBr →

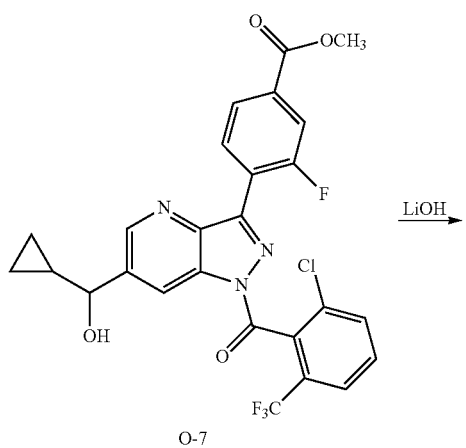

O-7

LiOH →

124
-continued

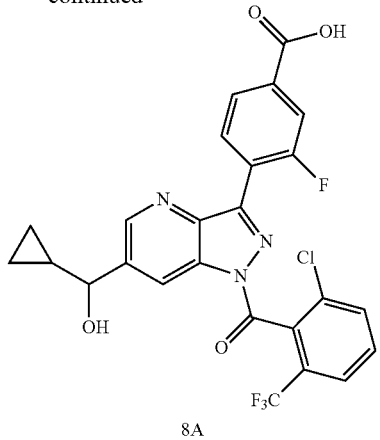

8A

Step 1. Preparation of methyl 3-bromo-1H-pyrazolo[4,3-b]pyridine-6-carboxylate (O-2)

To a solution of methyl 1H-pyrazolo[4,3-b]pyridine-6-carboxylate (O-1) (2 g, 11.3 mmol) in THF (50 mL) was added NBS (3 g, 16.9 mmoL). The reaction mixture was stirred overnight at room temperature, then methanol was added to quench the reaction. The reaction mixture was concentrated to give a crude product, triturated with EtOAc, and filtered, and 2.5 g (87%) of title compound as a white solid was collected. LCMS (ESI): calc'd for $C_8H_6BrN_3O_2$ [M+H]$^+$: 256. found: 256.

Step 2. Preparation of methyl 3-bromo-1-(2-chloro-6-(trifluoromethyl)benzoyl)-1H-pyrazolo[4,3-b]pyridine-6-carboxylate (O-3)

To a solution of methyl 3-bromo 1H-pyrazolo[4,3-b]pyridine-6-carboxylate (O-2) (2.5 g, 9.8 mmol) in DCM (100 mL) was added TEA (2 mL, 14.7 mmol), DMAP (240 mg, 2 mmol), then 2-chloro-6-(trifluoromethyl)benzoyl chloride (3.1 g, 12.7 mmol) in DCM (10 mL) dropwise. The reaction was stirred for 3 h at room temperature, then diluted with EtOAc (200 mL), and the organic layer was washed with sat. NaHCO$_3$ aqueous, washed with water and brine, dried over Na$_2$SO$_4$, concentrated, and purified by flash chromatography (PE:EA=10:1) to give 4.3 g (95%) of the title compound as a light yellow solid. LCMS (ESI): calc'd for $C_{16}H_8BrClF_3N_3O_3$ [M+H]$^+$: 462. found: 462.

Step 3. Preparation of (3-bromo-6-(hydroxymethyl)-1H-pyrazolo[4,3-b]pyridin-1-yl)(2-chloro-6-(trifluoromethyl)phenyl)methanone (O-4)

To a solution of methyl 3-bromo-1-(2-chloro-6-(trifluoromethyl)benzoyl)-1H-pyrazolo[4,3-b]pyridine-6-carboxylate (O-3) (2 g, 4.3 mmol) in dried THF (50 mL) was added DIBAL (1M in THF, 13 mL) slowly at −40° C., then the reaction mixture was warmed to room temperature and stirred for 3 h. The reaction mixture was cooled to 0° C., and 15% NaOH aqueous (5 ml) and water (5 mL) were added successively and slowly, and the mixture was stirred for another 30 min, filtered, concentrated, and purified with flash chromatography (PE:EA=3:1) to give 1.4 g (75%) of title compound as a light yellow solid. LCMS (ESI): calc'd for $C_{16}H_8BrClF_3N_3O_3$ [M+H]$^+$: 434. found: 434.

Step 4. Preparation of methyl 4-(1-(2-chloro-6-(trifluoromethyl)benzoyl)-6-(hydroxymethyl)-1H-pyrazolo[4,3-b]pyridin-3-yl)-3-fluorobenzoate (O-5)

A mixture of (3-bromo-6-(hydroxymethyl)-1H-pyrazolo[4,3-b]pyridin-1-yl) (2-chloro-6-(trifluoromethyl)phenyl)methanone (O-4) (1.3 g, 3.0 mmol), 2-fluoro-4-(methoxycarbonyl)phenylboronic acid (1.2 g, 6.0 mmol), Pd(dppf)Cl$_2$ (367 mg, 0.45 mmol), and K$_3$PO$_4$ (1.9 g, 9.0 mmol) in 8 mL dioxane and water (7:1) was heated at 10° C. for 1 h with an oil-bath. The reaction mixture was filtrated and washed with EtOAc, the organic phase was concentrated, and the product was purified with column chromatography (PE:EA=3:1) to obtain a yellow solid O-5 (800 mg), yield 52.6%. Physical characterization data for O-5 was as follows: LCMS (ESI): calc. C$_{23}$H$_{14}$ClF$_4$N$_3$O$_4$, 507.7. found: M+H=508.7.

Step 5. Preparation of methyl 4-(1-(2-chloro-6-(trifluoromethyl)benzoyl)-6-formyl-1H-pyrazolo[4,3-b]pyridin-3-yl)-3-fluorobenzoate (O-6)

4-(1-(2-Chloro-6-(trifluoromethyl)benzoyl)-6-(hydroxymethyl)-1H-pyrazolo[4,3-b]pyridine-3-yl)-3-fluorobenzoate (O-5) (670 mg, 1.32 mmol) was dissolved in DCM (15 mL), Dess-Martin reagent (840 mg, 1.98 mmol) was added, then the mixture was stirred at room temperature for 2 h. The solvent was evaporated and the product was purified with column chromatography (PE:EA=3:1) to obtain solid O-6 (580 mg), yield 87%. Physical characterization data for O-6 was as follows: LCMS (ESI): calc. C$_{23}$H$_{12}$ClF$_4$N$_3$O$_4$, 505.7. found: M+H=506.7.

Step 6. Preparation of methyl 4-(1-(2-chloro-6-(trifluoromethyl)benzoyl)-6-(cyclopropyl(hydroxy)methyl)-1H-pyrazolo[4,3-b]pyridin-3-yl)-3-fluorobenzoate (O-7)

A 50 ml, round-bottomed flask was degassed with nitrogen and cooled to −78° C., cyclopropylmagnesium bromide (4 mL, 2.0 mmol) was added, then methyl 4-(1-(2-chloro-6-(trifluoromethyl)benzoyl)-6-formyl-1H-pyrazolo[4,3-b]pyridine-3-yl)-3-fluorobenzoate (O-6) (80 mg, 0.16 mmol) in THF (3 mL, anhydrous) was added slowly. The mixture was stirred from −78° C. to room temperature for 4 h. Water was added, and the solvent was evaporated. The product was purified with Prep-HPLC to obtain white solid O-7 (26 mg), yield 29.7%. Physical characterization data for O-7 was as follows: LCMS (ESI): calc. C$_{26}$H$_{18}$ClF$_4$N$_3$O$_4$, 547.7. found: M+H=548.7.

Step 7. Preparation of 4-(1-(2-chloro-6-(trifluoromethyl)benzoyl)-6-(cyclopropyl(hydroxy)methyl)-1H-pyrazolo[4,3-b]pyridin-3-yl)-3-fluorobenzoic acid (8A)

A mixture of methyl 4-(1-(2-chloro-6-(trifluoromethyl)benzoyl)-6-(cyclopropyl(hydroxy)methyl)-1H-pyrazolo[4,3-b]pyridin-3-yl)-3-fluorobenzoate (O-7) (26 mg, 0.05 mmol) and LiOH.H$_2$O (10 mg, 0.24 mmol) in 2 ml THF and 2 ml H$_2$O was stirred at room temperature for 2 hours. The solvent was evaporated and the residue was dissolved in water. HCl (5% sol in water) was added until pH 4-5. The product was extracted by EtOAc, and concentrated to obtain crude solid. The product was purified by prep-HPLC to obtain O-8 (4 mg), yield 15.79%. Physical characterization data for 8A was as follows: LCMS (ESI): calc. C$_{25}$H$_{16}$ClF$_4$N$_3$O$_4$, 533.7. found: M+H=533.7. $^1$HNMR (400 MHz, MeOD) δ 8.97-9.00 (2H, d, J=12 Hz), 8.26-8.30 (1H, m), 7.98-8.00 (1H, d, J=8 Hz), 7.84-7.90 (3H, m), 7.77-7.81 (1H, m), 4.37-4.39 (1H, d, J=8.4 Hz), 1.29-1.33 (1H, m), 0.74-0.78 (1H, m), 0.67-0.72 (2H, m), 0.57-0.63 (1H, m).

Example 8B: Preparation of 4-(1-(2-chloro-6-(trifluoromethyl)benzoyl)-6-(cyclopropane-carbonyl)-1H-pyrazolo[4,3-b]pyridin-3-yl)-3-fluorobenzoic acid (8B)

SCHEME P

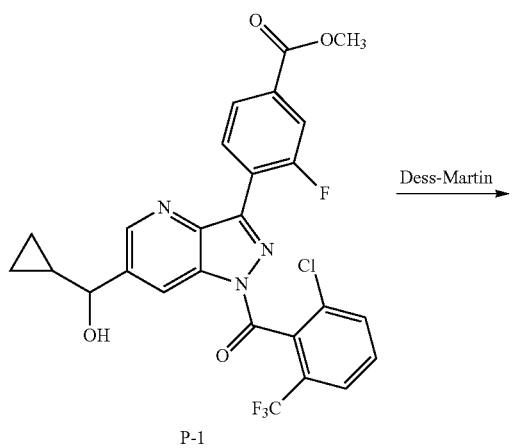

P-1

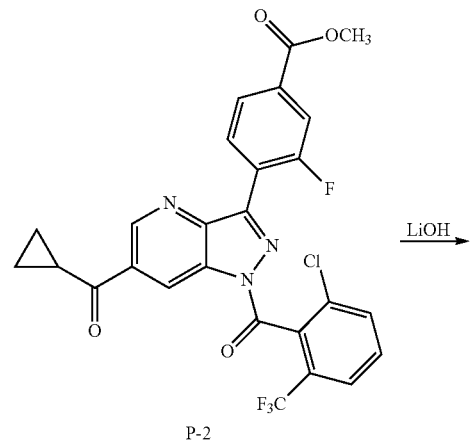

P-2

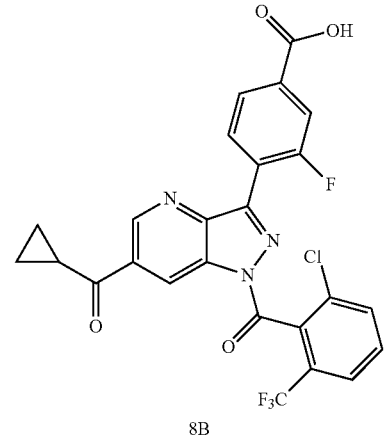

8B

Step 1. Preparation of methyl 4-(1-(2-chloro-6-(trifluoromethyl)benzoyl)-6-(cyclopropanecarbonyl)-1H-pyrazolo[4,3-b]pyridin-3-yl)-3-fluorobenzoate (P-2)

Methyl 4-(1-(2-chloro-6-(trifluoromethyl)benzoyl)-6-(cyclopropyl(hydroxy)methyl)-1H-pyrazolo[4,3-b]pyridin-3-yl)-3-fluorobenzoate (P-1) (25 mg, 0.05 mmol) was dissolved in DCM (5 mL), Dess-Martin reagent (29 mg, 0.069 mmol) was added, then the mixture was stirred at room temperature for 3 h. The solvent was evaporated and the product was purified with column chromatography (PE:EA=4:1) to obtain crude solid P-2 (10 mg). Physical characterization data for P-2 was as follows: LCMS (ESI): calc. $C_{26}H_{16}ClF_4N_3O_4$, 545.7. found: M+H=546.7.

Step 2. Preparation of 4-(1-(2-chloro-6-(trifluoromethyl)benzoyl)-6-(cyclopropanecarbonyl)-1H-pyrazolo[4,3-b]pyridin-3-yl)-3-fluorobenzoic acid (8B)

A mixture of methyl 4-(1-(2-chloro-6-(trifluoromethyl)benzoyl)-6-(cyclopropanecarbonyl)-1H-pyrazolo[4,3-b]pyridin-3-yl)-3-fluorobenzoate (P-2) (10 mg, 0.02 mmol) and LiOH.H$_2$O (8 mg, 0.18 mmol) in 2 mL THF and 2 mL H$_2$O was stirred at room temperature for 2 hours. The solvent was evaporated and the residue was dissolved in water. HCl (5% sol. in water) was added until pH 4-5. The product was extracted by EtOAc, and concentrated to obtain crude solid. The product was purified by Prep-HPLC to obtain 8B (2 mg), yield 2.35%. Physical characterization data for 8B was as follows: LCMS (ESI): calc. $C_{25}H_{14}ClF_4N_3O_4$, 531.7. found: M+H=531.7. $^1$HNMR (400 MHz, DMSO) δ 9.553 (1H, s), 9.312 (1H, s), 8.377 (1H, s), 8.04-8.08 (1H, m), 7.96-8.01 (1H, m), 7.88-7.92 (1H, m), 7.01-7.84 (1H, d, J=10.4 Hz), 3.16-3.18 (1H, m), 1.15-1.22 (4H, m).

The following examples shown in TABLE 8 were prepared following similar procedures described for Examples 8A, 8B in Schemes O, P, which can be achieved by those of ordinary skill in the art of organic synthesis in light of the present disclosure.

TABLE 8

| Ex. | Chemical Name | A ring | P | Q | LCMS [M + H]$^+$ Found |
|---|---|---|---|---|---|
| 8C | 4-(1-(2-chloro-6-(trifluoromethyl)benzoyl)-6-(hydroxy(oxazol-2-yl)methyl)-1H-pyrazolo[4,3-b]pyridine-3-yl)-3-fluorobenzoic acid | | | | 561 |
| 8D | 4-(1-(2-chloro-6-(trifluoromethyl)benzoyl)-6-(oxazole-2-carbonyl)-1H-pyrazolo[4,3-b]pyridin-3-yl)-3-fluorobenzoic acid | | | | 559 |

Example 9A: Preparation of sodium 4-(1-(2-chloro-6-(trifluoromethyl)benzoyl)-6-(5-methyloxazol-2-yl)-1H-indazol-3-yl)benzoate (9A)
SCHEME Q
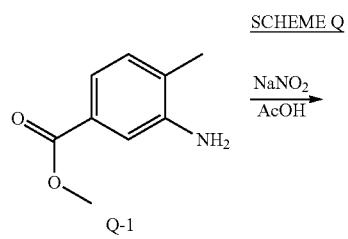
Q-1
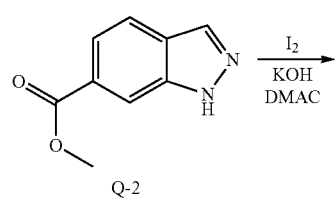
Q-2
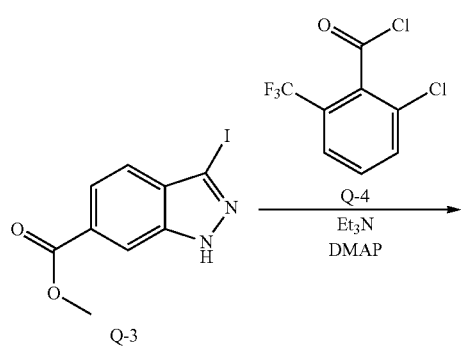
Q-3
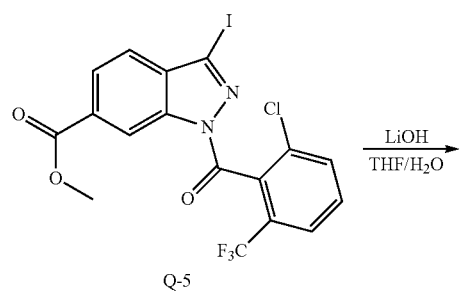
Q-5
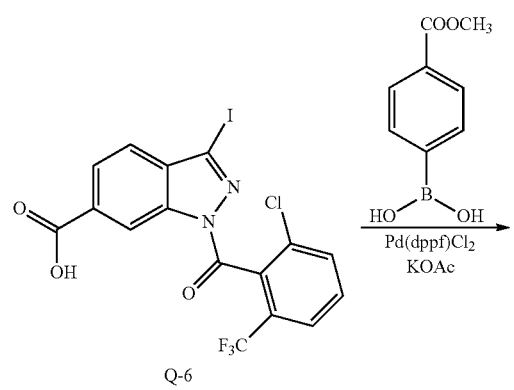
Q-6
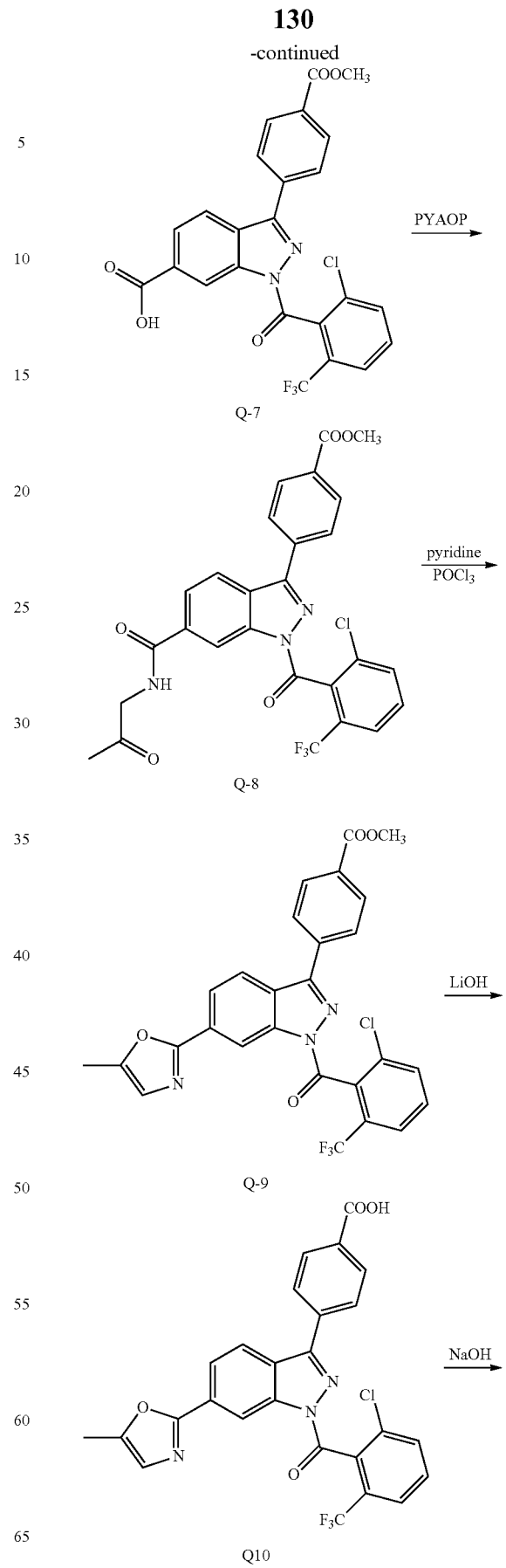

-continued

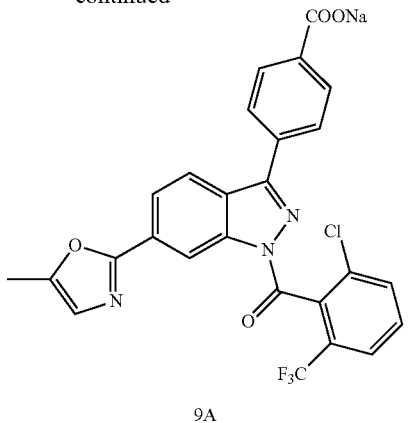

9A

Step 1: Preparation of methyl
1H-indazole-6-carboxylate (Q-2)

Methyl 3-amino-4-methylbenzoate (Q-1) (5.0 g, 30.2 mmol) was dissolved in AcOH (140 mL). Sodium nitrite (2.1 g, 30.2 mmol) in water (3.5 mL) was added dropwise to the solution of starting material under ice-cooling at room temperature. The ice-bath was removed and the mixture was stirred overnight. Half of the solvents were evaporated, and the mixture was diluted with water (80 mL) and extracted with EtOAc (30 mL×3). The collected organic phase was washed with water and brine (200 mL×2), dried, and evaporated to afford the crude product Q-2 (4.4 g). LCMS (ESI): calc'd for $C_9H_8N_2O_2$, [M+H]$^+$: 177.1. found: 177.1.

Step 2: Preparation of methyl
3-iodo-1H-indazole-6-carboxylate (Q-3)

Methyl 1H-indazole-6-carboxylate (Q-2) (5.0 g, 28.3 mmol) was dissolved in anhydrous DMAC (50 mL). Iodine (14.4 g, 56.7 mmol) and potassium hydroxide (6.3 g, 113.5 mmol) were added in portions under ice-cooling at room temperature. The ice-bath was removed and the mixture was stirred at room temperature for 1 h. The reaction was monitored by TLC (25% MeOH in chloroform) then slowly quenched with $Na_2S_2O_3$ (sat. sol. in water, 100 mL), diluted with water (50 mL), and extracted with EtOAC (100 mL×3). The organic phase was evaporated and triturated with n-hexane. The precipitated material was filtered and dried to afford a brown solid Q-3 5.3 g (62%). LCMS (ESI): calc'd for $C_9H_7IN_2O_2$, [M+H]$^+$: 302.9. found: 302.9.

Step 3: Preparation of methyl 1-(2-chloro-6-(trifluoromethyl)benzoyl)-3-iodo-1H indazole-6-carboxylate (Q-5)

To a 250 mL round-bottomed flask was added compound methyl 3-iodo-1H-indazole-6-carboxylate (Q-3) (11.7 g, 38.7 mmol), 2-chloro-6-(trifluoromethyl)benzoyl chloride (Q-4) (10.3 g, 42.6 mmol), DMAP (4.72 g, 38.7 mmol) and $CH_2Cl_2$ (100 mL). After stirring at room temperature for 3 minutes, TEA (11.2 mL, 77 mmol) was added slowly. The reaction mixture was stirred at room temperature overnight. LCMS showed that no starting materials remained. Then the mixture was poured into 30 mL water, and the lower (organic) and upper (aqueous) phases were separated. The aqueous phase was extracted twice with 20 mL $CH_2Cl_2$. The combined organic phases were washed successively with two 20 mL portions of water and 10 mL of brine. The resulting organic phase was dried over anhydrous sodium sulfate, filtered and concentrated at reduced pressure to give a yellow solid. The residue was purified by column chromatography on 60 g on silica gel eluting with PE/EA from 50/1 to 10/1, to give a fawn solid Q-5 16.5 g (84%). LCMS (ESI): calc'd for $C_{17}H_9ClF_3IN_2O_3$, [M+H]$^+$: 508.9. found: 508.9.

Step 4: Preparation of 1-(2-chloro-6-(trifluoromethyl)benzoyl)-3-iodo-1H-indazole-6-carboxylic acid (Q-6)

A mixture of 1-(2-chloro-6-(trifluoromethyl)benzoyl)-3-iodo-1H-indazole-6-carboxylate (Q-5) (16.5 g, 32.48 mmol) and LiOH (3.40 g, 162.40 mmol) in 10 mL THF and 50 mL pure $H_2O$ was stirred at room temperature overnight. The solvent was evaporated and the residue was dissolved in water. HCl (5% sol. in water) was added until pH 4-5. The precipitated solid was filtered, washed with water and n-hexane, and dried to afford an off-white solid Q-6 16.0 g (83%). LCMS (ESI): calc'd for $C_{16}H_7ClF_3IN_2O_3$, [M+H]$^+$: 494.9. found: 494.9.

Step 5: Preparation of 1-(2-chloro-6-(trifluoromethyl)benzoyl)-3-(4-(methoxycarbonyl)phenyl)-1H-indazole-6-carboxylic acid (Q-7)

A mixture of 1-(2-chloro-6-(trifluoromethyl)benzoyl)-3-iodo-1H-indazole-6-carboxylic acid (Q-6) (300 mg, 0.61 mmol), 4-(methoxycarbonyl)phenylboronic acid (165 mg, 0.92 mmol), Pd(dppf)Cl$_2$ (50 mg, 0.061 mmol) and KOAc (181 mg, 1.83 mmol) in 10 mL dioxane and 2 mL pure $H_2O$ was heated to 95° C. for 2 h under microwave. Then the reaction mixture was diluted with EA (50 mL), washed with brine (50 mL×2), dried over anhydrous $Na_2SO_4$, concentrated, and purified by silica gel column (Petroleum ether/EtOAc=20/1) to obtain white solid Q-7 180 mg (59%). LCMS (ESI): calc'd for $C_{24}H_{14}ClF_3N_2O_5$, [M+H]$^+$: 503.1. found: 503.1.

Step 6: Preparation of methyl 4-(1-(2-chloro-6-(trifluoromethyl)benzoyl)-6-(2-oxopropylcarbamoyl)-1H-indazol-3-yl)benzoate (Q-8)

1-(2-Chloro-6-(trifluoromethyl)benzoyl)-3-(4-(methoxycarbonyl)phenyl)-1H-indazole-6-carboxylic acid (Q-7) (180 mg, 0.36 mmol) was dissolved in $CH_2Cl_2$ (15 mL). 1-aminopropan-2-one hydrochloride (47 mg, 0.43 mmol) and PYAOP (374 mg, 0.72 mmol) were added and the mixture was stirred at room temperature for 2 mins. TEA (0.16 mL, 1.08 mmol) was added and the mixture was stirred at room temperature for 2 h. Then the mixture was diluted with EtOAC (20 ml), washed with brine (20 ml×2), dried over anhydrous $Na_2SO_4$, and concentrated to obtain crude product Q-8 (191 mg), which was used in the next step without further purification. LCMS (ESI): calc'd for $C_{27}H_{19}ClF_3N_3O_5$, $[M+H]^+$: 558.1. found: 558.1.

Step 7: Preparation of methyl 4-(1-(2-chloro-6-(trifluoromethyl)benzoyl)-6-(5-methyloxazol-2-yl)-1H-indazol-3-yl)benzoate (Q-9)

$POCl_3$ (3.5 mL) was added to a solution of methyl 4-(1-(2-chloro-6-(trifluoromethyl)benzoyl)-6-(2-oxopropylcarbamoyl)-1H-indazol-3-yl)benzoate (Q-8) (191 mg, 0.34 mmol) in pyridine (7 mL) at 25° C. The resulting solution was then warmed to 70° C. and stirred for 6 hours. Upon completion, the reaction mixture was cooled to 25° C., diluted with EtOAc (10 mL), poured into a cold (0° C.) solution of saturated aqueous $NaHCO_3$ (50 mL), and extracted with EtOAc (25 mL×3). The combined organic layers were then washed with water (50 mL) and brine (50 mL), dried ($MgSO_4$), and concentrated to obtain a crude product Q-9 (40 mg). LCMS (ESI): calc'd for $C_{27}H_{17}ClF_3N_3O_4$, $[M+H]^+$: 540.1. found: 540.1.

Step 8: Preparation of 4-(1-(2-chloro-6-(trifluoromethyl)benzoyl)-6-(5-methyloxazol-2-yl)-1H-indazol-3-yl)benzoic acid (Q-10)

A mixture of methyl 4-(1-(2-chloro-6-(trifluoromethyl)benzoyl)-6-(5-methyloxazol-2-yl)-1H-indazol-3-yl)benzoate (Q-9) (40 mg, 0.07 mmol) and LiOH (16 mg, 0.37 mmol) in 10 mL THF and 10 mL pure $H_2O$ was stirred at room temperature for 2 hours. The solvent was evaporated and the residue was dissolved in water. HCl (5% sol in water) was added until pH was 4-5. The precipitated solid was filtered, washed with water and n-hexane, and dried to afford an off-white solid Q-10 36 mg (98%). LCMS (ESI): calc'd for $C_{26}H_{15}ClF_3N_3O_4$, $[M+H]^+$: 526 found: 526.

Step 9: Preparation of sodium 4-(1-(2-chloro-6-(trifluoromethyl)benzoyl)-6-(5-methyloxazol-2-yl)-1H-indazol-3-yl)benzoate (9A)

4-(1-(2-Chloro-6-(trifluoro methyl)benzoyl)-6-(5-methyloxazol-2-yl)-1H-indazol-3-yl)benzoic acid (Q-10) (36 mg, 0.069 mmol) was added to $H_2O$ (10 mL) and the mixture was sonicated for 10 min. Then 0.1 mol/L NaOH (0.7 mL, 0.07 mmol) was added to the solution at 0° C. and the reaction mixture was stirred at 0° C. for 30 mins. Then the mixture was dried by Freeze dryer to obtain compound 9A 38 mg (100%). LCMS (ESI): calc'd for $C_{26}H_{14}ClF_3N_3NaO_4$, $[M+H]^+$: 548. found: 548. $^1$HNMR (400 MHz, DMSO) δ 9.04 (1H, s), 8.37-8.39 (1H, d, J=8 Hz), 8.18-8.20 (1H, d, J=8 Hz), 8.06-8.08 (1H, d, J=8 Hz), 8.00-8.02 (3H, d, J=8.8 Hz), 7.87-7.91 (1H, m), 7.78-7.80 (2H, d, J=8 Hz), 7.16 (1H, s), 2.48 (3H, s).

The following example shown in TABLE 9 was prepared following similar procedures described for Example 9A in Scheme Q, which can be achieved by those of ordinary skill in the art of organic synthesis in light of the present disclosure.

TABLE 9

| Ex. | Chemical Name | A ring | P | Q | LCMS [M + H]+ Found |
|---|---|---|---|---|---|
| 9B | 4-(1-(2-chloro-6-(trifluoromethyl)benzoyl)-6-(5-methyloxazol-2-yl)-1H-indazol-3-yl)-3-fluorobenzoic acid | | | | 544 |

Example 11A: Preparation of 4-(1-(2-chloro-6-(trifluoromethyl)benzoyl)-6-(3-hydroxyprop-1-ynyl)-1H-indazol-3-yl)benzoic acid (11A)

SCHEME S

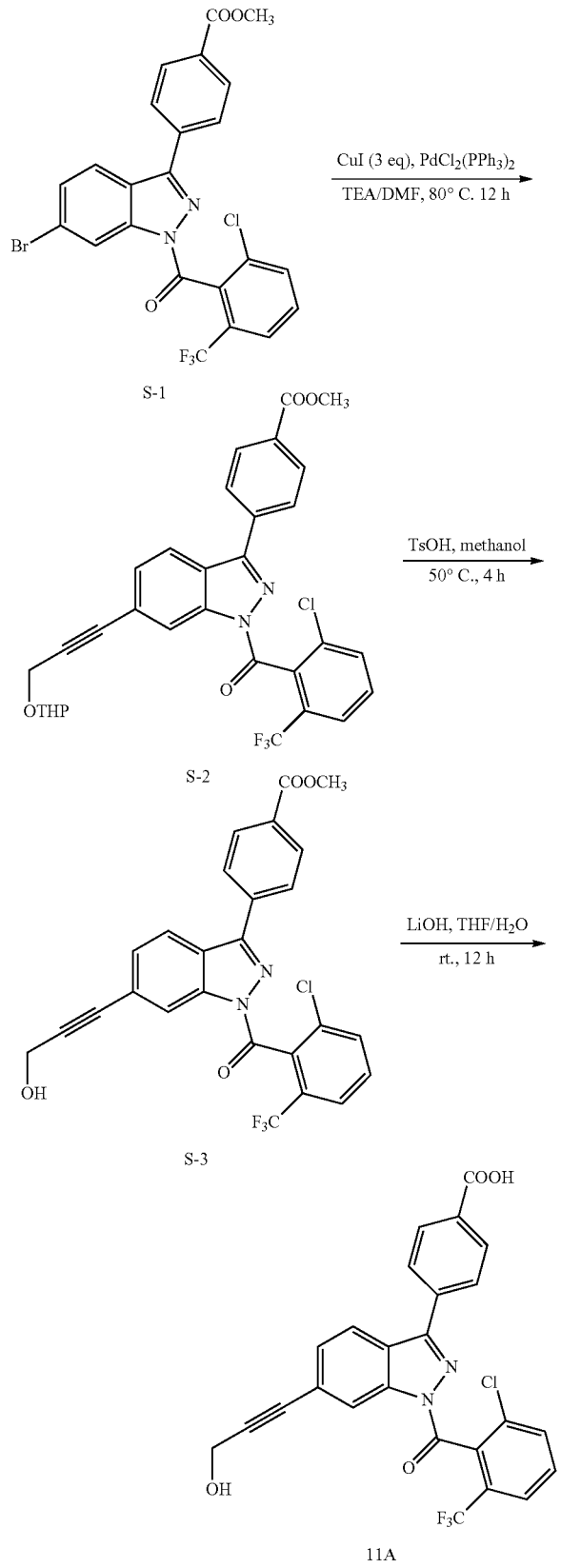

Step 1. Preparation of methyl 4-(1-(2-chloro-6-(trifluoromethyl)benzoyl)-6-(3-(tetrahydro-2H-pyran-2-yloxy)prop-1-ynyl)-1H-indazol-3-yl)benzoate (S-2)

To a solution of methyl 4-(6-bromo-1-(2-chloro-6-(trifluoromethyl)benzoyl)-1H-indazol-3-yl)benzoate (S-1) (53.5 mg, 0.1 mmol) in DMF (5 mL) and TEA (10 mL) was added 2-(prop-2-ynyloxy)-tetrahydro-2H-pyran (16.8 mg, 0.12 mmol), copper(I) iodide (10 mg, 0.01 mmol) and $PdCl_2(PPh_3)_2$ (10 mg, 0.01 mmol) under argon. The mixture was stirred under argon for 2 hours at 80° C. The mixture was diluted with $H_2O$. The aqueous layer was extracted with $CH_2Cl_2$ (3×50 mL). The combined organics were washed with $H_2O$, brine, dried over $Na_2SO_4$, and concentrated. The residue was purified by Prep-TLC (Pentane/EtOAc, 5/1) to afford 48 mg (58%) of the title compound. LCMS (ESI) calc'd for $C_{31}H_{24}ClF_3N_2O_5$ $[M+H]^+$: 597.1. found: 597.1.

Step 2. Preparation of methyl 4-(1-(2-chloro-6-(trifluoromethyl)benzoyl)-6-(3-hydroxyprop-1-ynyl)-1H-indazol-3-yl)benzoate (S-3)

To a solution of methyl 4-(1-(2-chloro-6-(trifluoromethyl)benzoyl)-6-(3-(tetrahydro-2H-pyran-2-yloxy)prop-1-ynyl)-1H-indazol-3-yl)benzoate (S-2) (200 mg, 0.34 mmol) in MeOH (10 mL) was added TsOH (12 mg, 0.07 mmol) at 0° C. The mixture was stirred for 12 hours at room temperature. The mixture was diluted with $H_2O$. The aqueous layer was extracted with $CH_2Cl_2$ (3×80 mL). The combined organics were washed with $H_2O$, brine, dried over $Na_2SO_4$, and concentrated. The residue was purified by Prep-TLC (Pentane/EtOAc, 3/1) to afford 110 mg (64%) of the title compound. LCMS (ESI) calc'd for $C_{26}H_{16}ClF_3N_2O_4[M+H]^+$: 513.1. found: 513.1.

Step 3. Preparation of 4-(1-(2-chloro-6-(trifluoromethyl)benzoyl)-6-(3-hydroxy prop-1-ynyl)-1H-indazol-3-yl)benzoic acid (11A)

To a stirred solution of methyl 4-(1-(2-chloro-6-(trifluoromethyl)benzoyl)-6-(3-hydroxyprop-1-ynyl)-1H-indazol-3-yl)benzoate (S-3) (300 mg, 0.5 mmol) was added THF (8.0 mL), $H_2O$ (2.0 mL) and $LiOH.H_2O$ (108 mg, 2.5 mmol) and the solution was stirred at room temperature overnight. LCMS showed disappearance of starting material. The solution was adjusted to pH 4.0 using 1N HCl and poured into THF (30 mL), and washed with brine (20 mL). The organic layer was dried over $Na_2SO_4$, evaporated, and submitted for Prep-HPLC. 100 mg of the product was collected. Yield: 32%. LCMS (ESI) calc'd for $C_{25}H_{14}ClF_3N_2O_4$ $[M+H]^+$: 499.1. found: 499.1. $^1$HNMR (400 MHz, DMSO) δ 8.544 (1H, s), 8.28 (1H, d), 8.10 (8H, m), 7.70 (1H, d), 4.41 (1H, s).

Example 12A: Preparation of 4-(1-(2-chloro-6-(trifluoromethyl)benzoyl)-6-(3-hydroxybut-1-ynyl)-1H-indazol-3-yl)-3-fluorobenzoic acid (12A)

SCHEME T

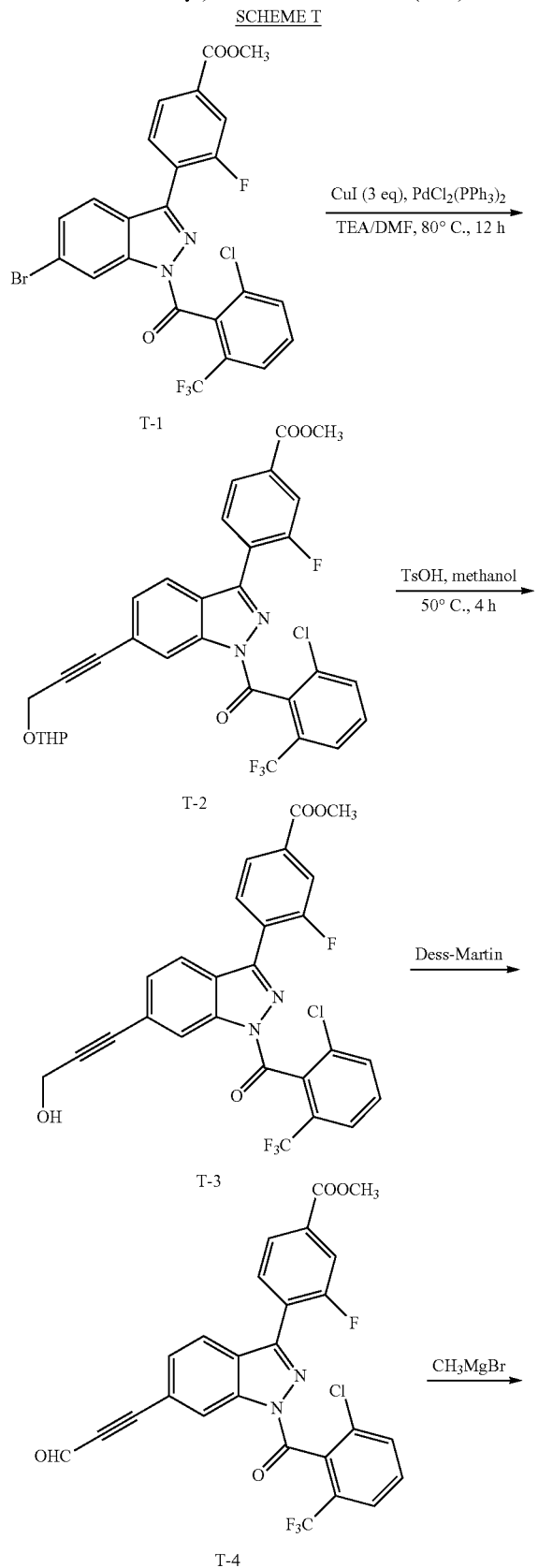

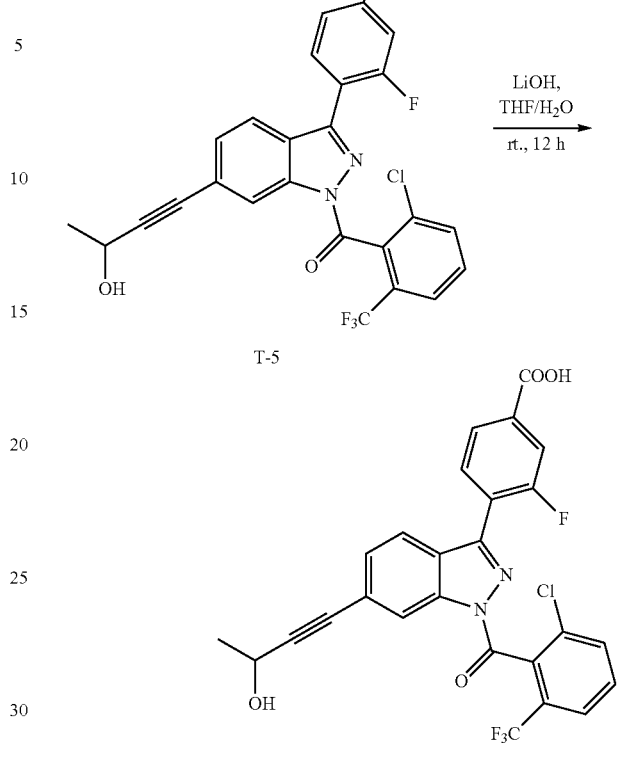

Step 1. Preparation of methyl 4-(1-(2-chloro-6-(trifluoromethyl)benzoyl)-6-(3-(tetrahydro-2H-pyran-2-yloxy)prop-1-ynyl)-1H-indazol-3-yl)-3-fluorobenzoate (T-2)

To a solution of methyl 4-(6-bromo-1-(2-chloro-6-(trifluoromethyl)benzoyl)-1H-indazol-3-yl)-3-fluorobenzoate (T-1) (200 mg, 0.36 mmol) in DMF (10 mL) and TEA (20 mL) was added 2-(prop-2-ynyloxy)-tetrahydro-2H-pyran (60 mg, 0.43 mmol), copper(I) iodide (6.8 mg, 0.036 mmol) and $PdCl_2(PPh_3)_2$ (25 mg, 0.036 mmol) under argon. The mixture was stirred under argon for 2 hours at 80° C. The mixture was diluted with $H_2O$, and the aqueous layer was extracted with $CH_2Cl_2$ (3×50 mL). The combined organics were washed with $H_2O$, brine, dried over $Na_2SO_4$, and concentrated. The residue was purified by Prep-TLC (Pentane/EtOAc, 5/1) to afford 111 mg (51%) of the title compound. LCMS (ESI) calc'd for $C_{31}H_{23}ClF_4N_2O_5$ [M+H]$^+$: 615. found: 615.

Step 2. Preparation of methyl 4-(1-(2-chloro-6-(trifluoromethyl)benzoyl)-6-(3-hydroxyprop-1-ynyl)-1H-indazol-3-yl)-3-fluorobenzoate (T-3)

To a solution of methyl 4-(1-(2-chloro-6-(trifluoromethyl)benzoyl)-6-(3-(tetrahydro-2H-pyran-2-yloxy)prop-1-ynyl)-1H-indazol-3-yl)-3-fluorobenzoate (T-2) (111 mg, 0.18 mmol) in MeOH/$H_2O$ (20/2 mL) was added TsOH (15 mg, 0.09 mmol) at 0° C. The mixture was stirred for 12 hours at room temperature. The mixture was diluted with H₂O, and the aqueous layer was extracted with CH₂Cl₂ (3×80 mL). The combined organics were washed with H₂O, brine, dried over Na₂SO₄, and concentrated. The residue was purified by Prep-TLC (Pentane/EtOAc, 3/1) to give 45 mg (47%) of the title compound. LCMS (ESI) calc'd for $C_{26}H_{15}ClF_4N_2O_4$ [M+H]⁺: 531. found: 531.

Step 3. Preparation of methyl 4-(1-(2-chloro-6-(trifluoromethyl)benzoyl)-6-(3-oxoprop-1-ynyl)-1H-indazol-3-yl)-3-fluorobenzoate (T-4)

To a solution of methyl 4-(1-(2-chloro-6-(trifluoromethyl)benzoyl)-6-(3-hydroxyprop-1-ynyl)-1H-indazol-3-yl)-3-fluorobenzoate (T-3) (45 mg, 0.085 mmol) in DCM (20 mL) was added Dess-Martin reagent (108 mg, 0.25 mmol) at 0° C. The mixture was stirred for 12 hours at room temperature. The mixture was diluted with H₂O and extracted with CH₂Cl₂ (3×80 mL). The combined organics were washed with H₂O, brine, dried over Na₂SO₄, and concentrated. The residue was purified by Prep-TLC (Pentane/EtOAc, 3/1) to afford 40 mg (88%) of the title compound. LCMS (ESI) calc'd for $C_{26}H_{13}ClF_4N_2O_4$ [M+H]⁺: 529.1. found: 529.1.

Step 4. Preparation of methyl 4-(1-(2-chloro-6-(trifluoromethyl)benzoyl)-6-(3-hydroxybut-1-ynyl)-1H-indazol-3-yl)-3-fluorobenzoate (T-5)

To a solution of methyl 4-(1-(2-chloro-6-(trifluoromethyl)benzoyl)-6-(3-oxoprop-1-ynyl)-1H-indazol-3-yl)-3-fluorobenzoate (T-4) (40 mg, 0.076 mmol) in dry THF (5 mL) was added MeMgBr (0.18 mL, 0.53 mmol, 3 M in ether) at −60° C. The mixture was stirred for 2 hours at room temperature, the mixture was quenched with saturated NH₄Cl, the aqueous layer was extracted with EtOAc (3×80 mL), and the combined organics were washed with H₂O, brine, dried over Na₂SO₄, and concentrated. The residue was purified by Prep-TLC (Pentane/EtOAc, 3/1) to afford 41 mg (85%) of the title compound. LCMS (ESI) calc'd for $C_{27}H_{17}ClF_4N_2O_4$ [M+H]⁺: 545.1. found: 545.1.

Step 5. Preparation of methyl 4-(1-(2-chloro-6-(trifluoromethyl)benzoyl)-6-(3-hydroxybut-1-ynyl)-1H-indazol-3-yl)-3-fluorobenzoate (12A)

To a stirred solution of methyl 4-(1-(2-chloro-6-(trifluoromethyl)benzoyl-6-(3-hydroxybut-1-ynyl)-1H-indazol-3-yl)-3-fluorobenzoate (T-5) (41 mg, 0.075 mmol) was added THF (8.0 mL), H₂O (2.0 mL) and LiOH.H₂O (32 mg, 0.75 mmol), and the solution was stirred at room temperature overnight. LCMS showed disappearance of starting material. The solution was adjusted to pH 4.0 using 1N HCl and poured into THF (30 mL), and washed with brine (20 mL). The organic layer was dried over Na₂SO₄, evaporated, and submitted for Prep-HPLC to give 5 mg of product (yield 12%). LCMS (ESI) calc'd for $C_{26}H_{15}ClF_4N_2O_4$ [M+H]⁺: 531. found: 531. ¹HNMR (400 MHz, DMSO) δ 13.5 (1H, bs), 8.526 (1H, s), 7.95 (6H, m), 7.76 (1H, t), 7.63 (1H, t), 5.61 (1H, d), 4.57 (1H, t), 1.449-1.464 (3H, d).

Example 13A: Preparation of 4-(6-(3-aminoprop-1-ynyl)-1-(2-chloro-6-(trifluoromethyl)benzoyl)-1H-indazol-3-yl)-3-fluorobenzoic acid (13A)

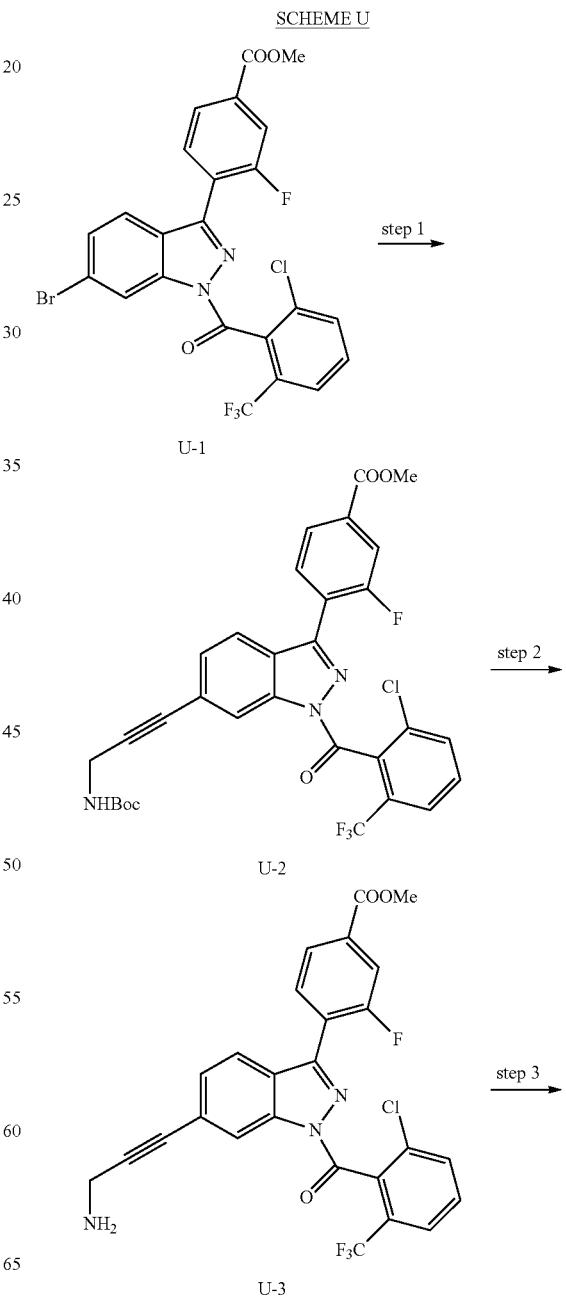

141
-continued

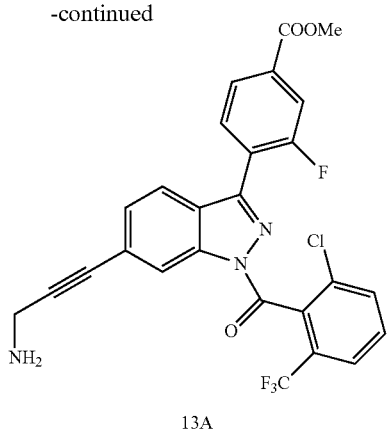

13A

Step 1. Preparation of methyl 4-(6-(3-(tert-butoxy-carbonylamino)prop-1-ynyl)-1-(2-chloro-6-(trifluoromethyl)benzoyl)-1H-indazol-3-yl)-3-fluorobenzoate (U-2)

The mixture of methyl 4-(6-bromo-1-(2-chloro-6-(trifluoromethyl)benzoyl)-1H-indazol-3-yl)-3-fluorobenzoate (U-1) (554 mg, 1.0 mmol), Pd(PPh₃)₂Cl₂ (105 mg, 0.1 mmol), CuI (60 mg, 0.15 mmol), Et₃N (20 mL) and DMF (20 mL) was purged with N₂ and stirred at 80° C. overnight. LCMS showed that the starting material was completely consumed, and showed formation of the desired product. The resulting solution was filtered, concentrated, and purified by column chromatography to give 432 mg of product as a white solid (68.7%). LCMS (ESI) calc'd for [M+H]⁺: 629.99. found: 630.1.

Step 2. Preparation of methyl 4-(6-(3-aminoprop-1-ynyl)-1-(2-chloro-6-(trifluoro methyl)benzoyl)-1H-indazol-3-yl)-3-fluorobenzoate (U-3)

To the solution of methyl 4-(6-(3-(tert-butoxycarbonylamino)prop-1-ynyl)-1-(2-chloro-6-(trifluoromethyl)benzoyl)-1H-indazol-3-yl)-3-fluorobenzoate (U-2) (629 mg, 1.0 mmol) in THF (30 mL) and water (10 mL) was added TFA (970 mg, 10 mmol). The mixture solution was stirred at room temperature for 10 h. The mixture was diluted with H₂O and extracted with EtOAc (30 mL×3). The combined organic layer was concentrated and purified by chromatography column (EA:PE=1:1) to afford 461 mg of product (yield: 87.5%). LCMS (ESI) calc'd [M+H]⁺: 529.87. found: 530.1.

Step 3. Preparation of 4-(6-(3-aminoprop-1-ynyl)-1-(2-chloro-6-(trifluoromethyl)benzoyl)-1H-indazol-3-yl)-3-fluorobenzoic acid (13A)

To the solution of methyl 4-(6-(3-aminoprop-1-ynyl)-1-(2-chloro-6-(trifluoromethyl)benzoyl)-1H-indazol-3-yl)

142

3-fluorobenzoate (U-3) (529 mg, 1.0 mmol) in THF (30 mL) and water (10 mL) was added LiOH (240 mg, 10 mmol). The mixture solution was stirred at room temperature for 10 h. The mixture was acidified with 2N HCl and extracted with EtOAc (30 mL×3). The combined organic layer was purified by flash chromatography (EA:PE=1:1) to afford 431 mg of final product (yield: 84%). LCMS (ESI) calc'd [M+H]⁺: 515.84. found: 516.1. ¹HNMR (400 MHz, CDCl₃) δ: 8.63 (1H, s), 8.41 (2H, w), 8.02 (3H, m), 7.89 (3H, m), 7.76 (1H, t), 7.68 (1H, s), 4.12 (1H, s).

Example 14A: Preparation of 4-(1-(2-chloro-6-(trifluoromethyl)benzoyl)-6-ethynyl-1H-indazol-3-yl) benzoic acid (14A)

SCHEME V

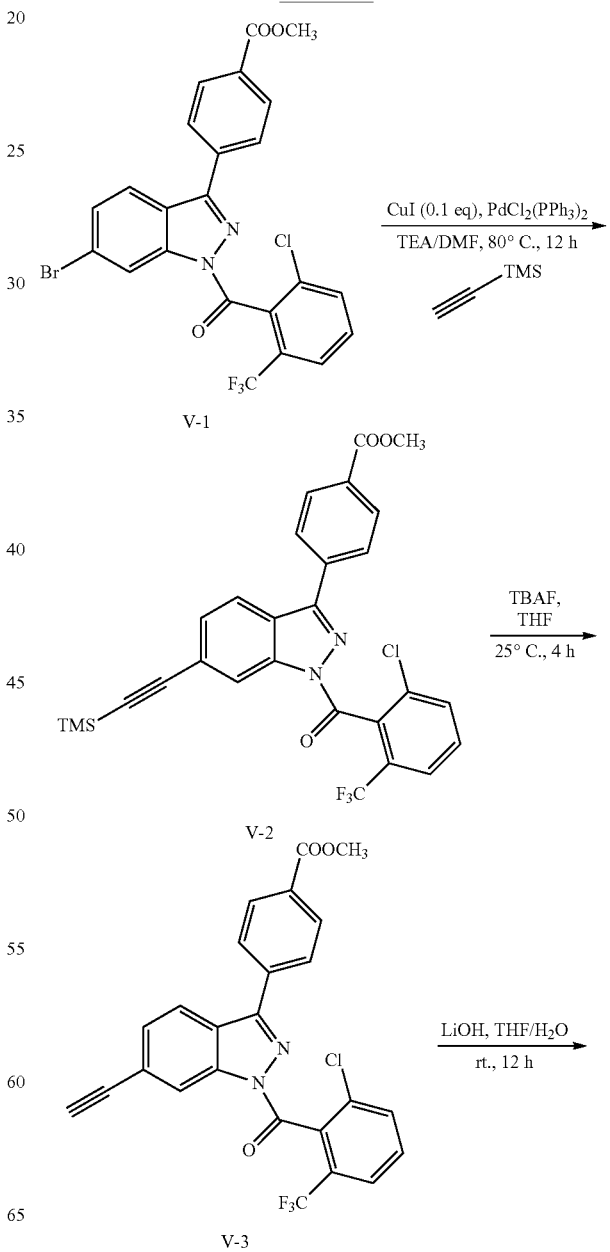

-continued

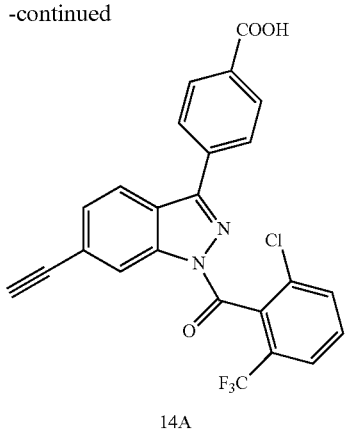

14A

Step 1. Preparation of methyl 4-(1-(2-chloro-6-(trifluoromethyl)benzoyl)-6-((trimethylsilyl)ethynyl)-1H-indazol-3-yl)benzoate (V-2)

To a solution of methyl 4-(6-bromo-1-(2-chloro-6-(trifluoromethyl)benzoyl)-1H-indazol-3-yl)benzoate (V-1) (108 mg, 0.2 mmol) in DMF (10 mL) and TEA (20 mL) was added ethynyltrimethylsilane (24 mg, 0.24 mmol), copper(I) iodide (4 mg, 0.02 mmol) and PdCl$_2$(PPh$_3$)$_2$ (14 mg, 0.02 mmol) under argon. The mixture was stirred under argon for 2 hours at 80° C. The mixture was diluted with H$_2$O. The aqueous layer was extracted with CH$_2$Cl$_2$ (3×50 mL). The combined organics were washed with H$_2$O, brine, dried over Na$_2$SO$_4$, and concentrated. The residue was purified by Prep-TLC (Pentane/EtOAc, 5/1) to afford 90 mg (87%) of the title compound. LCMS (ESI) calc'd for C$_{28}$H$_{22}$ClF$_3$N$_2$O$_3$Si [M+H]$^+$: 555.1. found: 555.1.

Step 2. Preparation of methyl 4-(1-(2-chloro-6-(trifluoromethyl)benzoyl)-6-ethynyl-1H-indazol-3-yl)benzoate (V-3)

To a solution of methyl 4-(1-(2-chloro-6-(trifluoromethyl)benzoyl)-6-((trimethylsilyl)ethynyl)-1H-indazol-3-yl)benzoate (V-2) (50 mg, 0.09 mmol) in THF (10 mL) at 0° C. was added TBAF (23 mg, 0.09 mmol). The mixture was stirred for 12 hours at room temperature. The mixture was diluted with H$_2$O. The aqueous layer was extracted with CH$_2$Cl$_2$ (3×80 mL). The combined organics were washed with H$_2$O, brine, dried over Na$_2$SO$_4$, and concentrated. The residue was purified by Prep-TLC (Pentane/EtOAc, 5/1) to afford 35 mg (92%) of the title compound. LCMS (ESI) calc'd for C$_{25}$H$_{14}$ClF$_3$N$_2$O$_3$ [M+H]+: 483. found: 483.

Step 3. Preparation of 4-(1-(2-chloro-6-(trifluoromethyl)benzoyl)-6-ethynyl-1H-indazol-3-yl)benzoic acid (14A)

To a stirred solution of methyl 4-(1-(2-chloro-6-(trifluoromethyl)benzoyl)-6-ethynyl-1H-indazol-3-yl)benzoate (V-3) (170 mg, 0.35 mmol) was added THF (8.0 mL), H$_2$O (2.0 mL) and LiOH.H$_2$O (74 mg, 1.76 mmol), and the solution was stirred at room temperature overnight. The solution was acidified with 1N HCl to pH=4.0, and diluted with THF (30 mL). The organic layer was separated and washed with brine (20 mL). The organic layer was dried over Na$_2$SO$_4$, concentrated, and purified by Prep-HPLC to afford 43 mg of the final product (yield: 26%). LCMS (ESI) calc'd for C$_{25}$H$_{14}$ClF$_3$N$_2$O$_3$ [M+H]+: 483.1. found: 483.1.

$^1$HNMR (500 MHz, DMSO) δ 13.36 (1H, bs), 8.56 (1H, s), 8.30 (1H, d), 8.10 (4H, d), 8.05 (3H, m), 7.76 (1H, d), 4.59 (1H, s).

Example 15A: Preparation of 4-(1-(2-chloro-6-(trifluoromethyl)benzoyl)-6-(3-methyl-1,2,4-oxadiazol-5-yl)-1H-indazol-3-yl)-3-fluorobenzoic acid (15A)

SCHEME W

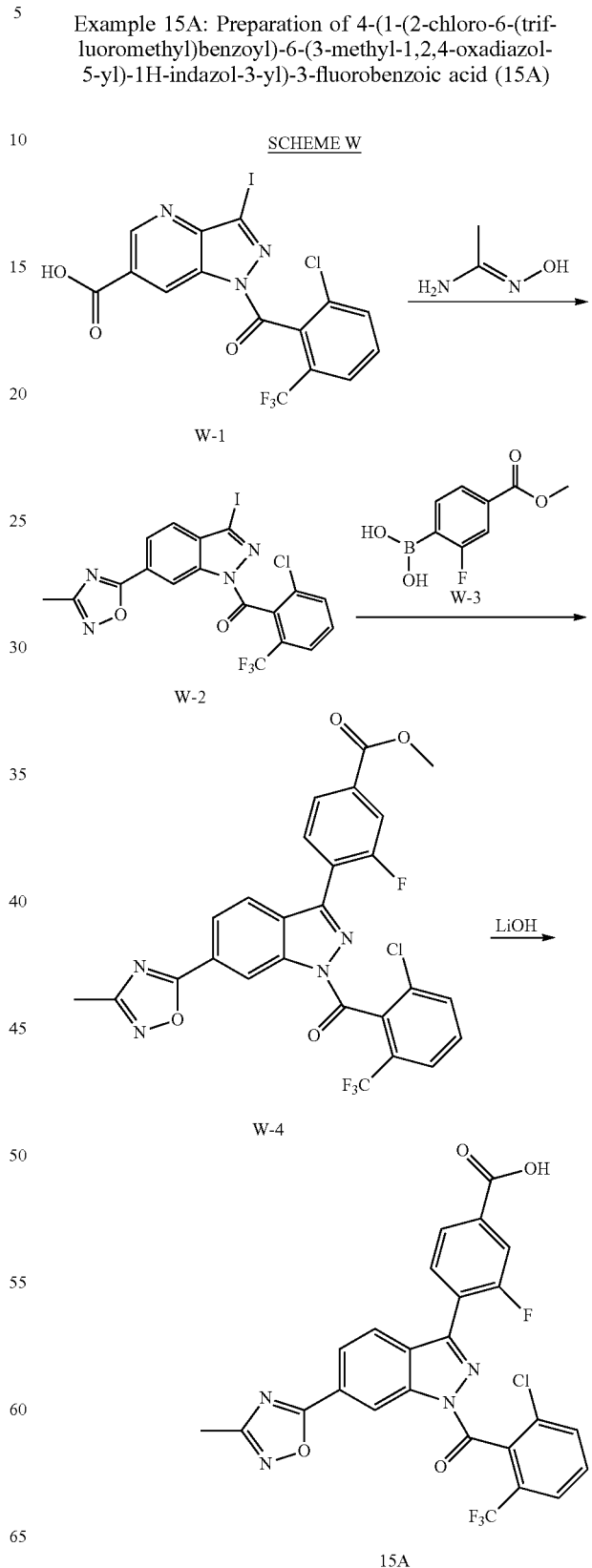

Step 1. Preparation of (2-chloro-6-(trifluoromethyl)phenyl)(3-iodo-6-(3-methyl-1,2,4-oxadiazol-5-yl)-1H-indazol-1-yl)methanone (W-2)

The mixture of 1-(2-chloro-6-(trifluoromethyl)benzoyl)-3-iodo-1H-indazole-6-carboxylic acid (W–1) (0.2 g, 0.4 mmol), N'-hydroxyacetimidamide (59 mg, 0.8 mmol), and HATU (0.3 g, 0.8 mmol) and DIPEA (0.13 mL, 0.80 mmol) in DCM (20 mL) was stirred at room temperature overnight. The reaction mixture was washed with 1M HCl solution, saturated NaHCO$_3$ solution, and brine respectively, dried over anhydrous Na$_2$SO$_4$ and concentrated. The residue was dissolved in 1,4-dioxane (20 mL) and heated at 100° C. overnight. The solvent was removed under reduced pressure, the residue was diluted with H$_2$O (50 mL), and the aqueous layer was extracted with ethyl acetate (50 mL×3). The combined organic layers were washed with brine (50 mL×1), dried over anhydrous Na$_2$SO$_4$, and concentrated. The residue was purified with Prep-TLC (PE:EA=5:2) to obtain the desired product W-2 as a white solid (85 mg, 40%). LCMS (ESI) calc'd for C$_{18}$H$_9$ClF$_3$IN$_4$O$_2$ [M+H]$^+$: 533. found: 533.

Step 2. Preparation of methyl 4-(1-(2-chloro-6-(trifluoromethyl)benzoyl)-6-(3-methyl-1,2,4-oxadiazol-5-yl)-1H-indazol-3-yl)-3-fluorobenzoate (W-4)

A mixture of (2-chloro-6-(trifluoromethyl)phenyl)(3-iodo-6-(3-methyl-1,2,4-oxadiazol-5-yl)-1H-indazol-1-yl)methanone (W-2) (100 mg, 0.19 mol), W-3 (56 mg, 0.29 mol), Pd(OAc)$_2$ (4 mg, 0.019 mol), s-phos (8 mg, 0.019 mol) and K$_3$PO$_4$ (121 mg, 0.57 mol) was suspended in 1,4-dioxane (5 mL) and H$_2$O (1 mL). The reaction mixture was heated at 100° C. in a microwave reactor for 2 h. The resulting mixture was diluted with H$_2$O (50 mL) and the aqueous layer was extracted with ethyl acetate (50 mL×3). The combined organic layers were washed with brine (50 mL×1), dried over anhydrous Na$_2$SO$_4$, and concentrated to obtain the desired product W-4 as a yellow solid (65 mg, 45%). LCMS (ESI) calc'd for C$_{26}$H$_{15}$ClF$_4$N$_4$O$_4$ [M+H]$^+$: 559. found: 559.

Step 3. Preparation of 4-(1-(2-chloro-6-(trifluoromethyl)benzoyl)-6-(3-methyl-1,2,4-oxadiazol-5-yl)-1H-indazol-3-yl)-3-fluorobenzoic acid (15A)

A mixture of methyl 4-(1-(2-chloro-6-(trifluoromethyl)benzoyl)-6-(3-methyl-1,2,4-oxadiazol-5-yl)-1H-indazol-3-yl)-3-fluorobenzoate (W-4) (150 mg, 0.27 mmol) and LiOH (57 mg, 1.35 mmol) in THF (4 mL) and H$_2$O (2 mL) was stirred at room temperature for 4 h. The reaction mixture was diluted with H$_2$O (20 mL), and acidified with 2N HCl solution to pH=~3. The mixture was extracted with ethyl acetate (20 mL×3). The combined organic layers were washed with brine (20 mL×1), dried over anhydrous Na$_2$SO$_4$, and concentrated. The residue was purified with Prep-HPLC to obtain the desired product 15A as a white solid (130 mg, 90%). LCMS (ESI): calc'd for C$_{25}$H$_{13}$ClF$_4$N$_4$O$_4$ [M+H]$^+$: 545. found: 545; $^1$HNMR (400 MHz, MeOD) δ 8.36 (1H, s), 8.34 (1H, d, J=8.4 Hz), 8.17 (1H, d, J=8.4 Hz), 7.97-7.99 (2H, m), 7.89-7.94 (2H, m), 7.81 (1H, d, J=8.4 Hz), 7.73-7.78 (1H, m), 2.54 (3H, s).

Example 16A: Preparation 4-(1-(2-chloro-6-(trifluoromethyl)benzoyl)-6-(5-(hydroxymethyl)oxazol-2-yl)-1H-indazol-3-yl)-3-fluorobenzoic acid (16A)

SCHEME X

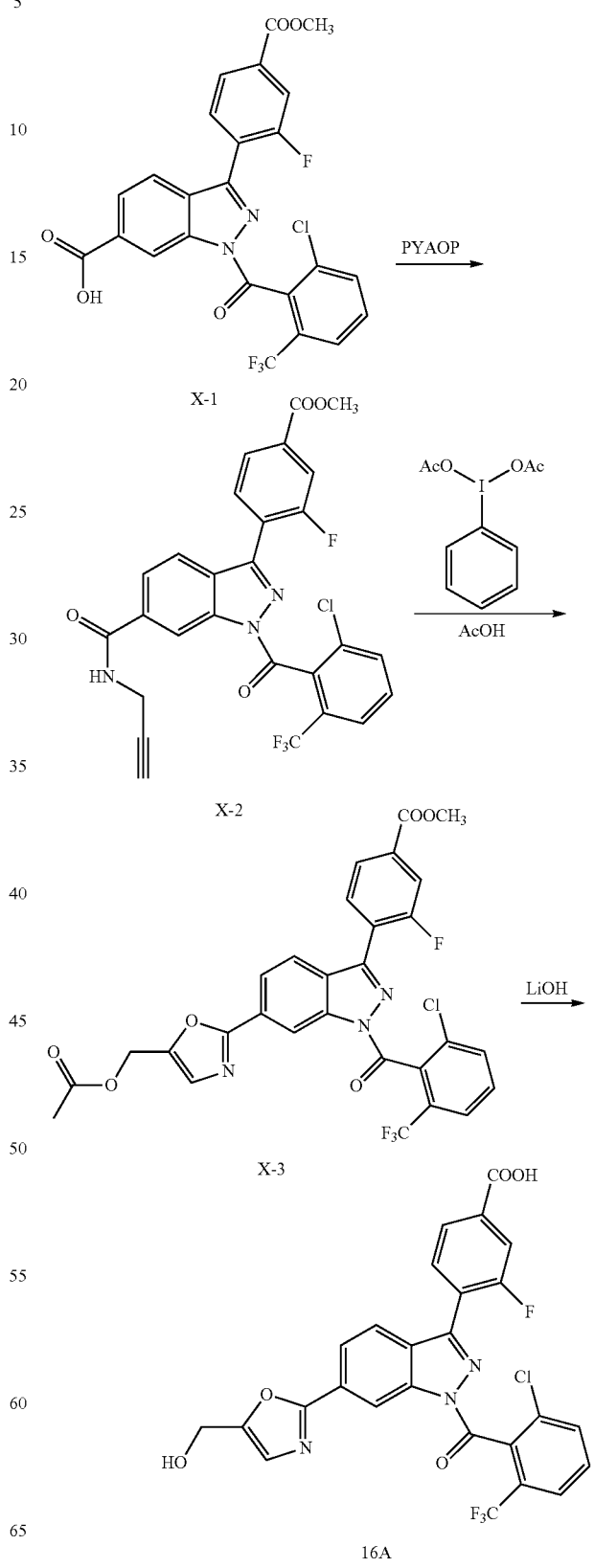

Step 1: Preparation of methyl 4-(1-(2-chloro-6-(trifluoromethyl)benzoyl)-6-(prop 2-ynylcarbamoyl)-1H-indazol-3-yl)-3-fluorobenzoate (X-2)

1-(2-Chloro-6-trifluoromethyl)benzoyl)-3-(2-fluoro-4-(methoxycarbonyl)phenyl)-1H-indazole-6-carboxylic acid (X-1) (100 mg, 0.2 mmol) was dissolved in CH$_2$Cl$_2$ (15 mL), followed by the addition of prop-2-yn-1-amine (13 mg, 0.24 mmol) and PYAOP (208 mg, 0.4 mmol). The mixture was stirred at room temperature for 2 mins, followed by the addition of TEA (0.16 mL, 1.08 mmol). The mixture was stirred at room temperature for 2 h, diluted with EtOAC (20 mL), washed with brine (20 mL×2), dried over anhydrous Na$_2$SO$_4$, and concentrated to give 85 mg of crude product, which was used in the next step without further purification. LCMS (ESI): calc'd for C$_{27}$H$_{16}$ClF$_4$N$_3$O$_4$, [M+H]$^+$: 557.1. found: 557.1.

Step 2: Preparation of methyl 4-(6-(5-(acetoxymethyl)oxazol-2-yl)-1-(2-chloro-6-(trifluoromethyl)benzoyl)-1H-indazol-3-yl)-3-fluorobenzoate (X-3)

Methyl-(1-(2-chloro-6-(trifluoromethyl)benzoyl)-6-(prop-2-ynylcarbamoyl)-1H-indazol-3-yl)-3-fluorobenzoate (X-2) (85 mg, 0.15 mmol) was dissolved in AcOH (15 mL), followed by the addition of (diacetoxyiodo)benzene (73 mg, 0.23 mmol). The mixture was stirred at 90° C. for 12 hours. Then the mixture was diluted with EtOAC (20 mL), washed with brine (20 mL×2), dried over anhydrous Na$_2$SO$_4$, and concentrated to obtain the crude product X-3 (60 mg), which was used in the next step without further purification. LCMS (ESI): calc'd for C$_{30}$H$_{19}$ClF$_4$N$_2$O$_6$, [M+H]$^+$: 614.1. found: 614.1.

Step 3: Preparation of 4-(1-(2-chloro-6-(trifluoromethyl)benzoyl)-6-(5-(hydroxyl methyl)oxazol-2-yl)-1H-indazol-3-yl)-3-fluorobenzoic acid (16A)

A mixture of methyl 4-(1-(2-chloro-6-(trifluoromethyl)benzoyl)-6-(prop-2-ynyl carbamoyl)-1H-indazol-3-yl)-3-fluorobenzoate (X-3) (25 mg, 0.04 mmol) and LiOH.H$_2$O (10 mg, 0.25 mmol) in 10 mL THF and 10 mL pure H$_2$O was stirred at room temperature for 2 hours. The solvent was evaporated and the residue was dissolved in water. HCl (5% sol. in water) was added until pH 4-5. The precipitated solid was filtered, washed with water and n-hexane, and dried to afford an off-white solid 16A (15 mg, 80%). LCMS (ESI): calc'd for C$_{27}$H$_{15}$ClF$_4$N$_2$O$_5$, [M+H]$^+$: 558.1 found: 558.1. $^1$HNMR (400 MHz, DMSO) δ 9.09 (1H, s), 8.22-8.24 (1H, d, J=8 Hz), 8.11-8.13 (1H, d, J=8 Hz), 8.05-8.07 (1H, d, J=8 Hz), 8.00-8.02 (1H, d, J=8 Hz), 7.88-7.95 (3H, m), 7.77-7.81 (1H, m), 7.35 (1H, s), 4.63 (2H, s).

Example 17A: Preparation of 4-(1-(2-chloro-6-(trifluoromethyl)benzoyl)-6-(1-methyl-1H-imidazol-4-yl)-1H-indazol-3-yl)-3-fluorobenzoic acid (17A)

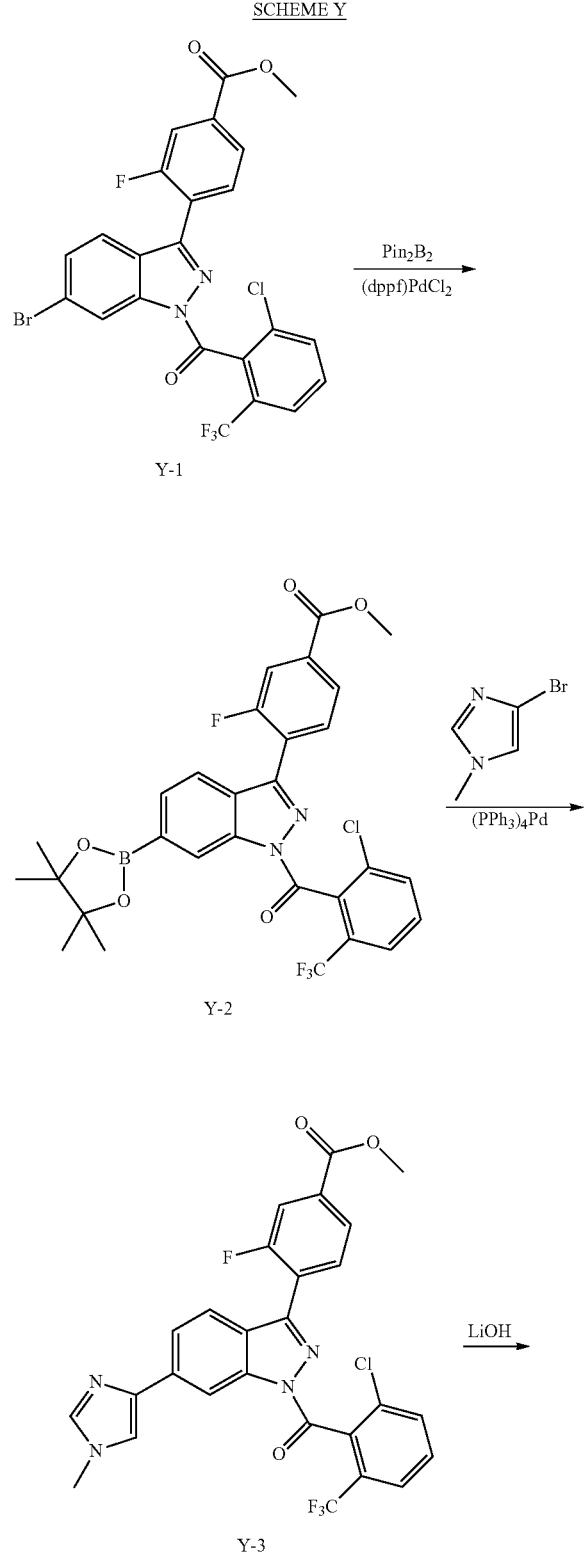

SCHEME Y

149
-continued

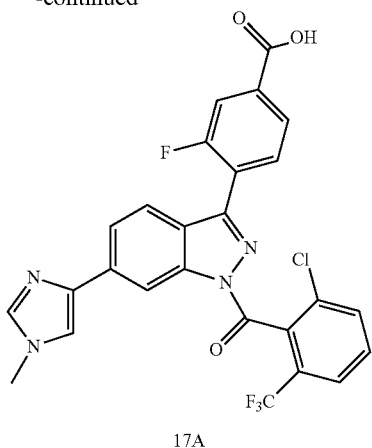

17A

Step 1. Preparation of methyl 4-(1-(2-chloro-6-(trifluoromethyl)benzoyl)-6-(4,4,5,5-tetramethyl-1,3,2-dioxaborolan-2-yl)-1H-indazol-3-yl)-3-fluorobenzoate (Y-2)

To the solution of methyl 4-(6-bromo-1-(2-chloro-6-(trifluoromethyl)benzoyl)-1H-indazol-3-yl)-3-fluorobenzoate (Y-1) (161 mg, 0.29 mmol) in dioxane (5 mL) was added $Pin_2B_2$ (151 mg, 0.58 mmol), KOAc (115 mg, 1.16 mmol) and (dppf)PdCl$_2$ (21 mg, 0.029 mmol) under $N_2$ protection. The mixture was heated at 90° C. for 6 h. Then the mixture was cooled down and diluted with EtOAc (100 mL), washed with $H_2O$ (20 mL×3), brine (20 mL), dried and concentrated. The residue was purified with chromatography (PE:EA=6:1) to afford 125 mg of the final product (yield: 71%). LCMS (ESI) calc'd [M+H]$^+$: 602.0. found: 602.1.

150

Step 2. Preparation of methyl 4-(1-(2-chloro-6-(trifluoromethyl)benzoyl)-6-(1-methyl-1H-imidazol-4-yl)-1H-indazol-3-yl)-3-fluorobenzoate (Y-3)

To the solution of methyl 4-(6-bromo-1-(2-chloro-6-(trifluoromethyl)benzoyl)-1H-indazol-3-yl)-3-fluorobenzoate (Y-2) (50 mg, 0.083 mmol) in dioxane (5 mL) was added 4-bromo-1-methyl-1H-imidazole (20 mg, 0.1 mmol), $K_2CO_3$ (30 mg, 0.2 mmol) and (PPh$_3$)$_4$Pd (10 mg, 0.0083 mmol) under $N_2$ protection. The mixture was protected by $N_2$ and stirred at 85° C. for 16 h. The solution was cooled down, concentrated, and purified by Prep-HPLC (ACN:$H_2O$) to afford 5 mg of product (yield: 7.2%). LCMS (ESI) calc'd [M+H]$^+$: 557. found: 557.

Step 3. Preparation of 4-(1-(2-chloro-6-(trifluoromethyl)benzoyl)-6-(1-methyl-1H imidazol-4-yl)-1H-indazol-3-yl)-3-fluorobenzoic acid (17A)

To the solution of methyl 4-(1-(2-chloro-6-(trifluoromethyl)benzoyl)-6-(1-methyl-1H-imidazol-4-yl)-1H-indazol-3-yl)-3-fluorobenzoate (Y-3) (5 mg, 0.009 mmol) in THF (2 mL) and $H_2O$ (0.5 mL) was added LiOH (1 mg, 0.045 mmol). The mixture solution was stirred at room temperature for 16 h, acidified by HCl (2N), and extracted with EtOAc (10 mL×3). The organic layer was dried, concentrated, and purified by Prep-HPLC (ACN:$H_2O$) to afford 5 mg of final product (yield: 100%). LCMS (ESI) calc'd [M+H]$^+$: 543. found: 543.

Example 18A: Preparation of 4-(1-(2-chloro-6-(trifluoromethyl)benzoyl)-6-(oxazol-2-yl)-1H-indazol-3-yl)-3-fluorobenzoic acid (18A)

SCHEME Z

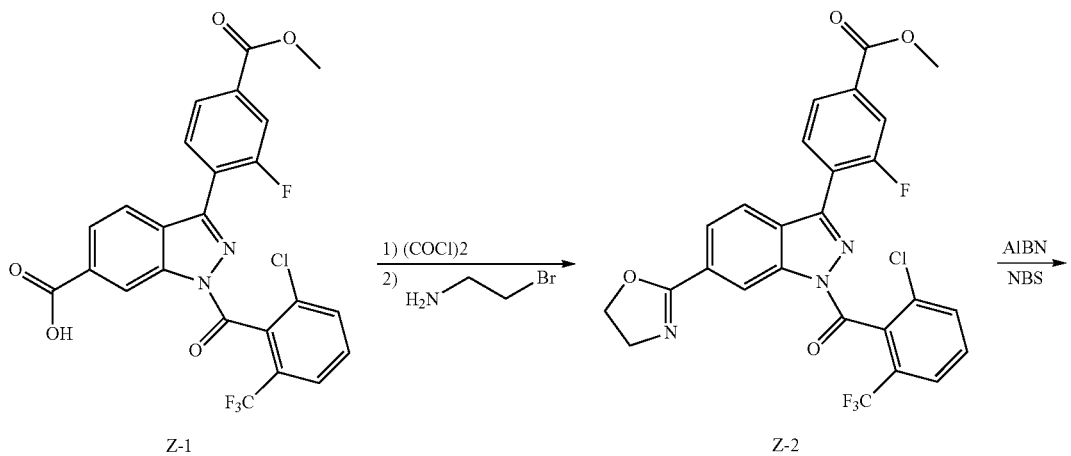

Z-1     Z-2

-continued

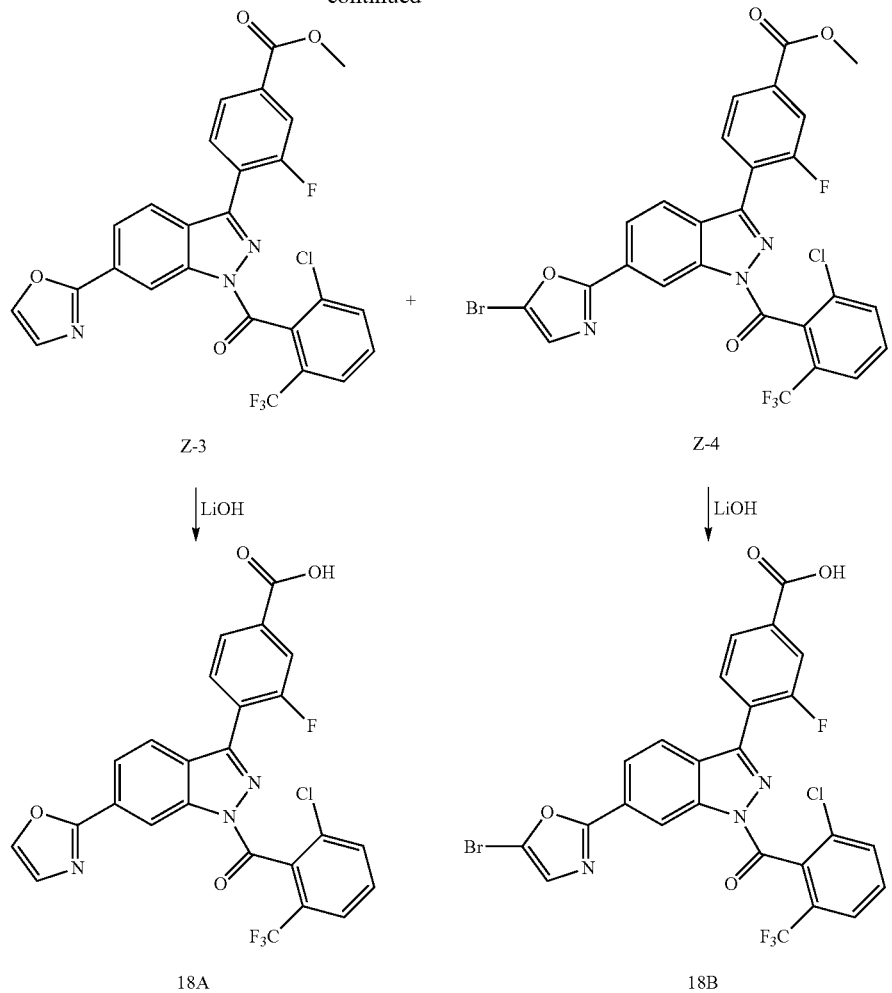

Step 1. Preparation of methyl 4-(1-(2-chloro-6-(trifluoromethyl)benzoyl)-6-(4,5-dihydrooxazol-2-yl)-1H-indazol-3-yl)-3-fluorobenzoate (Z-2)

A mixture of 1-(2-chloro-6-(trifluoromethyl)benzoyl)-3-(2-fluoro-4-(methoxycarbonyl)phenyl)-1H-indazole-6-carboxylic acid (Z-1) (286 mg, 0.55 mmol) and (COCl)$_2$ (0.14 mL, 1.65 mmol) in DCM (5 mL) and DMF (2 drops) was stirred at room temperature for 1 h. The solvent was removed and the residue was dissolved in anhydrous toluene (5 mL). The resulting solution was added to a mixture of 2-bromoethanamine (86 mg, 0.7 mmol) and Et$_3$N (167 mg, 1.65 mmol) in anhydrous toluene (5 mL). The reaction mixture was stirred at 85° C. for 3 hours. The solvent was evaporated and the residue was purified by flash chromatography (PE:DCM=1:10) to give the desired product Z-2. LCMS (ESI) calc'd for C$_{26}$H$_{16}$ClF$_4$N$_3$O$_4$ [M+H]$^+$: 546. found: 546.

Step 2. Preparation of methyl 4-(1-(2-chloro-6-(trifluoromethyl)benzoyl)-6-(oxazol-2-yl)-1H-indazol-3-yl)-3-fluorobenzoate (Z-3) and Step 3. Preparation of methyl 4-(6-(5-bromooxazol-2-yl)-1-(2-chloro-6-(trifluoromethyl)benzoyl)-1H-indazol-3-yl)-3-fluorobenzoate (Z-4)

A mixture of methyl 4-(1-(2-chloro-6-(trifluoromethyl)benzoyl)-6-(4,5-dihydrooxazol-2-yl)-1H-indazol-3-yl)-3-fluorobenzoate (Z-2) (300 mg, 0.55 mmol), AIBN (9 mg, 0.055 mmol) and NBS (587 mg, 3.3 mmol) in CCl$_4$ (15 mL) under argon was made, and the reaction mixture was refluxed for 12 hours. The solvent was evaporated and the residue was purified by column chromatography on silica gel eluting with (PE:DCM=1:4) to afford two products:

Z-3. (200 mg, 66%). LCMS (ESI) calc'd for C$_{26}$H$_{14}$ClF$_4$N$_3$O$_4$ [M+H]$^+$: 544. found: 544.

Z-4. LCMS (ESI) calc'd for C$_{26}$H$_{13}$BrClF$_4$N$_3$O [M+H]+: 622. found: 622.

Step 4. Preparation of 4-(1-(2-chloro-6-(trifluoromethyl)benzoyl)-6-(oxazol-2-yl)-1H-indazol-3-yl)-3-fluorobenzoic acid (18A)

A mixture of methyl 4-(1-(2-chloro-6-(trifluoromethyl)benzoyl)-6-(oxazol-2-yl)-1H-indazol-3-yl)-3-fluorobenzoate (Z-3) (38 mg, 0.07 mmol) and LiOH.H$_2$O (16 mg, 0.37 mmol) in 10 mL THF and 10 mL pure H$_2$O was stirred at room temperature for 2 hours. The solvent was evaporated and the residue was dissolved in water. HCl (5% sol. in water) was added until pH=4-5. The precipitated solid was filtered, washed with water (10 mL) and n-hexane (10 mL), and dried to afford an off-white solid 18A (32 mg, 93%). LCMS (ESI): calc'd for C$_{25}$H$_{12}$ClF$_4$N$_3$O$_4$, [M+H]$^+$: 530 found: 530; ¹HNMR (400 MHz, DMSO) δ 13.57 (1H, s), 9.12 (1H, s), 8.40 (1H, s), 8.24-8.26 (1H, d, J=8 Hz), 8.12-8.14 (1H, d, J=8 Hz), 8.00-8.07 (2H, m), 7.88-7.95 (3H, m), 7.78-7.81 (1H, m), 7.55 (1H, s).

Step 5. Preparation of 4-(6-(5-bromooxazol-2-yl)-1-(2-chloro-6-(trifluoro methyl)benzoyl)-1H-indazol-3-yl)-3-fluorobenzoic acid (18B)

By following the same method as for the synthesis of compound 18A, but starting from Z-4, the desired product 18B was prepared. LCMS (ESI): calc'd for C₂₅H₁₁BrClF₄N₃O₄, [M+H]+: 608 found: 608; ¹HNMR (400 MHz, DMSO) δ 13.57 (1H, s), 9.05 (1H, s), 8.19-8.21 (1H, d, J=8 Hz), 8.12-8.14 (1H, d, J=8 Hz), 8.05-8.06 (1H, d, J=4 Hz), 8.00-8.02 (1H, d, J=8 Hz), 7.93-7.95 (1H, d, J=8 Hz), 7.86-7.88 (2H, m), 7.77-7.80 (1H, m), 7.61 (1H, s).

Example 19A: Preparation of (E)-4-(1-(2-chloro-6-(trifluoromethyl)benzoyl)-6-(N'-cyano-N,N-dimethylcarbamimidoyl)-1H-indazol-3-yl)-3-fluorobenzoic acid (19A)

SCHEME AA

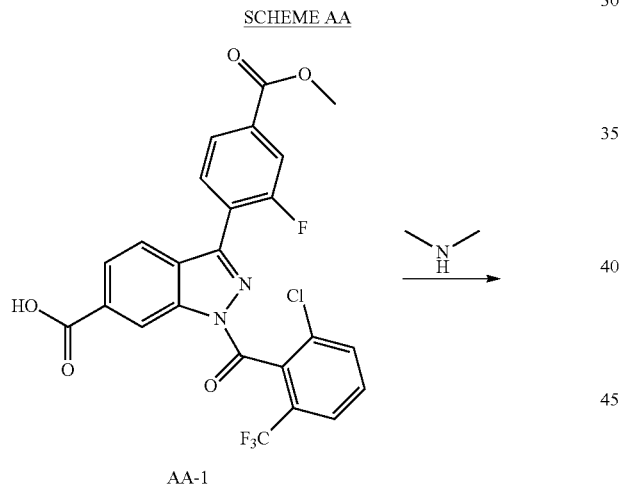

AA-1

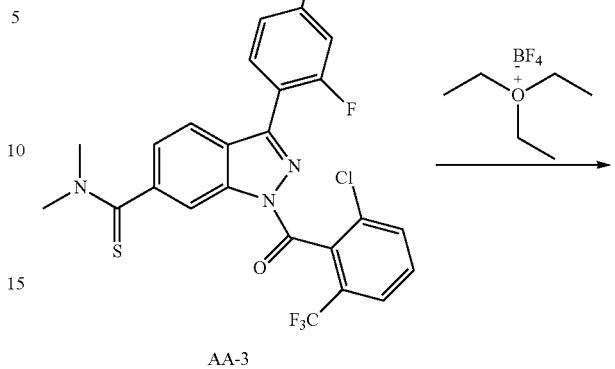

AA-3

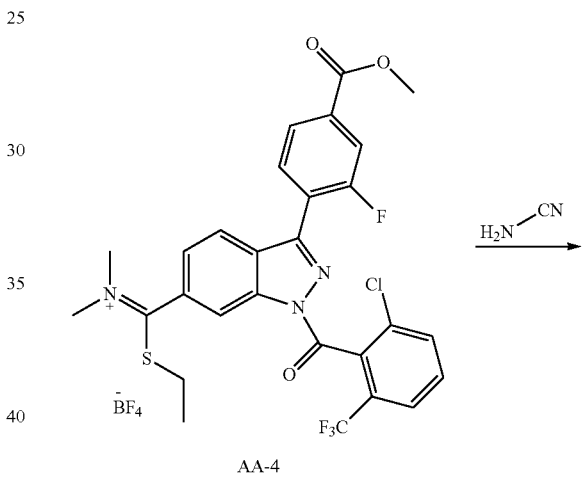

AA-4

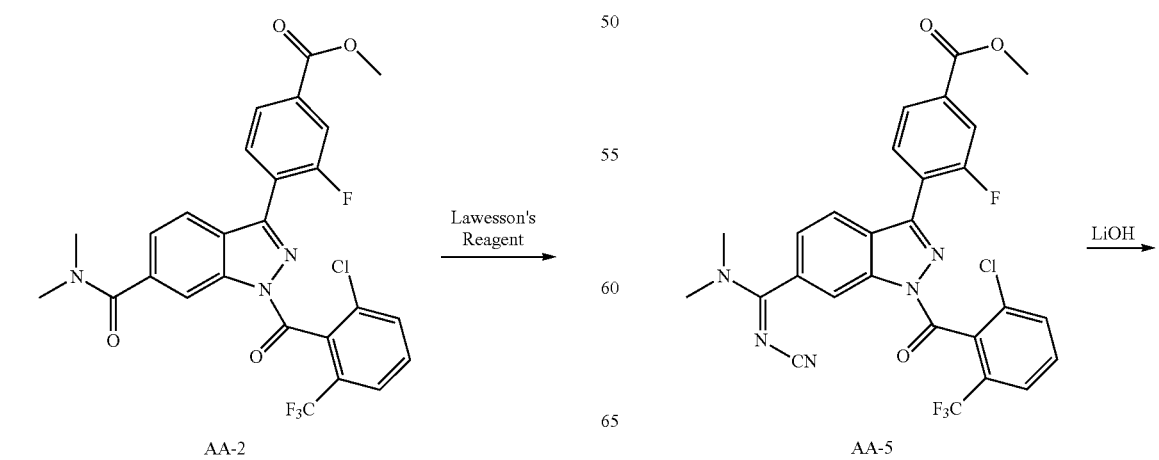

AA-2

AA-5

-continued

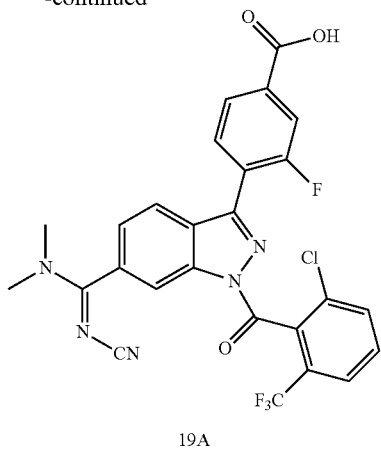

19A

Step 1. Preparation of methyl 4-(1-(2-chloro-6-(trifluoromethyl)benzoyl)-6-(dimethylcarbamoyl)-1H-indazol-3-yl)-3-fluorobenzoate (AA-2)

The mixture of 1-(2-chloro-6-(trifluoromethyl)benzoyl)-3-(2-fluoro-4-(methoxycarbonyl)phenyl)-1H-indazole-6-carboxylic acid (AA-1) (250 mg, 0.48 mmol), dimethylamine (2.0 M solution in THF, 0.36 mL, 0.72 mmol), HATU (220 mg, 0.58 mmol) and Et$_3$N (0.13 mL, 0.96 mmol) in DCM (10 mL) was stirred at room temperature for 1 h. The solvent was removed under reduced pressure and the residue was chromatographed on silica gel (PE:EA 1:1) to obtain the desired product as a white solid (200 mg, 86%). LCMS (ESI) calc'd for $C_{26}H_{18}ClF_4N_3O_4$ [M+H]$^+$: 548. found: 548.

Step 2. Preparation of methyl 4-(1-(2-chloro-6-(trifluoromethyl)benzoyl)-6-(dime thylcarbamothioyl)-1H-indazol-3-yl)-3-fluorobenzoate (AA-3)

The mixture of methyl 4-(1-(2-chloro-6-(trifluoromethyl)benzoyl)-6-(dimethylcarbamoyl)-1H-indazol-3-yl)-3-fluorobenzoate (AA-2) (240 mg, 0.44 mmol) and Lawesson Reagent (360 mg, 0.88 mmol) in toluene (10 mL) was stirred at 100° C. for 4 h. The solvent was removed under reduced pressure and the residue was chromatographed on silica gel (PE:EA 5:1) to obtain the desired product as a yellow solid (180 mg, 70%). LCMS (ESI) calc'd for $C_{26}H_{18}ClF_4N_3O_3S$ [M+H]$^+$: 564. found: 564.

Step 3. Preparation of tetrafluoroborate of methyl 4-(1-(2-chloro-6-(trifluoro methyl)benzoyl)-6-((dimethylamino)(ethylthio)methyl)-1H-indazol-3-yl)-3-fluorobenzoate (AA-4)

The mixture of methyl 4-(1-(2-chloro-6-(trifluoromethyl)benzoyl)-6-(dimethylcarbamothioyl)-1H-indazol-3-yl)-3-fluorobenzoate (AA-3) (145 mg, 0.26 mmol) and triethyloxonium tetrafluoroborate (1.0 M solution in DCM, 0.31 mL, 0.31 mmol) in DCE (6 mL) was stirred at 85° C. overnight. The solvent was removed under reduced pressure to obtain the crude product as a yellow solid. The crude product was used in the next step without further purification. LCMS (ESI) calc'd for $C_{28}H_{23}BClF_8N_3O_3S$ [M+H]$^+$: 592. found: 592.

Step 4. Preparation of (E)-methyl 4-(1-(2-chloro-6-(trifluoromethyl)benzoyl)-6-(N'-cyano-N,N-dimethylcarbamimidoyl)-1H-indazol-3-yl)-3-fluorobenzoate (AA-5)

The mixture of methyl 4-(1-(2-chloro-6-(trifluoromethyl)benzoyl)-6-((dimethyl amino)(ethylthio)methyl)-1H-indazol-3-yl)-3-fluorobenzoate (AA-4) (150 mg, 0.26 mmol), cyanamide (37 mg, 0.88 mmol) and Et$_3$N (44 mg, 0.44 mmol) in MeOH (5 mL) was stirred at room temperature for 2 h. The resulting solution was diluted with water (30 mL) and the aqueous layer was extracted with EtOAc (20 mL×3). The combined organic layers were washed with 1N HCl solution (20 mL×1) then brine (20 mL×1), dried over anhydrous Na$_2$SO$_4$ and concentrated to obtain the desired crude product AA-5 (160 mg) as a yellow solid. LCMS (ESI) calc'd for $C_{27}H_{18}ClF_4N_5O_3$ [M+H]$^+$: 572. found: 572.

Step 5. Preparation of (E)-4-(1-(2-chloro-6-(trifluoromethyl)benzoyl)-6-(N'-cyano-N,N-dimethylcarbamimidoyl)-1H-indazol-3-yl)-3-fluorobenzoic acid (19A)

The mixture of (E)-methyl 4-(1-(2-chloro-6-(trifluoromethyl)benzoyl)-6-(N'-cyano-N, N-dimethylcarbamimidoyl)-1H-indazol-3-yl)-3-fluorobenzoate (AA-5) (100 mg, 0.18 mmol) and LiOH (30 mg, 0.72 mmol) in THF (4 mL) and H$_2$O (2 mL) was stirred at room temperature for 3 h. The reaction mixture was diluted with H$_2$O (20 mL). 2 M HCl solution was added to adjust the pH to 3 and the aqueous layer was extracted with ethyl acetate (20 mL×3). The combined organic layers were washed with brine (20 mL×1), dried over anhydrous Na$_2$SO$_4$ and concentrated. The residue was purified with Prep-HPLC (acetonitrile-water system) to obtain the desired product 6 as a white solid (50 mg, 50%). LCMS (ESI) calc'd for $C_{26}H_{16}ClF_4N_5O_3$ [M+H]$^+$: 558. found: 558; $^1$HNMR (400 MHz, MeOD) δ 8.68 (1H, s), 8.15-8.18 (1H, m), 7.93-7.98 (2H, m), 7.87-7.91 (2H, m), 7.77-7.81 (1H, m), 7.72-7.76 (1H, m), 7.61 (1H, d, J=8.4 Hz), 3.37 (3H, s), 3.09 (3H, s).

Example 20A: Preparation of 4-(1-(2-chloro-6-(trifluoromethyl)benzoyl)-6-(5-oxo-4,5-dihydro-1,3,4-oxadiazol-2-yl)-1H-indazol-3-yl)-3-fluorobenzoic acid (20A)

SCHEME AB

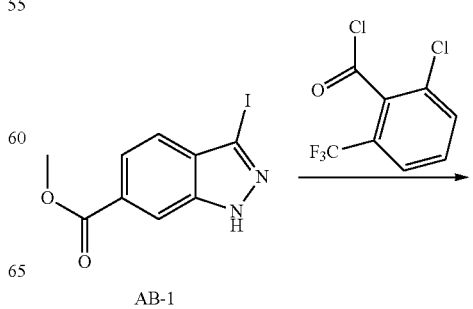

AB-1

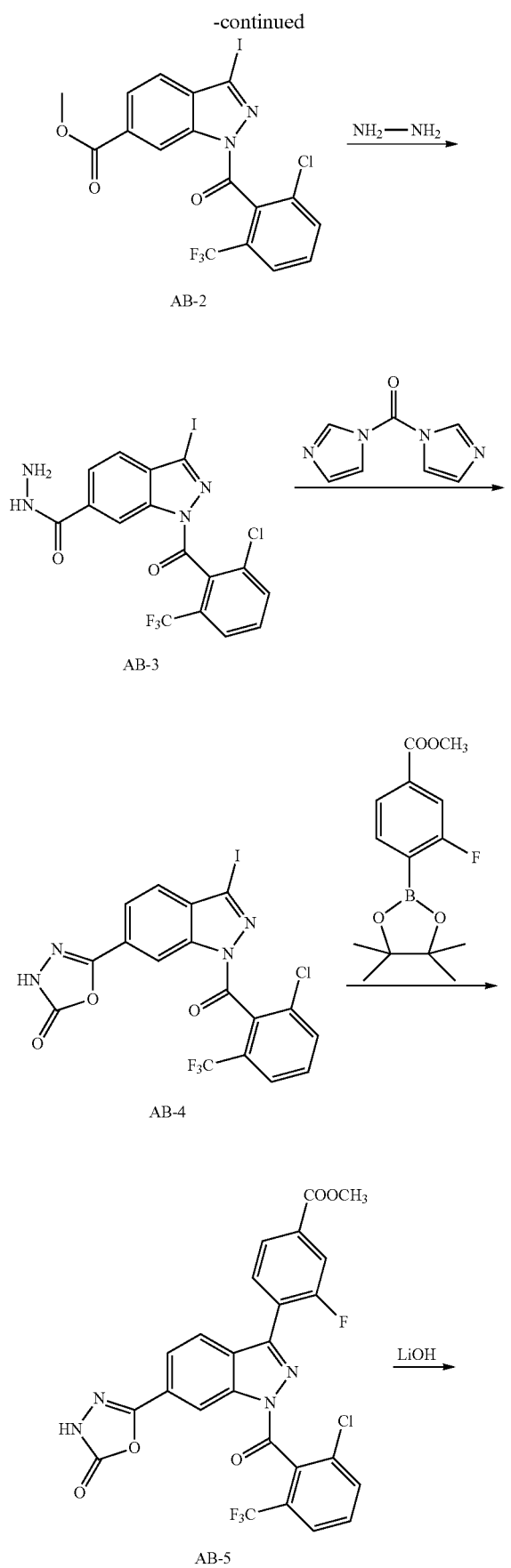

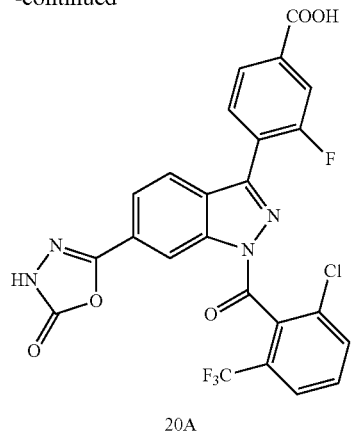

Step 1. Preparation of methyl 1-(2-chloro-6-(trifluoromethyl)benzoyl)-3-iodo-1H-indazole-6-carboxylate (AB-2)

To a stirred solution of methyl 3-iodo-1H-indazole 6-carboxylate (AB-1) (2 g, 6.62 mmol) in anhydrous DCM (60 mL) at room temperature was added 2-chloro-6-(trifluoromethyl)benzoyl chloride (2.4 g, 9.93 mmol), DMAP (161 mg, 1.32 mmol), and Et$_3$N (1.47 mg, 14.57 mmol). The solution was stirred at room temperature overnight. The solution was diluted with EtOAc (50 mL), filtered through celite and washed with DCM (40 mL). The combined organic layer was washed with H$_2$O (20 mL), brine (20 mL) and dried over anhydrous Na$_2$SO$_4$. The solution was evaporated with silica gel and loaded on a column. SGC (DCM) afforded 3.25 g product. Yield 98.5%. LCMS (ESI) calc'd for C$_{17}$H$_9$ClF$_3$IN$_2$O$_3$ [M+H]$^+$: 509. found: 509.

Step 2. Preparation of 1-(2-chloro-6-(trifluoromethyl)benzoyl)-3-iodo-1H-indazole-6-carbohydrazide (AB-3)

To a stirred solution of methyl1-(2-chloro-6-(trifluoromethyl)benzoyl)-3-iodo-1H-indazole-6-carboxylate (AB-2) (1000 mg, 1.97 mmol) in ethanol (40 mL) was added NH$_2$NH$_2$H$_2$O (0.31 ml, 9.83 mmol). The solution was stirred at reflux temperature overnight. LCMS showed complete transformation to the product. The solution was diluted with H$_2$O (100 mL), and extracted with EtOAc (3×60 mL). The combined organic layer was washed with H$_2$O (2×20 mL), brine (30 mL) and dried over anhydrous Na$_2$SO$_4$. The solution was evaporated with silica gel and loaded on a column. Prep-TLC (DCM) afforded 176 mg product. Yield 18%. LCMS (ESI) calc'd for C$_{16}$H$_9$ClF$_3$IN$_4$O$_2$ [M+H]$^+$: 509. found: 509.

Step 3. Preparation of 5-(1-(2-chloro-6-(trifluoromethyl)benzoyl)-3-iodo-1H-indazol-6-yl)-1,3,4-oxadiazol-2(3H)-one (AB-4)

To a stirred solution of 1-(2-chloro-6-(trifluoromethyl)benzoyl)-3-iodo-1H-indazole-6-carbohydrazide (AB-3) (100 mg, 0.196 mmol) in THF (2 mL) was added CDI (48 mg, 0.294 mmol) and Et$_3$N (30 mg, 0.294 mmol). The solution was stirred at room temperature overnight. The solution was diluted with H$_2$O (30 mL) and extracted with EtOAc (2×30 mL), and the organic layer was washed with H<sub>2</sub>O (30 mL) and brine (30 mL) and dried over anhydrous Na<sub>2</sub>SO<sub>4</sub>. The organic layer was evaporated with silica gel and loaded on a silica gel column. SGC (PE/EA: 2/1) gave 60 mg product, yield 57%. LCMS (ESI) calc'd for $C_{17}H_7ClF_3IN_4O_3$ [M+H]$^+$: 535. found: 535.

Step 4. Preparation of methyl 4-(1-(2-chloro-6-(trifluoromethyl)benzoyl)-6-(5-oxo-4,5-dihydro-1,3,4-oxadiazol-2-yl)-1H-indazol-3-yl)-3-fluorobenzoate (AB-5)

To a microwave tube was added 5-(1-(2-chloro-6-(trifluoromethyl)benzoyl)-3-iodo-1H-indazol-6-yl)-1,3,4-oxadiazol-2(3H)-one (AB-4) (60 mg, 0.11 mmol), methyl 3-fluoro 4-(4,4,5,5-tetramethyl-1,3,2-dioxaborolan-2-yl)benzoate (44 mg, 0.22 mmol), Pd(OAc)<sub>2</sub> (trimer) (1.23 mg, 0.01 mmol), s-Phos (4.4 mg, 0.01 mmol), K<sub>3</sub>PO<sub>4</sub> (80 mg, 0.33 mmol), THF (1.5 mL), H<sub>2</sub>O (0.3 mL). The solution was microwaved under argon at 110° C. for 2 hours. LCMS showed major product peak. The upper solution was filtered and used in the next step without further purification. LCMS (ESI) calc'd for $C_{25}H_{13}ClF_4N_4O_5$[M+H]$^+$: 560. found: 560.

Step 5. Preparation of 4-(1-(2-chloro-6-(trifluoromethyl)benzoyl)-6-(5-oxo-4,5-dihydro-1,3,4-oxadiazol-2-yl)-1H-indazol-3-yl)-3-fluorobenzoic acid (20A)

To a stirred solution of methyl4-(1-(2-chloro-6-(trifluoromethyl)benzoyl)-6-(5-oxo-4,5-dihydro-1,3,4-oxadiazol-2-yl)-1H-indazol-3-yl)-3-fluorobenzoate (AB-5) (as generated in step 4) was added LiOH.H<sub>2</sub>O (10 mg, 0.4 mmol) and H<sub>2</sub>O (0.1 mL). The solution was stirred overnight and LCMS showed major product peak. The solution was adjusted to PH=3.0 using 1 N HCl. The upper organic layer was collected and the aqueous layer was extracted with THF (3×1 mL). To the combined organic layer was added 0.5 mL MeOH, submitting for Prep-HPLC (H<sub>2</sub>O/ACN, 0.05% TFA) gave 15 mg product, and the yield for two steps was 25%. LCMS (ESI) calc'd for $C_{24}H_{11}ClF_4N_4O_5$ [M+H]$^+$: 547. found: 547. <sup>1</sup>HNMR (400 MHz, DMSO) δ 13.60 (1H, s), 13.00 (1H, s), 8.87 (1H, s), 8.15-8.07 (1H, m), 8.06-8.03 (3H, m), 8.02-8.00 (3H, m), 7.79-7.76 (1H, m).

Example 21A: Preparation of 4-(1-(2-chloro-6-(trifluoromethyl)benzoyl)-6-(4H-1,2,4-triazol-3-yl)-1H-indazol-3-yl)-3-fluorobenzoic acid (21A)

SCHEME AC

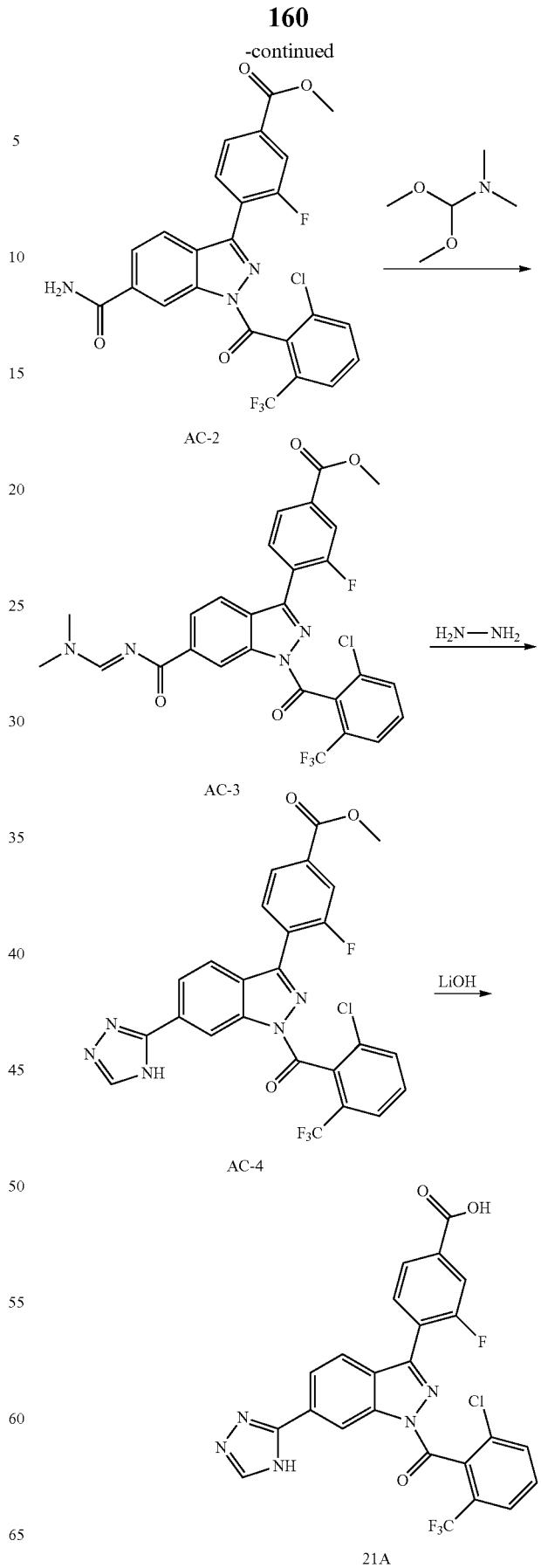

Step 1. Preparation of methyl 4-(6-carbamoyl-1-(2-chloro-6-(trifluoromethyl)benzoyl)-1H-indazol-3-yl)-3-fluorobenzoate (AC-2)

The mixture of 1-(2-chloro-6-(trifluoromethyl)benzoyl)-3-(2-fluoro-4-(methoxycarbonyl)phenyl)-1H-indazole-6-carboxylic acid (AC-1) (95 mg, 0.18 mmol), ammonium chloride (14.3 mg, 0.27 mmol), HATU (82 mg, 0.22 mmol) and Et$_3$N (76 uL, 0.54 mmol) in DCM (5 mL) was stirred at room temperature for 1 h. The solvent was removed under reduced pressure and the residue was chromatographed on silica gel (PE:EA 1:1) to obtain the desired product as a white solid (60 mg, 68%). LCMS (ESI) calc'd for $C_{24}H_{14}ClF_4N_3O_4$ [M+H]$^+$: 520. found: 520.

Step 2. Preparation of (E)-methyl 4-(1-(2-chloro-6-(trifluoromethyl)benzoyl)-6-((dimethylamino)methylenecarbamoyl)-1H-indazol-3-yl)-3-fluorobenzoate (AC-3)

The mixture of methyl 4-(6-carbamoyl-1-(2-chloro-6-(trifluoromethyl)benzoyl)-1H-indazol-3-yl)-3-fluorobenzoate (AC-2) (80 mg, 0.15 mmol) and dimethoxy-N,N-dimethylmethanamine (92 mg, 0.75 mmol) in EtOAc (5 mL) was stirred at 60° C. overnight. The solvent was removed under reduced pressure to obtain the crude product as a white solid. The crude product was used in the next step without further purification. LCMS (ESI) calc'd for $C_{27}H_{19}ClF_4N_4O_4$ [M+H]$^+$: 575. found: 575.

Step 3. Preparation of methyl 4-(1-(2-chloro-6-(trifluoromethyl)benzoyl)-6-(4H-1,2,4-triazol-3-yl)-1H-indazol-3-yl)-3-fluorobenzoate (AC-4)

The mixture of (E)-methyl 4-(1-(2-chloro-6-(trifluoromethyl)benzoyl)-6-(((dimethylamino)methylene carbamoyl)-1H-indazol-3-yl)-3-fluorobenzoate (AC-3) (100 mg, 0.17 mmol) and hydrazine (27 mg, 0.85 mmol) in AcOH (5 mL) was stirred at room temperature for 2 h. The resulting solution was diluted with water (30 mL). NaHCO$_3$ solid was added to adjust the pH to 8 and the aqueous layer was extracted with EtOAc (20 mL×3). The combined organic layers were washed with brine (20 mL×1), dried over anhydrous Na$_2$SO$_4$ and concentrated to obtain the desired product as a white solid (50 mg, 50%). LCMS (ESI) calc'd for $C_{25}H_{14}ClF_4N_5O_3$ [M+H]$^+$: 544. found: 544.

Step 4. Preparation of 4-(1-(2-chloro-6-(trifluoromethyl)benzoyl)-6-(4H-1,2,4-triazol-3-yl)-1H-indazol-3-yl)-3-fluorobenzoic acid (21A)

The mixture of methyl 4-(1-(2-chloro-6-(trifluoromethyl)benzoyl)-6-(4H-1,2,4-triazol-3-yl)-1H-indazol-3-yl)-3-fluorobenzoate (AC-4) (100 mg, 0.18 mmol) and LiOH (38 mg, 0.90 mmol) in THF (4 mL) and H$_2$O (2 mL) was stirred at 30° C. for 1 h. The reaction mixture was diluted with H$_2$O (20 mL). 2M HCl solution was added to adjust the pH to 3 and the aqueous layer was extracted with ethyl acetate (20 mL×3). The combined organic layers were washed with brine (20 mL×1), dried over anhydrous Na$_2$SO$_4$ and concentrated. The residue was purified with Prep-HPLC (acetonitrile-water system) to obtain the desired product 21A as a white solid (95 mg, 96%). LCMS (ESI) calc'd for $C_{24}H_{12}ClF_4N_5O_3$ [M+H]$^+$: 530. found: 530. $^1$HNMR (400 MHz, MeOD) δ 9.32 (1H, s), 8.56 (1H, s), 8.30 (1H, d, J=8.4 Hz), 8.02-8.05 (1H, m), 7.92-7.97 (2H, m), 7.86-7.90 (2H, m), 7.72-7.80 (2H, m).

The following examples shown in TABLE 10 were prepared following similar procedures described for Example 21A in Scheme AC, which can be achieved by those of ordinary skill in the art of organic synthesis in light of the present disclosure.

TABLE 10

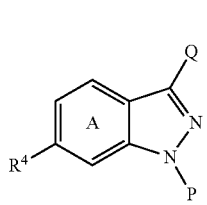
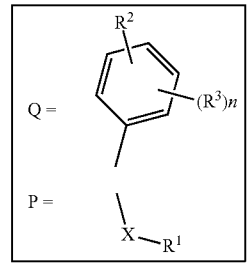

| Example | Chemical Name | A ring | P | Q | LCMS [M + H]$^+$ Found |
|---|---|---|---|---|---|
| 21B | 4-(1-(2-chloro-6-(trifluoromethyl)benzoyl)-6-(5-methyl-1,3,4-oxadiazol-2-yl)-1H-indazol-3-yl)-3-fluorobenzoic acid | | | -phenyl-F) | 545 |

TABLE 10-continued

| Example | Chemical Name | A ring | P | Q | LCMS [M + H]+ Found |
|---------|---------------|--------|---|---|---------------------|
| 21C | 4-(1-(2-chloro-6-(trifluoromethyl)benzoyl)-6-(1-methyl-1H-imidazol-2-yl)-1H-indazol-3-yl)-3-fluorobenzoic acid | | | | 543 |

Example 22A: Preparation of 4-(1-(2-chloro-6-trifluorobenzoyl)-6-(thiazol-2-yl)-1H indazol-3-yl)benzoic acid (22A)

SCHEME AD

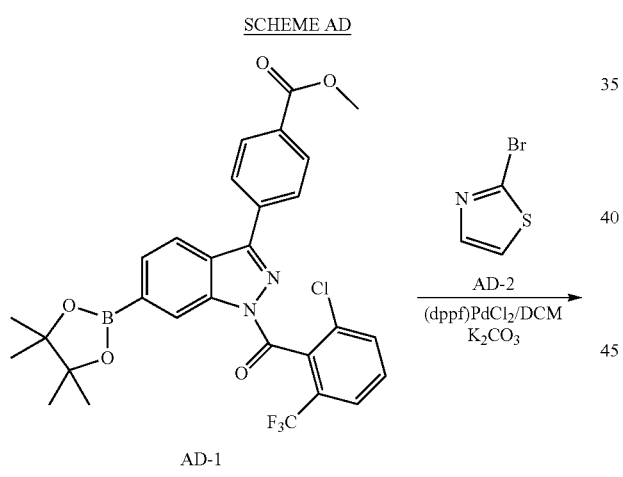

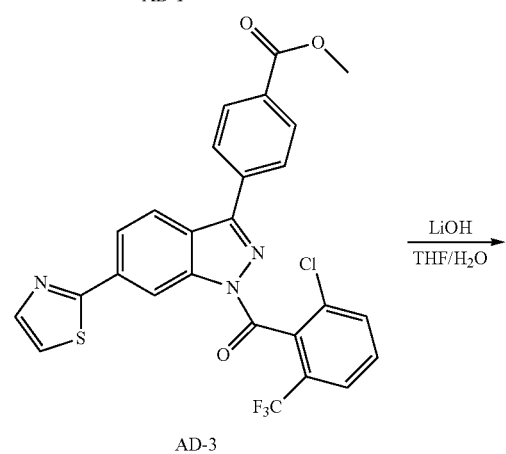

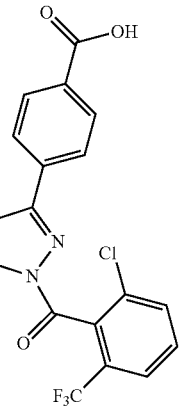

Step: Preparation of 4-(1-(2-chloro-6-trifluorobenzoyl)-6-(thiazol-2-yl)-1H-indazol 3-yl)benzoic acid (22A)

To a 1 dram vial was added methyl 4-(1-(2-chloro-6-trifluorobenzoyl)-6-(4,4,5,5-tetramethyl-1,3,2-dioxaborolan-2-yl)-1H-indazol-3-yl)benzoate (AD-1) (20 mg, 0.034 mmol), 2-bromothiazole (AD-2) (0.051 mmol), potassium carbonate (0.093 mL, 2M), dichloro 1-1'-bis(diphenylphosphino)ferrocine palladium (II) dichloromethane adduct (5.59 mg, 6.84 umol), and 1,4-dioxane (1 mL). The vessel was flushed with argon and stirred overnight at 90° C. The reactions were concentrated under reduced pressure. The remaining residue was dissolved in a 1:1 DCM/Methanol solution (1 mL) and SiliaBond DMT Resin (78 mg, 0.045 mmol) was then added. The mixture was stirred overnight at room temperature. The mixture was then filtered and concentrated under reduced pressure. Lithium hydroxide (1M, 0.186 mL), methanol (0.25 mL), and THF (0.5 mL) was then added and the reaction was stirred overnight at room temperature. The reactions were concentrated under reduced pressure. The reaction was then diluted with 1.0 mL DMSO, filtered, and purified by mass-triggered reverse phase HPLC, eluting with a 1% trifluoroacetic acid buffered water/acetonitrile gradient over a Waters X-Bridge C-18 column, to afford desired product (5 mg, 18% over two steps). LCMS (ESI) calc'd for $C_{24}H_{13}ClFN_3O_3S$ [M+H]$^+$: 478. found: 478.

The following examples shown in TABLE 11 were prepared following similar procedures described for Example 22A in Scheme AD, which can be achieved by those of ordinary skill in the art of organic synthesis in light of the present disclosure.

TABLE 11

| Ex. | Chemical Name | Structure | LCMS [M + H]$^+$ Calc'd/Found |
|---|---|---|---|
| 22B | 4-[1-{[2-chloro-6-(trifluoromethyl)phenyl]carbonyl}-6-(1-methyl-1H-imidazol-5-yl)-1H-indazol-3-yl]benzoic acid | 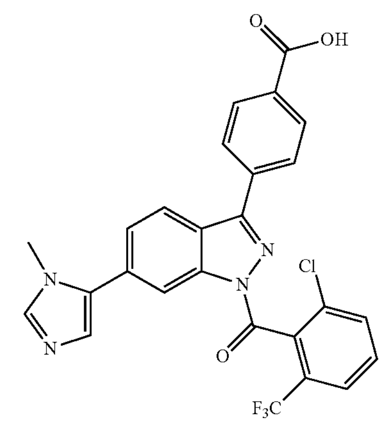 [SMILES: Cn1cncc1-c1ccc2c(-c3ccc(C(=O)O)cc3)nn(C(=O)c3c(Cl)cccc3C(F)(F)F)c2c1] | 475/475 |
| 22C | 4-[1-{[2-chloro-6-(trifluoromethyl)phenyl]carbonyl}-6-(5-methylthiophen-3-yl)-1H-indazol-3-yl]benzoic acid | 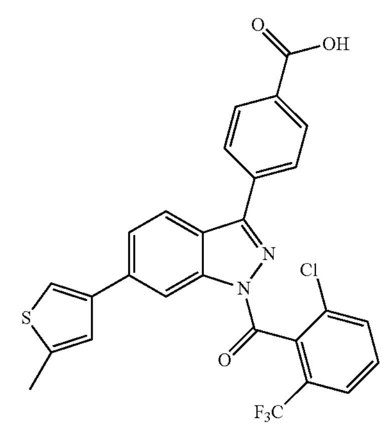 [SMILES: Cc1cc(-c2ccc3c(-c4ccc(C(=O)O)cc4)nn(C(=O)c4c(Cl)cccc4C(F)(F)F)c3c2)cs1] | 491/491 |

TABLE 11-continued
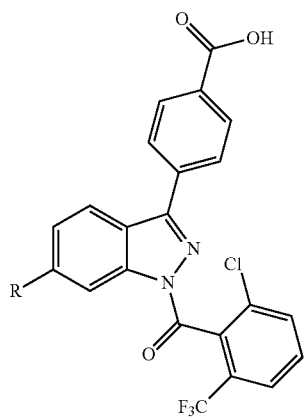
| Ex. | Chemical Name | Structure | LCMS [M + H]+ Calc'd/Found |
|---|---|---|---|
| 22D | 4-(1-{[2-chloro-6-(trifluoromethyl)phenyl]carbonyl}-6-pyrimidin-2-yl-1H-indazol-3-yl)benzoic acid | 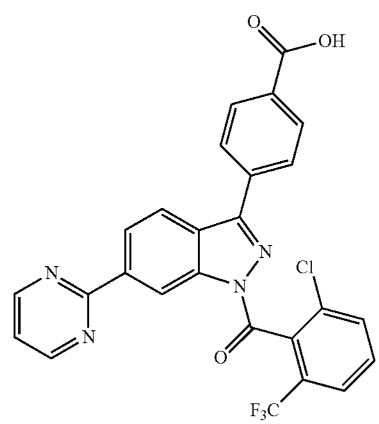 [SMILES: O=C(O)c1ccc(-c2nn(C(=O)c3c(Cl)cccc3C(F)(F)F)c3cc(-c4ncccn4)ccc23)cc1] | 473/473 |
| 22E | 4-(1-{[2-chloro-6-(trifluoromethyl)phenyl]carbonyl}-6-pyrimidin-4-yl-1H-indazol-3-yl)benzoic acid | 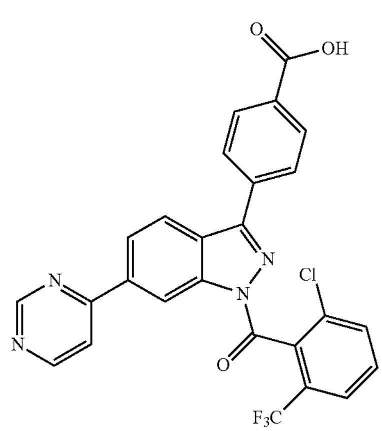 [SMILES: O=C(O)c1ccc(-c2nn(C(=O)c3c(Cl)cccc3C(F)(F)F)c3cc(-c4ccncn4)ccc23)cc1] | 473/473 |

TABLE 11-continued
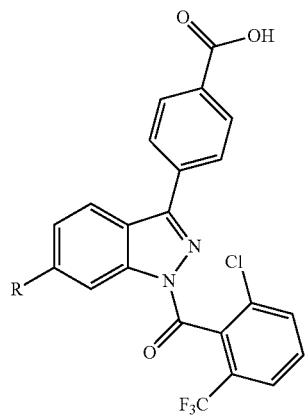
| Ex. | Chemical Name | Structure | LCMS [M + H]+ Calc'd/Found |
|---|---|---|---|
| 22F | 4-[1-{[2-chloro-6-(trifluoromethyl)phenyl]carbonyl}-6-(1-methyl-1H-imidazol-4-yl)-1H-indazol-3-yl]benzoic acid | 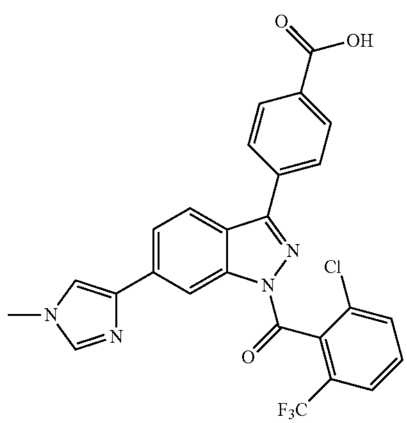 [SMILES: Cn1cnc(-c2ccc3c(-c4ccc(C(=O)O)cc4)nn(C(=O)c4c(Cl)cccc4C(F)(F)F)c3c2)c1] | 475/475 |
| 22G | 4-[1-{[2-chloro-6-(trifluoromethyl)phenyl]carbonyl}-6-(1,3-thiazol-4-yl)-1H-indazol-3-yl]benzoic acid | 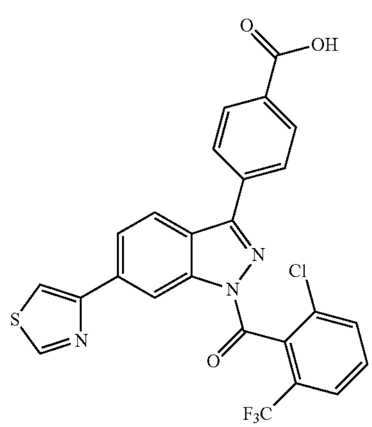 [SMILES: O=C(O)c1ccc(-c2nn(C(=O)c3c(Cl)cccc3C(F)(F)F)c3cc(-c4cscn4)ccc23)cc1] | 478/478 |

TABLE 11-continued
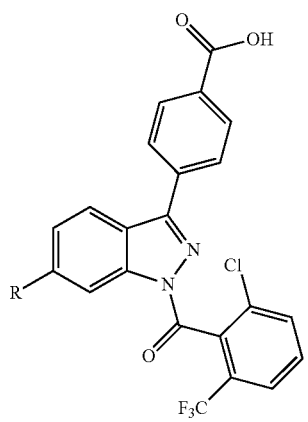
| Ex. | Chemical Name | Structure | LCMS [M + H]+ Calc'd/Found |
|---|---|---|---|
| 22H | 4-(6-[4-(aminomethyl)pyridin-2-yl]-1-{[2-chloro-6-(trifluoromethyl)phenyl]carbonyl}-1H-indazol-3-yl)benzoic acid | 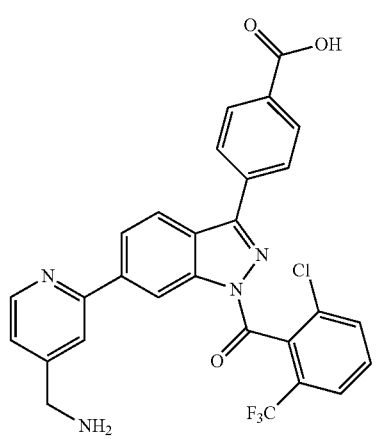 [SMILES: NCc1ccnc(-c2ccc3c(-c4ccc(C(=O)O)cc4)nn(C(=O)c4c(Cl)cccc4C(F)(F)F)c3c2)c1] | 501/501 |
| 22I | 4-(1-{[2-chloro-6-(trifluoromethyl)phenyl]carbonyl}-6-pyridin-2-yl-1H-indazol-3-yl)benzoic acid | 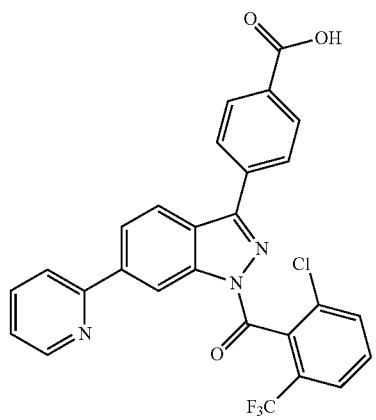 [SMILES: O=C(O)c1ccc(-c2nn(C(=O)c3c(Cl)cccc3C(F)(F)F)c3cc(-c4ccccn4)ccc23)cc1] | 472/472 |

TABLE 11-continued
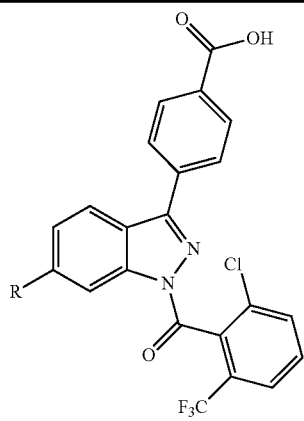
| Ex. | Chemical Name | Structure | LCMS [M + H]+ Calc'd/Found |
|---|---|---|---|
| 22J | 4-[1-{[2-chloro-6-(trifluoromethyl)phenyl]carbonyl}-6-(1,3-thiazol-5-yl)-1H-indazol-3-yl]benzoic acid | 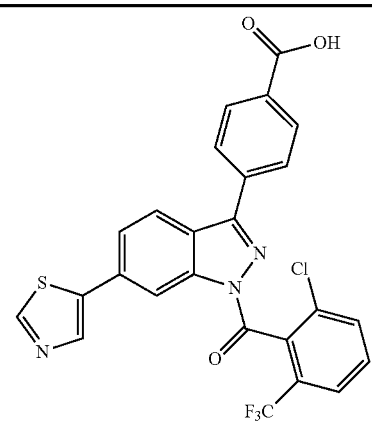 | 478/478 |
Example 23A: Preparation of 4-(1-(2-chloro-6-trifluorobenzoyl)-6-(thiazol-2-yl)-1H-indazol-3-yl)benzoic acid (23A)
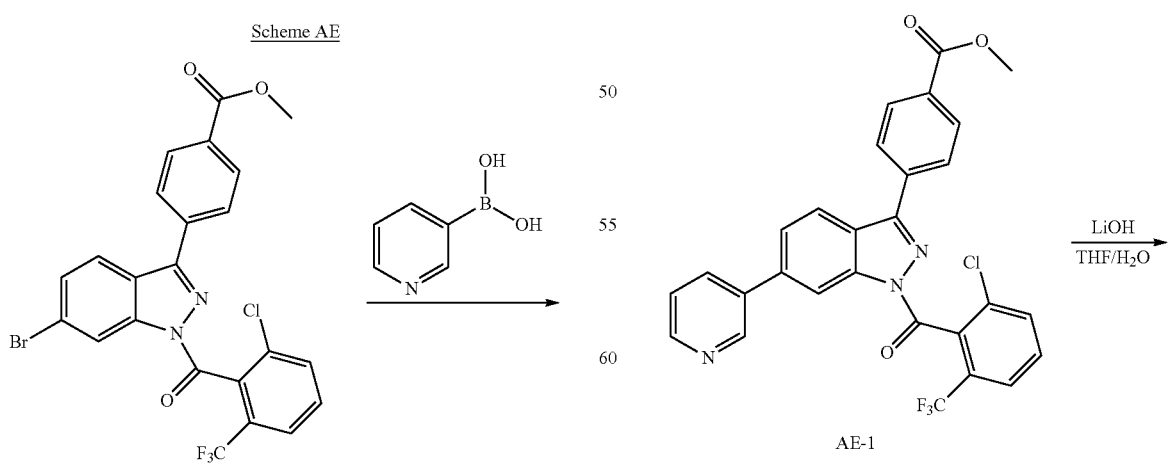
-continued -continued

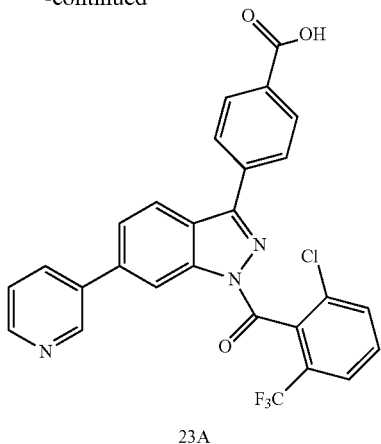

23A

Step 1: Preparation of 4-(1-(2-chloro-6-trifluorobenzoyl)-6-(pyridin-3-yl)-1H-indazol-3-yl)benzoic acid (23A)

To a 1 dram vial was added methyl 4-(6-bromo-1-(2-chloro-6-trifluorobenzoyl)-1H-indazol-3-yl)benzoate (i-9) (20 mg, 0.037 mmol), pyridin-3-ylboronic acid (6.9 mg, 0.056 mmol), potassium carbonate (2 M, 0.093 mL, 0.186 mmol), dichloro 1-1'-bis(diphenylphosphino)ferrocine palladium(II) dichloromethane adduct (6.07 mg, 7.44 umol), and 1,4-dioxane (1 mL). The vessel was flushed with argon and stirred overnight at 90° C. The reactions were concentrated under reduced pressure. The remaining residue was dissolved in a 1:1 DCM/Methanol solution (1 mL) and SiliaBond DMT Resin (78 mg, 0.045 mmol) was then added. The mixture was stirred overnight at room temperature. The mixture was then filtered and concentrated under reduced pressure. Lithium hydroxide (1M, 0.186 mL), methanol (0.25 mL) and THF (0.5 mL) were then added and the reaction was stirred overnight at room temperature. The reactions were concentrated under reduced pressure. The reaction was then diluted with 1.0 mL DMSO, filtered, and purified by mass-triggered reverse phase HPLC, eluting with a 1% trifluoroacetic acid buffered water/acetonitrile gradient over a Waters X-Bridge C-18 column, to afford the desired product. LCMS (ESI) calc'd for $C_{26}H_{15}ClFN_3O_3$ [M+H]$^+$: 472. found: 472. 1H $^1$H NMR δ (ppm)(DMSO-d$_6$): 7.66 (1H, t, J=6.33 Hz), 7.85 (1H, t, J=8.15 Hz), 7.99-7.98 (6H, m), 8.08 (2H, d, J=8.17 Hz), 8.37 (2H, d, J=8.35 Hz), 8.71 (1H, d, J=4.84 Hz), 8.78 (1H, s), 9.09 (1H, s).

The following examples shown in TABLE 12 were prepared following similar procedures described for Example 23A in Scheme AE, which can be achieved by those of ordinary skill in the art of organic synthesis in light of the present disclosure.

TABLE 12

| Ex. | Chemical Name | Structure | LCMS [M + H]$^+$ Found |
|---|---|---|---|
| 23B | 4-(1-{[2-chloro-6-(trifluoromethyl)phenyl]carbonyl}-6-pyridin-4-yl-1H-indazol-3-yl)benzoic acid | 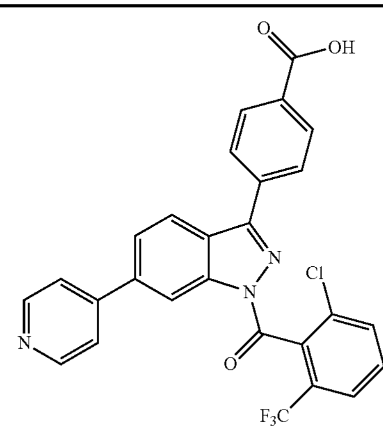 | 472 |

TABLE 12-continued
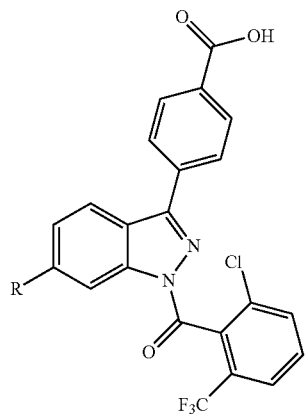
| Ex. | Chemical Name | Structure | LCMS [M + H]+ Found |
|---|---|---|---|
| 23C | 4-[1-{[2-chloro-6-(trifluoromethyl)phenyl]carbonyl}-6-(4-cyanophenyl)-1H-indazol-3-yl]benzoic acid | 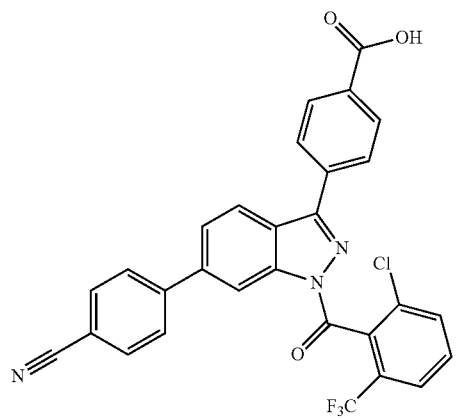 [SMILES: N#Cc1ccc(-c2ccc3c(-c4ccc(C(=O)O)cc4)nn(C(=O)c4c(Cl)cccc4C(F)(F)F)c3c2)cc1] | 496 |
| 23D | 4-[1-{[2-chloro-6-(trifluoromethyl)phenyl]carbonyl}-6-(3-cyanophenyl)-1H-indazol-3-yl]benzoic acid | 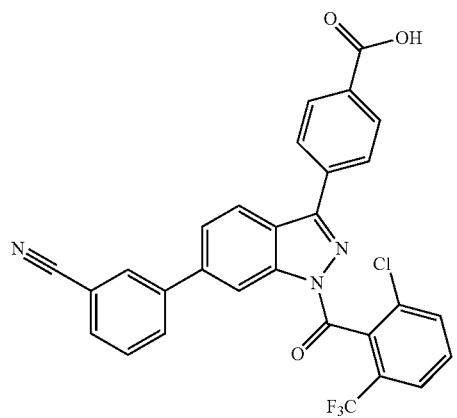 [SMILES: N#Cc1cccc(-c2ccc3c(-c4ccc(C(=O)O)cc4)nn(C(=O)c4c(Cl)cccc4C(F)(F)F)c3c2)c1] | 496 |

TABLE 12-continued
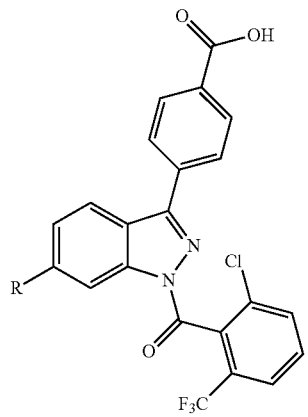
| Ex. | Chemical Name | Structure | LCMS [M + H]+ Found |
|---|---|---|---|
| 23E | 4-[1-{[2-chloro-6-(trifluoromethyl)phenyl]carbonyl}-6-(2-cyanophenyl)-1H-indazol-3-yl]benzoic acid | 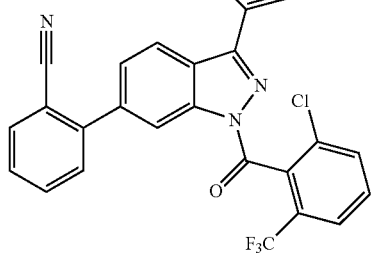 | 496 |
| 23F | 4-(1-{[2-chloro-6-(trifluoromethyl)phenyl]carbonyl}-6-thiophen-2-yl-1H-indazol-3-yl)benzoic acid | 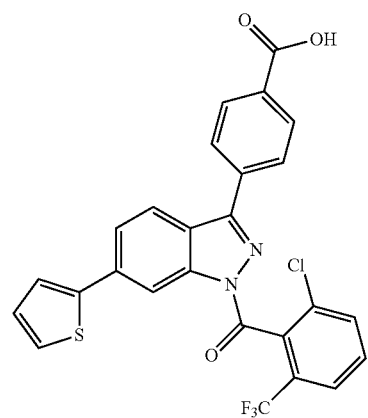 [SMILES: O=C(O)c1ccc(-c2nn(C(=O)c3c(Cl)cccc3C(F)(F)F)c3cc(-c4cccs4)ccc23)cc1] | 477 |

TABLE 12-continued
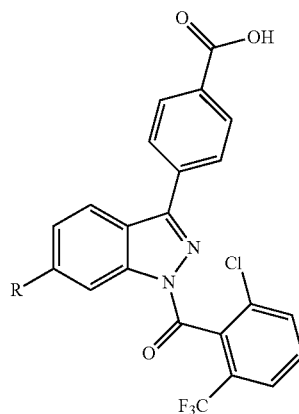
| Ex. | Chemical Name | Structure | LCMS [M + H]+ Found |
|---|---|---|---|
| 23G | 4-[1-{[2-chloro-6-(trifluoromethyl)phenyl]carbonyl}-6-(2-fluorophenyl)-1H-indazol-3-yl]benzoic acid | 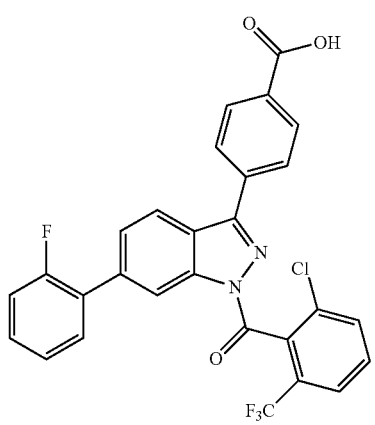 [SMILES: O=C(O)c1ccc(-c2nn(C(=O)c3c(Cl)cccc3C(F)(F)F)c3cc(-c4ccccc4F)ccc23)cc1] | 489 |
| 23H | 4-[1-{[2-chloro-6-(trifluoromethyl)phenyl]carbonyl}-6-(3-fluorophenyl)-1H-indazol-3-yl]benzoic acid | 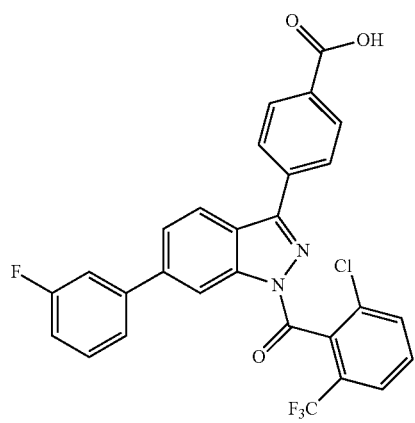 [SMILES: O=C(O)c1ccc(-c2nn(C(=O)c3c(Cl)cccc3C(F)(F)F)c3cc(-c4cccc(F)c4)ccc23)cc1] | 489 |

TABLE 12-continued
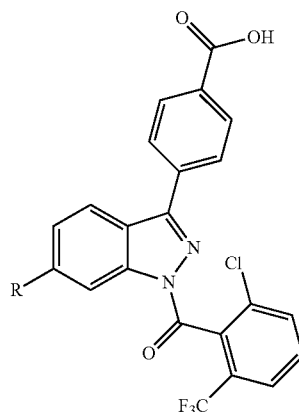
| Ex. | Chemical Name | Structure | LCMS [M + H]+ Found |
|---|---|---|---|
| 23I | 4-[1-{[2-chloro-6-(trifluoromethyl)phenyl]carbonyl}-6-(4-fluorophenyl)-1H-indazol-3-yl]benzoic acid | 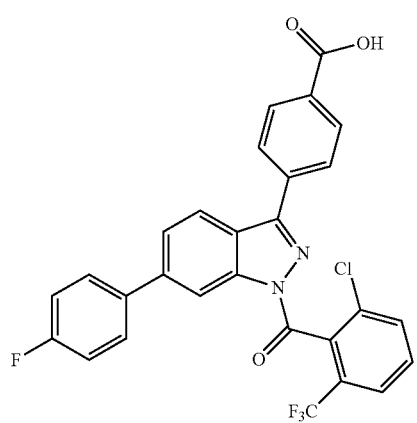 [SMILES: O=C(O)c1ccc(-c2nn(C(=O)c3c(Cl)cccc3C(F)(F)F)c3cc(-c4ccc(F)cc4)ccc23)cc1] | 489 |
| 23J | 4-[1-{[2-chloro-6-(trifluoromethyl)phenyl]carbonyl}-6-(1-methyl-1H-pyrazol-5-yl)-1H-indazol-3-yl]benzoic acid | 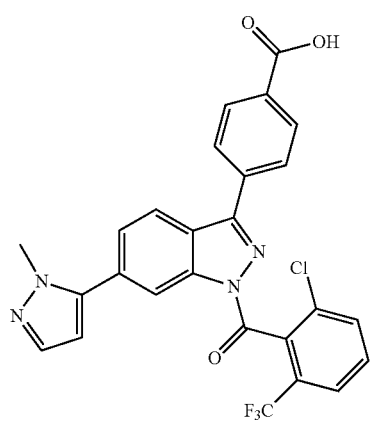 [SMILES: Cn1nccc1-c1ccc2c(-c3ccc(C(=O)O)cc3)nn(C(=O)c3c(Cl)cccc3C(F)(F)F)c2c1] | 475 |

TABLE 12-continued
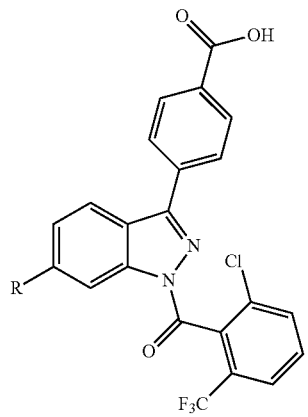
| Ex. | Chemical Name | Structure | LCMS [M + H]+ Found |
|---|---|---|---|
| 23K | methyl 4-(1-(2-chloro-6-trifluorobenzoyl)-6-(4-hydroxyphenyl)-1H-indazol-3-yl)benzoate | 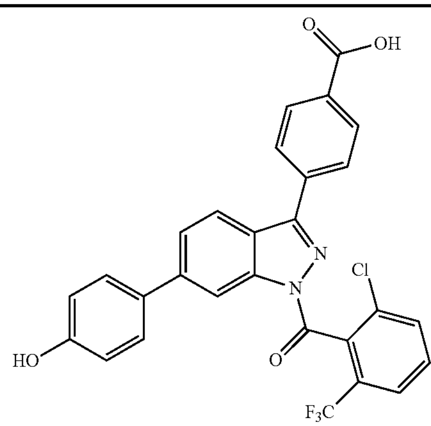 | 487 |
Example 26A: Preparation of 4-(1-(2-chloro-6-(trifluoromethyl)benzoyl)-6-(methylsulfonamidomethyl)-1H-indazol-3-yl)benzoic acid (26A)
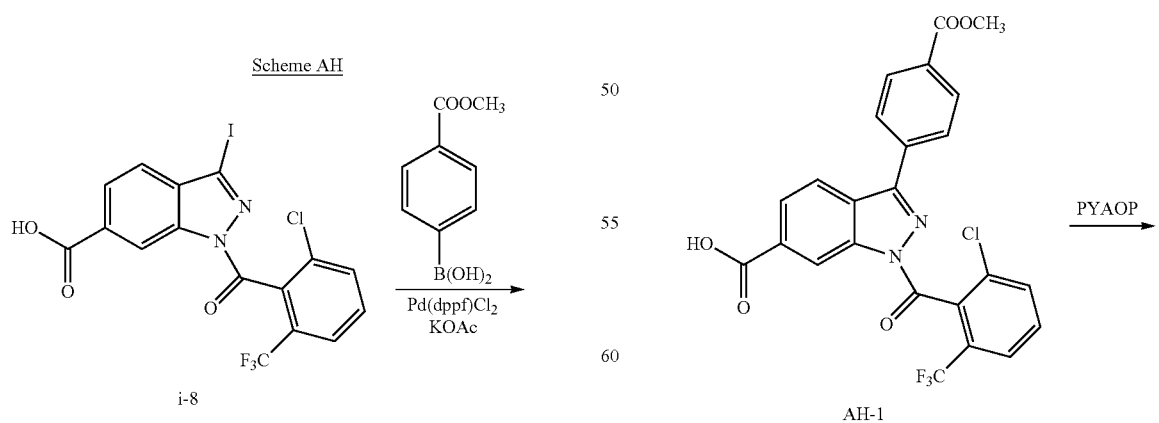

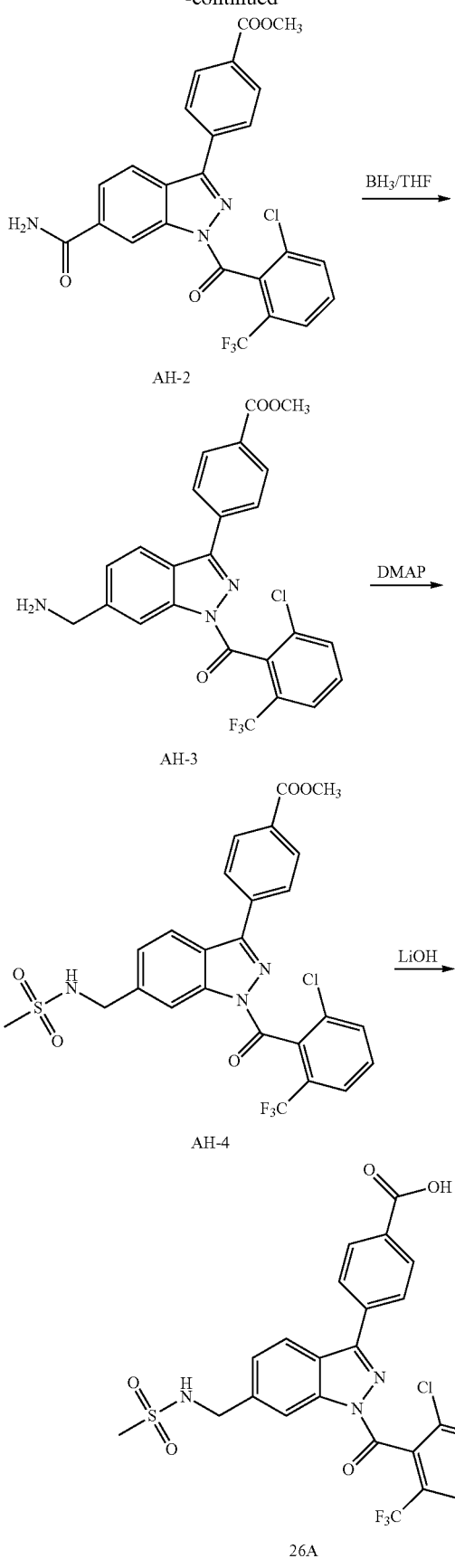

Step 1. Preparation of 1-(2-chloro-6-(trifluoromethyl)benzoyl)-3-(4-(methoxycarbonyl)phenyl)-1H-indazole-6-carboxylic acid (AH-1)

A mixture of i-8 (300 mg, 0.61 mmol), 4-(methoxycarbonyl)phenylboronic acid (165 mg, 0.92 mmol), Pd(dppf)Cl$_2$ (50 mg, 0.061 mmol) and KOAc (181 mg, 1.83 mmol) in 10 mL dioxane and 2 mL pure H$_2$O was heated to 95° C. for 2 h under microwave. Then the reaction mixture was diluted with EtOAC (50 mL), washed with brine (50 mL×2), dried over anhydrous Na$_2$SO$_4$, concentrated, and purified by silica gel column (PE/EtOAc=20/1) to obtain a white solid (180 mg; 59%). LCMS (ESI): calc'd for C$_{24}$H$_{14}$ClF$_3$N$_2$O$_5$, [M+H]$^+$: 503.1. found: 503.1

Step 2. Preparation of methyl 4-(6-carbamoyl-1-(2-chloro-6-(trifluoromethyl)-benzoyl)-1H-indazol-3-yl)benzoate (AH-2)

The compound AH-1 (100 mg, 0.2 mmol) was dissolved in CH$_2$Cl$_2$ (15 mL). NH$_4$Cl (13 mg, 0.24 mmol). PYAOP (208 mg, 0.4 mmol) was added and the mixture was stirred at room temperature for 2 min. TEA (0.16 mL, 1.08 mmol) was added and the mixture was stirred at room temperature for 2 h. Then the reaction mixture was diluted with EtOAC (20 mL), washed with brine (20 mL×2), dried over anhydrous Na$_2$SO$_4$, and concentrated to obtain a white solid AH-2 (90 mg; 90%). LCMS (ESI): calc'd for C$_{24}$H$_{15}$ClF$_3$N$_3$O$_4$, [M+H]$^+$: 502. found: 502.

Step 3. Preparation of methyl 4-(6-(aminomethyl)-1-(2-chloro-6-(trifluoromethyl)benzoyl)-1H-indazol-3-yl)benzoate (AH-3)

The compound AH-2 (90 mg, 0.18 mmol) was dissolved in anhydrous THF (20 mL) under argon, BH$_3$.THF (0.9 mL, 0.9 mmol) was added, and the mixture was refluxed for 12 h. MeOH was added to quench the excess BH$_3$. The mixture was evaporated and a white solid (75 mg) was obtained. LCMS (ESI): calc'd for C$_{24}$H$_{17}$ClF$_3$N$_3$O$_3$, [M+H]$^+$: 488.1. found: 488.1.

Step 4. Preparation of methyl 4-(1-(2-chloro-6-(trifluoromethyl)benzoyl)-6-(methylsulfonamidomethyl)-1H-indazol-3-yl)benzoate (AH-4)

To a 50 mL round-bottomed flask was added compound AH-3 (100 mg, 0.2 mmol), methanesulfonyl chloride (23 mg, 0.2 mmol) and CH$_2$Cl$_2$ (10 mL). After stirring at room temperature for 3 min, TEA (0.1 mL, 0.6 mmol) was added slowly. The reaction mixture was stirred at room temperature overnight. Then the mixture was poured into 30 mL water, and the lower (organic) and upper (aqueous) phases were separated. The aqueous phase was extracted CH$_2$Cl$_2$ (20 mL×2). The combined organic phases were washed successively with water (20 mL×2) and 10 mL of brine. The organic phase was dried over anhydrous sodium sulfate, filtered and concentrated at reduced pressure to give a solid (22 mg). LCMS (ESI): calc'd for C$_{25}$H$_{19}$ClF$_3$N$_3$O$_5$S [M+H]$^+$: 566.1. found: 566.1.

Step 5. Preparation of 4-(1-(2-chloro-6-(trifluoromethyl)benzoyl)-6-(methylsulfonamidomethyl)-1H-indazol-3-yl)benzoic acid (26A)

A mixture of methyl 4-(1-(2-chloro-6-(trifluoromethyl)benzoyl)-6-(methylsulfonamidomethyl)-1H-indazol-3-yl)benzoate (AH-4) (22 mg, 0.04 mmol) and LiOH.H$_2$O (8 mg, 0.19 mmol) in 10 mL THF and 10 mL pure H$_2$O was stirred at room temperature for 2 h. The solvent was evaporated and the residue was dissolved in water. HCl (5% sol in water) was added until the pH was 4-5. The precipitated solid was filtered, washed with water and n-hexane, and dried to afford an off-white solid 15 mg (80%). LCMS (ESI): calc'd for C$_{24}$H$_{17}$ClF$_3$N$_3$O$_5$S, [M+H]$^+$: 552.1 found: 552.1; $^1$HNMR (400 MHz, DMSO-d$_6$) δ 8.59 (s, 1H), 8.23-8.25 (d, 1H, J=8 Hz), 8.09-8.11 (d, 2H, J=8 Hz), 8.04-8.06 (d, 1H, J=8 Hz), 7.99-8.01 (d, 1H, J=8 Hz), 7.94-7.96 (d, 2H, J=8 Hz), 7.86-7.90 (m, 2H), 7.64-7.66 (d, 1H, J=8 Hz), 4.46-4.48 (d, 2H, J=8 Hz), 2.99 (s, 3H).

Example 27A: Preparation of 4-(1-(2-chloro-6-(trifluoromethyl)benzoyl)-6-(2,5-dioxoimidazolidin-4-yl)-1H-indazol-3-yl)-3-fluorobenzoic acid (27A)

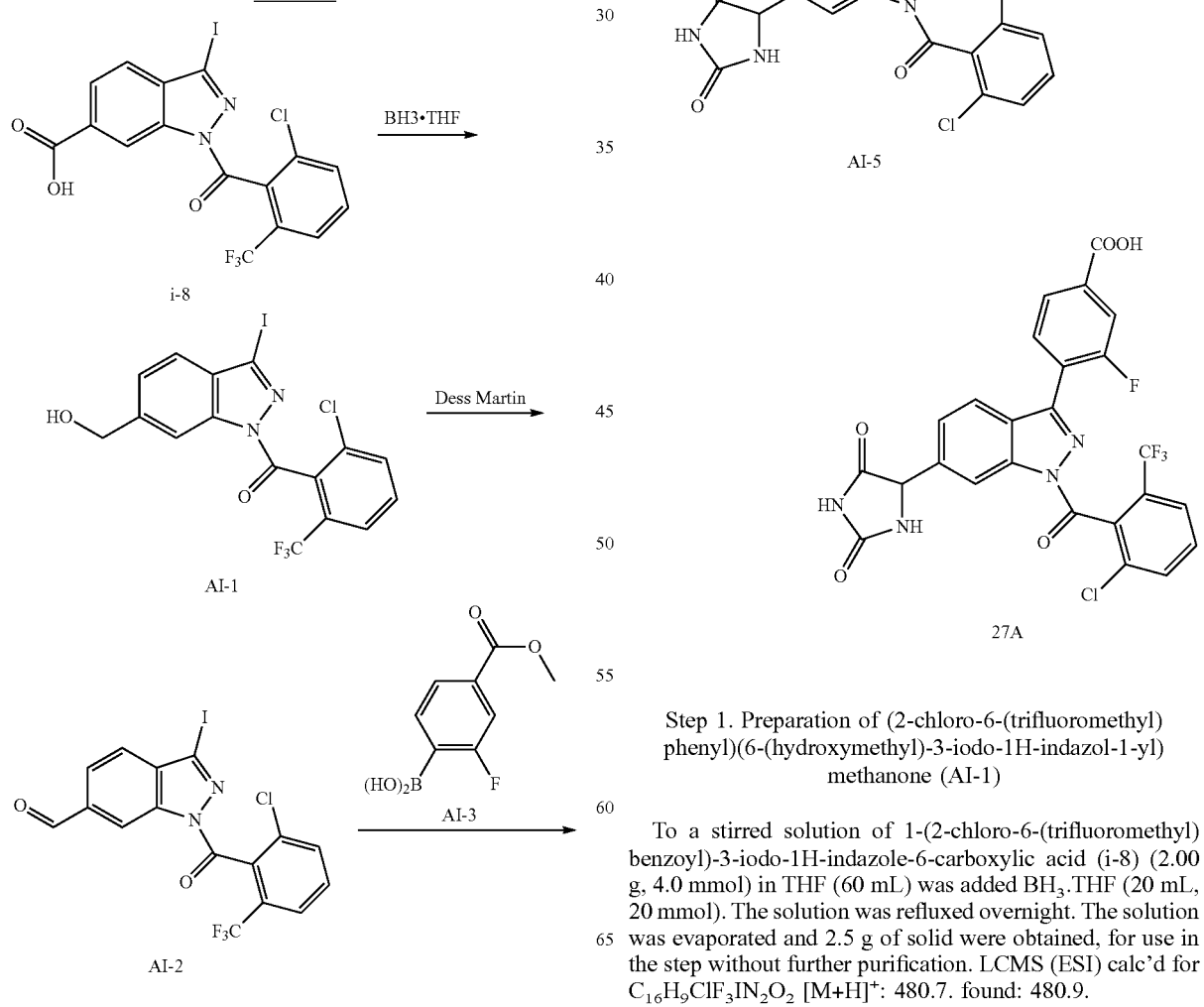

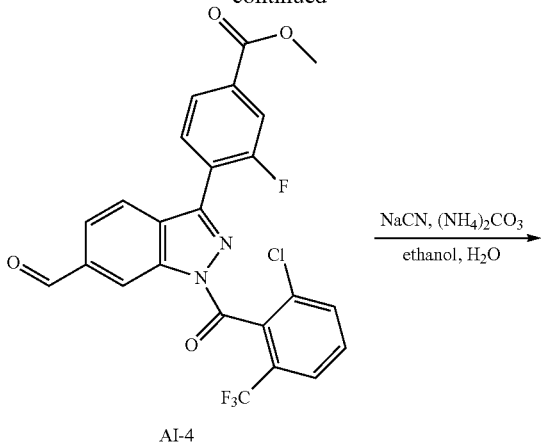

Step 1. Preparation of (2-chloro-6-(trifluoromethyl)phenyl)(6-(hydroxymethyl)-3-iodo-1H-indazol-1-yl)methanone (AI-1)

To a stirred solution of 1-(2-chloro-6-(trifluoromethyl)benzoyl)-3-iodo-1H-indazole-6-carboxylic acid (i-8) (2.00 g, 4.0 mmol) in THF (60 mL) was added BH$_3$.THF (20 mL, 20 mmol). The solution was refluxed overnight. The solution was evaporated and 2.5 g of solid were obtained, for use in the step without further purification. LCMS (ESI) calc'd for C$_{16}$H$_9$ClF$_3$IN$_2$O$_2$ [M+H]$^+$: 480.7. found: 480.9.

Step 2. Preparation of 1-(2-chloro-6-(trifluoromethyl)benzoyl)-3-iodo-1H-indazole-6-carbaldehyde (AI-2)

To a stirred solution of (2-chloro-6-(trifluoromethyl)phenyl)(6-(hydroxymethyl)-3-iodo-1H-indazol-1-yl)methanone (AI-1) (2.5 g, 0.52 mmol) in DCM (160 mL) was added Dess-Martin Periodinane (3.7 g, 0.78 mmol). The solution was stirred for 1 h. The mixture was filtered, and the filtrate was washed with H$_2$O (100 mL) and brine (100 mL) and dried over Na$_2$SO$_4$. The solvent was then evaporated and purified with column chromatography (EtOAc/Hexanes=1/10) to give 1.2 g of product. Yield for two steps 60%. LCMS (ESI) calc'd for C$_{16}$H$_7$ClF$_3$IN$_2$O$_2$ [M+H]$^+$: 478.7. found: 479.0.

Step 3. Preparation of methyl 4-(1-(2-chloro-6-(trifluoromethyl)benzoyl)-6-formyl-1H-indazol-3-yl)-3-fluorobenzoate (AI-4)

To a microwave tube was added 1-(2-chloro-6-(trifluoromethyl)benzoyl)-3-iodo-1H-indazole-6-carbaldehyde (AI-2) (400 mg, 0.83 mmol), 2-fluoro-4-(methoxycarbonyl)phenylboronic acid (AI-3) (320 mg, 1.66 mmol), Pd(OAc)$_2$ trimer (28 mg, 0.125 mmol), K$_3$PO$_4$ (600 mg, 2.5 mmol), s-Phos (100 mg, 0.25 mmol), THF (8 mL), H$_2$O (2 mL). The mixture was microwaved at 110° C. for 2 hours and the compound was submitted for Prep-HPLC. 178 mg product was obtained with a yield of 40%. LCMS (ESI) calc'd for C$_{24}$H$_{13}$ClF$_4$N$_2$O$_4$ [M+H]$^+$: 505. found: 505.

Step 4. Preparation of methyl 4-(1-(2-chloro-6-(trifluoromethyl)benzoyl)-6-(2,5-dioxoimidazolidin-4-yl)-1H-indazol-3-yl)-3-fluorobenzoate (AI-5)

To a microwave tube was added methyl 4-(1-(2-chloro-6-(trifluoromethyl)benzoyl)-6-formyl-1H-indazol-3-yl)-3-fluorobenzoate (AI-4) (100 mg, 0.20 mmol), NaCN (19.6 mg, 0.40 mmol), (NH$_4$)$_2$CO$_3$ (76.8 mg, 0.8 mmol), ethanol (0.8 mL) and H$_2$O (0.8 mL). The mixture was microwaved under argon at 110° C. for 2 hours. The mixture was filtered and the obtained product was used in the next step without further purification. LCMS (ESI) calc'd for C$_{26}$H$_{15}$ClF$_4$N$_4$O$_5$[M+H]$^+$: 575. found: 575.

Step 5. Preparation of 4-(1-(2-chloro-6-(trifluoromethyl)benzoyl)-6-(2,5-dioxoimidazolidin-4-yl)-1H-indazol-3-yl)-3-fluorobenzoic acid (27A)

To a stirred solution of the above-made methyl 4-(1-(2-chloro-6-(trifluoromethyl)benzoyl)-6-(2,5-dioxoimidazolidin-4-yl)-1H-indazol-3-yl)-3-fluorobenzoate (AI-5) was added LiOH.H$_2$O (60 mg, 1.5 mmol) and H$_2$O (0.1 mL). The solution was stirred overnight. The solution was adjusted to PH=3.0 using 1 N HCl. The reaction mixture was extracted with THF (1 mL×3). To the combined organic layer was added 0.5 mL MeOH, submitting to Prep-HPLC (H$_2$O/ACN, 0.05% TFA) gave 5 mg of product, and the yield for two steps was 4.5%. LCMS (ESI) calc'd for C$_{25}$H$_{13}$ClF$_4$N$_4$O$_5$ [M+H]$^+$: 561. found: 561; $^1$HNMR (400 MHz, DMSO-d$_6$) δ 13.60 (s, 1H), 10.99 (s, 1H), 8.68 (s, 1H), 8.66 (s, 1H), 8.56-7.98 (m, 3H), 7.93-7.88 (m, 3H), 7.84-7.75 (d, 1H), 7.73-7.60 (d, 1H).

Example 28A: Preparation of 4-(5-(tert-butoxycarbonylamino)-1-(2-chloro-6-(trifluoromethyl)benzoyl)-1H-pyrrolo[2,3-c]pyridin-3-yl)-3-fluorobenzoic acid (28A)

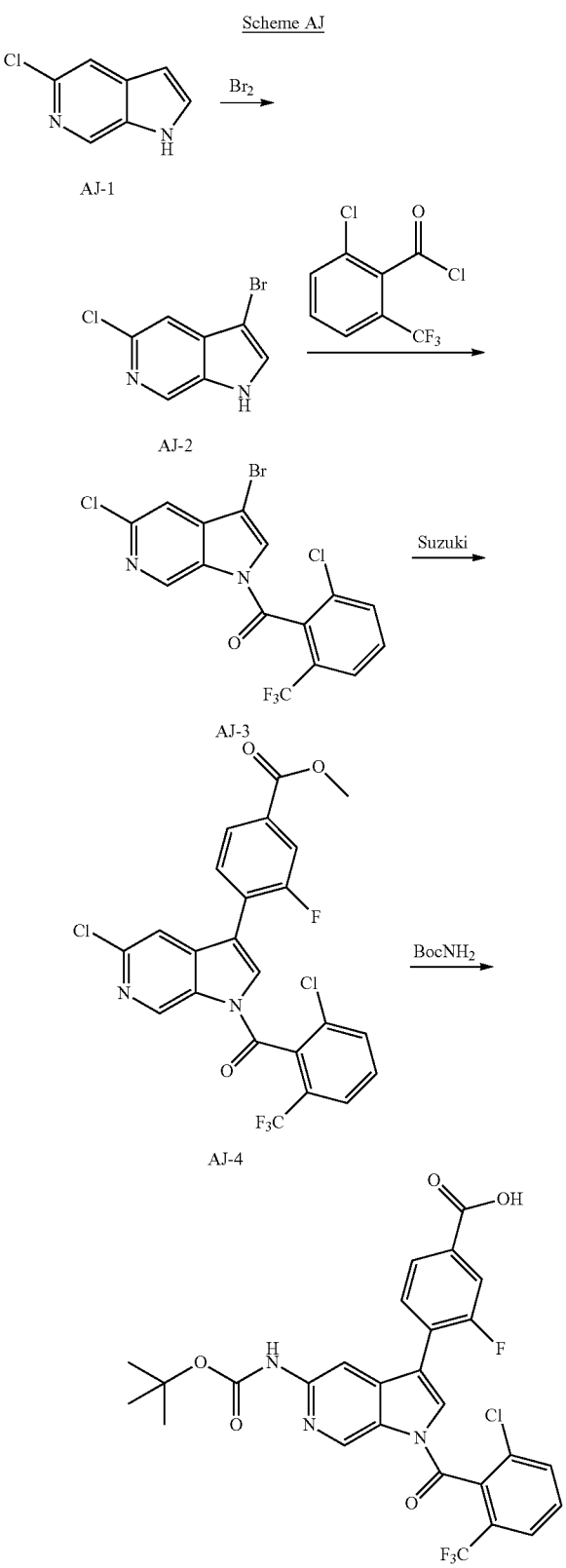

Scheme AJ

Step 1. 3-bromo-5-chloro-1H-pyrrolo[2,3-c]pyridine (AJ-2)

To a stirred solution of 5-chloro-1H-pyrrolo[2,3-c]pyridine (AJ-1) (2.0 g, 13.3 mmol) in anhydrous DMF (80 mL) at room temperature was added $Br_2$ (0.68 mL, 13.3 mmol) dropwise. The solution was stirred at room temperature for one hour. The solution was quenched with 10% $Na_2S_2O_3$ solution (100 mL) and diluted with $H_2O$ (400 mL). The aqueous layer was extracted with EtOAc (100 mL×4) and combined organic layer was washed with $H_2O$ (50 mL×3) and brine (50 mL×3) and dried over anhydrous $Na_2SO_4$. The solution was evaporated and dried over vacuo and 2.9 g product (95%) was collected. LCMS (ESI) calc'd for $C_7H_4BrClN_2[M+H]^+$: 231. found: 231.

Step 2. (3-bromo-5-chloro-1H-pyrrolo[2,3-c]pyridin-1-yl)(2-chloro-6-(trifluoro-methyl)phenyl)methanone (AJ-3)

To a stirred solution of 3-bromo-5-chloro-1H-pyrrolo[2,3-c]pyridine (AJ-2) (2.9 g, 12.6 mmol) in anhydrous DMF (100 mL) was added 2-chloro-6-(trifluoromethyl)benzoyl chloride (4.6 g, 18.9 mmol) and NaH (60%) (1 g, 25.2 mmol). The solution was stirred at room temperature for 2 hours. The solution was quenched with $H_2O$ (400 mL). The suspension was extracted with EtOAc (150 mL×3). The combined organic layer was washed with $H_2O$ (100 mL×2) and brine (100 mL×2) and dried over anhydrous $Na_2SO_4$. The solution was evaporated and dried over vacuo and 5.7 g product was obtained. LCMS (ESI) calc'd for $C_{15}H_6BrCl_2F_3N_2O$ $[M+H]^+$: 437. found: 437.

Step 3. methyl 4-(5-chloro-1-(2-chloro-6-(trifluoromethyl)benzoyl)-1H-pyrrolo[2,3-c]pyridin-3-yl)-3-fluorobenzoate (AJ-4)

To a microwave tube was added (3-bromo-5-chloro-1H-pyrrolo[2,3-c]pyridin-1-yl)(2-chloro-6-(trifluoromethyl)phenyl)-methanone (AJ-3) (650 mg, 1.5 mmol), 2-fluoro-4-(methoxycarbonyl)phenylboronic acid (450 mg, 2.25 mmol), Pd(dppf)$Cl_2$ (73 mg, 0.10 mmol), KOAc (300 mg, 3.0 mmol) and dioxane (12 mL). The mixture was microwaved at 110° C. for three hours and filtered through celite. The solvent was evaporated, and the crude product was purified with column chromatography (DCM/Hexanes: 1/1) to give 450 mg product (yield 60%). LCMS (ESI) calc'd for $C_{23}H_{12}Cl_2F_4N_2O_3$ $[M+H]^+$: 511. found: 511.

Step 4. 4-(5-(tert-butoxycarbonylamino)-1-(2-chloro-6-(trifluoromethyl)benzoyl)-1H-pyrrolo[2,3-c]pyridin-3-yl)-3-fluorobenzoic acid (28A)

To a microwave tube was added 4-(5-chloro-1-(2-chloro-6-(trifluoromethyl)benzoyl)-1H-pyrrolo[2,3-c]pyridin-3-yl)-3-fluorobenzoic acid (AJ-4) (50 mg, 0.1 mmol), $BocNH_2$ (35 mg, 0.3 mmol), NaOH (20 mg, 0.5 mmol), Pd(OAc)$_2$ (4 mg, 0.02 mmol), xant-Phos (20 mg, 0.04 mmol), dioxane (1 mL) and $H_2O$ (0.05 mL). The mixture was microwaved at 90° C. for 1 hr. After filtration and evaporation, the crude product was submitted for prep-HPLC purification, which gave 5 mg of the title product (yield 17%). LCMS (ESI) calc'd for $C_{27}H_{20}ClF_4N_3O_5$ $[M+H]^+$: 578. found: 578; $^1$HNMR (400 MHz, DMSO-d$_6$) δ 13.40 (bs, 1H), 10.00 (s, 1H), 9.37 (s, 1H), 8.02-8.09 (m, 3H), 7.88-7.93 (m, 3H), 7.81-7.84 (d, 1H), 7.70-7.74 (m, 1H), 1.48 (s, 9H).

Example 29A: Preparation of 4-(6-(tert-butoxycarbonylamino)-1-(2-chloro-6-(trifluoromethyl)benzoyl)-1H-pyrazolo[4,3-b]pyridin-3-yl)-3-fluorobenzoic acid (29A) and 4-(1-(2-chloro-6-(trifluoromethyl)benzoyl)-6-(methylamino)-1H-pyrazolo[4,3-b]pyridin-3-yl)-3-fluorobenzoic acid (29B)

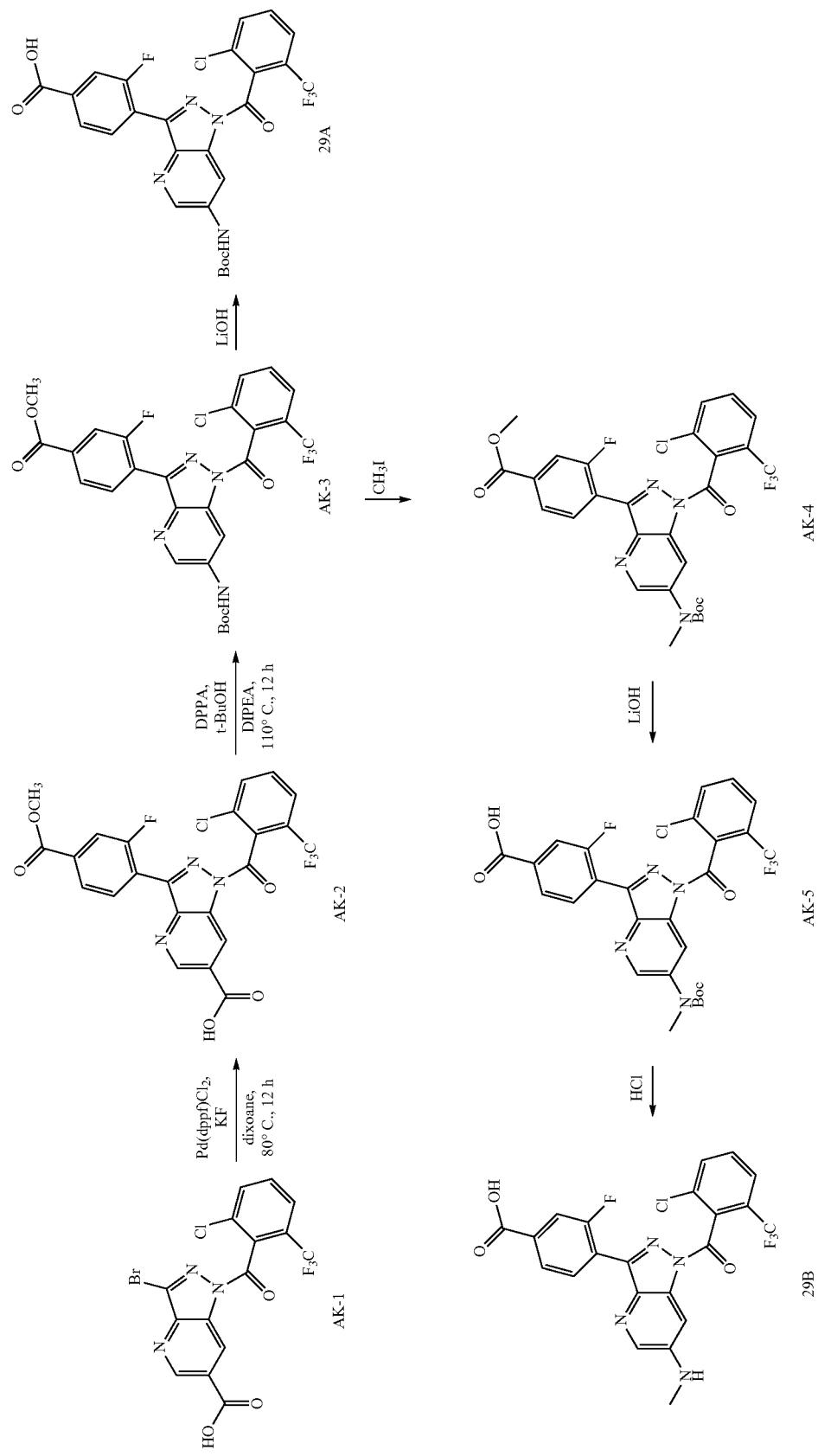

Step 1. Preparation of 1-(2-chloro-6-(trifluoromethyl)benzoyl)-3-(2-fluoro-4-(methoxycarbonyl)phenyl)-1H-pyrazolo[4,3-b]pyridine-6-carboxylic acid (AK-2)

To a mixture of 3-bromo-1-(2-chloro-6-(trifluoromethyl)benzoyl)-1H-pyrazolo[4,3-b]pyridine-6-carboxylic acid (AK-1) (224 mg, 0.5 mmol), boric acid (128 mg, 0.60 mmol), PdCl$_2$(dppf)$_2$ (48 mg, 0.05 mmol) and KF (90 mg, 1.5 mmol) was added dioxane (25 mL) and H$_2$O (0.5 mL), and the mixture was heated at 90° C. under argon for 16 h. The mixture was cooled down, and diluted with CH$_2$Cl$_2$ (80 mL). The organic layer was separated, washed with brine, dried over Na$_2$SO$_4$, and concentrated. The residue was purified by Prep-TLC (EtOAc) to afford 220 mg (85%) of the title compound as a white solid. LCMS (ESI) calc'd for C$_{23}$H$_{12}$ClF$_4$N$_3$O$_5$ [M+H]$^+$: 522.1. found: 522.1.

Step 2. Preparation of methyl 4-(6-(tert-butoxycarbonylamino)-1-(2-chloro-6-(trifluoromethyl)benzoyl)-1H-pyrazolo[4,3-b]pyridin-3-yl)-3-fluorobenzoate (AK-3)

To a mixture of 1-(2-chloro-6-(trifluoromethyl)benzoyl)-3-(2-fluoro-4-(methoxycarbonyl)phenyl)-1H-pyrazolo[4,3-b]pyridine-6-carboxylic acid (AK-2) (50 mg, 0.1 mmol), DPPA (41 mg, 0.15 mmol), DIPEA (38 mg, 0.3 mmol) and t-BuOH (10 mL) was heated at 90° C. under argon for 16 h. The mixture was cooled down, and diluted with CH$_2$Cl$_2$ (80 mL). The organic layer was separated, washed with brine, dried over Na$_2$SO$_4$, and concentrated. The residue was purified by Prep-TLC (EtOAc) to afford 38 mg (64%) of the title compound as a white solid. LCMS (ESI) calc'd for C27H21ClF4N4O5 [M+H]$^+$: 593.1. found: 593.1.

Step 3. Preparation of 4-(6-(tert-butoxycarbonylamino)-1-(2-chloro-6-(trifluoromethyl)benzoyl)-1H-pyrazolo[4,3-b]pyridin-3-yl)-3-fluorobenzoic acid (29A)

To a stirred solution of methyl 4-(6-(tert-butoxycarbonylamino)-1-(2-chloro-6-(trifluoromethyl)benzoyl)-1H-pyrazolo[4,3-b]pyridin-3-yl)-3-fluorobenzoate (AK-3) (80 mg, 0.14 mmol) was added THF (5.0 mL), H$_2$O (1.0 mL) and LiOH.H$_2$O (57 mg, 1.4 mmol) and the solution was stirred at room temperature overnight. The solution was adjusted to PH=4.0 using 1N HCl, poured into THF (30 mL), and washed with brine (20 mL). The organic layer was dried over Na$_2$SO$_4$ and the solvent was evaporated. Submitting the residue for Prep-HPLC resulted in 60 mg of the title product, Yield: 73%. LCMS (ESI) calc'd for C$_{26}$H$_{19}$ClF$_4$N$_4$O$_5$ [M+H]$^+$: 579.1. found: 579.1; $^1$HNMR (500 MHz, DMSO-d$_6$) δ 13.75 (bs, 1H), 10.35 (s, 1H), 9.25 (s, 1H), 8.81-8.81 (d, 1H), 8.34 (t, 1H), 7.98 (m, 5H), 1.55 (s, 9H).

Step 4. Preparation of methyl 4-(6-(tert-butoxycarbonyl(methyl)amino)-1-(2-chloro-6-(trifluoromethyl)benzoyl)-1H-pyrazolo[4,3-b]pyridin-3-yl)-3-fluorobenzoate (AK-4)

To a solution of methyl 4-(6-(tert-butoxycarbonylamino)-1-(2-chloro-6-(trifluoromethyl)benzoyl)-1H-pyrazolo[4,3-b]pyridin-3-yl)-3-fluorobenzoate (AK-3) (300 mg, 0.5 mmol) in DMF (10 mL) was added NaH (81 mg, 2 mmol, 60%) in portions over 5 min, and the mixture was stirred at 0° C. for 1 h. CH$_3$I (108 mg, 0.76 mmol) in THF (1 mL) was added dropwise by syringe, the reaction mixture was stirred at 0° C. for 12 h and quenched with ice-water, and the aqueous layer was extracted with CH$_2$Cl$_2$ (50 mL×3). The combined organics were washed with H$_2$O, brine, dried over Na$_2$SO$_4$, and concentrated. The residue was purified by silica gel column chromatography (Pentane/EtOAc=10/1) to afford 280 mg (91%) of the title compound. LCMS (ESI) calc'd for C$_{28}$H$_{23}$ClF$_4$N$_4$O$_5$ [M+H]$^+$: 607. found: 607.

Step 5. Preparation of 4-(6-(tert-butoxycarbonyl)methyl)amino)-1-(2-chloro-6-(trifluoromethyl)benzoyl)-1H-pyrazolo[4,3-b]pyridin-3-yl)-3-fluorobenzoic acid (AK-5)

To a stirred solution of methyl 4-(6-(tert-butoxycarbonyl(methyl)amino)-1-(2-chloro-6-(trifluoromethyl)benzoyl)-1H-pyrazolo[4,3-b]pyridin-3-yl)-3-fluorobenzoate (AK-4) (85 mg, 0.14 mmol) was added THF (5.0 mL), H$_2$O (1.0 mL) and LiOH.H$_2$O (57 mg, 1.4 mmol), and the solution was stirred at room temperature overnight. The solution was adjusted to pH=4.0 using 1N HCl, poured into THF (30 mL), and washed with brine (20 mL). The organic layer was dried over Na$_2$SO$_4$ and the organic solvent was evaporated. Submitting the residue for Prep-HPLC resulted in 61 mg of product, Yield: 71%. LCMS (ESI) calc'd for C$_{27}$H$_{21}$ClF$_4$N$_4$O$_5$[M+H]$^+$: 593.1. found: 593.1.

Step 6. Preparation of 4-(1-(2-chloro-6-(trifluoromethyl)benzoyl)-6-(methyl-amino)-1H-pyrazolo[4,3-b]pyridin-3-yl)-3-fluorobenzoic acid (28B)

To a stirred solution of 4-(6-(tert-butoxycarbonyl(methyl)amino)-1-(2-chloro-6-(trifluoromethyl)benzoyl)-1H-pyrazolo[4,3-b]pyridin-3-yl)-3-fluorobenzoic acid (AK-5) (100 mg, 0.17 mmol) was added THF (5.0 mL), and 6 N HCl (4 mL) and the solution was stirred at room temperature for 4 h. The solution was adjusted to pH=4.0 using 2N NaOH, poured into THF (30 mL), and washed with brine (20 mL). The organic layer was dried over Na$_2$SO$_4$, the organic solvent was evaporated and the residue was purified by prep-HPLC to give 20 mg of the desired product. Yield 25%. LCMS (ESI) calc'd for C$_{22}$H$_{13}$ClF$_4$N$_4$O$_3$ [M+H]$^+$: 493.1. found: 493.1; $^1$HNMR (500 MHz, DMSO-d$_6$) δ 13.74 (bs, 1H), 8.328 (s, 1H), 8.268 (t, 1H), 8.01 (d, 1H), 7.94 (d, 1H), 7.89 (m, 1H), 7.84 (d, 1H), 7.74 (m, 1H), 7.19 (d, 1H), 2.87 (d, 1H).

Example 30A: Preparation of 4-(5-acetamido-1-(2-chloro-6-(trifluoromethyl)-benzoyl)-1H-pyrrolo[2,3-c]pyridin-3-yl)-3-fluorobenzoic acid (30A) and 4-(1-(2-chloro-6-(trifluoromethyl)benzoyl)-5-(methylamino)-1H-pyrrolo[2,3-c]pyridin-3-yl)-3-fluorobenzoic acid (30B)
Scheme AL
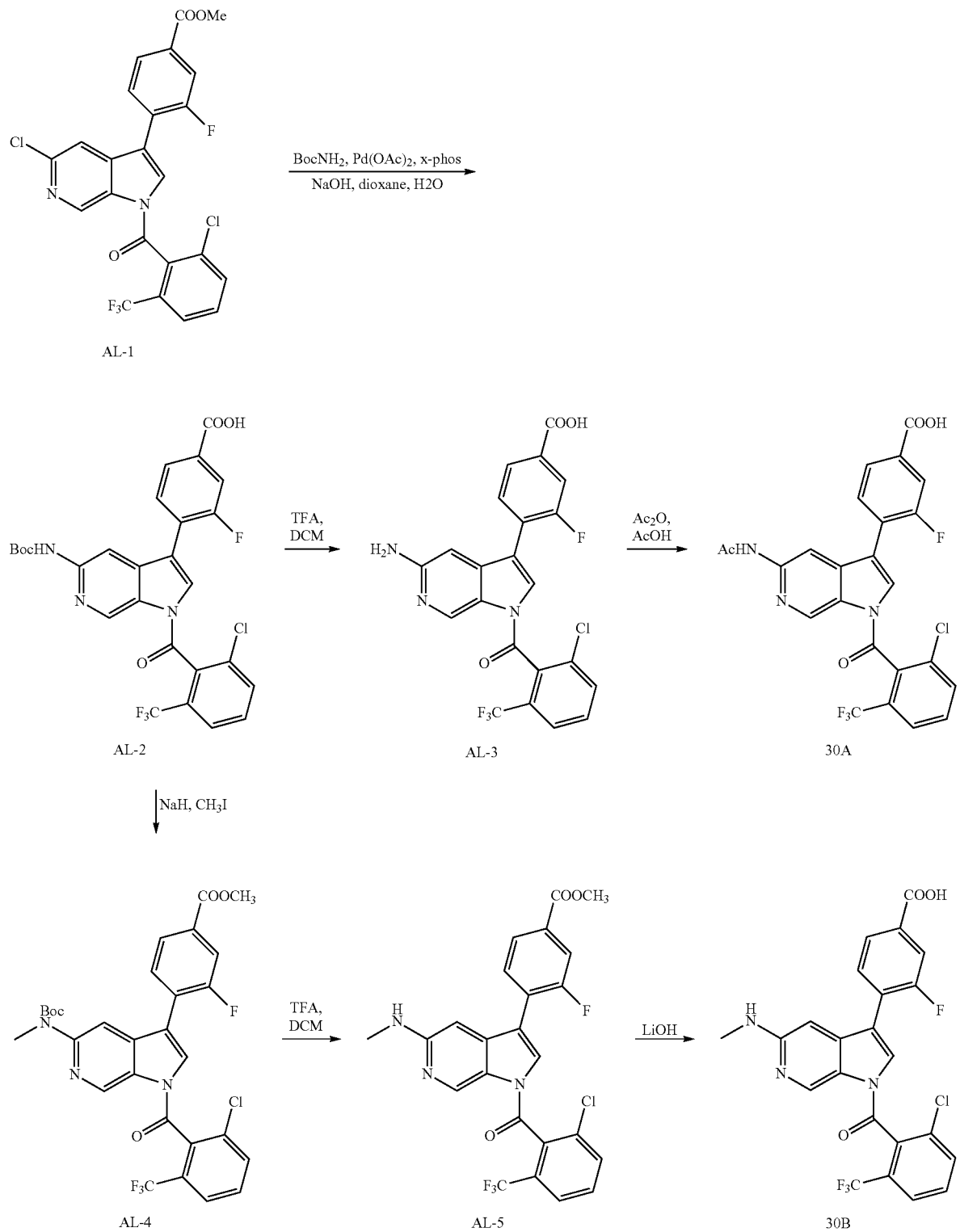

Step 1. 4-(5-(tert-butoxycarbonylamino)-1-(2-chloro-6-(trifluoromethyl)benzoyl)-1H-pyrrolo[2,3-c]pyridin-3-yl)-3-fluorobenzoic acid (AL-2)

To a stirred solution of methyl 4-(5-chloro-1-(2-chloro-6-(trifluoromethyl)benzoyl)-1H-pyrrolo[2,3-c]pyridin-3-yl)-3-fluorobenzoate (AL-1) (550 mg, 1.1 mmol) in dioxane (14 mL) and water (0.5 mL) was added BocNH$_2$ (389 mg, 3.3 mmol), Pd(OAc)$_2$ (50 mg, 0.22 mmol), xant-phos (256 mg, 0.44 mmol) and NaOH (222 mg, 5.5 mmol). The mixture was stirred under argon at 90° C. for 1 h in the microwave reactor. The mixture was filtered and evaporated, and MeOH (5 mL) was added. The resultant solution was submitted for Prep-HPLC under 0.01% TFA, 300 mg solid was obtained, yield: 47%. LCMS (ESI) calc'd for $C_{27}H_{20}ClF_4N_3O_5$ [M+H]$^+$: 578. found: 578.

Step 2. 4-(5-amino-1-(2-chloro-6-(trifluoromethyl)benzoyl)-1H-pyrrolo[2,3-c]pyridin-3-yl)-3-fluorobenzoic acid (AL-3)

To a stirred solution of 4-(5-(tert-butoxy carbonylamino)-1-(2-chloro-6-(trifluoromethyl)benzoyl)-1H-pyrrolo[2,3-c]pyridin-3-yl)-3-fluorobenzoic acid (AL-2) (40 mg, 0.07 mmol) in DCM (0.5 mL) was added TFA (0.5 mL), and the solution was stirred under argon at room temperature for 5 h. The mixture was evaporated, and the crude product was used in the next step directly. LCMS (ESI) calc'd for $C_{22}H_{12}ClF_4N_3O_3$ [M+H]$^+$: 478. found: 478.

Step 3. 4-(5-acetamido-1-(2-chloro-6-(trifluoromethyl)benzoyl)-1H-pyrrolo[2,3-c]pyridin-3-yl)-3-fluorobenzoic acid (30A)

To a stirred solution of 4-(5-amino-1-(2-chloro-6-(trifluoromethyl)benzoyl)-1H-pyrrolo[2,3-c]pyridin-3-yl)-3-fluorobenzoic acid (AL-3) (30 mg, 0.06 mmol) in Ac$_2$O (1 mL) was added AcOH (0.2 mL), and the reaction mixture was stirred under argon at 100° C. for 1 h. The solvent was evaporated, then H$_2$O (1 mL) as added, and the mixture was stirred at room temperature for 2 h. The mixture was purified by Prep-HPLC under 0.01% TFA twice to obtain 10 mg of product (yield: 24.5%). LCMS (ESI) calc'd for $C_{24}H_{14}ClF_4N_3O_4$ [M+H]$^+$: 520. found: 520; $^1$HNMR (400 MHz, DMSO-d$_6$) δ 13.37 (bs, 1H), 10.78 (s, 1H), 9.43 (s, 1H), 8.43 (s, 1H), 8.04 (dd, 2H), 7.9-37.87 (m, 3H), 7.81 (d, 1H), 7.71 (t, 1H), 2.12 (s, 3H).

Step 4. Methyl 4-(5-(tert-butoxycarbonyl)methyl)amino)-1-(2-chloro-6-(trifluoro-methyl)benzoyl)-1H-pyrrolo[2,3-c]pyridin-3-yl)-3-fluorobenzoate (AL-4)

To a stirred solution of 4-(5-acetamido-1-(2-chloro-6-(trifluoromethyl)benzoyl)-1H-pyrrolo[2,3-c]pyridin-3-yl)-3-fluorobenzoic acid (AL-2) (100 mg, 0.17 mmol) in anhydrous DMF (5 mL) at room temperature was added NaH (42 mg, 60%, 1 mmol) and then MeI (98 mg, 0.69 mmol). The solution was stirred at room temperature for 3 hours. Ethyl Acetate (200 mL) was added and the solution was washed with brine (70 mL×2). The solution was evaporated and 120 mg of crude product was obtained for use in the next step without further purification. LCMS (ESI) calc'd for $C_{29}H_{24}ClF_4N_3O_5$ [M+H]$^+$: 606. found: 606.

Step 5. Methyl 4-(1-(2-chloro-6-(trifluoromethyl)benzoyl)-5-(methylamino)-1H-pyrrolo[2,3-c]pyridin-3-yl)-3-fluorobenzoate (AL-5)

To a stirred solution of methyl 4-(5-(tert-butoxycarbonyl(methyl)amino)-1-(2-chloro-6-(trifluoromethyl)-benzoyl)-1H-pyrrolo[2,3-c]pyridin-3-yl)-3-fluorobenzoate (AL-4) (120 mg, as generated from step 4) in DCM (4 mL) was added TFA (2 mL) under N$_2$. The solution was stirred at room temperature for 3 hours and evaporated. 70 mg crude product was collected. It was used the next step without further purification. LCMS (ESI) calc'd for $C_{24}H_{16}ClF_4N_3O_3$ [M+H]$^+$: 506. found: 506.

Step 6. 4-(1-(2-chloro-6-(trifluoromethyl)benzoyl)-5-(methylamino)-1H-pyrrolo[2,3-c]pyridin-3-yl)-3-fluorobenzoic acid (30B)

To a stirred solution of methyl 4-(1-(2-chloro-6-(trifluoromethyl)benzoyl)-5-(methylamino)-1H-pyrrolo[2,3-c]pyridin-3-yl)-3-fluorobenzoate (AL-5) (71 mg, as generated from step 5) in THF (2 mL) was added H$_2$O (2 mL) and LiOH.H$_2$O (58 mg, 1.4 mmol). The solution was stirred at room temperature overnight and adjusted to PH~2 using 1N HCl. The mixture was concentrated and the residue was purified by Prep-HPLC (CH$_3$CN/H$_2$O) to give the title compound. 52 mg product, yield for three steps was 60%. LCMS (ESI) calc'd for $C_{23}H_{14}ClF_4N_3O_3$ [M+H]$^+$: 492. found: 492.

Example 31A: Preparation of 4-(1-(2-chloro-6-(trifluoromethyl)benzoyl)-6-(2-methoxyethyl amino)-1H-pyrazolo[4,3-b]pyridin-3-yl)-3-fluorobenzoic acid

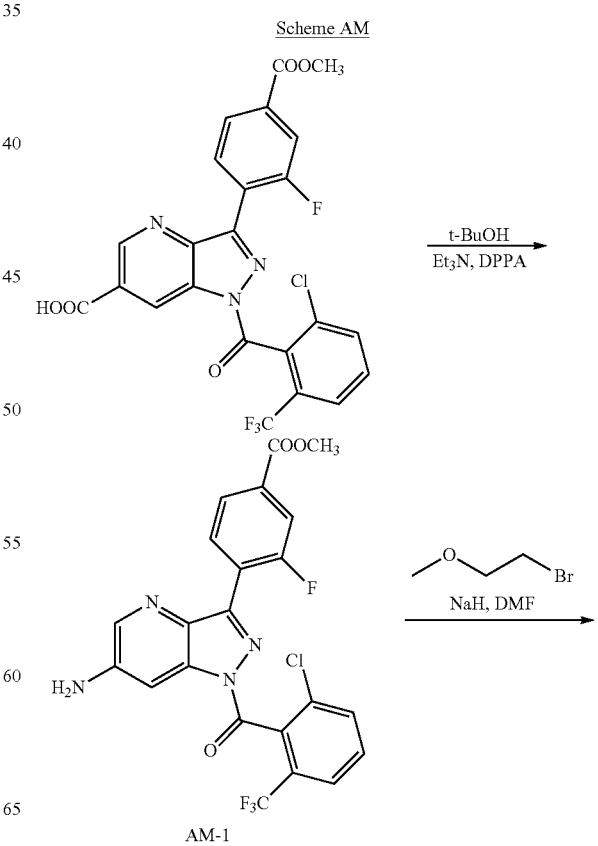

Scheme AM

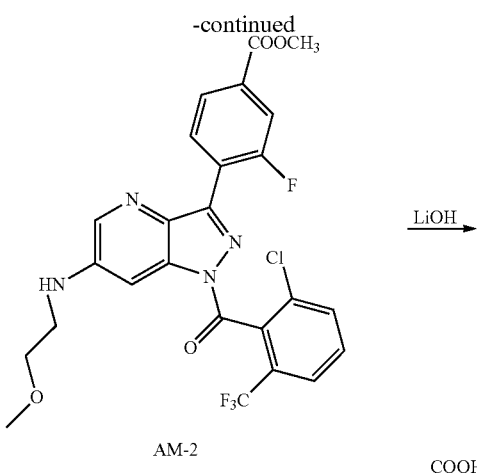

AM-2

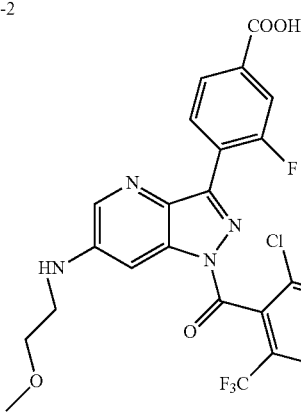

Step 1. Preparation of methyl 4-(6-amino-1-(2-chloro-6-(trifluoromethyl)benzoyl)-1H-pyrazolo[4,3-b]pyridin-3-yl)-3-fluorobenzoate (AM-1)

A mixture of 1-(2-chloro-6-(trifluoromethyl)benzoyl)-3-(2-fluoro-4-(methoxycarbonyl)phenyl)-1H-pyrazolo[4,3-b]pyridine-6-carboxylic acid (313 mg, 0.6 mmol), Et$_3$N (303 mg, 3 mmol) and DPPA (349 mg, 1.2 mmol) in 15 mL of t-BuOH and 2 mL of water was heated to 90° C. for 12 hrs. The reaction mixture was then diluted with EtOAc (50 mL), washed with brine (50 mL*2), dried over anhydrous Na$_2$SO$_4$, and concentrated in vacuo. The crude residue was purified by silica gel column (DCM/MeOH=50/1) to obtain the title compound. LCMS (ESI): calc'd for C$_{22}$H$_{13}$ClF$_4$N$_4$O$_3$, [M+H]$^+$: 493. found: 493.

Step 2. Preparation of methyl 4-(1-(2-chloro-6-(trifluoromethyl)benzoyl)-6-(2-methoxyethylamino)-1H-pyrazolo[4,3-b]pyridin-3-yl)-3-fluorobenzoate (AM-2)

A mixture of methyl 4-(6-amino-1-(2-chloro-6-(trifluoromethyl)benzoyl)-1H-pyrazolo[4,3-b]pyridin-3-yl)-3-fluorobenzoate (AM-1) (148 mg, 0.3 mmol) and NaH (36 mg, 1.5 mmol) in 10 mL of DMF was stirred for 10 mins. Next, 1-bromo-2-methoxyethane (83 mg, 0.6 mmol) was added and the resulting mixture was stirred for 12 h. Then NH$_4$Cl (1 M) was added until pH=9-10, and the mixture was diluted with EtOAc (50 mL), washed with brine (50 mL*2), dried over anhydrous Na$_2$SO$_4$ and concentrated. The residue was purified by silica gel column (DCM/MeOH=40/1) to obtain the title compound. LCMS (ESI): calc'd for C$_{25}$H$_{19}$ClF$_4$N$_4$O$_4$, [M+H]$^+$: 551. found: 551.

Step 3. Preparation of 4-(1-(2-chloro-6-(trifluoromethyl)benzoyl)-6-(2-methoxy ethylamino)-1H-pyrazolo[4,3-b]pyridin-3-yl)-3-fluorobenzoic acid (31A)

A mixture of methyl 4-(1-(2-chloro-6-(trifluoromethyl)benzoyl)-6-(2-methoxyethylamino)-1H-pyrazolo[4,3-b]pyridin-3-yl)-3-fluorobenzoate (AM-2) (39 mg, 0.07 mmol) and LiOH.H$_2$O (16 mg, 0.37 mmol) in 10 mL of THF and 10 mL of pure H$_2$O was stirred at room temperature for 2 hrs. The solvent was evaporated and the residue was dissolved in water. HCl (5% sol in water) was added until pH=4-5. The precipitated solid was filtered, washed with water (10 mL) followed by n-hexane (10 mL) and then dried to afford the title compound as a solid. LCMS (ESI): calc'd for C$_{24}$H$_{17}$ClF$_4$N$_4$O$_4$, [M+H]$^+$: 537 found: 537; $^1$HNMR (400 MHz, DMSO) δ 8.42 (1H, s), 8.25-8.29 (1H, m), 8.01 (1H, d, J=8 Hz), 7.96 (1H, d, J=8 Hz), 7.91 (1H, d, J=8 Hz), 7.82-7.86 (1H, m), 7.76 (1H, d, J=12 Hz), 7.70 (1H, d, J=4 Hz), 7.16-7.19 (1H, m), 3.60-3.62 (2H, m), 3.38-3.42 (2H, m), 3.33 (3H, s).

Example 32A: Preparation of 4-(1-(2-chloro-6-(trifluoromethyl)benzoyl)-2-methyl-1H-indol-3-yl)-3-fluorobenzoic acid

SCHEME AN

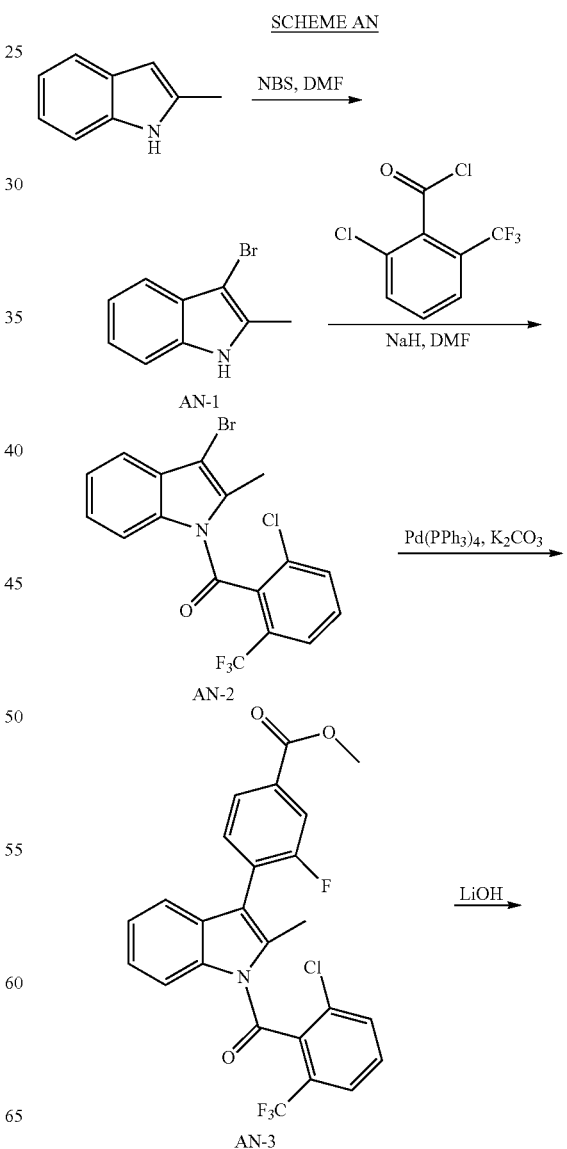

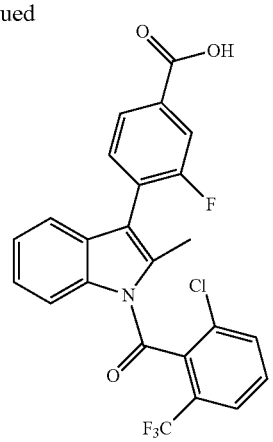

Step 1. 3-bromo-2-methyl-1H-indole (AN-1)

A mixture of 2-methyl-1H-indole (0.4 g, 3.05 mmol) and NBS (0.6 g, 3.36 mmol) in DMF (5 mL) was stirred at room temperature for 1.5 h. The reaction mixture was diluted with water (50 mL) and the aqueous layer was extracted with EA (50 mL×3). The combined organic layers were washed with brine (50 mL×1), dried over anhydrous $Na_2SO_4$ and concentrated. The residue was chromatographed on silica gel (PE:EA 5:1) to obtain the title compound as a pale red solid. LCMS (ESI) calc'd for $C_9H_8BrN$ [M+H]$^+$: 210. found: 210.

Step 2. Preparation of (3-bromo-2-methyl-1H-indol-1-yl)(2-chloro-6-(trifluoro methyl)phenyl)methanone (AN-2)

A mixture of 3-bromo-2-methyl-1H-indole (AN-1) (0.56 g, 2.67 mmol) in DMF (4 mL) was cooled to 0° C. in an ice-water bath and NaH (0.27 g, 6.68 mmol) was added slowly. Then a solution of 2-chloro-6-(trifluoromethyl)benzoyl chloride (0.71 g, 2.94 mmol) in DMF (2 mL) was added dropwise. The reaction mixture was warmed to room temperature and stirred for 14 h. Saturated $NH_4Cl$ solution was added to quench the reaction. The aqueous layer was extracted with EA (50 mL×2). The combined organic layers were washed with brine (50 mL×1), dried over anhydrous $Na_2SO_4$ and concentrated to obtain the title compound as a brown solid. LCMS (ESI) calc'd for $C_{17}H_{10}BrClF_3NO$ [M+H]$^+$: 416. found: 416.

Step 3. Preparation of methyl 4-(1-(2-chloro-6-(trifluoromethyl)benzoyl)-2-methyl-1H-indol-3-yl)-3-fluorobenzoate (AN-3)

A mixture of (3-bromo-2-methyl-1H-indol-1-yl)(2-chloro-6-(trifluoro methyl)phenyl)methanone (AN-2) (0.15 mg, 0.36 mmol), 2-fluoro-4-(methoxycarbonyl)phenylboronic acid (0.11 g, 0.54 mmol), Pd(PPh$_3$)$_4$ (42 mg, 0.036 mmol) and $K_2CO_3$ (0.15 g, 1.08 mmol) was suspended in 1,4-dioxane (5 mL) and $H_2O$ (1 mL). The reaction mixture was heated at 120° C. in a microwave reactor for 2 h. The resulting mixture was diluted with $H_2O$ (30 mL) and the aqueous layer was extracted with ethyl acetate (30 mL×3). The combined organic layers were washed with brine (20 mL×1), dried over anhydrous $Na_2SO_4$ and concentrated to obtain the title compound as brown oil. LCMS (ESI) calc'd for $C_{25}H_{16}ClF_4NO_3$ [M+H]$^+$: 490. found: 490.

Step 4. Preparation of 4-(1-(2-chloro-6-(trifluoromethyl)benzoyl)-2-methyl-1H-indol-3-yl)-3-fluorobenzoic acid (32A)

A mixture of methyl 4-(1-(2-chloro-6-(trifluoromethyl)benzoyl)-2-methyl-1H-indol-3-yl)-3-fluorobenzoate (AN-3) (100 mg, 0.20 mmol) and LiOH (34 mg, 0.80 mmol) in THF (4 mL) and $H_2O$ (2 mL) was stirred at room temperature overnight. The reaction mixture was diluted with $H_2O$ (20 mL). 2M HCl solution was added to adjust to pH=3 and the aqueous layer was extracted with ethyl acetate (20 mL×3). The combined organic layers were washed with brine (20 mL×1), dried over anhydrous $Na_2SO_4$ and concentrated. The residue was purified with prep-HPLC (acetonitrile-water system) to obtain the title compound as white solid. LCMS (ESI) calc'd for $C_{24}H_{14}ClF_4NO_3$ [M+H]$^+$: 476. found: 476; $^1$HNMR (400 MHz, MeOD) δ 7.80-8.62 (6H, m), 7.54-7.64 (1H, m), 7.19-7.44 (2H, m), 6.00-7.42 (1H, m), 2.71 (1H, s), 1.73 (2H, s).

The following example shown in TABLE 13 was prepared following similar procedures described for Example 32A in Scheme AN, which can be achieved by those of ordinary skill in the art of organic synthesis in light of the present disclosure.

TABLE 13

| Ex. | Chemical Name | Structure | LCMS [M + H]$^+$ Found |
|---|---|---|---|
| 32B | 4-(2-methyl-1-(2-(trifluoromethyl)benzoyl)-1H-indol-3-yl)benzoic acid | 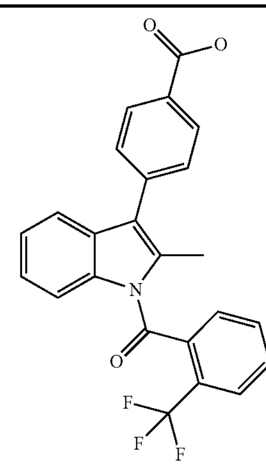 | 424 |

Example 33A: Preparation of 4-(1-(2-chloro-6-cyclopropylbenzoyl)-1H-pyrazolo[4,3-b]pyridin-3-yl)-3,5-difluorobenzoic acid Scheme AO

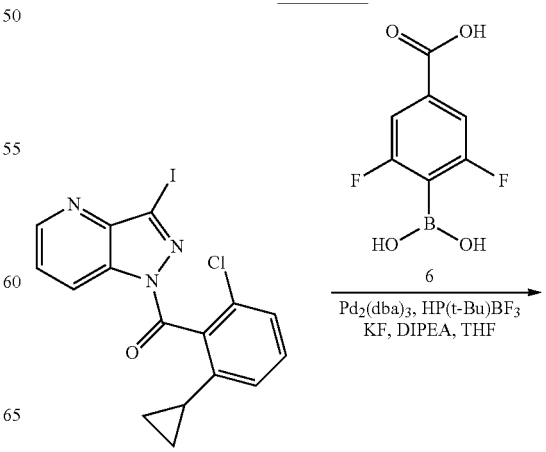

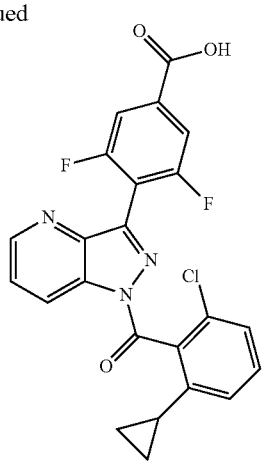

Step 1. Preparation of 4-(1-(2-chloro-6-cyclopropyl-benzoyl)-1H-pyrazolo[4,3-b]pyridin-3-yl)-3,5-difluorobenzoic acid (33A)

(2-chloro-6-cyclopropylphenyl)(3-iodo-1H-pyrazolo[4,3-b]pyridin-1-yl)methanone (200 mg, 0.47 mmol), 4-borono-3,5-difluorobenzoic acid (191 mg, 0.94 mmol), $Pd_2(dba)_3$ (132 mg, 0.19 mmol), HP(t-Bu)$BF_3$ (35 mg, 0.12 mmol), KF (164 mg, 2.8 mmol) and DIPEA (182 mg, 1.4 mmol) were mixed in THF (10 ml). The mixture was stirred at 60° C. for 2 h and then stirred at 70° C. for 1 h under microwave. The reaction mixture was next cooled to room temperature, diluted with THF (30 ml) and filtered. The filtrate was concentrated to obtain a residue that was purified by prep-HPLC (solvents: $CH_3CN/H_2O$) to afford 20 mg (8%) of the title compound as white solid. LCMS (ESI): calc'd for $C_{23}H_{14}ClF_2N_3O_3$ [M+H]$^+$: 454. found: 454; $^1$HNMR (400 MHz, DMSO) δ 9.04-9.02 (1H, d), 8.84-8.82 (1H, d), 7.83-7.80 (1H, m), 7.76-7.74 (2H, d), 7.46-7.42 (1H, t), 7.37-7.35 (1H, d), 7.15-7.13 (1H, d), 1.91-1.86 (1H, m), 0.90-0.81 (2H, m), 0.76-0.70 (1H, m), 0.60-0.55 (1H, m).

The following examples shown in TABLE 14 were prepared following similar procedures described for Example 33A in Scheme AO, which can be achieved by those of ordinary skill in the art of organic synthesis in light of the present disclosure.

TABLE 14

| Ex. | Chemical Name | Structure | LCMS [M + H]$^+$ Found |
|---|---|---|---|
| 33B | 4-(1-(2-chloro-6-cyclopropylbenzoyl)-1H-indazol-3-yl)-3,5-difluorobenzoic acid | | 453 |
| 33C | 4-(1-(2-chloro-6-cyclopropylbenzoyl)-4-fluoro-1H-indazol-3-yl)-3,5-difluorobenzoic acid | 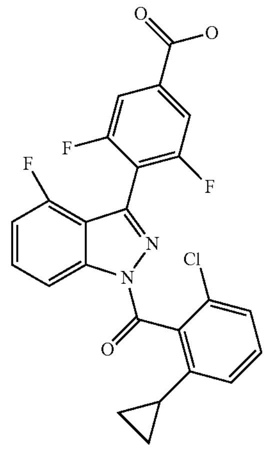 [SMILES: O=C(O)c1cc(F)c(-c2nn(C(=O)c3c(Cl)cccc3C3CC3)c3cccc(F)c23)c(F)c1] | 471 |
| 33D | 4-(1-(2-chloro-6-cyclopropylbenzoyl)-1H-pyrrolo[3,2-b]pyridin-3-yl)-3,5-difluorobenzoic acid | 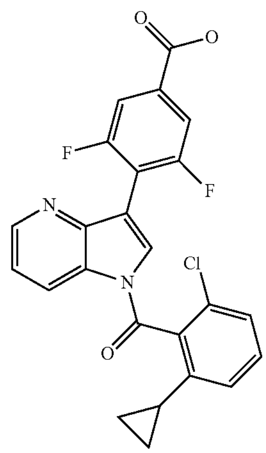 [SMILES: O=C(O)c1cc(F)c(-c2cn(C(=O)c3c(Cl)cccc3C3CC3)c3cccnc23)c(F)c1] | 453 |

Example 34A: Preparation of 4-(1-(2-chloro-6-cyclobutylbenzoyl)-1H-pyrazolo[4,3-b]pyridin-3-yl)-3,5-difluorobenzoic acid Scheme AP

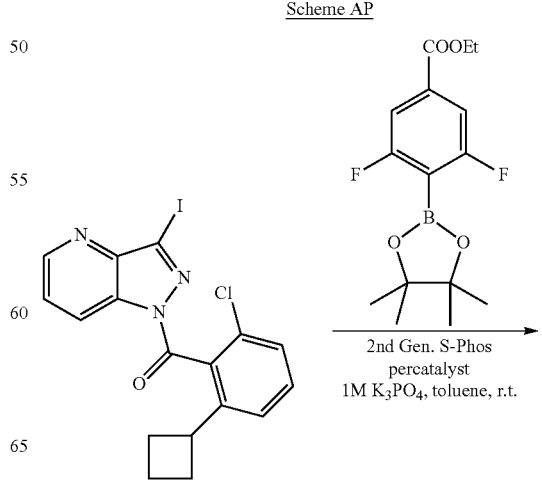

2nd Gen. S-Phos percatalyst
1M $K_3PO_4$, toluene, r.t.

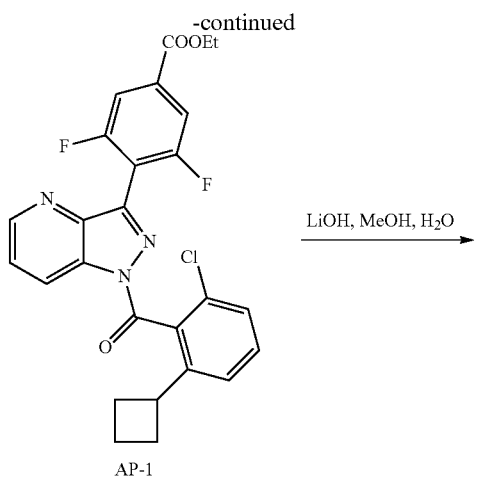

AP-1

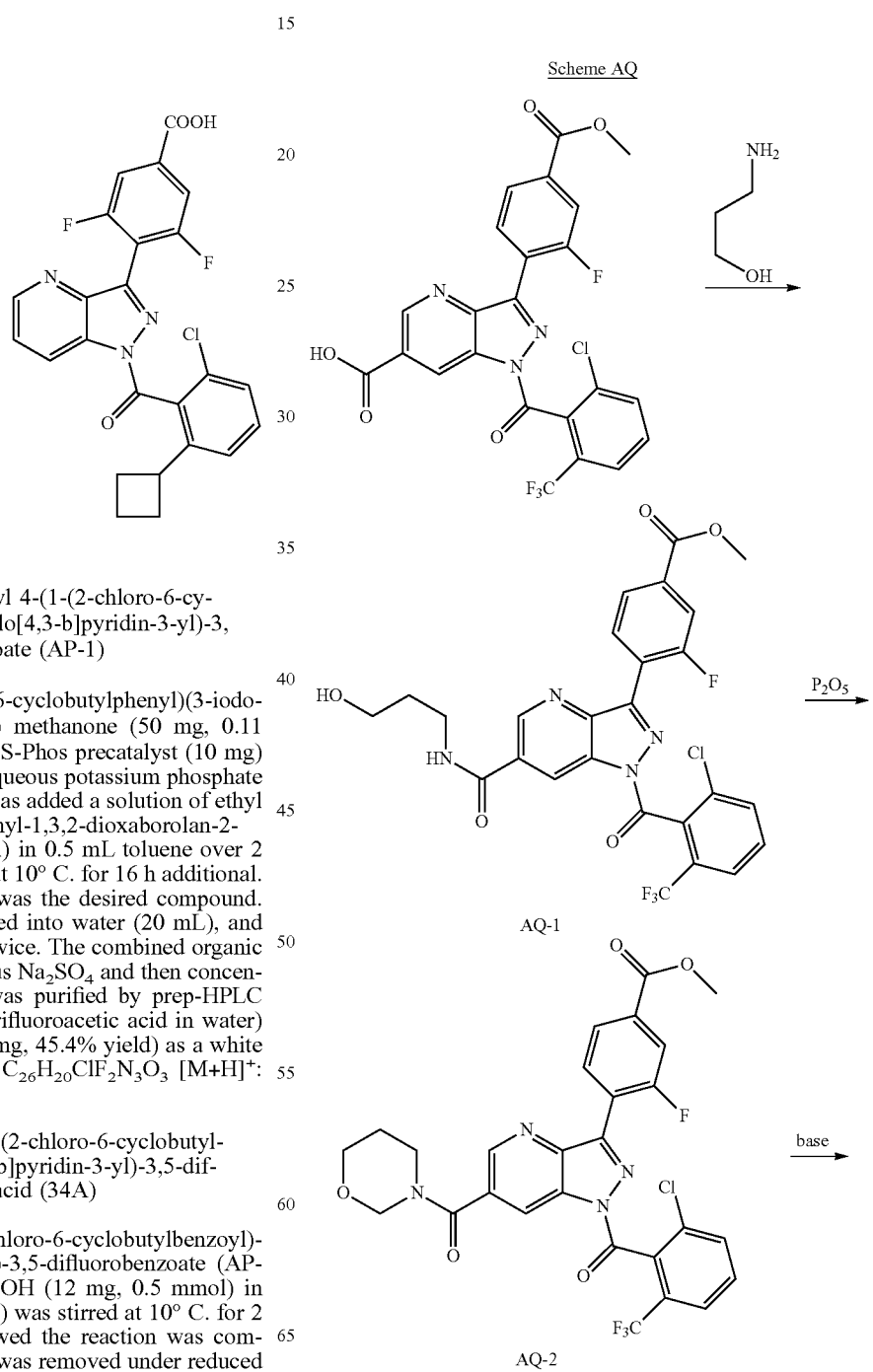

The aqueous layer was adjusted to pH=5 with 2 M HCl, and extracted with DCM (10 mL×3). The combined organic layers were washed with brine (20 mL), dried over anhydrous $Na_2SO_4$, and concentrated in vacuo to give the title compound (15 mg, 61.8% yield) as a white solid. LCMS (ESI): calc'd for $C_{24}H_{16}ClF_2N_3O_3$ [M+H]$^+$: 468, found: 468; $^1$H NMR (400 MHz, DMSO-$d_6$) δ 8.93-8.86 (2H, m), 7.85 (1H, dd, J=4.5, 8.5 Hz), 7.74 (2H, d, J=7.8 Hz), 7.58-7.53 (1H, m), 7.48-7.44 (2H, m), 3.59-3.43 (1H, m), 2.27-2.07 (2H, m), 2.00-1.75 (3H, m), 1.69-1.55 (1H, m).

Example 35A: Preparation of 4-(1-(2-chloro-6-(trifluoromethyl)benzoyl)-6-(1,3-oxazinane-3-carbonyl)-1H-pyrazolo[4,3-b]pyridin-3-yl)-3-fluorobenzoic acid Step 1. Preparation of ethyl 4-(1-(2-chloro-6-cyclobutylbenzoyl)-1H-pyrazolo[4,3-b]pyridin-3-yl)-3,5-difluorobenzoate (AP-1)

To a mixture of (2-chloro-6-cyclobutylphenyl)(3-iodo-1H-pyrazolo[4,3-b]pyridin-1-yl) methanone (50 mg, 0.11 mmol) and Buchwald 2$^{nd}$ Gen. S-Phos precatalyst (10 mg) in 1 mL toluene and 1.0 M of aqueous potassium phosphate (73 mg, 0.34 mmol) at 10° C. was added a solution of ethyl 3,5-difluoro-4-(4,4,5,5-tetramethyl-1,3,2-dioxaborolan-2-yl)benzoate (54 mg, 0.17 mmol) in 0.5 mL toluene over 2 hours. The mixture was stirred at 10° C. for 16 h additional. LCMS showed major product was the desired compound. The reaction mixture was poured into water (20 mL), and extracted with DCM (20 mL) twice. The combined organic layers were dried over anhydrous $Na_2SO_4$ and then concentrated in vacuo. The residue was purified by prep-HPLC (60-90% acetonitrile+0.75%0 trifluoroacetic acid in water) to give the title compound (25 mg, 45.4% yield) as a white solid. LCMS (ESI): calc'd for $C_{26}H_{20}ClF_2N_3O_3$ [M+H]$^+$: 496. found: 496.

Step 2. Preparation of 4-(1-(2-chloro-6-cyclobutylbenzoyl)-1H-pyrazolo[4,3-b]pyridin-3-yl)-3,5-difluorobenzoic acid (34A)

A mixture of ethyl 4-(1-(2-chloro-6-cyclobutylbenzoyl)-1H-pyrazolo[4,3-b]pyridin-3-yl)-3,5-difluorobenzoate (AP-1) (25 mg, 0.05 mmol) and LiOH (12 mg, 0.5 mmol) in MeOH (2 mL) and water (1 mL) was stirred at 10° C. for 2 hours, after which LCMS showed the reaction was complete. Then most of the solvent was removed under reduced pressure, and the residue was dissolved in water (10 mL).

-continued

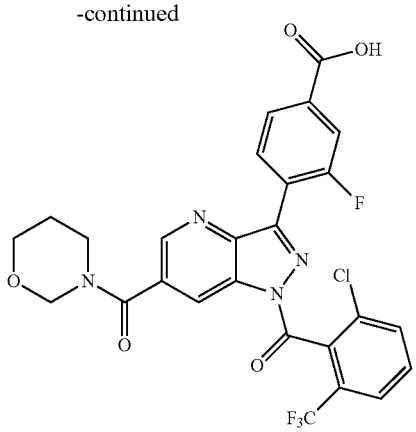

Step 1: Preparation of methyl 4-(1-(2-chloro-6-(trifluoromethyl)benzoyl)-6-((3-hydroxypropyl)carbamoyl)-1H-pyrazolo[4,3-b]pyridin-3-yl)-3-fluorobenzoate (AQ-1)

To a vial were added 1-(2-chloro-6-(trifluoromethyl)benzoyl)-3-(2-fluoro-4-(methoxycarbonyl)phenyl)-1H-pyrazolo[4,3-b]pyridine-6-carboxylic acid (75 mg, 0.144 mmol), 3-aminopropan-1-ol (21.59 mg, 0.287 mmol), BOP (95 mg, 0.216 mmol), THF (1437 µl), and finally DIPEA (75 µl, 0.431 mmol). The reaction was then allowed to stir at room temperature for 14 h. The reaction was then concentrated and the residue was purified by flash chromatography (EtOAc/Hexane 5-75%) to give the title compound as a colorless solid. (57 mg, 68%) LCMS (ESI) calc'd for $C_{26}H_{19}ClF_4N_4O_5$ [M+H]$^+$: 579. found: 579.

Step 2: Preparation of 4-(1-(2-chloro-6-(trifluoromethyl)benzoyl)-6-(1,3-oxazinane-3-carbonyl)-1H-pyrazolo[4,3-b]pyridin-3-yl)-3-fluorobenzoate (AQ-2)

To a vial were added methyl 4-(1-(2-chloro-6-(trifluoromethyl)benzoyl)-6-((3-hydroxypropyl)carbamoyl)-1H-pyrazolo[4,3-b]pyridin-3-yl)-3-fluorobenzoate (AQ-1) (55 mg, 0.095 mmol), dimethoxymethane (50.4 µl, 0.570 mmol), CHCl$_3$ (950 µl), and phosphorus pentoxide (53.9 mg, 0.380 mmol), and the reaction was heated to 70° C. for 4 hours. The mixture was then cooled, neutralized with 2N HCl, diluted with EtOAc, washed 2× with aqueous NaHCO$_3$ and 1× with brine. Aqueous layers were back extracted 1× with ethyl acetate, combined organic layers were dried with Na$_2$SO$_4$, filtered and the solvent was evaporated under reduced pressure. The residue was purified by flash chromatography (EtOAc/Hexane 10-100%) to give the title compound as a colorless solid. (30 mg, 53%) LCMS (ESI) calc'd for $C_{27}H_{19}ClF_4N_4O_5$ [M+H]$^+$: 591. found: 591.

Step 3: Preparation of 4-(1-(2-chloro-6-(trifluoromethyl)benzoyl)-6-(1,3-oxazinane-3-carbonyl)-1H-pyrazolo[4,3-b]pyridin-3-yl)-3-fluorobenzoic acid (35A)

To a vial were added methyl 4-(1-(2-chloro-6-(trifluoromethyl)benzoyl)-6-(1,3-oxazinane-3-carbonyl)-1H-pyrazolo[4,3-b]pyridin-3-yl)-3-fluorobenzoate (AQ-2) (30 mg, 0.051 mmol), THF (254 µl), water (254 µl) and lithium hydroxide (4.86 mg, 0.203 mmol). The reaction was allowed to stir for 1 hour at room temperature, acidified with 2N HCl, and then concentrated in vacuo. The residue was purified by prep-HPLC (Acetonitrile/Water+0.10% TFA 50-100%) to give the title compound as a colorless solid. (20 mg, 68%) LCMS (ESI) calc'd for $C_{26}H_{17}ClF_4N_4O_5$ [M+H]$^+$: 577. found: 577.

The following example shown in TABLE 15 was prepared following similar procedures described for Example 35A in Scheme AQ, which can be achieved by those of ordinary skill in the art of organic synthesis in light of the present disclosure.

TABLE 15

| Ex. | Chemical Name | Structure | LCMS [M + H]$^+$ Found |
|-----|---------------|-----------|------------------------|
| 35B | 4-(1-(2-chloro-6-(trifluoromethyl)benzoyl)-6-(oxazolidine-3-carbonyl)-1H-pyrazolo[4,3-b]pyridin-3-yl)-3-fluorobenzoic acid | 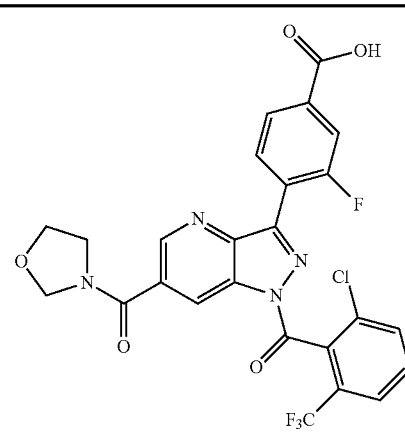 | 563 |

213

Example 36A: Preparation of 4-(6-(azetidine-1-carbonyl)-1-(2-chloro-6-(trifluoromethyl)benzoyl)-1H-indol-3-yl)-3-fluorobenzoic acid

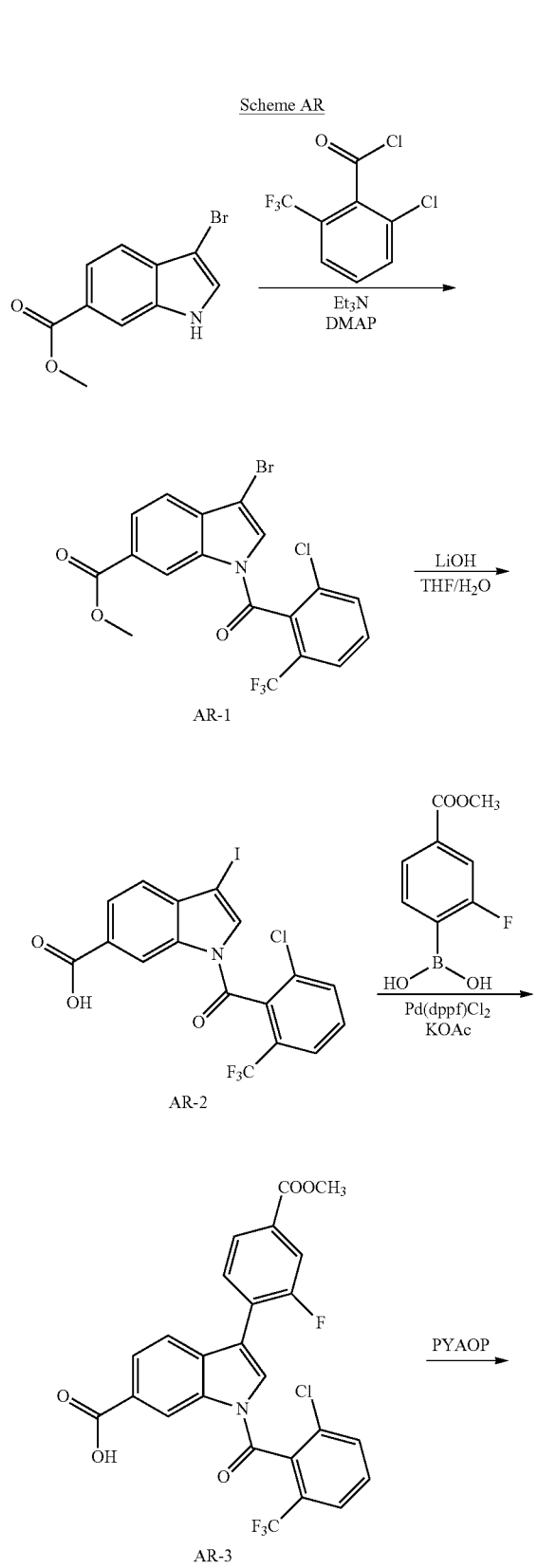

214

-continued

Step 1. Preparation of methyl 3-bromo-1-(2-chloro-6-(trifluoromethyl)benzoyl)-1H-indole-6-carboxylate (AR-1)

To a 250 mL round-bottomed flask, were added methyl 3-iodo-1H-indazole-6-carboxylate (9.8 g, 38.7 mmol), 2-chloro-6-(trifluoromethyl)benzoyl chloride (10.3 g, 42.6 mmol), DMAP (4.72 g, 38.7 mmol) and $CH_2Cl_2$ (100 mL). After stirring at room temperature for 3 min, TEA (11.2 mL, 77 mmol) was added slowly. The reaction mixture was stirred at room temperature overnight, after which LC-MS showed no starting materials remaining. Then the mixture was poured into 30 mL water. The organic phase was separated, and the aqueous phase was extracted twice with 20 mL $CH_2Cl_2$. The combined organic extracts were washed successively with two 20 mL portions of water and 10 mL of brine, dried over anhydrous sodium sulfate, filtered and concentrated at reduced pressure to give a yellow solid. The residue was purified by column chromatography on 60 g of silica gel eluting with Petroleum ether/EtOAc from 50/1 to 10/1, to give a fawn solid of the title compound. LCMS (ESI): calc'd for $C_{18}H_{10}BrClF_3NO_3$, $[M+H]^+$: 460. found: 460.

Step 2. Preparation of 1-(2-chloro-6-(trifluoromethyl)benzoyl)-3-iodo-1H-indole-6-carboxylic acid (AR-2)

A mixture of methyl 3-bromo-1-(2-chloro-6-(trifluoromethyl)benzoyl)-1H-indole-6-carboxylate (AR-1) (14.5 g, 32.48 mmol) and LiOH (3.40 g, 162.40 mmol) in 10 mL THF and 50 mL pure H$_2$O was stirred at room temperature overnight. The solvent was evaporated and the residue was dissolved in water. HCl (5% sol in water) was added until pH 4-5. The precipitated solid was filtered, washed with water and n-hexane, and dried over Na$_2$SO$_4$ to afford an off-white solid of the title compound: calc'd for C$_{17}$H$_8$ClF$_3$INO$_3$, [M+H]$^+$: 494. found: 494.

Step 3. Preparation of 1-(2-chloro-6-(trifluoromethyl)benzoyl)-3-(2-fluoro-4-(methoxycarbonyl)phenyl)-1H-indole-6-carboxylic acid (AR-3)

A mixture of 1-(2-chloro-6-(trifluoromethyl)benzoyl)-3-iodo-1H-indole-6-carboxylic acid (AR-2) (301 mg, 0.61 mmol), 2-fluoro-4-(methoxycarbonyl)phenylboronic acid (182 mg, 0.92 mmol), Pd(dppf)Cl$_2$ (50 mg, 0.061 mmol) and KOAc (181 mg, 1.83 mmol) in 10 mL dioxane and 2 mL pure H$_2$O was heated to 95° C. for 2 h under microwave. The reaction mixture was then diluted with EtOAc (50 mL), washed with brine (50 mL*2), dried over anhydrous Na$_2$SO$_4$, and concentrated. The residue was purified by silica gel column (Petroleum ether/EtOAc=20/1) to obtain the title compound as a white solid. LCMS (ESI): calc'd for C$_{25}$H$_{14}$ClF$_4$NO$_5$, [M+H]$^+$: 520. found: 520

Step 4. Preparation of methyl 4-(6-(azetidine-1-carbonyl)-1-(2-chloro-6-(trifluoromethyl)benzoyl)-1H-indol-3-yl)-3-fluorobenzoate (AR-4)

1-(2-chloro-6-(trifluoromethyl)benzoyl)-3-(2-fluoro-4-(methoxycarbonyl)phenyl)-1H-indole-6-carboxylic acid (AR-3) (187 mg, 0.36 mmol) was dissolved in CH$_2$Cl$_2$ (15 mL). Azetidine hydrochloride (40 mg, 0.43 mmol) and PYAOP (374 mg, 0.72 mmol) were added, and the mixture was stirred at room temperature for 2 mins. TEA (0.16 mL, 1.08 mmol) was added and the mixture was stirred at room temperature for 2 h. The reaction mixture was diluted with EtOAc (20 mL), washed with brine (20 mL*2), dried over anhydrous Na$_2$SO$_4$, and concentrated to afford the title compound as white solid. LCMS (ESI): calc'd for C$_{28}$H$_{19}$ClF$_4$N$_2$O$_4$, [M+H]$^+$: 559. found: 559.

Step 5. Preparation of 4-(6-(azetidine-1-carbonyl)-1-(2-chloro-6-(trifluoro-methyl)benzoyl)-1H-indol-3-yl)-3-fluorobenzoic acid (36A)

A mixture of methyl 4-(6-(azetidine-1-carbonyl)-1-(2-chloro-6-(trifluoromethyl)benzoyl)-1H-indol-3-yl)-3-fluorobenzoate (AR-4) (39 mg, 0.07 mmol) and LiOH.H$_2$O (16 mg, 0.37 mmol) in 10 mL THF and 10 mL pure H$_2$O was stirred at room temperature for 2 hrs. The solvent was evaporated and the residue was dissolved in water. HCl (5% sol in water) was added until pH=4-5. The precipitated solid was filtered, washed sequentially with water (10 mL) and n-hexane (10 mL), and dried to afford the title compound as a solid. LCMS (ESI): calc'd for C$_{27}$H$_{17}$ClF$_4$N$_2$O$_4$, [M+H]$^+$: 545 found: 545; $^1$HNMR (400 MHz, DMSO) δ 8.82 (1H, s), 7.96-8.03 (2H, m), 7.83-7.90 (2H, m), 7.72-7.77 (4H, m), 7.56 (1H, s), 4.24-4.27 (4H, m), 2.29-2.34 (2H, m).

The following example shown in TABLE 16 was prepared following similar procedures described for Example 35A in Scheme AR, which can be achieved by those of ordinary skill in the art of organic synthesis in light of the present disclosure.

TABLE 16

| Ex. | Chemical Name | Structure | LCMS [M + H]$^+$ Found |
|---|---|---|---|
| 36B | 4-(1-(2-chloro-6-(trifluoromethyl)benzoyl)-6-(3-methoxy-azetidine-1-carbonyl)-1H-indol-3-yl)-3-fluorobenzoic acid | 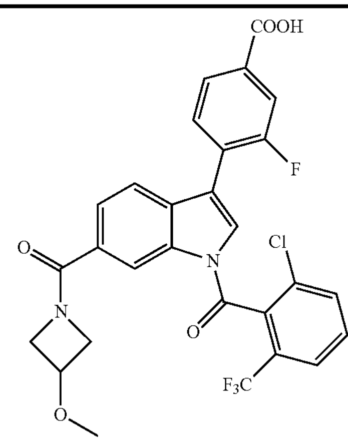 | 575 |

Example 37A: Preparation of 4-(6-(2-amino-2-oxo-ethyl)-1-(2-chloro-6-(trifluoromethyl)benzoyl)-1H-pyrazolo[4,3-b]pyridin-3-yl)-3-fluorobenzoic acid

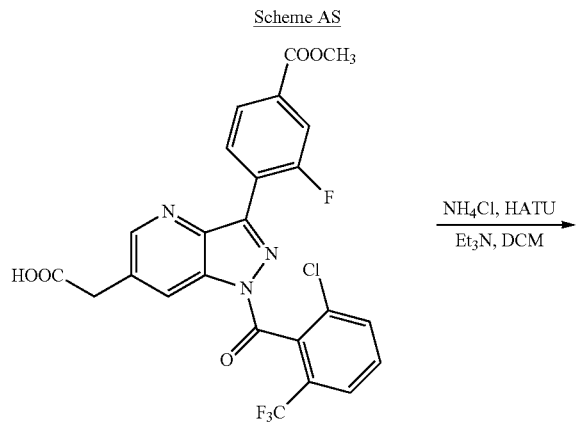

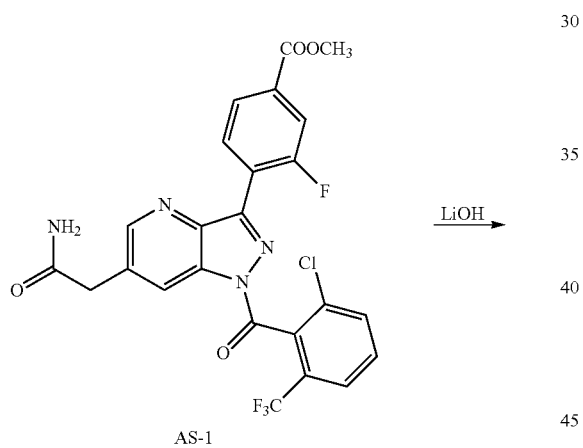

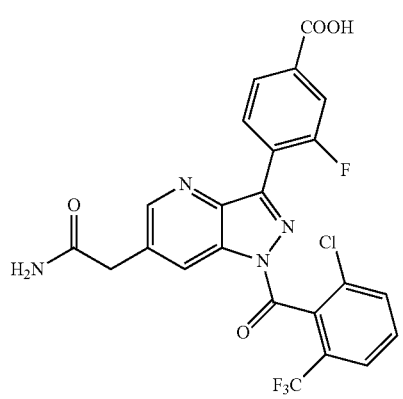

Step 1. Preparation of methyl 4-(6-(2-amino-2-oxo-ethyl)-1-(2-chloro-6-(trifluoro methyl)benzoyl)-1H-pyrazolo[4,3-b]pyridin-3-yl)-3-fluorobenzoate (AS-1)

A mixture of 2-(1-(2-chloro-6-(trifluoromethyl)benzoyl)-3-(2-fluoro-4-(methoxycarbonyl)phenyl)-1H-pyrazolo[4,3-b]pyridin-6-yl)acetic acid (50 mg, 0.09 mmol), NH$_4$Cl (10 mg, 0.19 mmol), HATU (72 mg, 0.19 mmol), and NEt$_3$ (28 mg, 0.28 mmol) in DCM (20 mL) was stirred at room temperature for 10 h. The mixture was extracted with EtOAc and water. The organic phase was washed with brine, dried over Na$_2$SO$_4$, filtered, and concentrated to give the crude title compound. LCMS (ESI) calc'd for C$_{24}$H$_{15}$ClF$_4$N$_4$O$_4$ [M+H]$^+$: 535.0. found: 535.0.

Step 2. Preparation of 4-(6-(2-amino-2-oxoethyl)-1-(2-chloro-6-(trifluoromethyl)benzoyl)-1H-pyrazolo[4,3-b]pyridin-3-yl)-3-fluorobenzoic acid (37A)

To a solution of methyl 4-(6-(2-amino-2-oxoethyl)-1-(2-chloro-6-(trifluoro methyl)benzoyl)-1H-pyrazolo[4,3-b]pyridin-3-yl)-3-fluorobenzoate (AS-1) (40 mg, 0.07 mmol) in THF (20 mL) and water (10 mL) was added LiOH.H$_2$O (16 mg, 0.35 mmol) at 0° C. The mixture was stirred at room temperature for 12 h. The solvents were removed under reduced pressure. The mixture was acidified with 1 M HCl to pH 1-2 and then extracted with EtOAc, washed with brine, dried over anhydrous Na$_2$SO$_4$, filtered and concentrated under reduced pressure to give the title compound. LCMS (ESI) calc'd for C$_{23}$H$_{13}$ClF$_4$N$_4$O$_4$ [M+H]$^+$: 521.0. found: 521.0. $^1$H NMR (400 MHz, DMSO) δ 8.80 (d, 2H), 8.30 (s, 1H), 7.79-8.02 (m, 5H), 3.80 (s, 2H).

The following examples shown in TABLE 17 were prepared following similar procedures described for Example 37A in Scheme AS, which can be achieved by those of ordinary skill in the art of organic synthesis in light of the present disclosure.

TABLE 17

| Ex. | Chemical Name | Structure | LCMS [M + H]+ Found |
|---|---|---|---|
| 37B | 4-(6-(2-(azetidin-1-yl)-2-oxoethyl)-1-(2-chloro-6-(trifluoromethyl)benzoyl)-1H-pyrazolo[4,3-b]pyridin-3-yl)-3-fluorobenzoic acid | 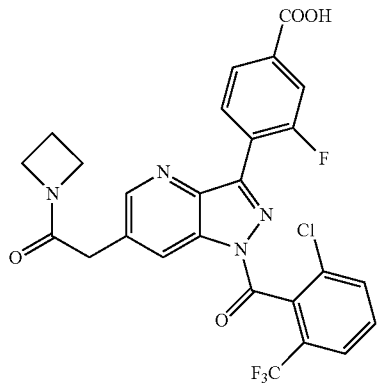 [SMILES: O=C(O)c1ccc(-c2nn(C(=O)c3c(Cl)cccc3C(F)(F)F)c3cc(CC(=O)N4CCC4)cnc23)c(F)c1] | 561 |
| 37C | 4-(1-(2-chloro-6-(trifluoromethyl)benzoyl)-6-(2-(methylamino)-2-oxoethyl)-1H-pyrazolo[4,3-b]pyridin-3-yl)-3-fluorobenzoic acid | 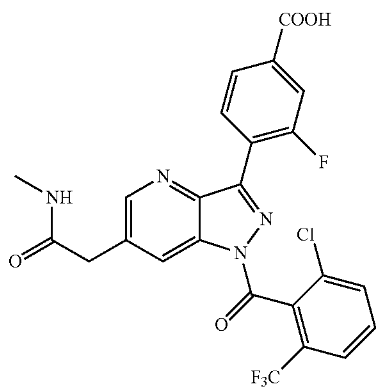 [SMILES: CNC(=O)Cc1cnc2c(-c3ccc(C(=O)O)cc3F)nn(C(=O)c3c(Cl)cccc3C(F)(F)F)c2c1] | 535 |
| 37D | 4-(1-(2-chloro-6-(trifluoromethyl)benzoyl)-6-(2-(dimethylamino)-2-oxoethyl)-1H-pyrazolo[4,3-b]pyridin-3-yl)-3-fluorobenzoic acid | 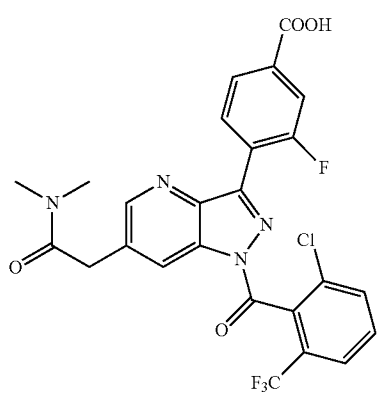 [SMILES: CN(C)C(=O)Cc1cnc2c(-c3ccc(C(=O)O)cc3F)nn(C(=O)c3c(Cl)cccc3C(F)(F)F)c2c1] | 549 |

Example 38A: Preparation of 4-(1-(2-chloro-6-(trifluoromethyl)benzoyl)-6-(oxetan-3-yl)-1H-indazol-3-yl)-3-fluorobenzoic acid

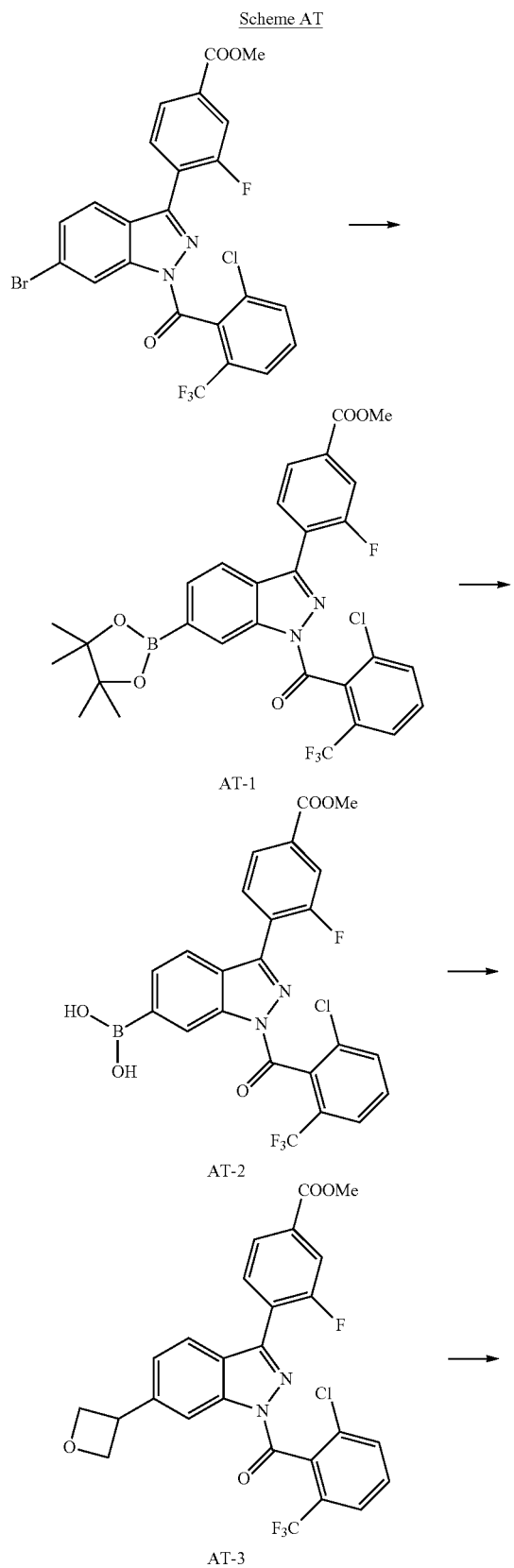

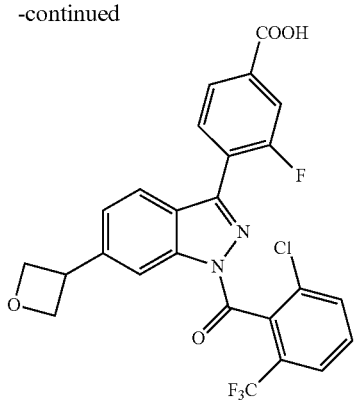

Step 1. Preparation of methyl 4-(1-(2-chloro-6-(trifluoromethyl)benzoyl)-6-(4,4,5,5-tetramethyl-1,3,2-dioxaborolan-2-yl)-1H-indazol-3-yl)-3-fluorobenzoate (AT-1)

A mixture of methyl 4-(6-bromo-1-(2-chloro-6-(trifluoromethyl)benzoyl)-1H-indazol-3-yl)-3-fluorobenzoate (554 mg, 1.0 mmol), 4,4,4',4',5,5,5',5'-octamethyl-2,2'-bi(1,3,2-dioxaborolane) (763 mg, 3.0 mmol), Pd(dppf)Cl$_2$ (40.9 mg, 0.05 mmol), KOAc (294 mg, 3.0 mmol), and dioxane (30 ml) was degassed, placed under an atmosphere of N$_2$ (g) and stirred at 80° C. for 4 h. Then the solution was filtered, concentrated, and purified by silica gel chromatography (EA:PE=1:4) to afford 425 mg of the title compound (yield: 70.8%). LCMS (ESI) calc'd C$_{29}$H$_{24}$BClF$_4$N$_2$O$_5$ [M+H]$^+$: 603. found: 603.

Step 2. Preparation of 1-(2-chloro-6-(trifluoromethyl)benzoyl)-3-(2-fluoro-4-(methoxycarbonyl)phenyl)-1H-indazol-6-ylboronic acid (AT-2)

To a solution of methyl 4-(1-(2-chloro-6-(trifluoromethyl)benzoyl)-6-(4,4,5,5-tetramethyl-1,3,2-dioxaborolan-2-yl)-1H-indazol-3-yl)-3-fluorobenzoate (AT-1) (602 mg, 1.0 mmol) in THF (15 ml) and H$_2$O (10 ml) was added NH$_4$OAc (154 mg, 2.0 mmol) and NaIO$_4$ (428 mg, 2.0 mmol). The mixture solution was stirred at room temperature for 16 h. Then the solution was concentrated and purified by chromatography column (EA:PE=1:4) to afford 411 mg of the title compound (yield: 79.2%). LCMS (ESI) calc'd C$_{15}$H$_6$BrClF$_3$IN$_2$O [M+H]$^+$: 521. found: 521.

Step 3. Preparation of methyl 4-(1-(2-chloro-6-(trifluoromethyl)benzoyl)-6-(oxetan-3-yl)-1H-indazol-3-yl)-3-fluorobenzoate (AT-3)

A mixture of 1-(2-chloro-6-(trifluoromethyl)benzoyl)-3-(2-fluoro-4-(methoxycarbonyl)phenyl)-1H-indazol-6-ylboronic acid (AT-2) (52 mg, 0.1 mmol), NiI$_2$ (3.1 mg, 0.01 mmol), NaHMDS (18.3 mg, 0.1 mmol), (1S,2S)-2-aminocyclohexanol (1.15 mg, 0.01 mmol), 3-iodooxetane (18.4 mg, 0.1 mmol) and iPrOH (2 ml) was placed under an atmosphere of N₂ (g) and stirred at 80° C. for 0.5 h in microwave. Then the reaction mixture was filtered, concentrated, and purified by silica gel chromatography (EA:PE=1:10) to afford 9 mg of the title compound (yield: 16.9%). LCMS (ESI) calc'd $C_{26}H_{17}ClF_4N_2O_4$ [M+H]$^+$: 533. found: 533.

Step 4. Preparation of 4-(1-(2-chloro-6-(trifluoromethyl)benzoyl)-6-(oxetan-3-yl)-1H-indazol-3-yl)-3-fluorobenzoic acid (38A)

To a solution of methyl 4-(1-(2-chloro-6-(trifluoromethyl)benzoyl)-6-(oxetan-3-yl)-1H-indazol-3-yl)-3-fluorobenzoate (AT-3) (9.0 mg, 0.017 mmol) in THF (10 ml) and H₂O (5 ml) was added LiOH (7.14 mg, 1.7 mmol). The mixture solution was stirred at room temperature for 16 h. The reaction mixture was next treated with water (10 ml), acidified by HCl (2M), and extracted with EA (20 ml×3). The combined organic extracts were dried, concentrated, and purified by Prep-HPLC to afford 6.0 mg of the title compound (yield: 68.9%). LCMS (ESI) calc'd $C_{22}H_{12}ClF_4N_3O_4$ [M+H]$^+$: 519. found: 519. ¹HNMR (400 MHz, DMSO) δ 13.58 (1H, s), 8.53 (1H, s), 7.63 (6H, m), 7.75 (2H, m), 5.08 (2H, m), 4.73 (2H, m), 4.58 (1H, m).

Example 39A: Preparation of 4-(1-(2-chloro-4-(2-methoxyethoxy)-6-methylbenzoyl)-1H-pyrazolo[4,3-b]pyridin-3-yl)-3-fluorobenzoic acid Scheme AU

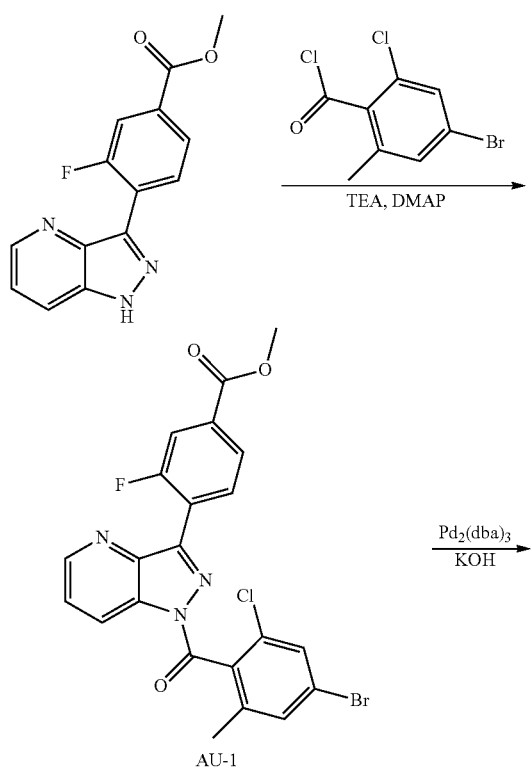

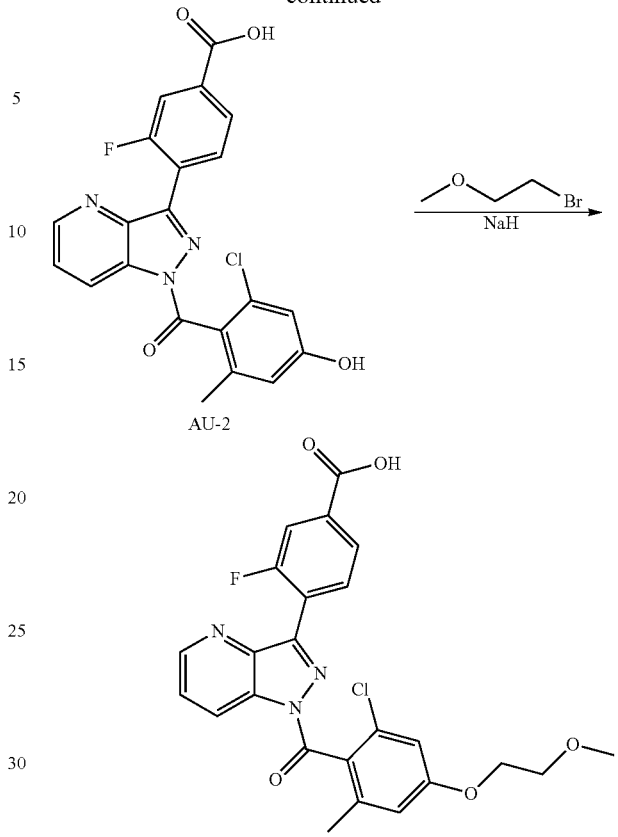

Step 1. Preparation of methyl 4-(1-(4-bromo-2-chloro-6-methylbenzoyl)-1H-pyrazolo[4,3-b]pyridin-3-yl)-3-fluorobenzoate (AU-1)

To a solution of methyl 3-fluoro-4-(1H-pyrazolo[4,3-b]pyridin-3-yl)benzoate (271 mg, 1 mmol) and TEA (202 mg, 2 mmol) in DCM (10 ml), DMAP (15 mg) and 4-bromo-2-chloro-6-methylbenzoyl chloride (267 mg, 1 mmol) were added. Following stirring for 2 h at room temperature, 100 ml EA was added. The resulting mixture was washed sequentially with H₂O (10 ml*2) and brine (20 ml), dried and concentrated in vacuo. The residue was purified by silica gel chromatography (PE: EA=6:1) to afford the title compound 426 mg (yield: 85%). LCMS (ESI) calc'd for $C_{22}H_{14}BrClFN_3O_3$ [M+H]$^+$: 502. found: 502.

Step 2. Preparation of 4-(1-(2-chloro-4-hydroxy-6-methylbenzoyl)-1H-pyrazolo[4,3-b]pyridin-3-yl)-3-fluorobenzoic acid (AU-2)

Methyl 4-(1-(4-bromo-2-chloro-6-methylbenzoyl)-1H-pyrazolo[4,3-b]pyridin-3-yl)-3-fluorobenzoate (AU-1) (100 mg, 0.2 mmol), Pd₂(dba)₃ (18 mg, 0.02 mmol), tBu-XPhos (34 mg, 0.08 mmol) and KOH (44 mg, 0.8 mmol) were mixed in 5 ml dioxane and 5 ml H₂O under N₂. After stirring at 100° C. for 2 h, the reaction mixture was cooled to room temperature, acidified with 1N HCl, and poured into 100 ml EA. The resulting mixture was washed sequentially with H₂O (20 ml*3) and brine (20 ml), dried and concentrated in vacuo. Silica gel chromatography (PE: EA=3:1) afforded the title compound (68 mg, yield: 80%). LCMS (ESI) calc'd for $C_{21}H_{13}ClFN_3O_4$ [M+H]$^+$: 426. found: 426. ¹HNMR (400

MHz, DMSO) δ 13.5 (1H, s), 10.35 (1H, s), 8.85~8.95 (2H, t), 8.32~8.38 (1H, t), 7.94~7.99 (1H, d), 7.80~7.88 (2H, t), 6.73~6.85 (2H, d), 2.19 (3H, s).

Step 3. Preparation of 4-(1-(2-chloro-4-(2-methoxyethoxy)-6-methylbenzoyl)-1H-pyrazolo[4,3-b]pyridin-3-yl)-3-fluorobenzoic acid (39A)

To a solution of 4-(1-(2-chloro-4-hydroxy-6-methylbenzoyl)-1H-pyrazolo[4,3-b]pyridin-3-yl)-3-fluorobenzoic acid (AU-2) (43 mg, 0.1 mmol) in 2 ml of anhydrous DMF, NaH (8 mg, 0.2 mmol) was added. The mixture was stirred for 0.5 h, and then 1-bromo-2-methoxyethane (29 mg, 0.2 mmol) was added. After 3 h, 2 ml H$_2$O was added and the resulting mixture was poured into 100 ml EA, washed sequentially with H$_2$O (10 ml*2) and brine (10 ml), dried and concentrated. The residue was purified with prep-HPLC (ACN: H$_2$O) to give 11 mg (yield: 23%) of the title compound. LCMS (ESI) calc'd for C$_{24}$H$_{19}$ClFN$_3$O$_5$ [M+H]$^+$: 484. found: 484. $^1$HNMR (400 MHz, DMSO) δ 13.5 (1H, s), 8.88~8.95 (2H, t), 8.32~8.38 (1H, t), 7.94~7.99 (1H, t), 7.80~7.88 (2H, t), 6.96~7.10 (2H, d), 4.18~4.23 (2H, t), 3.66~3.70 (2H, t), 3.32 (3H, s), 2.35 (3H, s).

Example 40A: Preparation of 4-(1-(2-chloro-6-methyl-4-morpholinobenzoyl)-1H-pyrazolo[4,3-b]pyridin-3-yl)-3-fluorobenzoic acid Scheme AV

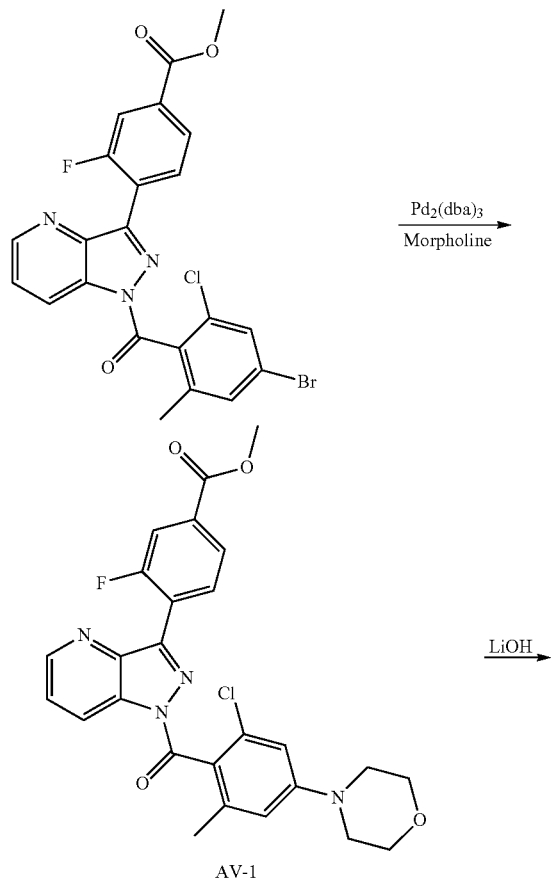

AV-1

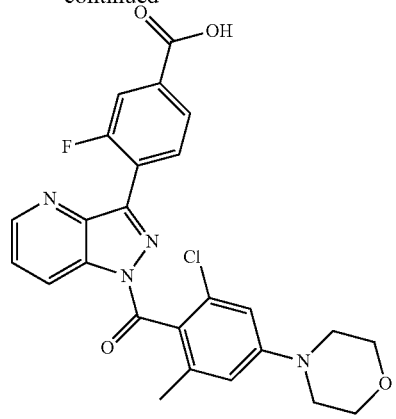

Step 1. Preparation of methyl 4-(1-(2-chloro-6-methyl-4-morpholinobenzoyl)-1H-pyrazolo[4,3-b]pyridin-3-yl)-3-fluorobenzoate (AV-1)

A mixture of methyl 4-(1-(4-bromo-2-chloro-6-methylbenzoyl)-1H-pyrazolo[4,3-b]pyridin-3-yl)-3-fluorobenzoate (50 mg, 0.1 mmol), Pd$_2$(dba)$_3$ (9 mg, 0.01 mmol), DavePhos (8 mg, 0.02 mmol), t-BuONa (19 mg, 0.2 mmol) and morpholine (17 mg, 0.2 mmol) were mixed in 5 ml toluene under N$_2$ and then stirred at 100° C. for 2 h. The reaction mixture was next cooled to room temperature, acidified with 1N HCl, and then poured into 100 ml EA. The mixture was washed sequentially with H$_2$O (20 ml*3) and brine (20 ml), dried and concentrated in vacuo. The residue was purified by Prep-TLC (PE: EA=3:1) to afford the title compound. (15 mg, yield: 30%). LCMS (ESI) calc'd for C$_{26}$H$_{22}$ClFN$_4$O$_4$ [M+H]$^+$: 509. found: 509.

Step 2. Preparation of 4-(1-(2-chloro-6-methyl-4-morpholinobenzoyl)-1H-pyrazolo[4,3-b]pyridin-3-yl)-3-fluorobenzoic acid (40A)

A mixture of methyl 4-(1-(2-chloro-4-hydroxy-6-methylbenzoyl)-1H-pyrazolo[4,3-b]pyridin-3-yl)-3-fluorobenzoate (AV-1) (15 mg, 0.03 mmol) and LiOH (7 mg, 0.3 mmol) in 5 ml THF and 1 ml H$_2$O was stirred for 4 h at room temperature, acidified with 1N HCl and concentrated. The residue was purified by Prep-HPLC (ACN: H$_2$O) to afford the title compound 10 mg (yield: 67%). LCMS (ESI) calc'd for C$_{25}$H$_{20}$ClFN$_4$O$_4$ [M+H]$^+$: 495. found: 495. $^1$HNMR (400 MHz, DMSO) δ 13.5 (1H, s), 8.88~8.92 (1H, d), 8.28~8.34 (1H, t), 7.94~7.99 (1H, d), 7.80~7.86 (2H, m), 6.90~6.96 (2H, d), 3.72~3.77 (4H, t), 3.24~3.29 (4H, t), 2.21 (3H, s).

Example 41A: Preparation of 4-(1-(2-chloro-6-(trifluoromethyl)benzoyl)-6-(dicyclopropylcarbamoyl)-1H-pyrazolo[4,3-b]pyridin-3-yl)-3-fluorobenzoic acid Scheme AW

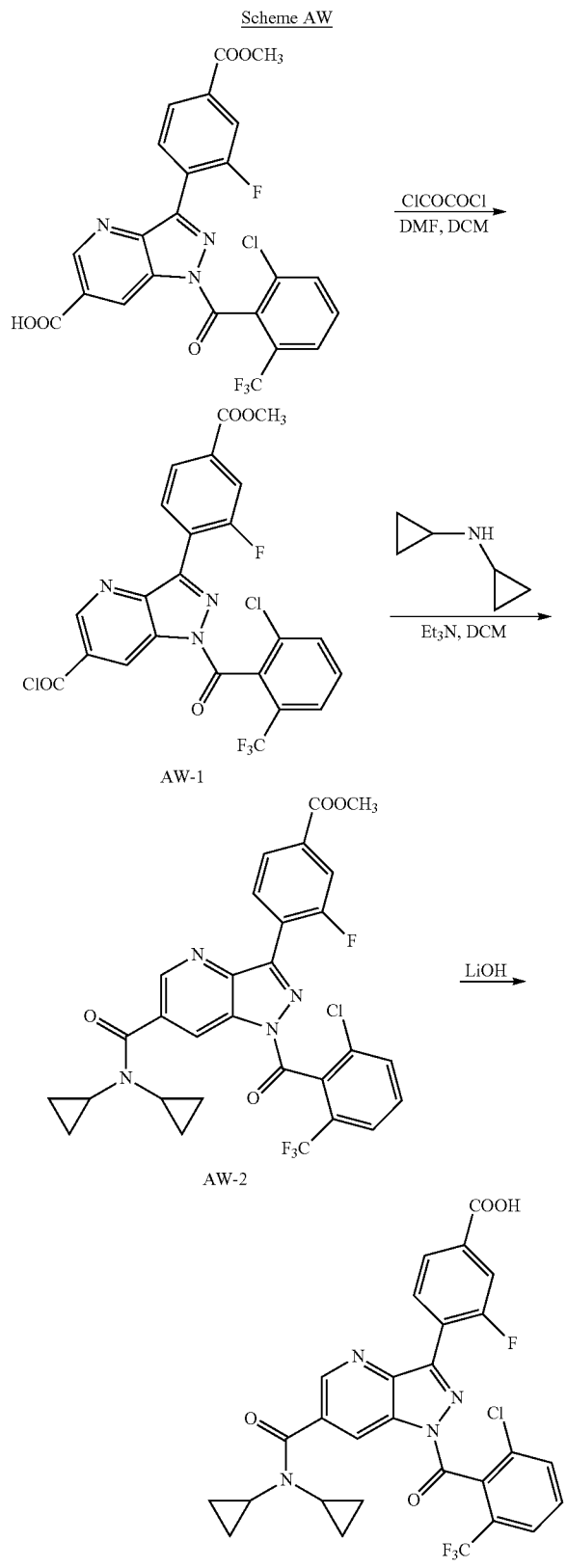

Step 1. Preparation of methyl 4-(1-(2-chloro-6-(trifluoromethyl)benzoyl)-6-(chlorocarbonyl)-1H-pyrazolo[4,3-b]pyridin-3-yl)-3-fluorobenzoate (AW-1)

To a solution of 1-(2-chloro-6-(trifluoromethyl)benzoyl)-3-(2-fluoro-4-(methoxycarbonyl)phenyl)-1H-pyrazolo[4,3-b]pyridine-6-carboxylic acid (50 mg, 0.1 mmol) in DCM (5 mL) was added oxalyl dichloride (51 mg, 0.2 mmol) with ice-cooling. Then DMF (2 drops) was added. The mixture was stirred at room temperature for 3 h. The solvent was evaporated to obtain the title compound as solid (53 mg), which was used in the next step without further purification. LCMS (ESI): calc. $C_{23}H_{11}Cl_2F_4N_3O_4$, $[M+H]^+$: 540. found: 540.

Step 2. Preparation of methyl 4-(1-(2-chloro-6-(trifluoromethyl)benzoyl)-6-(dicyclopropylcar-bamoyl)-1H-pyrazolo[4,3-b]pyridin-3-yl)-3-fluorobenzoate (AW-2)

To a solution of methyl 4-(1-(2-chloro-6-(trifluoromethyl)benzoyl)-6-(dicyclopropylcar-bamoyl)-1H-pyrazolo[4,3-b]pyridin-3-yl)-3-fluorobenzoate (AW-1) (53 mg, 0.1 mmol) in DCM (5 mL) was added dicyclopropylamine (27 mg, 0.2 mmol). Then Et$_3$N (15 mg, 0.15 mmol) was added. The mixture was stirred at room temperature for 14 h. Water (15 mL) was added, and the aqueous phase was extracted with DCM. The organic phase was collected, washed with brine, dried over anhydrous Na$_2$SO$_4$, and concentrated to obtain the title compound (50 mg), which was used subsequently without further purification. LCMS (ESI): calc. $C_{29}H_{21}ClF_4N_4O_4$, $[M+11]^+$: 601. found: 601.

Step 3. Preparation of 4-(1-(2-chloro-6-(trifluoromethyl)benzoyl)-6-(dicyclopropylcarbamoyl)-1H-pyrazolo[4,3-b]pyridin-3-yl)-3-fluorobenzoic acid (41A)

A mixture of methyl 4-(1-(2-chloro-6-(trifluoromethyl)benzoyl)-6-(dicyclopropylcar-bamoyl)-1H-pyrazolo[4,3-b]pyridin-3-yl)-3-fluorobenzoate (AW-2) (40 mg, 0.067 mmol) and LiOH.H$_2$O (28 mg, 0.67 mmol) in 4 ml THF and 4 ml H$_2$O was stirred at room temperature for 1 hour. The solvent was evaporated and the residue was dissolved in water. HCl (5% sol in water) was added until pH=4-5. The product was extracted by EtOAc, and the extracts were concentrated to obtain a crude solid. The product was purified by prep-HPLC to obtain the title compound (8 mg), yield 20.38%. LCMS (ESI): calc. $C_{28}H_{19}ClF_4N_4O_4$, $[M+H]^+$: 587. found: 587. $^1$HNMR (400 MHz, DMSO) δ 9.10 (1H, s), 8.99 (1H, s), 8.38-8.42 (1H, m), 7.96-8.07 (3H, m), 7.98-7.92 (1H, m), 7.83 (1H, d, J=10.8 Hz), 2.87 (2H, s), 0.73 (8H, s).

229
Example 42A: Preparation of 4-(1-(4-amino-2-chloro-6-methylbenzoyl)-1H-pyrazolo[4,3-b]pyridin-3-yl)-3-fluorobenzoic acid

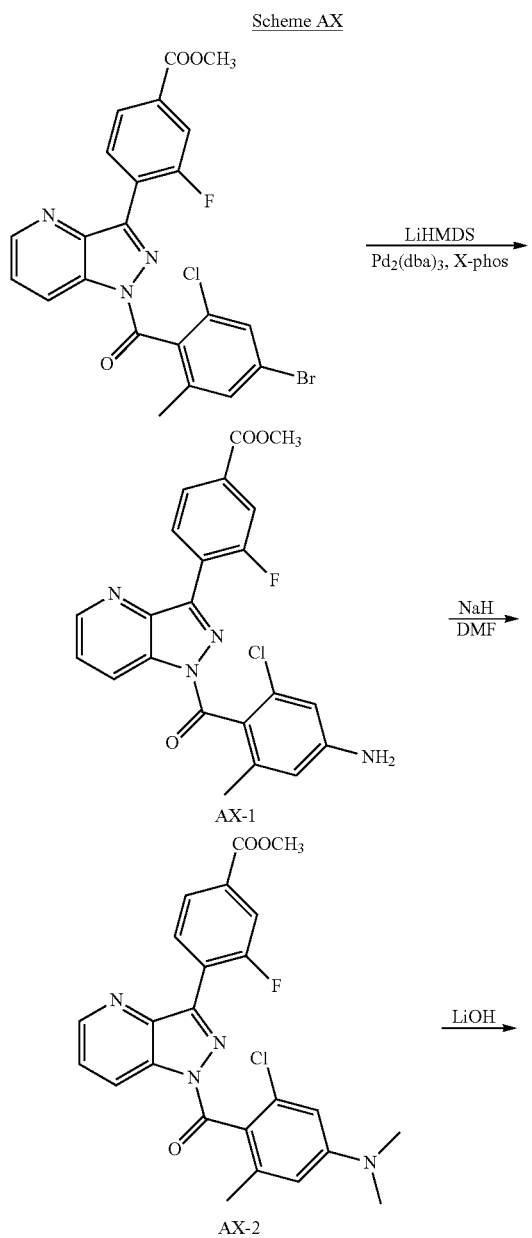

230
Step 1. Preparation of methyl 4-(1-(4-amino-2-chloro-6-methylbenzoyl)-1H-pyrazolo[4,3-b]pyridin-3-yl)-3-fluorobenzoate (AX-1)

A mixture of methyl 4-(1-(4-bromo-2-chloro-6-methylbenzoyl)-1H-pyrazolo[4,3-b]pyridin-3-yl)-3-fluorobenzoate (150 mg, 0.3 mmol), LiHMDS (251 mg, 1.5 mmol), Pd$_2$(dba)$_3$ (137 mg, 0.15 mmol), and X-phos (72 mg, 0.15 mmol)) in 4 mL THF was heated under argon to 80° C. for 2 hrs under microwave. HCl (1M) was added until PH=7, and the mixture was diluted with EtOAc (50 mL), washed with brine (50 mL*2), dried over anhydrous Na$_2$SO$_4$, and concentrated in vacuo. The residue was purified by silica gel column (DCM) to obtain the title compound as a white solid. LCMS (ESI): calc'd for $C_{22}H_{16}ClFN_4O_3$, [M+H]$^+$: 439. found: 439

Step 2. Preparation of methyl 4-(1-(2-chloro-4-(dimethylamino)-6-methylbenzoyl)-1H-pyrazolo[4,3-b]pyridin-3-yl)-3-fluorobenzoate (AX-2)

A mixture of methyl 4-(1-(4-amino-2-chloro-6-methylbenzoyl)-1H-pyrazolo[4,3-b]pyridin-3-yl)-3-fluorobenzoate (AX-1) (131 mg, 0.3 mmol) and NaH (36 mg, 1.5 mmol) in 10 mL DMF was stirred for 10 mins, after which CH$_3$I (86 mg, 0.6 mmol) was added and the reaction mixture was stirred for 14 h. NH$_3$.H$_2$O (1M) was added until PH=9-10, and the mixture was diluted with EtOAc (50 mL), washed with brine (50 mL*2), dried over anhydrous Na$_2$SO$_4$, and concentrated in vacuo. The residue was purified by silica gel column (DCM) to obtain the title compound. LCMS (ESI): calc'd for $C_{24}H_{20}ClFN_4O_3$, [M+H]$^+$: 467. found: 467

Step 3. Preparation of 4-(1-(2-chloro-4-(dimethylamino)-6-methylbenzoyl)-1H-pyrazolo[4,3-b]pyridin-3-yl)-3-fluorobenzoic acid (42A)

A mixture of methyl 4-(1-(2-chloro-4-(dimethylamino)-6-methylbenzoyl)-1H-pyrazolo[4,3-b]pyridin-3-yl)-3-fluorobenzoate (AX-2) (32 mg, 0.07 mmol) and LiOH.H$_2$O (16 mg, 0.37 mmol) in 10 mL THF and 10 mL pure H$_2$O was stirred at room temperature for 2 hrs. The solvent was evaporated and the residue was dissolved in water. HCl (5% sol in water) was added until pH=4-5. The precipitated solid was filtered, washed sequentially with water (10 mL) and n-hexane (10 mL), and dried to afford the title compound as a solid. LCMS (ESI): calc'd for $C_{23}H_{18}ClFN_4O_3$, [M+H]$^+$: 453 found: 453; $^1$HNMR (400 MHz, DMSO) δ 8.84-8.90 (2H, m), 8.29-8.33 (1H, m), 7.96-7.98 (1H, m), 7.80-7.86 (2H, m), 6.65-6.66 (2H, m), 3.00 (6H, s), 2.21 (3H, s)

Example 43A: Preparation of 4-(1-(2-chloro-6-cyclopentylbenzoyl)-1H-pyrazolo[4,3-b]pyridin-3-yl)-3-fluorobenzoic acid

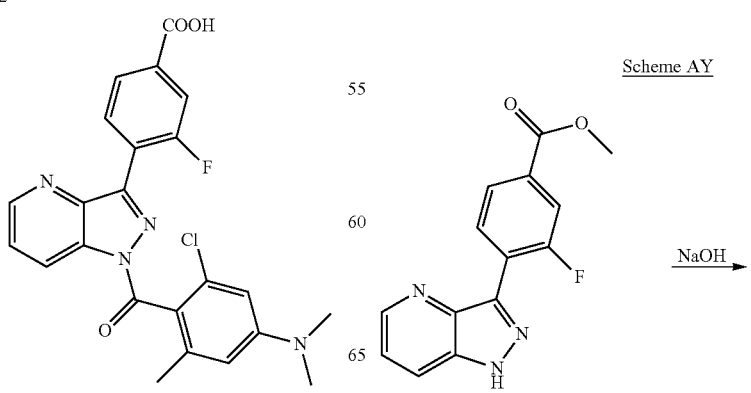

-continued

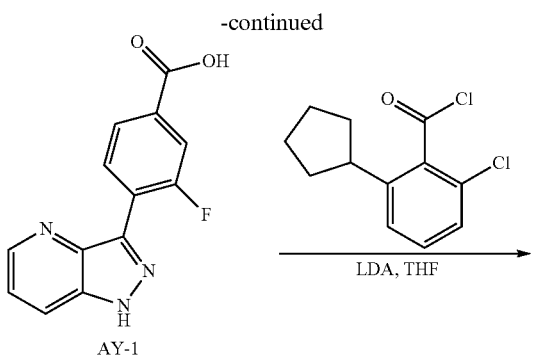

Step 1. Preparation of 3-fluoro-4-(1H-pyrazolo[4,3-b]pyridin-3-yl)benzoic acid (AY-1)

To a solution of methyl 3-fluoro-4-(1H-pyrazolo[4,3-b]pyridin-3-yl)benzoate (105 mg, 0.387 mmol) in MeOH (2.5 mL) was added water (2.5 mL) and sodium hydroxide (155 mg, 3.87 mmol). The mixture was stirred at 60° C. for 1 h. The mixture was acidified by aqueous HCl to pH=1, and the mixture was evaporated to dryness. The residue was purified by silica gel flash column (PE:EA=1:1) to afford the title compound (100 mg, yield: 100%). LCMS (ESI): calc'd for $C_{13}H_8FN_3O_2$ [M+H]$^+$: 258. found: 258.

Step 2. Preparation of 4-(1-(2-chloro-6-cyclopentylbenzoyl)-1H-pyrazolo[4,3-b]pyridin-3-yl)-3-fluorobenzoic acid (43A)

To a solution of 3-fluoro-4-(1H-pyrazolo[4,3-b]pyridin-3-yl)benzoic acid (AY-1) (80 mg, 0.31 mmol) in 5 mL of THF at –30° C. was added dropwise a solution of LDA (0.62 mL, 1.24 mmol), and the reaction mixture was stirred at 15° C. for 2 h. 2-chloro-6-cyclopentylbenzoyl chloride (82 mg, 0.34 mmol) in 5 mL of THF was added dropwise to the reaction mixture at 0° C., and the reaction mixture was stirred at the same temperature for 0.5 h and 15° C. for 4 h. After the reaction was completed, the reaction mixture was quenched by 5 mL of water and acidified with 2 M HCl to pH=3. The mixture was next extracted with EtOAc (100 mL*3). The combined organic extracts were washed with brine (100 mL*2), dried over $Na_2SO_4$ and concentrated. The crude product was purified by prep-HPLC (acetonitrile+ 0.75%0 trifluoroacetic acid in water) to give the title compound (10 mg, yield: 14%) as a white solid. LCMS (ESI): calc'd for $C_{25}H_{10}ClFN_3O_3$ [M+H]$^+$: 464. found: 464; $^1$H NMR (400 MHz, CDCl$_3$) δ 8.94 (1H, d, J=8.22 Hz), 8.81 (1H, d, J=3.52 Hz), 8.00-8.06 (1H, m), 7.86 (1H, d, J=7.84 Hz), 7.76 (1H, d, J=10.18 Hz), 7.59 (1H, dd, J=8.22, 4.70 Hz), 7.32-7.37 (1H, m), 7.26-7.31 (1H, m), 7.23 (1H, d, J=7.84 Hz), 2.86 (1H, t, J=8.02 Hz), 2.02-2.12 (1H, m,), 1.66-1.81 (3H, m), 1.44-1.60 (4H, m)

Example 44A: Preparation of 4-(1-(2-chloro-6-cyclobutylbenzoyl)-1H-pyrazolo[4,3-b]pyridin-3-yl)-3,5-difluorobenzoic acid Scheme AZ

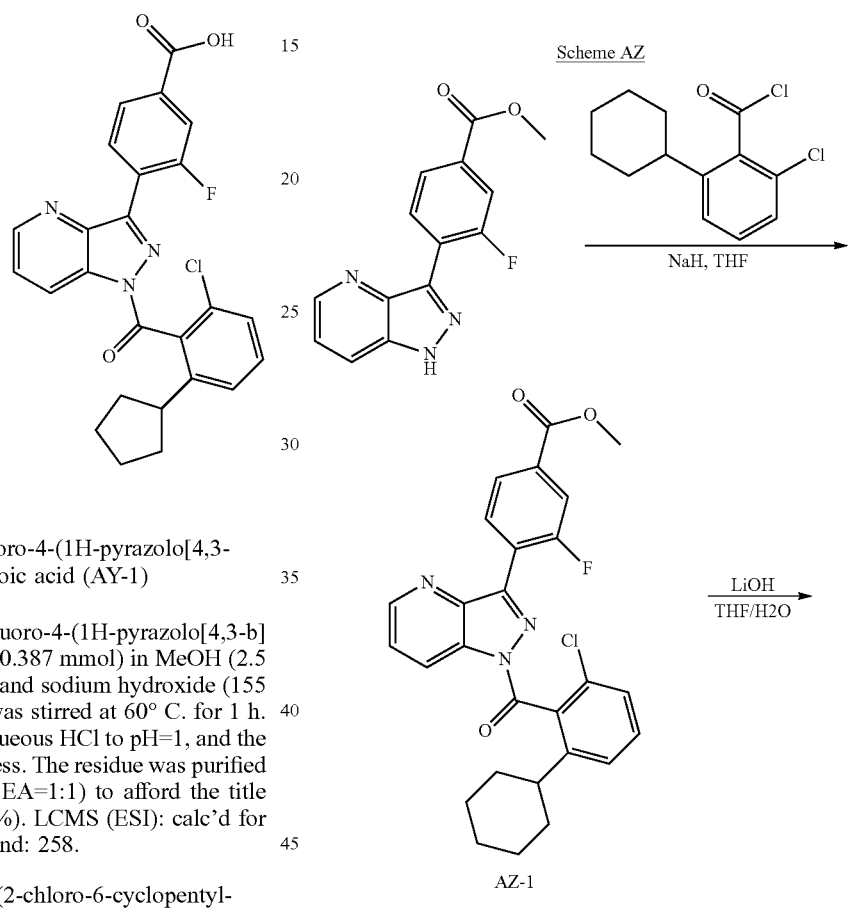

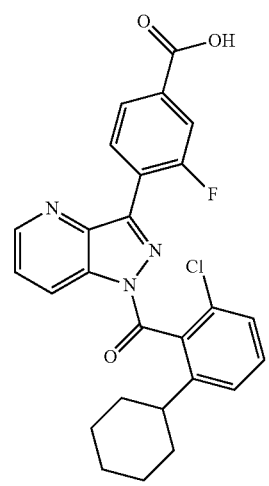

Step 1. Preparation of methyl 4-(1-(2-chloro-6-cyclohexylbenzoyl)-1H-pyrazolo[4,3-b]pyridin-3-yl)-3-fluorobenzoate (AZ-1)

To a solution of methyl 3-fluoro-4-(1H-pyrazolo[4,3-b]pyridin-3-yl)benzoate (147 mg, 0.54 mmol) in 10 mL of THF was added NaH (32 mg, 0.82 mmol) dropwise at 0° C., and the mixture was stirred at 15° C. for 30 min. 2-chloro-6-cyclohexylbenzoyl chloride (150 mg, 0.54 mmol) in 5 mL of THF was added dropwise, and then the mixture was stirred at 0° C. for 0.5 h before being allowed to come to 15° C. for 2 h. After the reaction was completed, the reaction mixture was quenched with 5 mL of water and extracted with EtOAc (100 mL*3). The combined organic layers were washed with brine (100 mL), dried over $Na_2SO_4$, filtered and concentrated in vacuo. The residue was purified by prep-TLC (PE: EtOAc=5:1) to give the title compound (70 mg, yield: 26%) as a white solid. LCMS (ESI): calc'd for $C_{27}H_{23}ClFN_3O_3$ $[M+H]^+$: 492. found: 492;

Step 2. Preparation of 4-(1-(2-chloro-6-cyclohexylbenzoyl)-1H-pyrazolo[4,3-b]pyridin-3-yl)-3-fluorobenzoic acid (44A)

To a solution of methyl 4-(1-(2-chloro-6-cyclohexylbenzoyl)-1H-pyrazolo[4,3-b]pyridin-3-yl)-3-fluorobenzoate (AZ-1) (50 mg, 0.1 mmol) in 5 mL of THF/$H_2O$ (4:1) was added lithium hydroxide hydrate (17 mg, 0.4 mmol), and the reaction mixture was stirred for 12 h at 15° C. After the reaction was completed, the mixture was acidified with 2 M HCl to pH=3 and then extracted with EtOAc (300 mL*3). The combined organic layers were washed with brine (200 mL*2), dried over $Na_2SO_4$ and concentrated. The residue was purified by prep-HPLC (acetonitrile+0.75%0 trifluoroacetic acid in water) to afford the title compound (15 mg, yield: 31%) as a white solid. LCMS (ESI): calc'd for $C_{26}H_{21}ClFN_3O_3$ $[M+H]^+$: 478. found: 478; $^1$H NMR (400 MHz, $CDCl_3$) δ 9.01 (1H, d, J=8.4 Hz), 8.88 (1H, d, J=3.6 Hz), 8.07 (1H, t, J=7.2 Hz), 7.93 (1H, d, J=7.6 Hz), 7.82 (1H, d, J=10.0 Hz), 7.66 (1H, dd, J=8.4, 4.50 Hz), 7.37-7.44 (1H, m), 7.27-7.35 (2H, m), 2.43 (1H, t, J=11.6 Hz), 1.98 (1H, d, J=12.4 Hz), 1.78 (2H, d, J=12.0 Hz), 1.58-1.71 (2H, m), 1.37-1.50 (2H, m), 1.24 (2H, t, J=13.6 Hz), 0.99-1.13 (1H, m).

Biological Assays

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was expressed in SF9 cells using a baculovirus expression system. The RORγ-LBD protein was purified by glutathione sepharose chromatography. Separately, SF9 cells not expressing any recombinant protein were lysed and the lysate was added to the purified RORγ-LBD at 0.25 μl lysate (from 10,000 SF9 cells)/nM purified protein. The mixture was then diluted in assay buffer (50 mM Tris pH 7.0, 50 mM KCl, 1 mM EDTA, 0.1 mM DTT) to obtain RORγ-LBD final concentration of 3 nM in 384-well assay plate.

Compounds to be tested were injected to the assay plate using Acoustic Droplet Ejection technology by Echo 550 liquid handler (Labcyte, CA).

A stock of biotinylated-LXXLL peptide from coactivator SRC1 (Biotin-CPSSHSSLTERHKILHRLLQEGSPS) (SEQ ID NO:2) was prepared in assay buffer and added to each well (100 nM final concentration). A solution of Europium tagged anti-HIS antibody (1.25 nM final concentration) and APC conjugated streptavidin (8 nM final concentration) were also added to each well.

The final assay mixture was incubated overnight at 4° C., and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

Biological Data

The following table tabulates the biological data disclosed for the instant invention.

| Examples | Fret $IC_{50}$ (nM) |
| --- | --- |
| 1A | 52 |
| 1B | 49 |
| 1C | 6 |
| 1D | >10000 |
| 1H | 39 |
| 1I | 4324 |
| 1J | 5569 |
| 1K | >10000 |
| 1L | >10000 |
| 1M | 335 |
| 1N | >10000 |
| 1O | 54 |
| 1P | 58 |
| 1Q | >10000 |
| 1R | 969 |
| 1S | 1477 |
| 1T | 159 |
| 1U | >10000 |
| 1V | 16 |
| 1W | 33 |
| 1X | 26 |
| 1Y | 40 |
| 1Z | 4 |
| 1AA | 2 |
| 1AB | 3 |
| 1AC | 2 |
| 1AD | 7 |
| 2A | 16 |
| 2B | 15 |
| 2C | 4 |
| 3A | 1466 |
| 3B | 1653 |
| 4A | 500 |
| 4B | 1326 |
| 4D | 130 |
| 4F | 23 |
| 4G | 1060 |
| 4H | 4321 |
| 5A | 255 |
| 5B | 153 |
| 5C | 314 |

| Examples | Fret IC$_{50}$ (nM) |
|---|---|
| 5D | 493 |
| 5E | 64 |
| 5F | 48 |
| 5G | 1502 |
| 5H | 491 |
| 6A | 85 |
| 6B | 25 |
| 6C | 22 |
| 6D | 1511 |
| 6E | 224 |
| 7A | 69 |
| 7B | 317 |
| 7C | 87 |
| 7D | 14 |
| 7E | 245 |
| 7F | 222 |
| 8A | 143 |
| 8B | 283 |
| 8C | 218 |
| 8D | 57 |
| 9A | 63 |
| 9B | 14 |
| 11A | 48 |
| 12A | 105 |
| 13A | 20 |
| 14A | 137 |
| 15A | 241 |
| 16A | 21 |
| 17A | 12 |
| 18A | 24 |
| 18B | 26 |
| 19A | 888 |
| 20A | 120 |
| 21A | 5 |
| 21B | 17 |
| 21C | 15 |
| 22A | 754 |
| 22B | 5606 |
| 22C | >10000 |
| 22D | 155 |
| 22E | 1441 |
| 22F | 39 |
| 22G | 356 |
| 22H | 37 |
| 22I | 274 |
| 22J | 6391 |
| 23A | >10000 |
| 23B | >10000 |
| 23C | >10000 |
| 23D | >10000 |
| 23E | >10000 |
| 23F | >10000 |
| 23G | >10000 |
| 23H | >10000 |
| 23I | >10000 |
| 23J | >10000 |
| 23K | >10000 |
| 26A | 876 |
| 27A | 53 |
| 28A | 182 |
| 29A | 191 |
| 29B | 13 |
| 30A | 6 |
| 30B | 209 |
| 31A | 80 |
| 32A | 29 |
| 32B | 384 |
| 33A | 8 |
| 33B | 5 |
| 33C | 5 |
| 33D | 8 |
| 34A | 3 |
| 35A | 11 |
| 35B | 3 |
| 36A | 2 |
| 36B | 1 |
| 37A | 81 |
| 37B | 225 |
| 37C | 363 |
| 37D | 458 |
| 38A | 784 |
| 39A | 821 |
| 40A | 6866 |
| 41A | 60 |
| 42A | 2323 |
| 43A | 11 |
| 44A | 16 |

What is claimed is:

1. A compound according to Formula I

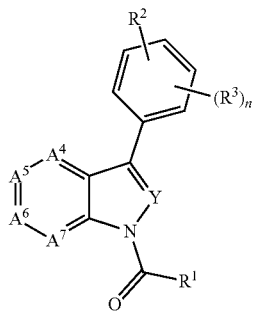

or a pharmaceutically acceptable salt or solvate thereof, wherein:

Y is CH, $CR^a$, or N;

n=0, 1, 2, or 3;

$A^4$ is N, $A^5$ is $CR^5$, $A^6$ is $CR^6$, $A^7$ is $CR^7$, $R^a$ is $(C_{1-4})$alkyl or $(C_{3-7})$cycloalkyl;

$R^1$ is
(i) $(C_{3-12})$carbocyclyl$(C_{0-4})$alkyl, or
(ii) a 4- to 12-membered heterocyclyl$(C_{0-4})$alkyl,
each being substituted with (i) one occurrence of $R^8$ that is $(C_{3-7})$cycloalkyl and (ii) optionally one, two, or three other occurrences of $R^8$;

$R^2$ is hydroxycarbonyl or hydroxycarbonyl$(C_{1-10})$alkyl;

$R^3$ is hydrogen, halogen, cyano, nitro, hydroxy, $(C_{1-4})$ alkylcarbonyloxy, $(C_{1-4})$ alkylsulfonylamino, $(C_{1-4})$ alkylcarbonylamino, $(C_{0-4})$ alkylamino, $(C_{1-4})$alkyl, hydroxyl$(C_{1-4})$alkyl or $(C_{1-4})$alkoxy, wherein $(C_{1-4})$ alkyl and $(C_{1-4})$alkoxy are optionally substituted with one or more halogen;

$R^5$-$R^7$ independently are hydrogen, halogen, amino, cyano, hydroxy, $(C_{1-3})$alkoxy, $(C_{1-4})$-alkyl, $(C_{1-6})$alkylcarbonylamino, $(C_{1-4})$alkylamino, amino$(C_{1-4})$alkyl or —C(O)H, wherein $(C_{1-3})$alkoxy, $(C_{1-4})$alkyl, $(C_{1-4})$ alkylamino and amino$(C_{1-4})$alkyl are optionally substituted with one or more halogen, hydroxyl or $(C_{1-3})$ alkoxy; or a group having the formula

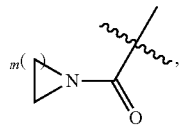

optionally substituted with one or more of the following: $(C_{1-10})$alkyl, halogen, or $(C_{1-3})$alkoxy, and wherein m is 1, 2, 3, or 4; or $R^6$ is additionally selected from:
(i) $(C_{3-7})$cycloalkyl or $(C_{3-5})$heterocycloalkyl, both optionally substituted with one or more groups selected from halogen, amino, hydroxyl, oxo (=O), $H_2NC(O)$, $(C_{1-4})$alkyl or $(C_{1-3})$alkoxy, wherein $(C_{1-4})$alkyl and $(C_{1-3})$alkoxy are optionally substituted with one or more halogen or hydroxyl;

(ii) $(C_{2-9})$heteroaryl, optionally substituted with one or more groups selected from halogen, amino, cyano, hydroxyl, $H_2NC(O)$, $(C_{1-4})$alkyl or $(C_{1-3})$alkoxy, wherein $(C_{1-4})$alkyl and $(C_{1-3})$alkoxy are optionally substituted with one or more halogen, amino or hydroxyl;

(iii) $(C_{6-14})$ aryl, optionally substituted with one or more groups selected from halogen, amino, cyano, hydroxyl, $H_2NC(O)$, $(C_{1-4})$alkyl or $(C_{1-3})$alkoxy, wherein $(C_{1-4})$ alkyl and $(C_{1-3})$alkoxy are optionally substituted with one or more halogen, amino or hydroxyl;

(iv) $(C_{3-5})$heterocycloalkylcarbonyl or $(C_{3-5})$heterocycloalkylcarbonyl$(C_{1-4})$alkyl, optionally substituted with one or more groups selected from halogen, amino, hydroxyl, oxo (=O), $H_2NC(O)$, $(C_{1-3})$alkoxycarbonyl, (di)$(C_{1-6})$alkylaminocarbonyl, $(C_{1-4})$alkyl or $(C_{1-3})$ alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one or more halogen, amino or hydroxyl;

(v) $(C_{3-5})$heterocycloalkylamino, $(C_{3-5})$cycloalkylaminocarbonyl, di$(C_{3-5})$cycloalkylaminocarbonyl, $(C_{3-5})$cycloalkylcarbonylamino, $(C_{3-5})$cycloalkyl$(C_{1-4})$alkyl, $(C_{3-5})$cycloalkylamino, or $(C_{3-5})$cycloalkylcarbonyl, each of which is optionally substituted with one or more groups selected from halogen, amino, hydroxyl, oxo (=O), $H_2NC(O)$, $(C_{1-4})$alkyl or $(C_{1-3})$alkoxy, wherein $(C_{1-4})$alkyl and $(C_{1-3})$alkoxy are optionally substituted with one or more halogen or hydroxyl;

(vi) $(C_{2-9})$heteroaryl$(C_{1-4})$alkyl or $(C_{2-9})$heteroarylcarbonyl, optionally substituted with one or more groups selected from halogen, amino, cyano, hydroxyl, $H_2NC(O)$, $(C_{1-4})$alkyl or $(C_{1-3})$alkoxy, wherein $(C_{1-4})$alkyl and $(C_{1-3})$alkoxy are optionally substituted with one or more halogen, amino or hydroxyl;

(vii) $(C_{2-4})$alkynyl, optionally substituted with hydroxyl or amino; or (viii) $(C_{1-6})$alkylsulfonylamino$(C_{0-4})$alkyl,
$(C_{1-6})$alkylaminocarbonylamino,
$(C_{1-6})$alkoxycarbonylamino$(C_{0-4})$alkyl,
Hydroxycarbonyl$(C_{1-4})$alkylamino,
$(C_{0-6})$alkylaminocarbonyl$(C_{1-6})$alkyl, or
di$(C_{1-6})$alkylaminocarbonyl$(C_{1-6})$alkyl,
each optionally substituted with one or more $(C_{1-4})$ alkyl, hydroxyl or amino; and $R^8$ is halogen, cyano, oxo (=O), di$(C_{1-3})$alkylamino, $(C_{1-3})$alkoxycarbonyl, (di)$(C_{1-6})$alkylaminocarbonyl, $(C_{1-4})$alkyl, $(C_{3-7})$cycloalkyl, $(C_{3-5})$heterocycloalkyl, $(C_{1-4})$alkenyl, $(C_{3-6})$cycloalkoxy or $(C_{1-3})$alkoxy, wherein $(C_{1-3})$alkoxycarbonyl, (di)$(C_{1-6})$alkylaminocarbonyl, $(C_{1-4})$alkyl and $(C_{1-3})$alkoxy are optionally substituted with one, two or three halogens.

2. The compound of claim 1 having Formula Ia

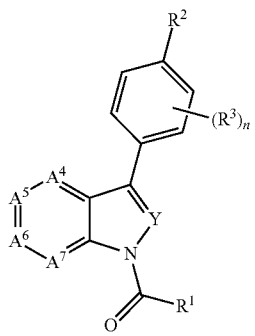

or a pharmaceutically acceptable salt or solvate thereof.

3. The compound of claim 1 having Formula Ib

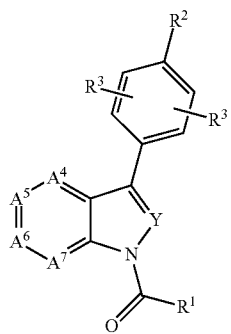

or a pharmaceutically acceptable salt or solvate thereof.

4. The compound of claim 3, wherein Y is N.

5. The compound of claim 3 having Formula Ic

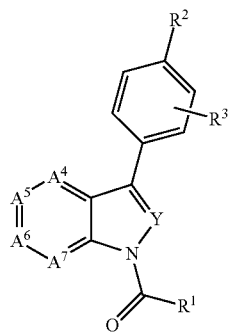

or a pharmaceutically acceptable salt or solvate thereof.

6. The compound of claim 5 having Formula Id

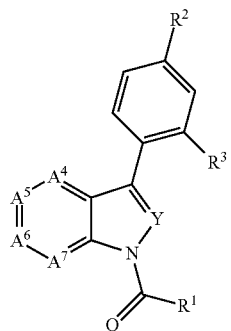

or a pharmaceutically acceptable salt or solvate thereof.

7. The compound of claim 6, wherein Y is N.

8. The compound of claim 2 having Formula Ie

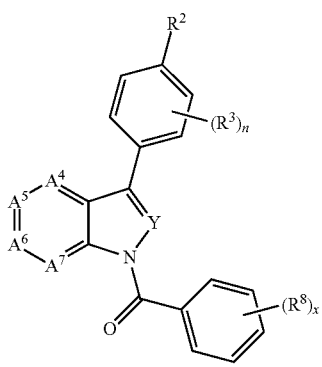

wherein x is 1, 2, 3, or 4;
at least one occurrence of $R^8$ is $(C_{3-7})$cycloalkyl;
or a pharmaceutically acceptable salt or solvate thereof.

9. The compound of claim 8 having Formula If

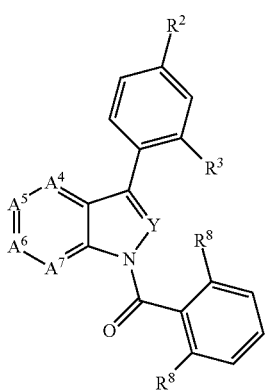

or a pharmaceutically acceptable salt or solvate thereof;
wherein at least one occurrence of $R^8$ is $(C_{3-7})$cycloalkyl.

10. The compound of claim 9 having Formula Ig

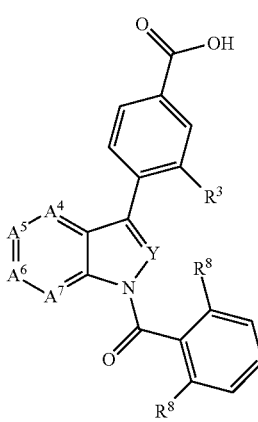

or a pharmaceutically acceptable salt or solvate thereof;
wherein at least one occurrence of $R^8$ is $(C_{3-7})$cycloalkyl.

11. The compound of claim 10 having Formula Ih

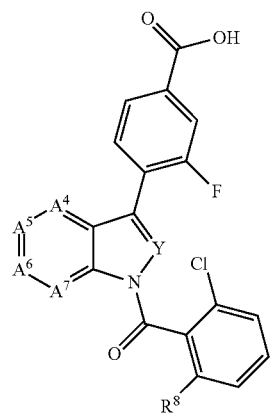

Ih or a pharmaceutically acceptable salt or solvate thereof; wherein $R^8$ is $(C_{3-7})$cycloalkyl.

12. The compound of claim 1, wherein Y is N.

13. The compound of claim 1, wherein $R^1$ is (i) $(C_{3-7})$cycloalkyl or $(C_{3-5})$heterocycloalkyl, both being substituted with (i) one occurrence of $R^8$ that is $(C_{3-7})$cycloalkyl and (ii) optionally one, two, or three other occurrences of $R^8$;

(ii) $(C_{2-9})$heteroaryl$(C_{0-4})$alkyl, being substituted with (i) one occurrence of $R^8$ that is $(C_{3-7})$cycloalkyl and (ii) optionally with one, two, or three other occurrences of $R^8$; or (iii) $(C_{6-14})$aryl$(C_{0-4})$alkyl, being substituted with (i) one occurrence of $R^8$ that is $(C_{3-7})$cycloalkyl and (ii) optionally with one, two, or three other occurrences of $R^8$.

14. The compound of claim 13, wherein $R^1$ is (i) $(C_{2-9})$heteroaryl, or (ii) $(C_{6-14})$aryl, both substituted with (i) one occurrence of $R^8$ that is $(C_{3-7})$cycloalkyl and (ii) optionally one, two, or three other occurrences of $R^8$.

15. The compound of claim 14, wherein $R^1$ is $(C_{6-14})_{aryl}$ substituted with (i) one occurrence of $R^8$ that is $(C_{3-7})$cycloalkyl and (ii) optionally one other occurrence of $R^8$.

16. The compound of claim 15, wherein $R^1$ is phenyl substituted with (i) one occurrence of $R^8$ that is $(C_{3-7})$cycloalkyl and (ii) optionally one other occurrence of $R^8$.

17. The compound of claim 16, wherein $R^2$ is C(O)OH.

18. The compound of claim 1, wherein $R^6$ is

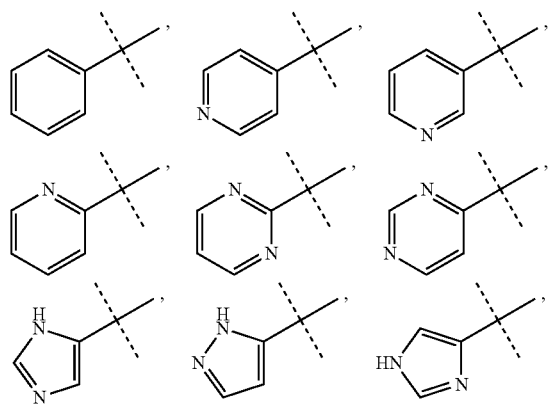

-continued

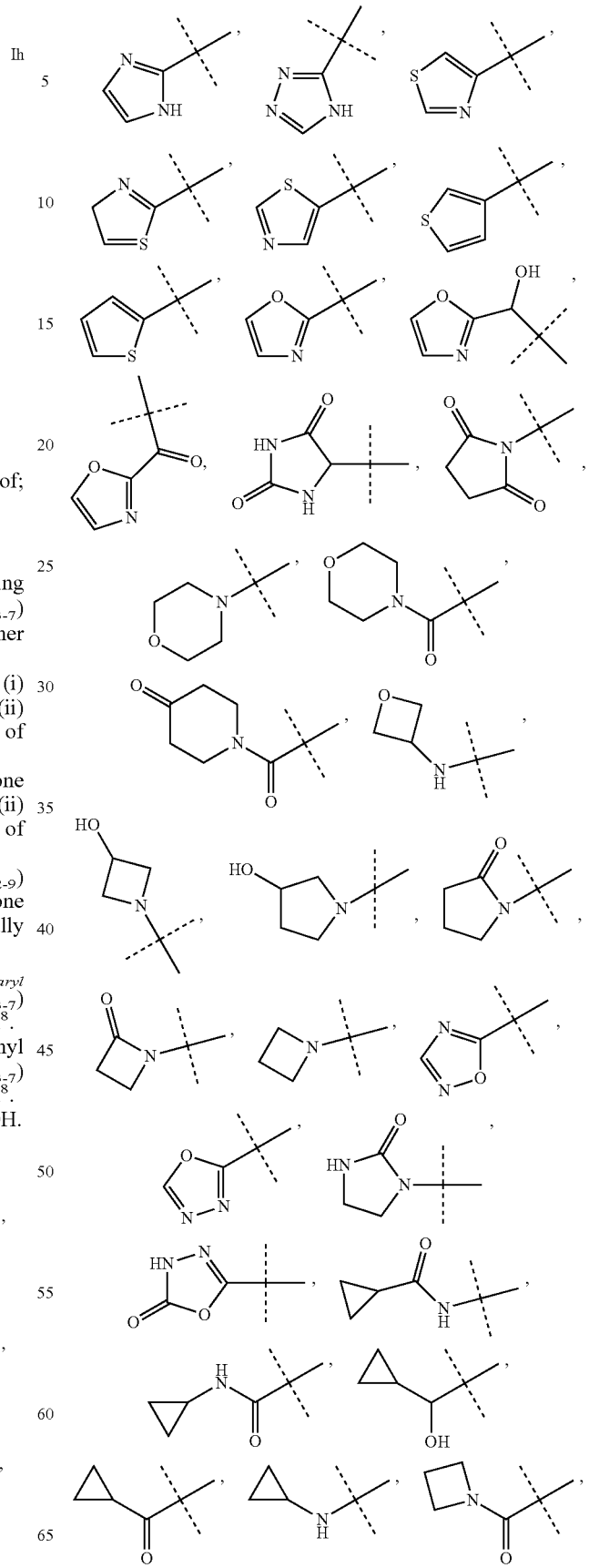

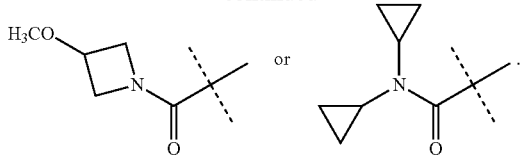

19. A compound selected from:
3-fluoro-4-[1-(pyridin-2-ylcarbonyl)-1H-indazol-3-yl] benzoic acid;
4-(1-(2-chloro-6-cyclypropoxybenzoyl)-1H-indazol-3-yl) benzoic acid;
(E)-4-(1-(2-chloro-6-(prop-1-enyl)benzoyl)-1H-pyrazolo [4,3-b]pyridin-3-yl)-3-fluorobenzoic acid;
4-(1-(2-chloro-6-(trifluoromethyl)benzoyl)-4-formyl-1H-indazol-3-yl)benzoic acid;
4-(1-(2-chloro-6-cyclopropoxybenzoyl)-1H-pyrazolo[4,3-b]pyridin-3-yl)benzoic acid;
3-fluoro-4-(1-(2-phenylpropanoyl)-1H-indazol-3-yl)benzoic acid;
3-fluoro-4-[1-(methoxyacetyl)-1H-indazol-3-yl]benzoic acid;
3-fluoro-4-[1-(pyridin-3-ylcarbonyl)-1H-indazol-3-yl] benzoic acid;
3-fluoro-4-{1-[(2-oxopyrrolidin-1-yl)acetyl]-1H-indazol-3-yl}benzoic acid;
3-fluoro-4-[1-(naphthalen-1-ylcarbonyl)-1H-indazol-3-yl]benzoic acid;
3-fluoro-4-{1-[(1-methyl-1H-indol-2-yl)carbonyl]-1H-indazol-3-yl}benzoic acid;
4-{1-[(2-bromo-3-methylphenyl)carbonyl]-1H-indazol-3-yl}-3-fluorobenzoic acid;
4-[1-(2,3-dihydro-1H-inden-4-ylcarbonyl)-1H-indazol-3-yl]-3-fluorobenzoic acid;
4-(1-{[3-(tertbutoxycarbonyl)-3-azabicyclo[3.1.0]hex-6-yl]carbonyl}-1H-indazol-3-yl)-3-fluorobenzoic acid;
4-[1-(2,3-dihydro-1-benzofuran-7-ylcarbonyl)-1H-indazol-3-yl]-3-fluorobenzoic acid;
4-[1-(1-benzofuran-7-ylcarbonyl)-1H-indazol-3-yl]-3-fluorobenzoic acid;
4-{1-[(2-bromo-3-chlorophenyl)carbonyl]-1H-indazol-3-yl}-3-fluorobenzoic acid;
3-fluoro-4-(1-(tetrahydrofuran-2-carbonyl)-1H-indazol-3-yl)benzoic acid;
4-(1-(2-chloro-6-(trifluoromethyl)benzoyl)-6-(morpholine-4-carbonyl)-1H-indazol-3-yl)benzoic acid;
4-(1-(2-chloro-6-(trifluoromethyl)benzoyl)-6-((2S,6R)-2,6-dimethylmorpholine-4-carbonyl)-1H-indazol-3-yl)-3-fluorobenzoic acid;
4-(1-(2-chloro-6-(trifluoromethyl)benzoyl)-6-(4-oxopiperidine-1-carbonyl)-1H-indazol-3-yl)-3-fluorobenzoic acid;
2-acetamido-4-(1-(2-chloro-6-(trifluoromethyl)benzoyl)-1H-indazol-3-yl)benzoic acid;
4-(1-(2-chloro-6-(trifluoromethyl)benzoyl)-1H-pyrazolo [4,3-b]pyridin-3-yl)-2-(methylsulfonamido)benzoic acid;
4-(1-(2-chloro-6-(trifluoromethyl) benzoyl)-6-(3-hydroxyazetidin-1-yl)-1H-indazol-3-yl)benzoic acid;
4-(6-(azetidin-1-yl)-1-(2-chloro-6-(trifluoromethyl)benzoyl)-1H-indazol-3-yl)-3-fluorobenzoic acid;
4-(1-(2-chloro-6-(trifluoromethyl)benzoyl)-6-(cyclopropylamino)-1H-indazol-3-yl)-3-fluorobenzoic acid;
4-(1-(2-chloro-6-(trifluoromethyl)benzoyl)-6-(oxetan-3-ylamino)-1H-indazol-3-yl)-3-fluorobenzoic acid;
4-(1-(2-chloro-6-(trifluoromethyl)benzoyl)-6-(3-hydroxypyrrolidin-1-yl)-1H-indazol-3-yl)-3-fluorobenzoic acid;
4-(1-(2-chloro-6-(trifluoromethyl)benzoyl)-6-morpholino-1H-indazol-3-yl)benzoic acid;
4-(1-(2-chloro-6-(trifluoromethyl)benzoyl)-6-(methoxycarbonylamino)-1H-indazol-3-yl)-3-fluorobenzoic acid;
4-(1-(2-chloro-6-(trifluoromethyl)benzoyl)-6-(N-methylacetamido)-1H-indazol-3-yl)-3-fluorobenzoic acid;
4-(1-(2-chloro-6-(trifluoromethyl)benzoyl)-6-(cyclopropanecarboxamido)-1H-indazol-3-yl)-3-fluorobenzoic acid;
4-(1-(2-chloro-6-(trifluoromethyl)benzoyl)-6-(methylsulfonamido)-1H-indazol-3-yl)-3-fluorobenzoic acid;
4-(1-(2-chloro-6-(trifluoromethyl)benzoyl)-6-(3-methylureido)-1H-indazol-3-yl)-3-fluorobenzoic acid;
4-(6-acetamido-1-(2-chloro-6-(trifluoromethyl)benzoyl)-1H-indazol-3-yl)-3-fluorobenzoic acid;
4-(1-(2-chloro-6-(trifluoromethyl)benzoyl)-6-(N-methylmethylsulfonamido)-1H-indazol-3-yl)-3-fluorobenzoic acid;
4-(1-(2-chloro-6-(trifluoromethyl)benzoyl)-6-(1,3-dimethylureido)-1H-indazol-3-yl)-3-fluorobenzoic acid;
4-(1-(2-chloro-6-(trifluoromethyl)benzoyl)-6-(2-oxo-imidazolidin-1-yl)-1H-indazol-3-yl)-3-fluorobenzoic acid;
4-(1-(2-chloro-6-(trifluoromethyl)benzoyl)-6-(2-oxoazetidin-1-yl)-1H-indazol-3-yl)-3-fluorobenzoic acid;
4-(6-(2-carboxyethylamino)-1-(2-chloro-6-(trifluoromethyl)benzoyl)-1H-indazol-3-yl)-3-fluorobenzoic acid;
4-(1-(2-chloro-6-(trifluoromethyl)benzoyl)-6-(3-methyl-2-oxoimidazolidin-1-yl)-1H-indazol-3-yl)-3-fluorobenzoic acid;
4-(1-(2-chloro-6-(trifluoromethyl)benzoyl)-6-(2-oxopyrrolidin-1-yl)-1H-indazol-3-yl)-3-fluorobenzoic acid;
4-(1-(2-chloro-6-(trifluoromethyl)benzoyl)-6-(morpholine-4-carbonyl)-1H-indazol-3-yl)benzoic acid;
3-(4-carboxyphenyl)-1-(2-chloro-6-(trifluoromethyl)benzoyl)-1H-indazole-6-carboxylic acid;
4-(1-(2-chloro-6-(trifluoromethyl)benzoyl)-6-(cyclopropylcarbamoyl)-1H-pyrazolo[4,3-b]pyridin-3-yl)-3-fluorobenzoic acid;
4-(1-(2-chloro-6-(trifluoromethyl)benzoyl)-6-(cyclopropyl(methyl)carbamoyl)-1H-pyrazolo[4,3-b]pyridin-3-yl)-3-fluorobenzoic acid;
4-(1-(2-chloro-6-(trifluoromethyl)benzoyl)-6-(cyclopropyl(hydroxy)methyl)-1H-pyrazolo[4,3-b]pyridin-3-yl)-3-fluorobenzoic acid;
4-(1-(2-chloro-6-(trifluoromethyl)benzoyl)-6-(cyclopropane-carbonyl)-1H-pyrazolo[4,3-b]pyridin-3-yl)-3-fluorobenzoic acid;
4-(1-(2-chloro-6-(trifluoromethyl)benzoyl)-6-(hydroxy (oxazol-2-yl)methyl)-1H-pyrazolo[4,3-b]pyridine-3-yl)-3-fluorobenzoic acid;
4-(1-(2-chloro-6-(trifluoromethyl)benzoyl)-6-(oxazole-2-carbonyl)-1H-pyrazolo[4,3-b]pyridin-3-yl)-3-fluorobenzoic acid;
sodium 4-(1-(2-chloro-6-(trifluoromethyl)benzoyl)-6-(5-methyloxazol-2-yl)-1H-indazol-3-yl)benzoate;
4-(1-(2-chloro-6-(trifluoromethyl)benzoyl)-6-(5-methyloxazol-2-yl)-1H-indazol-3-yl)-3-fluorobenzoic acid;
4-(1-(2-chloro-6-(trifluoromethyl)benzoyl)-6-(3-hydroxyprop-1-ynyl)-1H-indazol-3-yl)benzoic acid;
4-(1-(2-chloro-6-(trifluoromethyl)benzoyl)-6-(3-hydroxybut-1-ynyl)-1H-indazol-3-yl)-3-fluorobenzoic acid;

4-(6-(3-aminoprop-1-ynyl)-1-(2-chloro-6-(trifluoromethyl)benzoyl)-1H-indazol-3-yl)-3-fluorobenzoic acid;
4-(1-(2-chloro-6-(trifluoromethyl)benzoyl)-6-ethynyl-1H-indazol-3-yl)benzoic acid;
4-(1-(2-chloro-6-(trifluoromethyl)benzoyl)-6-(3-methyl-1,2,4-oxadiazol-5-yl)-1H-indazol-3-yl)-3-fluorobenzoic acid;
4-(1-(2-chloro-6-(trifluoromethyl)benzoyl)-6-(5-(hydroxymethyl)oxazol-2-yl)-1H-indazol-3-yl)-3-fluorobenzoic acid;
4-(1-(2-chloro-6-(trifluoromethyl)benzoyl)-6-(1-methyl-1H-imidazol-4-yl)-1H-indazol-3-yl)-3-fluorobenzoic acid;
4-(1-(2-chloro-6-(trifluoromethyl)benzoyl)-6-(oxazol-2-yl)-1H-indazol-3-yl)-3-fluorobenzoic acid;
4-(6-(5-bromooxazol-2-yl)-1-(2-chloro-6-(trifluoromethyl)benzoyl)-1H-indazol-3-yl)-3-fluorobenzoic acid;
(E)-4-(1-(2-chloro-6-(trifluoromethyl)benzoyl)-6-(N'-cyano-N,N-dimethylcarbamimidoyl)-1H-indazol-3-yl)-3-fluorobenzoic acid;
4-(1-(2-chloro-6-(trifluoromethyl)benzoyl)-6-(5-oxo-4,5-dihydro-1,3,4-oxadiazol-2-yl)-1H-indazol-3-yl)-3-fluorobenzoic acid;
4-(1-(2-chloro-6-(trifluoromethyl)benzoyl)-6-(4H-1,2,4-triazol-3-yl)-1H-indazol-3-yl)-3-fluorobenzoic acid;
4-(1-(2-chloro-6-(trifluoromethyl)benzoyl)-6-(5-methyl-1,3,4-oxadiazol-2-yl)-1H-indazol-3-yl)-3-fluorobenzoic acid;
4-(1-(2-chloro-6-(trifluoromethyl)benzoyl)-6-(1-methyl-1H-imidazol-2-yl)-1H-indazol-3-yl)-3-fluorobenzoic acid;
4-[1-{[2-chloro-6-(trifluoromethyl)phenyl]carbonyl}-6-(1-methyl-1H-imidazol-5-yl)-1H-indazol-3-yl]benzoic acid;
4-[1-{[2-chloro-6-(trifluoromethyl)phenyl]carbonyl}-6-(5-methylthiophen-3-yl)-1H-indazol-3-yl]benzoic acid;
4-(1-{[2-chloro-6-(trifluoromethyl)phenyl]carbonyl}-6-pyrimidin-2-yl-1H-indazol-3-yl)benzoic acid;
4-(1-{[2-chloro-6-(trifluoromethyl)phenyl]carbonyl}-6-pyrimidin-4-yl-1H-indazol-3-yl)benzoic acid;
4-[1-{[2-chloro-6-(trifluoromethyl)phenyl]carbonyl}-6-(1-methyl-1H-imidazol-4-yl)-1H-indazol-3-yl]benzoic acid;
4-[1-{[2-chloro-6-(trifluoromethyl)phenyl]carbonyl}-6-(1,3-thiazol-4-yl)-1H-indazol-3-yl]benzoic acid;
4-(6-[4-(aminomethyl)pyridin-2-yl]-1-{[2-chloro-6-(trifluoromethyl)phenyl]carbonyl}-1H-indazol-3-yl)benzoic acid;
4-(1-{[2-chloro-6-(trifluoromethyl)phenyl]carbonyl}-6-pyridin-2-yl-1H-indazol-3-yl)benzoic acid;
4-[1-{[2-chloro-6-(trifluoromethyl)phenyl]carbonyl}-6-(1,3-thiazol-5-yl)-1H-indazol-3-yl]benzoic acid;
4-(1-{[2-chloro-6-(trifluoromethyl)phenyl]carbonyl}-6-pyridin-4-yl-1H-indazol-3-yl)benzoic acid;
4-[1-{[2-chloro-6-(trifluoromethyl)phenyl]carbonyl}-6-(4-cyanophenyl)-1H-indazol-3-yl]benzoic acid;
4-[1-{[2-chloro-6-(trifluoromethyl)phenyl]carbonyl}-6-(3-cyanophenyl)-1H-indazol-3-yl]benzoic acid;
4-[1-{[2-chloro-6-(trifluoromethyl)phenyl]carbonyl}-6-(2-cyanophenyl)-1H-indazol-3-yl]benzoic acid;
4-[1-{[2-chloro-6-(trifluoromethyl)phenyl]carbonyl}-6-(2-fluorophenyl)-1H-indazol-3-yl]benzoic acid;
4-[1-{[2-chloro-6-(trifluoromethyl)phenyl]carbonyl}-6-(3-fluorophenyl)-1H-indazol-3-yl]benzoic acid;
4-[1-{[2-chloro-6-(trifluoromethyl)phenyl]carbonyl}-6-(4-fluorophenyl)-1H-indazol-3-yl]benzoic acid;
4-[1-{[2-chloro-6-(trifluoromethyl)phenyl]carbonyl}-6-(1-methyl-1H-pyrazol-5-yl)-1H-indazol-3-yl]benzoic acid;
4-(1-(2-chloro-6-(trifluoromethyl)benzoyl)-6-(methylsulfonamidomethyl)-1H-indazol-3-yl)benzoic acid;
4-(1-(2-chloro-6-(trifluoromethyl)benzoyl)-6-(2,5-dioxoimidazolidin-4-yl)-1H-indazol-3-yl)-3-fluorobenzoic acid;
4-(5-(tert-butoxycarbonylamino)-1-(2-chloro-6-(trifluoromethyl)benzoyl)-1H-pyrrolo[2,3-c]pyridin-3-yl)-3-fluorobenzoic acid;
4-(6-(tert-butoxycarbonylamino)-1-(2-chloro-6-(trifluoromethyl)benzoyl)-1H-pyrazolo[4,3-b]pyridin-3-yl)-3-fluorobenzoic acid;
4-(1-(2-chloro-6-(trifluoromethyl)benzoyl)-6-(methylamino)-1H-pyrazolo[4,3-b]pyridin-3-yl)-3-fluorobenzoic acid;
4-(5-acetamido-1-(2-chloro-6-(trifluoromethyl)-benzoyl)-1H-pyrrolo[2,3-c]pyridin-3-yl)-3-fluorobenzoic acid;
4-(1-(2-chloro-6-(trifluoromethyl)benzoyl)-5-(methylamino)-1H-pyrrolo[2,3-c]pyridin-3-yl)-3-fluorobenzoic acid;
4-(1-(2-chloro-6-cyclopropylbenzoyl)-1H-pyrazolo[4,3-b]pyridin-3-yl)-3-fluorobenzoic acid;
4-(1-(2-chloro-6-vinylbenzoyl)-1H-pyrazolo[4,3-b]pyridin-3-yl)-3-fluorobenzoic acid;
4-(1-(2-chloro-6-(prop-1-en-2-yl)benzoyl)-1H-pyrazolo[4,3-b]pyridin-3-yl)-3-fluorobenzoic acid;
4-(1-(6-chloro-2,3-dihydrobenzo[b][1,4]dioxine-5-carbonyl)-1H-pyrazolo[4,3-b]pyridin-3-yl)-3-fluorobenzoic acid;
4-(1-(2-(dimethylamino)-6-methylbenzoyl)-1H-pyrazolo[4,3-b]pyridin-3-yl)-3-fluorobenzoic acid;
4-(4-chloro-1-(2-chloro-6-cyclopropylbenzoyl)-1H-indazol-3-yl)-3-fluorobenzoic acid;
4-(1-(2-chloro-6-cyclopropylbenzoyl)-4-fluoro-1H-indazol-3-yl)-3-fluorobenzoic acid;
4-(1-(2-chloro-6-cyclobutylbenzoyl)-1H-pyrazolo[4,3-b]pyridin-3-yl)-3-fluorobenzoic acid;
4-(1-(2-chloro-6-cyclopropylbenzoyl)-1H-indazol-3-yl)-3-fluorobenzoic acid;
4-(1-(2-chloro-6-morpholinobenzoyl)-1H-pyrazolo[4,3-b]pyridin-3-yl)-3-fluorobenzoic acid;
4-(1-(2-chloro-6-(trifluoromethyl)benzoyl)-6-(3-methylmorpholine-4-carbonyl)-1H-pyrazolo[4,3-b]pyridin-3-yl)-3-fluorobenzoic acid;
4-(1-(2-chloro-6-(trifluoromethyl)benzoyl)-6-(3,5-dimethylmorpholine-4-carbonyl)-1H-pyrazolo[4,3-b]pyridin-3-yl)-3-fluorobenzoic acid;
4-(1-(2-chloro-6-(trifluoromethyl)benzoyl)-6-(2-methoxyethylamino)-1H-pyrazolo[4,3-b]pyridin-3-yl)-3-fluorobenzoic acid;
4-(1-(2-chloro-6-(trifluoromethyl)benzoyl)-2-methyl-1H-indol-3-yl)-3-fluorobenzoic acid;
4-(2-methyl-1-(2-(trifluoromethyl)benzoyl)-1H-indol-3-yl)benzoic acid;
4-(1-(2-chloro-6-cyclopropylbenzoyl)-1H-pyrazolo[4,3-b]pyridin-3-yl)-3,5-difluorobenzoic acid;
4-(1-(2-chloro-6-cyclopropylbenzoyl)-1H-indazol-3-yl)-3,5-difluorobenzoic acid;
4-(1-(2-chloro-6-cyclopropylbenzoyl)-4-fluoro-1H-indazol-3-yl)-3,5-difluorobenzoic acid;
4-(1-(2-chloro-6-cyclopropylbenzoyl)-1H-pyrrolo[3,2-b]pyridin-3-yl)-3,5-difluorobenzoic acid;
4-(1-(2-chloro-6-cyclobutylbenzoyl)-1H-pyrazolo[4,3-b]pyridin-3-yl)-3,5-difluorobenzoic acid;

4-(1-(2-chloro-6-(trifluoromethyl)benzoyl)-6-(1,3-oxazinane-3-carbonyl)-1H-pyrazolo[4,3-b]pyridin-3-yl)-3-fluorobenzoic acid;
4-(1-(2-chloro-6-(trifluoromethyl)benzoyl)-6-(oxazolidine-3-carbonyl)-1H-pyrazolo[4,3-b]pyridin-3-yl)-3-fluorobenzoic acid;
4-(6-(azetidine-1-carbonyl)-1-(2-chloro-6-(trifluoromethyl)benzoyl)-1H-indol-3-yl)-3-fluorobenzoic acid;
4-(1-(2-chloro-6-(trifluoromethyl)benzoyl)-6-(3-methoxy-azetidine-1-carbonyl)-1H-indol-3-yl)-3-fluorobenzoic acid;
4-(6-(2-amino-2-oxoethyl)-1-(2-chloro-6-(trifluoromethyl)benzoyl)-1H-pyrazolo[4,3-b]pyridin-3-yl)-3-fluorobenzoic acid;
4-(6-(2-(azetidin-1-yl)-2-oxoethyl)-1-(2-chloro-6-(trifluoromethyl)benzoyl)-1H-pyrazolo[4,3-b]pyridin-3-yl)-3-fluorobenzoic acid;
4-(1-(2-chloro-6-(trifluoromethyl)benzoyl)-6-(2-(methylamino)-2-oxoethyl)-1H-pyrazolo[4,3-b]pyridin-3-yl)-3-fluorobenzoic acid;
4-(1-(2-chloro-6-(trifluoromethyl)benzoyl)-6-(2-(dimethylamino)-2-oxoethyl)-1H-pyrazolo[4,3-b]pyridin-3-yl)-3-fluorobenzoic acid;
4-(1-(2-chloro-6-(trifluoromethyl)benzoyl)-6-(oxetan-3-yl)-1H-indazol-3-yl)-3-fluorobenzoic acid;
4-(1-(2-chloro-4-(2-methoxyethoxy)-6-methylbenzoyl)-1H-pyrazolo[4,3-b]pyridin-3-yl)-3-fluorobenzoic acid;
4-(1-(2-chloro-6-methyl-4-morpholinobenzoyl)-1H-pyrazolo[4,3-b]pyridin-3-yl)-3-fluorobenzoic acid;
4-(1-(2-chloro-6-(trifluoromethyl)benzoyl)-6-(dicyclopropylcarbamoyl)-1H-pyrazolo[4,3-b]pyridin-3-yl)-3-fluorobenzoic acid;
4-(1-(4-amino-2-chloro-6-methylbenzoyl)-1H-pyrazolo[4,3-b]pyridin-3-yl)-3-fluorobenzoic acid;
4-(1-(2-chloro-6-cyclopentylbenzoyl)-1H-pyrazolo[4,3-b]pyridin-3-yl)-3-fluorobenzoic acid; and
4-(1-(2-chloro-6-cyclobutylbenzoyl)-1H-pyrazolo[4,3-b]pyridin-3-yl)-3,5-difluorobenzoic acid.

20. A pharmaceutical composition comprising a compound of claim 1 or a pharmaceutically acceptable salt or solvate thereof, and one or more pharmaceutically acceptable excipients.

21. The pharmaceutical composition of claim 20, further comprising at least one additional therapeutically active agent.

22. A method for treating a disease or condition mediated by RORgammaT in a subject, comprising administering to the subject an amount of a compound of claim 1, or a pharmaceutically acceptable salt or solvate thereof, that is effective for treating the disease or condition mediated by RORgammaT in the subject, wherein the disease or condition is an autoimmune disease.

23. A method for treating a disease or condition selected from the group consisting of multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis, and mucosal leishmaniasis in a subject, comprising administering to the subject an amount of a compound of claim 1, or a pharmaceutically acceptable salt thereof, that is effective for treating the disease or condition.

24. The compound of claim 10, wherein $R^3$ is hydrogen or halogen.

25. The compound of claim 24, wherein $R^5$ and $R^7$ are hydrogen or halogen.

26. The compound of claim 25, wherein $R^6$ is $(C_{3-5})$heterocycloalkylcarbonyl or $(C_{3-5})$heterocycloalkylcarbonyl$(C_{1-4})$alkyl, optionally substituted with one or more groups selected from halogen, amino, hydroxyl, oxo (=O), $H_2NC(O)$—, $(C_{1-3})$alkoxycarbonyl, $(di)(C_{1-6})$alkylaminocarbonyl, $(C_{1-4})$alkyl or $(C_{1-3})$alkoxy, wherein $(C_{1-3})$alkoxycarbonyl, $(di)(C_{1-6})$alkylaminocarbonyl, $(C_{1-4})$alkyl and $(C_{1-3})$alkoxy are optionally substituted with one or more halogen, amino or hydroxyl.

27. The compound of claim 26, wherein $R^8$ is halogen, $(C_{1-4})$alkyl, or $(C_{3-7})$cycloalkyl, wherein the $(C_{1-4})$alkyl is optionally substituted with one, two or three halogens.

28. A pharmaceutical composition comprising a compound of claim 27 or a pharmaceutically acceptable salt thereof, and one or more pharmaceutically acceptable excipients.

29. A method for treating a disease or condition mediated by RORgammaT in a subject, comprising administering to the subject an amount of a compound of claim 19, or a pharmaceutically acceptable salt thereof, that is effective for treating the disease or condition mediated by RORgammaT in the subject, wherein the disease or condition is an autoimmune disease.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Leu Xaa Xaa Leu Leu
1               5

<210> SEQ ID NO 2
<211> LENGTH: 25
<212> TYPE: PRT
<213> ORGANISM: Artificial Sequence
<220> FEATURE:
<223> OTHER INFORMATION: SRC1_2 peptide

```
<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
                20                  25
```